US009297026B2

(12) United States Patent
Koepke et al.

(10) Patent No.: US 9,297,026 B2
(45) Date of Patent: Mar. 29, 2016

(54) RECOMBINANT MICROORGANISMS AND METHODS OF USE THEREOF

(71) Applicant: LanzaTech New Zealand Limited, Skokie, IL (US)

(72) Inventors: Michael Koepke, Skokie, IL (US); Shilpa Nagaraju, Skokie, IL (US); Wendy Yiting Chen, Sydney (AU)

(73) Assignee: LanzaTech New Zealand Limited, Auckland (NZ)

( * ) Notice: Subject to any disclaimer, the term of this patent is extended or adjusted under 35 U.S.C. 154(b) by 0 days.

(21) Appl. No.: 14/703,222

(22) Filed: May 4, 2015

(65) Prior Publication Data

US 2015/0299737 A1 Oct. 22, 2015

Related U.S. Application Data

(62) Division of application No. 13/876,563, filed as application No. PCT/NZ2013/000012 on Jan. 31, 2013, now Pat. No. 9,057,071.

(60) Provisional application No. 61/593,269, filed on Jan. 31, 2012.

(51) Int. Cl.

| | |
|---|---|
| ***C12P 7/06*** | (2006.01) |
| ***C12N 15/00*** | (2006.01) |
| ***C12N 15/52*** | (2006.01) |
| ***C12P 7/40*** | (2006.01) |
| ***C12N 1/20*** | (2006.01) |
| ***C12N 9/88*** | (2006.01) |
| ***C12N 9/04*** | (2006.01) |
| ***C12N 9/10*** | (2006.01) |
| ***C12P 7/46*** | (2006.01) |
| ***C12P 7/48*** | (2006.01) |
| ***C12P 7/50*** | (2006.01) |
| ***C12P 7/56*** | (2006.01) |
| ***C12P 13/06*** | (2006.01) |
| ***C12P 13/08*** | (2006.01) |
| ***C12N 15/74*** | (2006.01) |
| ***C12P 7/42*** | (2006.01) |

(52) U.S. Cl.

CPC . *C12P 7/065* (2013.01); *C12N 1/20* (2013.01); *C12N 9/0006* (2013.01); *C12N 9/1022* (2013.01); *C12N 9/88* (2013.01); *C12N 15/00* (2013.01); *C12N 15/52* (2013.01); *C12N 15/74* (2013.01); *C12P 7/40* (2013.01); *C12P 7/42* (2013.01); *C12P 7/46* (2013.01); *C12P 7/48* (2013.01); *C12P 7/50* (2013.01); *C12P 7/56* (2013.01); *C12P 13/06* (2013.01); *C12P 13/08* (2013.01); *C12Y 101/01004* (2013.01); *C12Y 202/01006* (2013.01); *C12Y 401/01005* (2013.01); *C12N 2510/02* (2013.01); *Y02E 50/17* (2013.01)

(58) Field of Classification Search

None

See application file for complete search history.

(56) References Cited

U.S. PATENT DOCUMENTS

2008/0293101 A1 11/2008 Peters et al.
2010/0285548 A1 11/2010 Friedmann et al.

FOREIGN PATENT DOCUMENTS

WO 2009113878 A1 9/2009
WO 2010121849 A1 10/2010

OTHER PUBLICATIONS

Abrini, Arch Microbiol, 161: 345-351, 1994.
Collins, Int J System Bacteriol, 44: 812-826, 1994.
Drake, Acetogenic Prokaryotes, In: The Prokaryotes (3rd Edition), Springer, New York, NY, 354-420, 2006.
Green, Microbiol, 142: 2079-2086, 1996.
Heap, J Microbiol Meth, 80: 49-55, 2010.
Köpke, Appl Environ Microbiol, 77: 5467-5475, 2011.
Köpke, Curr Opin Biotechnol, 22: 320-325, 2011.
Köpke, PNAS USA, 107: 13087-13092, 2010.
Nicholson, Appl Environ Microbiol, 74: 6832-6838, 2008.
Perez, Biotechnol Bioeng, 1-30, 2012.
Romero, Appl Environ Microbiol, 74: 5190-5198, 2007.
Smart, Nat Protoc, 5: 1709-1729, 2010.
Extended European Search Report, European Patent Application 13743087, Mar. 14, 2014.
Tanner, Int J System Bacteriol, 43: 232-236, 1993.
Tittmann, PNAS USA, 102: 553-558, 2005.
Tummala, J Bacteriol, 185: 1923-1934, 2003.
Tummala, J Bacteriol, 185: 3644-3653, 2003.
Vinogradov, Biochim Biophys Acta, 1760: 356-363, 2006.
Wood, Biotechnol Prog, 21: 1366-1372, 2005.
Yan, Organic Biomolecular Chem, 7: 3914-3917, 2009.
International Search Report, International Patent Application PCT/NZ2013/000012, Jul. 26, 2013.

*Primary Examiner* — Suzanne M Noakes
*Assistant Examiner* — Jae W Lee
(74) *Attorney, Agent, or Firm* — Andrea E. Schoen

(57) ABSTRACT

The invention relates to methods for the production of chemical compounds, particularly but not exclusively ethanol, by microbial fermentation. Also described are genetically modified micro-organisms capable of using carbon monoxide to produce one or more products, particularly but not exclusively ethanol as a main product, and producing a reduced amount or substantially no 2,3-butanediol and/or a precursor thereof.

17 Claims, 6 Drawing Sheets

RECOMBINANT MICROORGANISMS AND METHODS OF USE THEREOF

CROSS REFERENCE TO RELATED APPLICATIONS

This application claims the benefit of U.S. patent application Ser. No. 13/876,563 filed Mar. 28, 2013, which is a national phase of International Patent Application PCT/NZ2013/000012 filed Jan. 30, 2013, which claims priority to U.S. Provisional Patent Application 61/593,269 filed Jan. 31, 2012, the entirety of which are incorporated herein by reference.

STATEMENT REGARDING FEDERALLY SPONSORED RESEARCH

This invention was made with Government support under contract no W911NF-11C-0090 awarded by Defense Advanced Research Projects Agency (DARPA). The Government may have certain rights in this invention.

FIELD

The present invention relates to methods for the production of chemical compounds, particularly but not exclusively ethanol, by microbial fermentation and genetically modified micro-organisms of use in such methods.

BACKGROUND

Acetogenic microorganisms are known to be useful for the production of fuels (for example, ethanol or butanol) and other chemicals by fermentation of substrates including carbon monoxide, carbon dioxide, hydrogen and methanol, for example. Many of these microorganisms naturally produce at least two, if not more, products. However, where micoorganisms are being used to produce products, particularly on a commercial scale, it is not always desirable for the microorganisms to produce multiple products. For example, production of multiple products can come at the expense of production efficiency and yield of a product of particular value, as by-products can divert carbon away from the pathways involved in producing the main desired product. In addition, by-products may be toxic to the microorganism, the production of multiple products can make recovery and separation of desired products difficult and, it can be difficult to control fermentation conditions to favour production of one product over another. By-products may also be a potential source of contamination in a fermenter as they may be substrates for undesirable organisms.

In the case of ethanol production by microbial fermentation of substrates comprising carbon monoxide, 2,3-butanediol is typically produced as a by-product. This may reduce the ethanol production efficiency and yield, as well as cause other problems, as noted above.

It is an object of the invention to overcome one or more of the disadvantages of the prior art, or to at least to provide the public with a useful choice.

SUMMARY OF INVENTION

The invention relates, inter alia, to novel genetically modified microorganisms capable of using carbon monoxide to produce one or more product and producing a reduced amount of 2,3 butanediol and/or a precursor thereof compared to a parental microorganism. In one embodiment, the genetically modified microorganism produces substantially no 2,3 butanediol and/or a precursor thereof compared to a parental microorganism. In one particular embodiment the microorganism produces ethanol as the main product.

In a first aspect, the invention provides a carboxydotrophic acetogenic microorganism which is adapted to produce one or more product and a reduced amount or substantially no 2,3 butanediol and/or a precursor thereof upon fermentation of a substrate comprising carbon monoxide, the microorganism comprising one or more genetic modification which disrupts the 2,3-butanediol biosynthesis pathway compared to a parental microorganism.

In one particular embodiment, the invention provides a carboxydotrophic acetogenic microorganism which is adapted to produce ethanol as the main product and a reduced amount or substantially no 2,3 butanediol and/or a precursor thereof upon fermentation of a substrate comprising carbon monoxide, the microorganism comprising one or more genetic modification which disrupts the 2,3-butanediol biosynthesis pathway compared to a parental microorganism.

In one embodiment, the microorganism is adapted to further produce one or more of formate, lactate, pyruvate, succinate, valine, leucine, isoleucine, acetolactate, malate, fumerate, 2-oxogluterate, citrate.

In one embodiment, the microorganism is adapted to produce an increased amount of one or more of ethanol, formate, lactate, pyruvate, succinate, valine, leucine, isoleucine, acetolactate, malate, fumerate, 2-oxogluterate, citrate compared to a parental microorganism.

In one embodiment, the microorganism comprises at least one genetic modification which disrupts the expression and/or activity of one or more enzyme capable of converting pyruvate to acetolactate.

In one embodiment, the one or more enzyme capable of converting pyruvate to acetolactate is an acetolactate synthase (alsS).

In one embodiment, the microorganism comprises at least one genetic modification which disrupts the expression and/or activity of one or more capable of converting acetolactate to acetoin.

In one embodiment, the one or more enzyme capable of converting acetolactate to acetoin is an acetolactate decarboxylase (budA).

In one embodiment, the microorganism comprises at least one genetic modification which disrupts the expression and/or activity of one or more enzyme capable of converting acetoin to 2,3-butanediol.

In one embodiment, the one or more enzyme capable of converting acetoin to 2,3-butanediol is an enzyme chosen from 2,3-butanediol dehydrogenase (2,3bdh), an acetoin reductase, a primary:secondary alcohol dehydrogenase.

In one embodiment, the microorganism comprises at least one genetic modification which disrupts the expression and/or activity of a combination of two or more of the enzymes capable of converting pyruvate to acetolactate, acetolactate to acetoin, and/or acetoin to 2,3-butanediol.

In one embodiment, the genetic modification disrupts the expression and/or activity of one or more:

Acetolactate synthase (alsS);

Acetolactate decarboxylase (BudA);

2,3-Butanediol dehydrogenase (2,3 bdh);

Acetoin reductase; and,

Primary :secondary alcohol dehydrogenase.

In one embodiment, the genetic modification disrupts the expression and/or activity of one or more:

Acetolactate synthase (alsS);

Acetolactate decarboxylase (BudA); and, 2,3-Butanediol dehydrogenase (2,3 bdh).

In one embodiment, the one or more genetic modification disrupts one or more of the genes encoding one or more of the above enzymes. In one embodiment, the one or more genetic modification disrupts the activity of a compound required for the expression or activity of one or more of the above enzymes. In one embodiment, the one or more genetic modification increases the expression or activity of one or more compounds which inhibit the expression or activity of one or more of the above enzymes.

In one particular embodiment, the microorganism is selected from the group comprising *Clostridium autoethanogenum, Clostridium ljungdahlii*, and *Clostridium ragsdalei* and related isolates. In another embodiment, the group also comprises *Clostridium coskatii.*

In one particular embodiment, the microorganism is *Clostridium autoethanogenum* DSM23693.

In a second aspect, the invention provides a method for the production of a carboxydotrophic acetogenic microorganism which is adapted to produce one or more product and a reduced amount or substantially no 2,3 butanediol and/or a precursor thereof upon fermentation of a substrate comprising carbon monoxide, the method comprising genetically modifying a carboxydotrophic acetogenic parental microorganism to disrupt the 2,3-butanediol biosynthesis pathway.

In one embodiment, the method results in increased production of the one or more product compared to a parental microorganism.

In one particular embodiment, the invention provides a method for the production of a carboxydotrophic acetogenic microorganism which is adapted to produce ethanol as the main product and a reduced amount or substantially no 2,3 butanediol and/or a precursor thereof upon fermentation of a substrate comprising carbon monoxide, the method comprising genetically modifying a carboxydotrophic acetogenic parental microorganism to disrupt the 2,3-butanediol biosynthesis pathway.

The invention also provides microorganisms made by a method of the second aspect.

In one embodiment, the method comprises introducing to the parental microorganism one or more genetic modifications which disrupt one or more genes encoding one or more enzymes capable of converting pyruvate to acetolactate. In one embodiment, the one or more enzymes capable of converting pyruvate to acetolactate is an acetolactate synthase (alsS).

In one embodiment, the method comprises introducing to the parental microorganism one or more genetic modifications which disrupt one or more genes encoding one or more enzymes capable of converting acetolactate to acetoin. In one embodiment, the one or more enzymes capable of converting acetolactate to acetoin is an acetolactate decarboxylase (budA).

In one embodiment, the method comprises introducing to the parental microorganism one or more genetic modifications which disrupt one or more genes encoding one or more enzymes capable of converting acetoin to 2,3-butanediol. In one embodiment, the one or more enzymes capable of converting acetoin to 2,3-butanediol is chosen from a 2,3-butanediol dehydrogenase (2,3bdh), an acetoin reductase, a primary:secondary alcohol dehydrogenase.

In one embodiment, the method comprises introducing to the parental microorganism one or more genetic modifications which disrupt a combination of two or more of the genes encoding an an enzyme capable of converting pyruvate to acetolactate, acetolactate to acetoin, and/or acetoin to 2,3-butanediol.

In one embodiment, the method comprises introducing to the parental microorganism one or more genetic modifications which disrupts one or more of the genes encoding one or more acetolactate synthase (alsS), acetolactate decarboxylase (BudA) and 2,3-Butanediol dehydrogenase (2,3 bdh).

In one embodiment, the method comprises introducing a genetic modification which disrupts the activity of a compound required for the expression or activity of one or more of the above enzymes.

In one embodiment, the method comprises introducing a genetic modification which increases the expression or activity of one or more compounds which inhibit the expression or activity of one or more of the above enzymes.

In a third aspect, the invention provides a method for the production of one or more product. In one embodiment, the method is for the production of one or more of ethanol, formate, lactate, pyruvate, succinate, valine, leucine, isoleucine, acetolactate, malate, fumerate, 2-oxogluterate, citrate.

In one particular embodiment, the invention provides a method for the production of one or more products (in one embodiment including ethanol and one or more other products) by microbial fermentation comprising fermenting a substrate comprising CO using one or more microorganism of the first aspect of the invention and/or made by the method of the second aspect of the invention. In one embodiment, the one or more other products are chosen from the group consisting succinate, lactate, formate, valine, leucine, pyruvate, isoleucine, acetolactate, malate, fumerate, 2-oxogluterate, citrate.

The invention also provides a method for reducing the total atmospheric carbon emissions from an industrial process.

In one embodiment the method comprises the steps of:

(a) providing a substrate comprising CO to a bioreactor containing a culture of one or more microorganism of the first aspect of the invention and/or made by a method of the second aspect of the invention; and (b) anaerobically fermenting the culture in the bioreactor to produce one or more of the abovementioned products, preferably including ethanol.

In another embodiment the method comprises the steps of:

capturing CO-containing gas produced as a result of the industrial process, before the gas is released into the atmosphere;

the anaerobic fermentation of the CO-containing gas to produce one or more of the above mentioned products, preferably including ethanol, by a culture containing one or more microorganism of the first aspect of the invention and/or made by the method of the second aspect of the invention.

In particular embodiments of the method aspects, the microorganism is maintained in an aqueous culture medium.

In particular embodiments of the method aspects, the fermentation of the substrate takes place in a bioreactor.

Preferably, the substrate comprising CO is a gaseous substrate comprising CO. In one embodiment, the substrate comprises an industrial waste gas. In certain embodiments, the gas is steel mill waste gas or syngas.

In one embodiment, the substrate will typically contain a major proportion of CO, such as at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of 117:CO. In one embodiment the substrate comprises about 30% or less $H_2$ by volume, 20% or less $H_2$ by volume, about 15% or less $H_2$ by volume or about 10% or less $II_2$ by volume. In other embodiments, the substrate stream comprises low concentrations of $H_2$, for example, less than 5%, or less than 4%, or less than 3%, or less than 2%, or less than 1%, or is substantially hydrogen free. The substrate may also contain some CO, for example, such as about 1% to about 80% $CO_2$ by volume, or 1% to about 30% $CO_2$ by volume.

In certain embodiments the methods further comprise the step of recovering the one or more products from the fermentation broth. In one embodiment, ethanol is recovered from the fermentation broth. In one embodiment, one or more other products are recovered from the fermentation broth including formate, lactate, pyruvate, succinate, valine, leucine, isoleucine, acetolactate, malate, fumerate, citrate and 2-oxogluterate.

In a fourth aspect, the invention provides one or more product when produced by a method of the third aspect. In one embodiment, the one or more products are chosen from the group consisting of ethanol, formate, lactate, pyruvate, succinate, valine, leucine, isoleucine, acetolactate, malate, fumerate, citrate and 2-oxogluterate. In one particular embodiment, the one or more products at least comprises ethanol.

In a fifth aspect, the invention provides a carboxydotrophic acetogenic microorganism in which one or more non-essential gene has been disrupted compared to a parental microorganism.

In a sixth aspect, the invention provides a method of producing a carboxydotrophic acetogenic microorganism in which one or more non-essential gene has been disrupted, the method comprising genetically modifying one or more non-essential gene in a parental microorganism.

The invention also provides microorganisms made by the methods of the sixth aspect.

In one embodiment, the one or more non-essential gene is a gene encoding an enzyme that converts acetolactate to acetoin and/or encoding an enzyme that converts acetoin to 2,3 Butanediol. In one embodiment, the enzymes are as herein described.

In certain embodiments the microorganism is selected from the group comprising *Clostridium autoethanogenum, Clostridium ljungdahlii, Clostridium ragsdalei, Clostridium coskatii Butyribacterium limosum, Butyribacterium methylotrophicum, Acetobacterium woodii, Alkalibaculum bacchii, Blautia producta, Eubacterium limosum, Moorella thermoacetica, Moorella thermautotrophica, Oxobacter pfennigii*, and *Thermoanaerobacter kiuvi.*

In one particular embodiment, the microorganism is selected from the group comprising *Clostridium autoethanogenum, Clostridium ljungdahlii*, and *Clostridium ragsdalei*. In another embodiment, the group also comprises *Clostridium coskatii.*

In one particular embodiment, the microorganism is *Clostridium autoethanogenum* DSM23693.

In a seventh aspect, the invention provides a method for the production of one or more product by microbial fermentation using one or more microorganism of the fifth aspect and/or made by a method of the sixth aspect.

In one particular embodiment, the invention provides a method for the production of ethanol and one or more other products by microbial fermentation comprising fermenting a substrate comprising CO using one or more microorganism of the fifth aspect and/or made by a method of the sixth aspect.

In one embodiment the method comprises the steps of:

(a) providing a substrate comprising CO to a bioreactor containing a culture of one or more microorganism of the fifth aspect and/or made by a method of the sixth aspect; and (b) anaerobically fermenting the culture in the bioreactor to produce one or more products.

In another embodiment the method comprises the steps of:

(a) capturing CO-containing gas produced as a result of the industrial process, before the gas is released into the atmosphere;

b) the anaerobic fermentation of the CO-containing gas to produce one or more products by a culture containing one or more microorganism of the fifth aspect and/or made by a method of the sixth aspect.

In one embodiment, the one or more product is as herein described.

In one embodiment, the substrate comprising CO is as herein described.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE FIGURES

These and other aspects of the present invention, which should be considered in all its novel aspects, will become apparent from the following description, which is given by way of example only, with reference to the accompanying figures, in which:

FIG. 5 also shows an agarose gel electrophoresis image of PCR screening of *C. autoethanogenum* DSM23693 budA gene knockouts. Lane 1 and 9 show GeneRuler™ 1 kb Plus DNA Ladder. Lane 2-6 shows PCR amplication of budA target region from genomic DNA isolated from wildtype *C. autoethanogenum* DSM23693 (+ve, 2.7 kb) and six potential *C. autoethanogenum* DSM23693 budA gene knockouts (1-6, 2.2 kb) with primers Og09 and Og12r. Lane 10-16 shows PCR with genomic DNA isolated from wildtype (+ve) *C. autoethanogenum* DSM23693 and six potential *C. autoethanogenum* DSM23693 budA gene knockouts with primers Og44f and Og45r specific to 273 bp internal region of budA gene (*).

BRIEF DESCRIPTION OF SEQUENCE LISTING

Figure 1A:
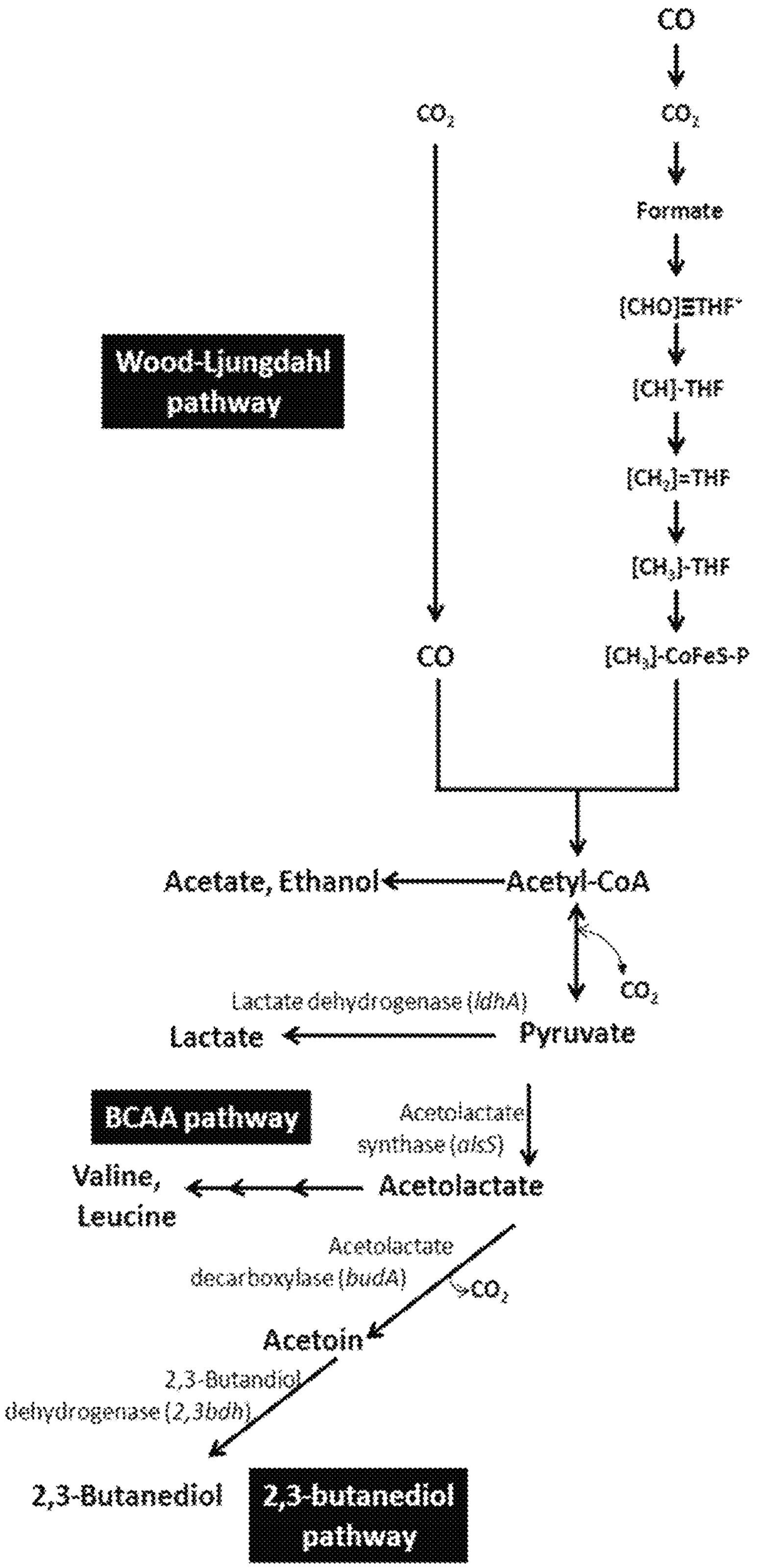
FIG. 1*a* shows the metabolic pathway from CO in 2,3 butanediol-producing carboxydotrophic aceotgens (for example *C. autoethanogenum* DSM23693).

This specification is accompanied by a sequence listing in which the following sequences are listed.

Seq. ID 1: Nucleotide sequence of the nucleotide sequence of *C. autoethanogenum* DSM23693 budA gene.

Seq. ID 2: Amino acid sequence of *C. autoethanogenum* DSM23693 budA protein.

Seq. ID 3: Nucleotide sequence of the 5' flanking region of *C. autoethanogenum* DSM23693 budA gene.

Seq. ID 4: Nucleotide sequence of 3' flanking sequence of budA gene

Seq ID 5 to 8 and 10 and 11: Are described in table 1 herein after.

Seq. ID 9: Nucleotide sequence of *E. coli-Clostridium* shuttle vector—plasmid pMTL85141

Seq. ID. 12: Nucleotide sequencing results of pMTL85141-budA-ko which demonstrates that the flanking DNA fragments found on the plasmid were free of mutations.

Seq ID 13: 16s rRNA gene of *C. autoethanogenum* (Y18178, GI:7271109)

Seq ID 14: 16s rRNA gene of colony 1 of potential budA knockout transformant of *C. autoethanogenum* DSM23693: (93%) identity Seq. ID 15: 16s rRNA gene of colony 2 of potential budA knockout transformant of *C. autoethanogenum* DSM23693: (94%)

Seq. ID 16: 16s rRNA gene of colony 3 of potential budA knockout transformant of *C. autoethanogenum* DSM23693: (95%)

Seq. ID 17: 16s rRNA gene of colony 4 of potential budA knockout transformant of *C. autoethanogenum* DSM23693: (93%).

Seq. ID 18: 16s rRNA gene of colony 5 of potential budA knockout transformant of *C. autoethanogenum* DSM23693: (94%).

Seq. ID 19: 16s rRNA gene of colony 6 of potential budA knockout transformant of *C. autoethanogenum* DSM23693: (92%).

Seq ID 20. Nucleotide sequencing result of Colony 1 PCR product of potential budA knockout transformant of *C. autoethanogenum* DSM23693 with primer Og09f. (92%)

Seq ID 21. Nucleotide sequencing result of Colony 1 PCR product of potential budA knockout transformant of *C. autoethanogenum* DSM23693 with primer Og12r. (92%)

Seq ID 22. Nucleotide sequencing result of Colony 3 PCR product of potential budA knockout transfbrmant of *C. autoethanogenum* DSM23693 with primer Og12r. (92%)

Seq ID 23. Nucleotide sequencing result of Colony 4 PCR product of potential budA knockout transformant of *C. autoethanogenum* DSM23693 with primer Og12r. (92%)

Seq ID 24. Nucleotide sequencing result of Colony 5 PCR product of potential budA knockout transformant of *C. autoethanogenum* DSM23693 with primer Og12r.

Seq ID 25. Nucleotide sequencing result of Colony 6 PCR product of potential budA knockout transformant of *C. autoethanogenum* DSM23693 with primer Og09f.

Seq ID 26. Nucleotide sequencing result of *C. autoethanogenum* DSM23693 budA target region from clone 6 with primer Og12r.

Seq ID 27 and 28: are described in table 4 herein after

Seq 29 and 30: are described in table 4 herein after

SEQ ID 31: nucleotide sequence of novel methyltransferase gene fused with an inducible lac promoter.

SEQ ID 32: protein sequence of a novel methyltransferase.

SEQ ID 33: nucleotide sequence of plasmid pGS20.

SEQ_ID NO 34: Amino acid sequence of a novel alcohol dehydrogenase from *C. autoethanogeum, C. ljungdahlii* and *C. ragsdalei.*

SEQ_ID NO 35: Nucleic acid sequence of novel alcohol dehydrogenase gene from *C. autoethanogeum.*

SEQ_ID NO 36: Nucleic acid sequence of novel alcohol dehydrogenase gene from *C. ljungdahlii.*

SEQ ID NO 37: Nucleic acid sequence of novel alcohol dehydrogenase gene from *C. ragsdalei.*

Seq. ID. 38: Nucleotide sequence of Malic enzyme 1 of *C. autoethanogenum*

Seq. ID. 39: Amino acid sequence of Malic enzyme 1 of *C. autoethanogenum:*

Seq. ID. 40: Nucleotide sequence of Malic enzyme 2 of *C. autoethanogenum*

Seq. ID. 41: Amino acid sequence of Malic enzyme 2 of *C. autoethanogenum*

Seq. ID. 42: Nucleotide sequence of Malate dehydrogenase of *C. autoethanogenum*

Seq. ID. 43: Amino acid sequence of Malate dehydrogenase of *C. autoethanogenum.*

Seq. ID. 44: Nucleotide sequence of Pyruvate phosphate dikinase of *C. autoethanogenum.*

Seq. ID. 45: Amino acid sequence of Pyruvate phosphate dikinase of *C. autoethanogenum.*

Seq. ID. 46: Nucleotide sequence of Pyruvate carboxylase of *C. autoethanogenum.*

Seq. ID. 47: Amino acid sequence of Pyruvate carboxylase of *C. autoethanogenum*

Seq. ID. 48: Nucleotide sequence of PEP carboxykinase of *C. autoethanogenum.*

Seq. ID. 49: Amino acid sequence of PEP carboxykinase of *C. autoethanogenum*

Seq. ID. 50: Nucleotide sequence of Fumarate hydratase subunit A of *C. autoethanogenum*

Seq. ID. 51: Amino acid sequence of Fumarate hydratase subunit A of *C. autoethanogenum.*

Seq. ID. 52: Nucleotide sequence of Fumarate hydratase subunit B of *C. autoethanogenum*

Seq. ID. 53: Amino acid sequence of Fumarate hydratase subunit B of *C. autoethanogenum.*

Seq. ID. 54: Nucleotide sequence of Fumarate reductase 1 of *C. autoethanogenum*

Seq. ID. 55: Amino acid sequence of Fumarate reductase 1 of *C. autoethanogenum.*

Seq. ID. 56: Nucleotide sequence of Fumarate reductase 2 of *C. autoethanogenum.*

Seq. ID. 57: Amino acid sequence of Fumarate reductase 2 of *C. autoethanogenum*

Seq. ID. 58: Nucleotide sequence of Fumarate reductase 3 of *C. autoethanogenum.*

Seq. ID. 59: Amino acid sequence of Fumarate reductase 3 of *C. autoethanogenum*

Seq. ID. 60: Nucleotide sequence of Malic enzyme 1 of *C. ragsdalei.*

Seq. ID. 61: Amino acid sequence of Malic enzyme 1 of *C. ragsdaiei.*

Seq. ID. 62: Nucleotide sequence of Malate dehydrogenase of *C. ragsdalei*

Seq. ID. 63: Amino acid sequence of Malate dehydrogenase of *C. ragsdalei.*

Seq. ID. 64: Nucleotide sequence of Pyruvate phosphate dikinase of *C. ragsdalei.*

Seq. ID. 65: Amino acid sequence of Pyruvate phosphate dikinase of *C. ragsdalei.*

Seq. ID. 66: Nucleotide sequence of Pyruvate carboxylase of *C. ragsdalei.*

Seq. ID. 67: Amino acid sequence of Pyruvate carboxylase of *C. ragsdalei*

Seq. ID. 68: Nucleotide sequence of PEP carboxykinase of *C. ragsdalei.*

Seq. ID. 69: Amino acid sequence of PEP carboxykinase of *C. ragsdalei*

Seq. ID. 70: Nucleotide sequence of Fumarate hydratase subunit A of *C. ragsdalei*

Seq. ID. 71: Amino acid sequence of Fumarate hydratase subunit A of *C. ragsdaiei*

Seq. ID. 72: Nucleotide sequence of Fumarate hydratase subunit B of *C. ragsdalei.*

Seq. ID. 73: Amino acid sequence of Fumarate hydratase subunit B of *C ragsdalei*

Seq. ID. 74: Nucleotide sequence of Fumarate reductase 1 of *C. ragsdalei.*

Seq. ID. 75: Amino acid sequence of :Fumarate reductase 1 of *C. ragsdalei*

Seq. ID. 76: Nucleotide sequence of Fumarate reductase 2 of *C. ragsdalei*

Seq. ID. 77: Amino acid sequence of Fumarate reductase 2 of *C. ragsdalei*

Seq. ID 78: 5' upstream sequence or homology arm of *Clostridium ljungdahlii* budA gene.

Seq. ID 79: 3' downstream sequence or homology arm of *Clostridium ljungdahlii* budA gene Seq. ID 80: 5' upstream sequence or homology arm of *Clostridium ragsdalei* budA gene Seq. ID 81: 3' downstream sequence or homology arm of *Clostridium ragsdalei* budA gene Seq ID 82: nucleotide sequence of ClosTron targeting region in *C. autoethanogenum* DSM23693 budA Seq ID 83 nucleotide sequence of ClosTron targeting region in *C. autoethanogenum* DSM23693 2.3bdh.

Seq ID 84: oligonucleotide Og42f used for screening Δ2,3bdh ClosTron mutants.

Seq ID 85: oligonucleotide Og43r used for screening Δ12, 3bdh ClosTron mutants.

Seq. ID 86: Nucleotide sequence of the 16s rRNA PCR product amplified from *C. autoethanogenum* DSM23693 Δ2, 3bdh ClosTron clone 2 obtained using primer fD1.

Seq ID 87: Nucleotide sequence of the 16s rRNA PCR product amplified from *C. autoethanogenum* DSM23693 Δ2, 3bdh ClosTron clone 2 obtained using primer rP2.

Seq. ID 88: Nucleotide sequence of the 16s rRNA PCR product of *C. autoethanogenum* DSM23693 Δ2,3bdh ClosTron clone 4 obtained using primer fD1

Seq ID 89: Nucleotide sequence of the 16s rRNA PCR product of *C. autoethanogenum* DSM23693 Δ2,3bdh ClosTron clone 4 obtained using primer rP2

Seq. ID 90: Nucleotide sequence of the 16s rRNA PCR product of *C. autoethanogenum* DSM23693 ΔbudA ClosTron clone 1 obtained using primer fD1.

Seq ID 91: Nucleotide sequence of the 16s rRNA PCR product of *C. autoethanogenum* DSM23693 ΔbudA ClosTron clone 1 obtained using primer rP2.

Seq. ID 92: Nucleotide sequence of the 16s rRNA PCR product of *C. autoethanogenum* DSM23693 ΔbudA ClosTron clone 3 obtained using primer fD1.

Seq ID and 93: Nucleotide sequence of the 16s rRNA PCR product of *C. autoethanogenum* DSM23693 ΔbudA ClosTron clone 3 obtained using primer rP2.

Seq ID 94 nucleotide sequence of 5' homology arm of *C. autoethanogenum* DSM23693 2,3bdh gene.

Seq ID 95: nucleotide sequence of 3' homology arm of *C. autoethanogenum* DSM23693 2,3bdh gene.

Seq. ID 96 and 97: the primers used to amplify 5' homology arm of *C. autoethanogenum* DSM23693 2,3bdh gene.

Seq. ID 98 and 99: the primers used to amplify 3' homology arm of *C. autoethanogenum* DSM23693 2,3bdh gene.

Seq. ID 100 and 101: flanking primers that can be used to confirm knockout of *C. autoethanogenum* DSM23693 2,3bdh gene.

Seq ID 102: nucleic acid sequence of 5' homology arm of *C. autoethanogenum* D5N423693 SecAdh gene Seq ID 103: nucleic acid sequence of 3' homology arm of *C. autoethanogenum* DSM23693 SecAdh gene.

Seq. ID 104 and 105: primers used to amplify 5' homology arm of *C. autoethanogenum* DSM23693 2,3bdh gene.

Seq. ID 106 and 107 primers used to amplify 3' homology arm of *C. autoethanogenum* DSM23693 2,3bdh gene.

Seq. ID 108 and 109: primers that can be used to confirm knockout of *C. autoethanogenum* DSM23693 SecAdh gene.

Seq ID 110: nucleotide sequence of group II intron targeting cassette for *C. autoethanogenum* DSM23693 SecAdh gene.

Seq. ID 111 and 112: flanking primers that can be used to confirm insertional inactivation of *C. autoethanogenum* DSM23693 SecAdh gene.

Seq ID 113: nucleotide sequence of 5' homology arm of *C. autoethanogenum* DSM23693 alsS gene.

Seq ID 114: nucleotide sequence of 3' homology arm of *C. autoethanogenum* DSM23693 alsS gene.

Seq. ID 115 and 116: sequences of primers used to amplify 5' homology arm of *C. autoethanogenum* DSM23693 alsS gene.

Seq. ID 117 and 118: sequences of primers used to amplify 3' homology arm of *C. autoethanogenum* DSM23693 alsS gene.

Seq. ID 119 and 120: sequences of flanking primers that can be used to confirm knockout of *C. autoethanogenum* DSM23693 alsS gene.

Seq ID 120: nucleotide sequence of 5' homology arm of *C. autoethanogenum* DSM23693 ilvC gene.

Seq ID 121: nucleic acid sequence of 3' homology arm of *C. autoethanogenum* DSM23693 ilvC gene.

Seq. ID 123 and 124: sequences of primers used to amplify 5' homology arm of *C. autoethanogenum* DSM23693 ilvC gene.

Seq. ID 125 and 126: sequences of primers used to amplify 3' homology arm of *C. autoethanogenum* DSM23693 ilvC gene.

Seq. ID 127 and 128: sequences of flanking primers that can be used to confirm knockout of *C. autoethanogenum* DSM23693 ilvC gene.

Seq ID 129: nucleotide sequence of 5' homology arm of *C. autoethanogenum* DSM23693 ilvl gene.

Seq ID 130: nucleotide sequence of 3' (Seq. ID 130) homology arm of *C. autoethanogenum* DSM23693 ilvl gene.

Seq. ID 131 and 132: sequences of primers used to amplify 5' homology arm of *C. autoethanogenum* DSM23693 ilvl gene.

Seq. ID 133 and 134: sequences of primers used to amplify 3' homology arm of *C. autoethanogenum* DSM23693 ilvl gene.

Seq. ID 135 and 136: sequences of flanking primers that can be used to confirm knockout of *C. autoethanogenum* DSM23693 ilvl gene.

Seq ID 137 nucleotide sequence of 5' homology arm of *C. autoethanogenum* DS14123693 ilvB gene.

Seq ID 138: nucleotide sequence of 3' homology arm of *C. autoethanogenum* DSM23693 ilvB gene.

Seq. ID 139 and 140: sequences of primers used to amplify 5' homology arm of *C. autoethanogenum* DSM23693 gene.

Seq. ID 141 and 142: sequences of primers used to amplify 3' homology arm of *C. autoethanogenum* DSM23693 ilvB gene.

Seq. ID 143 and 144: sequences of flanking primers that can be used to confirm knockout of *C. autoethanogenum* DSM23693 livB gene.

Seq ID 145: example ClosTron intron targeting nucleotide sequence of alsS

Seq ID 146: example ClosTron intron targeting nucleotide sequence of ilvC

Seq ID 147: example ClosTron intron targeting nucleotide sequence of ilvl

Seq ID 148: example ClosTron intron targeting nucleotide sequence of ilvB

Seq ID 149 and 150: oligonucleotides that can be used to screen alsS ClosTron mutants Seq ID 151 and 152: oligonucleotides that can be used to screen ilvC ClosTron mutants Seq ID 153 and 154: oligonucleotides that can be used to screen ilvl ClosTron mutants Seq ID 155 and 156: oligonucleotides that can be used to screen ilvB ClosTron mutants.

Standard IUPAC abbreviations are used for all sequences, see http://en.m.wikipedia.org/wiki/Nucleic_acid_notation#section_1. By way of example:

A Adenosine
C Cytidine
G Guanosine
T Thymidine
W A or T
S C or G
M A or C
K G or T
R A or G
Y C or T
B C, G or T
D A, G or T
H A, C or T
V A, C or G
N or—any base (not a gap), A, C, G, T

DETAILED DESCRIPTION OF THE INVENTION

The following is a description of the present invention, including preferred embodiments thereof, given in general terms. The invention is further elucidated from the disclosure given under the heading "Examples" herein below, which provides experimental data supporting the invention, specific examples of various aspects of the invention, and means of performing the invention.

The invention provides microorganisms capable of producing one or more products by fermentation of a substrate comprising CO. In one particular embodiment, the invention provides microorganisms capable of producing ethanol or, ethanol and one or more other products, by fermentation of a substrate comprising CO. The recombinant microorganism produces at least a reduced amount of 2,3 butanediol and/or a precursor thereof compared to a parental microorganism. In one embodiment the microorganism produces substantially no 2,3 butanediol or a precursor thereof compared to a parental microorganism.

Through various gene knockout studies, the inventors have surprisingly identified that if the 2,3-butanediol biosynthesis pathway is disrupted in a carboxydotrophic acetogenic microorganism, the microorganism is able to produce increased levels of thrmate, lactate, succinate, 2-oxogluterate, valine, leucine, isoleucine and ethanol, as compared to a parental microorganism. The inventors also believe that the microorganisms produce increased levels of pyruvate and TCA cycle intermediate compounds acetolactate, malate, fumarate, citrate as these are precursors of succinate, 2-oxogluterate and valine, leucine and isoleucine production. This has a number of significant advantages. One primary advantage is an increase in the efficiency of ethanol production including higher levels of ethanol produced. Without wanting to be bound by any particular theoty, the inventors believe that the increased levels of valine, leucine, formate, lactate and pyruvate, result in more of these chemicals being available to the microorganisms to feed ethanol production. In addition, fermentation broths must often be supplemented with amino acids and other chemicals to ensure the viability and production efficiency of the microorganisms during fermentation. The production of valine, leucine, formate, lactate and pyruvate by a recombinant microorganism of the invention obviates the need to supplement the fermentation broth with these chemicals, which can result in cost savings. Further, the reduction or removal of 2,3-butanediol production in the microorganisms of the invention has advantages. 2,3-butanediol can be toxic to microorganisms and thus may have a negative effect on fermentation and growth. Reducing or removing 2,3-butanediol from the fermentation broth also allows for easier recovery of ethanol from the broth; typically both ethanol and 2,3-butanediol must be recovered together and then separated in a subsequent step. 2,3-butanediol is also a source for potential microbial contamination in a fermenter as it is a substrate for many undesirable organisms. In addition, succinate, 2-oxogluterate, formate, lactate, pyruvate, leucine and isoleucine have independent economic value as they may be used in a number of commercial processes and as intermediate compounds in the production of downstream chemical products.

The inventor's have for the first time demonstrated the disruption or knock out of a non-essential gene in a carboxydotrophic acetogenic microorganism. Accordingly, in another aspect, the invention also provides carboxydotrophic acetogenic microorganisms in which one or more non-essential gene has been disrupted compared to a parental microorganism, along with methods of producing such microorganisms and methods of using these microorganisms. A "non-essential" gene is one which encodes a protein which is not necessary for the survival of a microorganism, such that the microorganism can survive without supplementation of the protein. Examples of non-essential genes include those encoding acetolactate decarboxylase and 2,3 butanediol dehydrogenase. Skilled persons will be able to identify non-essential genes using standard techniques in the art, including recombinant techniques to disrupt genes (as described herein) along with standard assays to test whether such genetic modifications have an effect on the survival of the microorganisms.

While the description of the invention herein after focuses on disruption of the 2,3-butanediol biosynthesis pathway by genetic modification, it should be appreciated that microorganisms of the invention may also include one or more additional genetic modifications if desired (including disruption of one or more non-essential gene not associated with the 2,3-butanediol biosynthesis pathway). In the case of the aspect of the invention relating to disruption of non-essential genes it should be appreciated that genetic modifications in genes encoding enzymes other than in the 2,3-butanediol pathway is encompassed.

In addition, while the description hereinafter may focus on the production and recovery of ethanol as a main product, it should be appreciated that the invention may be used to increase the level of production of one or more product other than ethanol or in addition to ethanol.

Definitions

As referred to herein, a "fermentation broth" is a culture medium comprising at least a nutrient media and bacterial cells.

As referred to herein, a shuttle microorganism is a microorganism in which a methyltransferase enzyme is expressed and is distinct from the destination microorganism.

As referred to herein, a destination microorganism is a microorganism in which the genes included on an expression construct/vector are expressed and is distinct from the shuttle microorganism.

The term "main fermentation product" is intended to mean the one fermentation product which is produced in the highest concentration and/or yield.

The terms "increasing the efficiency", "increased efficiency" and the like, when used in relation to a fermentation process, include, but are not limited to, increasing one or more of the rate of growth of microorganisms catalysing the fermentation, the growth and/or product production rate, the volume of desired product (such as alcohols) produced per volume of substrate consumed, the rate of production or level of production of the desired product, and the relative proportion of the desired product rodt ced compared with other by-products of the fermentation.

The phrase "substrate comprising carbon monoxide" and like terms should be understood to include any substrate in which carbon monoxide is available to one or more strains of bacteria for growth and/or fermentation, for example.

The phrase "gaseous substrate comprising carbon monoxide" and like phrases and terms includes any gas which contains a level of carbon monoxide. In certain embodiments the substrate contains at least about 20% to about 100% CO by volume, from 20% to 70% CO by volume, from 30% to 60% CO by volume, and from 40% to 55% CO by volume. In particular embodiments, the substrate comprises about 25%, or about 30%, or about 35%, or about 40%, or about 45%, or about 50% CO, or about 55% CO, or about 60% CO by volume.

While it is not necessary for the substrate to contain any hydrogen, the presence of $H_2$ should not be detrimental to product formation in accordance with methods of the invention. In particular embodiments, the presence of hydrogen results in an improved overall efficiency of alcohol production. For example, in particular embodiments, the substrate may comprise an approx 2:1, or 1:1, or 1:2 ratio of H2:CO. In one embodiment the substrate comprises about 30% or less $H_2$ by volume, 20% or less $H_2$ by volume, about 15% or less $H_2$ by volume or about 10% or less $H_2$ by volume. In other embodiments, the substrate stream comprises low concentrations of H2, for example, less than 5%, or less than 4%, or less than 3%, or less than 2%, or less than 1%, or is substantially hydrogen free. The substrate may also contain some $CO_2$ for example, such as about 1% to about 80% $CO_2$ by volume, or 1% to about 30% $CO_2$ by volume. In one embodiment the substrate comprises less than or equal to about 20% $CO_2$ by volume. In particular embodiments the substrate comprises less than or equal to about 15% $CO_2$ by volume, less than or equal to about 10% $CO_2$ by volume, less than or equal to about 5% $CO_2$ by volume or substantially no $CO_2$.

In the description which follows, embodiments of the invention are described in terms of delivering and fermenting a "gaseous substrate containing CO". However, it should be appreciated that the gaseous substrate may be provided in alternative forms. For example, the gaseous substrate containing CO may be provided dissolved in a liquid. Essentially, a liquid is saturated with a carbon monoxide containing gas and then that liquid is added to the bioreactor. This may be achieved using standard methodology. By way of example, a microbubble dispersion generator (Hensirisak et. al. Scale-up of microbubble dispersion generator fur aerobic fermentation; Applied Biochemistry and Biotechnology Volume 101, Number 3/October, 2002) could be used. By way of further example, the gaseous substrate containing CO may be adsorbed onto a solid support. Such alternative methods are encompassed by use of the term "substrate containing CO" and the like.

In particular embodiments of the invention, the CO-containing gaseous substrate is an industrial off or waste gas. "Industrial waste or off gases" should be taken broadly to include any gases comprising CO produced by an industrial process and include gases produced as a result of ferrous metal products manufacturing, non-ferrous products manufacturing, petroleum refining processes, gasification of coal, gasification of biomass, electric power production, carbon black production, and coke manufacturing. Further examples may be provided elsewhere herein.

Unless the context requires otherwise, the phrases "fermenting", "fermentation process" or "fermentation reaction" and the like, as used herein, are intended to encompass both the growth phase and product biosynthesis phase of the process. As will be described further herein, in sonic embodiments the bioreactor may comprise a first growth reactor and a second fermentation reactor. As such, the addition of metals or compositions to a fermentation reaction should be understood to include addition to either or both of these reactors.

The term "bioreactor" includes a fermentation device consisting of one or more vessels and/or towers or piping arrangement, which includes the Continuous Stirred Tank Reactor (CSTR), immobilized Cell Reactor (ICR), Trickle Bed Reactor (TBR), Bubble Column, Gas Lift Fermenter, Static Mixer, or other vessel or other device suitable for gas-liquid contact. As is described herein after, in some embodiments the bioreactor may comprise a first growth reactor and a second fermentation reactor. As such, when referring to the addition of substrate to the bioreactor or fermentation reaction it should be understood to include addition to either or both of these reactors where appropriate.

When used in relation to the products of fermentation in accordance with the invention "one or more products" and like phrases is intended to include ethanol, succinate, pyruvate, lactate, valine, formate, isoleucine, and leucine, for example. In one embodiment, "one or more products" may also include one or more of acetolactate, malate, fumarate, citrate, and 2-oxogluterate. It should be appreciated that the methods of the invention are applicable to methods intended for the production and recovery of ethanol (alone or in combination with other products) or the production and recovery of products other than ethanol.

The term "acetate" includes both acetate salt alone and a mixture of molecular or free acetic acid and acetate salt, such as the mixture of acetate salt and free acetic acid present in a fermentation broth as described herein, The ratio of molecular acetic acid to acetate in the fermentation broth is dependent upon the pH of the system. The terms succinate, pyruvate, lactate, formate, acetolactate, malate, fumarate, citrate and 2-oxogluterate should be construed similarly.

Unless the context requires otherwise, reference to any compound herein which may exist in one or more isomeric forms (for example, D, L, meso, S, R, cis or trans form) should be taken generally to include refrence to any one or more such isomers of the compound. For example, reference to "acetoin" should be taken to include reference to either or both the D and L isomers thereof.

"Exogenous nucleic acids" are nucleic acids which originate outside of the microorganism to which they are introduced. Exogenous nucleic acids may be derived from any appropriate source, including, but not limited to, the microorganism to which they are to be introduced, strains or species of organisms which differ from the organism to which they are to be introduced, or they may be artificially or recombinantly created. The exogenous nucleic acid may be adapted to integrate into the genome of the microorganism to which it is to be introduced or to remain in an extra-chromosomal state.

The "2,3-butanediol biosynthesis pathway" is a pathway of reactions including the conversion of pyruvate into acetolactate, acetotatate into acetoin, and acetoin into 2,3-butanediol.

As used herein, "disrupt the 2,3-butanediol biosynthesis pathway" and like phrases, is intended to mean that the production of 2,3-butanediol is reduced, or in one embodiment substantially eliminated.

A "precursor of 2,3-butanediol" is intended to encompass acetoin and acetolactate.

An enzyme is "capable of converting" a first compound or substrate into a second compound or product, if in its active form it can catalyse a reaction in which at least a portion of the first compound is converted into the second compound.

Reference to "alcohol dehydrogenases" should be taken to include alcohol dehydrogenases which are capable of catalysing the conversion of ketones (such as acetoin) to secondary alcohols (such as 2,3-butanediol), or vice versa. Such alcohol dehydrogenases include secondary alcohol dehydrogenases and primary alcohol dehydrogenases. A "secondary alcohol dehydrogenase" is one which can convert ketones (such as acetoin) to secondary alcohols (such as 2,3-butanediol), or vice versa. A "primary alcohol dehydrogenase" is one which can convert aldehydes to primary alcohols, or vice versa; however, a number of primary alcohol dehydrogenases are also capable of catalysing the conversion of ketones to secondary alcohols, or vice versa. These alcohol dehydrogenases may also be referred to as "primary-secondary alcohol dehydrogenases". Accordingly, in certain embodiments of the invention, reference to "2,3-butanediol dehydrogenase" should be taken to include reference to 2,3-butanediol dehydrogenases which may be categorised as primary, secondary or primary-secondary alcohol dehydrogenases.

A "genetic modification which disrupts" the 2,3-butanediol biosynthesis pathway or the expression or activity of one or more enzyme in accordance with the invention should be taken broadly to include any genetic modification which at least reduces the biosynthesis of 2,3-butanediol, the expression or activity of one or more enzymes or in one embodiment substantially blocks the expression or activity of one or more enzymes or substantially prevents the production of 2,3-butanediol. The phrase should be taken to include, for example: modification to a gene encoding one or more of the enzymes, including a modification to a genetic regulatory element involved in the expression of a gene; introduction of a nucleic acid which produces a protein which reduces or inhibits the activity of one or more of the enzymes, or which reduces or prevents expression of one or more of the enzymes; introduction of a nucleic acid which expresses a nucleic acid which is adapted to block expression of a gene (for example, antisense RNA, siRNA (small interfering RNA), CRISPR (Clustered Regularly Interspaced Short Palindromic Repeats)); reducing or inhibiting a protein which is required for expression or activity of one or more of the enzymes by introducing a modification to a gene encoding the protein. It should be appreciated that a protein which is required for expression or activity of one or more of the enzymes may act directly on a gene or one or more enzymes, or may act indirectly via another compound. Similarly, a protein which reduces or inhibits the activity or expression of the one or more enzymes may act directly on the gene or the one or more enzymes, or may act indirectly via another compound.

A "genetic modification" should be taken broadly and is intended to include, for example, introducing one or more exogenous nucleic acids to a microorganism, introducing a mutation to a genetic site, adding to or removing from the genome one or more nucleotides, substitution of one or more nucleotides with different nucleotides, substitution of a gene, removal of a gene, addition of a gene and the like.

A "parental microorganism" is a microorganism used to generate a recombinant microorganism of the invention. In one embodiment, the parental microorganism may be one that occurs in nature (ie a wild type microorganism) or one which has been previously modified (a genetically modified or recombinant microorganism). In embodiments of the invention relating to microorganisms which produce a reduced amount or substantially no 2,3-butanediol, the parental microorganism is one which includes a functional 2,3-butanediol pathway (including those that occur in nature or those that have been previously modified). Examples of parental microorganisms that include a functional 2,3-butanediol biosynthesis pathway include *Clostridium autoethanogenum, Clostridium ljungdahiii, Clostridium ragsdaiei, Clostridium coskatii* and related isolates.

A "functional" 2,3-butanediol biosynthesis pathway is one in which the microorganism can convert pyruvate to 2,3-butanediol. In one particular embodiment, the pathway includes conversion of pyruvate to acetolactate, acteolactate to aceotin, and acetoin to 2,3-butanediol. In one particular embodiment, conversion of pyruvate to acetolactate is catalysed by an acetolactate synthase, conversion of acteolactate to aceotin is catalysed by a aceotiatate decarboxylase, and conversion of acetoin to 2,3-butanediol is catalysed by a 2,3-butanediol dehydrogenase or an acetoin reductase.

The terms nucleic acid "constructs" or "vectors" and like terms should be taken broadly to include any nucleic acid (including DNA and RNA) suitable for use as a vehicle to transfer genetic material into a cell. The terms should be taken to include plasmids, viruses (including bacteriophage), cosmids and artificial chromosomes. Constructs or vectors may include one or more regulatory elements, an origin of replication, a multicloning site and/or a selectable marker, among other elements, sites and markers. In one particular embodiment, the constructs or vectors are adapted to allow for the disruption of a gene native to a parental microorganism. In another embodiment, the constructs or vectors are adapted to allow expression of one or more genes encoded by the construct or vector. Nucleic acid constructs or vectors include naked nucleic acids as well as nucleic acids formulated with one or more agents to facilitate delivery to a cell (for example, liposome-conjugated nucleic acid, an organism in which the nucleic acid is contained).

Throughout this specification exemplary sequence information is provided for enzymes applicable to the invention (for example, acetolactate synthase, aceotlactate decarboxylase, 2,3-butanediol dehydrogenase, acetoin reductase). This information is provided to identify exemplary enzymes applicable to the invention and to allow a skilled person to practise specific embodiments of the invention without undue experimentation. It should be appreciated that nucleic acid and amino acid sequences for the enzymes may differ from one microorganism to another. Accordingly, the invention should not be construed as being limited to these specific embodiments but rather to extend to the disruption of enzymes having different sequences but which are capable of catalysing the conversion of pyruvate to acetolactate, the conversion of acteolactate to aceotin, and/or the conversion of acetoin to 2,3-butanediol, Typically, such enzymes will have at least approximately 75% amino acid sequence identify to an enzyme exemplified herein. In particular embodiments, such enzymes will have at least approximately 80%, 85%, 90%, 95% or 99% sequence identify to an enzyme exemplified herein. At the nucleic acid level, genes encoding such variant enzymes will have at least approximately 75% sequence homology to a nucleic acid encoding an enzyme exemplified herein. In particular embodiments, such nucleic acidsw will have at least approximately 80%, 85%, 90%, 95% or 99% sequence homology to a nucleic acid encoding an enzyme exemplified herein.

It should also be appreciated that the variant enzyme need not have the same level of activity as an enzyme specifically exemplified herein. All that is required is that it has some level of activity in catalysing the conversion of interest. Skilled persons will readily appreciate other such enzymes, particularly in light of the information contained herein. Enzyme assays of use in assessing activities of enzymes for the 2,3-butanediol pathway include fore example the assay Voges-Proskauer testare described by Speckman and Collins (Specificity of the Westerfeld Adaptation of the Voges-Proskauer Test, 1982, *Appl. Environ. Microbiol.* 44: 40-43) or Dulieu and Poncelet (Spectrophotometric assay of a-acetolactate decarboxylase, 1999, *Enzy and Microbiol Technol,* 25, 537-42).

Microorganisms

As discussed herein before, the invention provides a recombinant microorganism capable of using carbon monoxide to produce one or more products (in one particular embodiment, ethanol as the main product) and producing a reduced amount or substantially no 2,3 butanediol and/or a precursor thereof compared to a parental microorganism. The microorganism comprises one or more genetic modifications (compared to a parental microorganism) which disrupts the 2,3-butanediol biosynthesis pathway.

As noted above, in one embodiment the microorganism produces ethanol as the main product. In one embodiment, the microorganism also produces one or more of formate, lactate, pyruvate, succinate, valine, leucine, isoleucine. In one particular embodiment, the microorganism is adapted to produce an increased amount of one or more of ethanol, formate, lactate, pyruvate, succinate, valine. leucine, isoleucine compared to a parental microorganism. In certain embodiments, the microorganism produces one or more of acetolactate, malate, citrate, fumerate, 2-oxogluterate. In one particular embodiment, the microorganism is adapted to produce an increased amount of one or more of acetolactate, malate, fumerate, 2-oxogluterate.

The one or more genetic modifications preferably disrupts the expression and/or activity of one or more enzymes capable of converting pyruvate to acetolactate, acteolactate to aceotin, acetoin to 2,3-butanediol. In certain embodiments, the one or more genetic modification disrupts the conversion of pyruvate to acetolactate only, the conversion of acetolactate to acetoin only, or the conversion of acetoin to 2,3-butanediol only. In other embodiments, the one or more genetic modifications disrupts two or three of these conversions.

In one embodiment, the one or more enzymes capable of converting pyruvate to aceotlacta e is an acetolactate synthase (alsS).

Figure 1B:
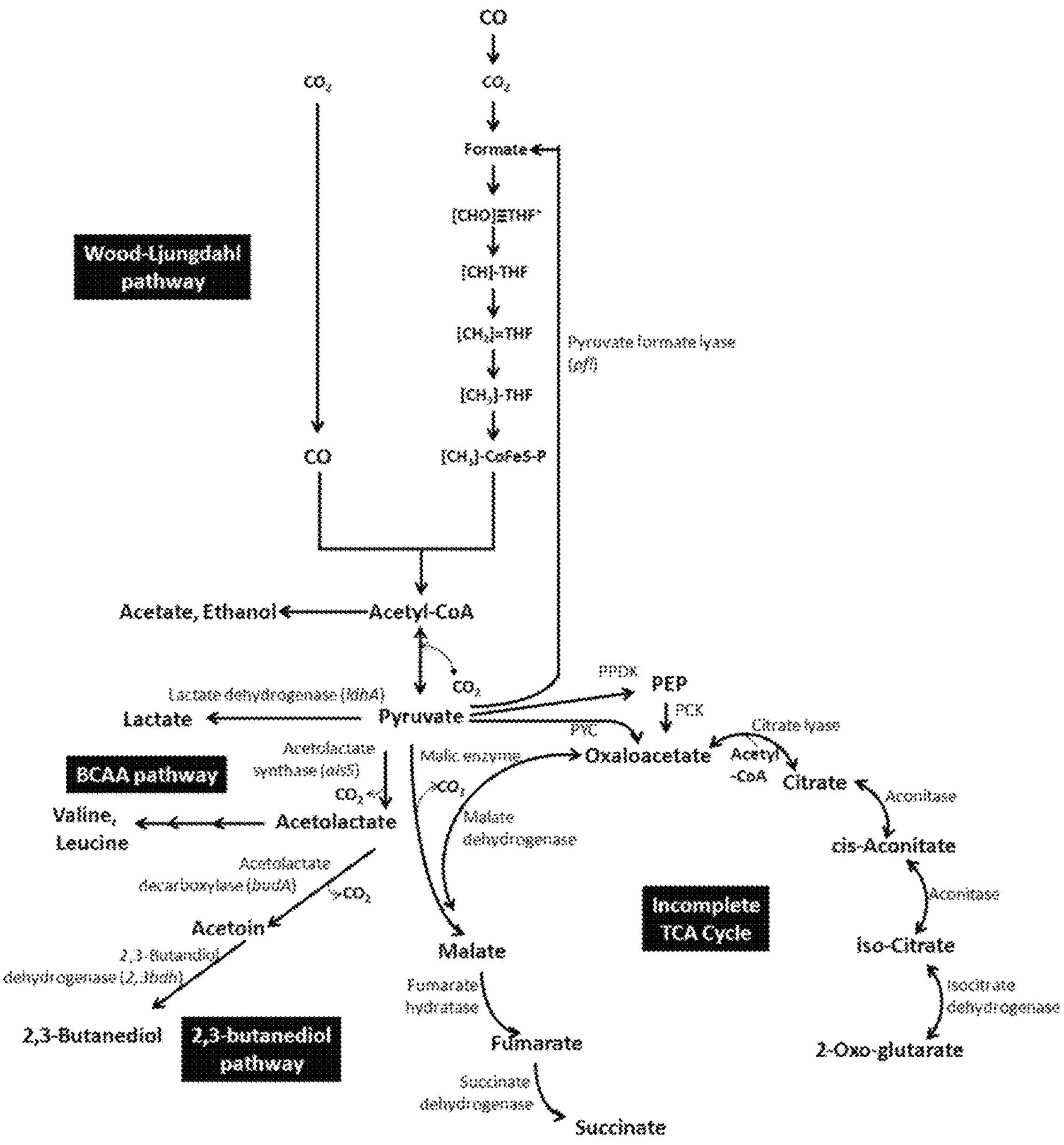
FIG. 1*b* illustrates the effects of knocking out the 2,3 butanediol biosynthesis pathway in 2,3-butanediol producing carboxydotrophic actogens with redistribution of carbon flux towards ethanol and shows production of new products, for example, succinate, 2-oxogluterate, formate, valine, leucine from CO.

Acetolactate synthase activity is capable of converting pyruvate to acetolactate and is essential for branched-chain amino acid (including valine, leucine, isoleucine) production FIGS. 1*a* and 1*b*. One or more enzyme having acetolactate synthase activity may be expressed. in a parental microorganism. Exemplary amino acid sequence from *C. autoethanogenum* (AEI90719.1, AEI90730.1, .AE190731.1, AE190713.1, AEI90714.1), *C. ljungdahlii* (ADK15104.1, ADK115104.1, ADK15105.1 ADK15400.1, ADK15400.1), and *C. ragsdalei* (AEI90734.1, AEI90734.1, AEI90735.1, AEI90727.1, AEI90727.1) and respective nucleic acid sequences from *C. autoethanogenum* (HQ876013.1, HQ876023.1, HQ876021.1), *C. ljungdahlii* (CP001666.1—CLJU_c38920, CLJU_c32420, CLJU_c20420-30), and *C. ragsdalei* (HQ876014.1, HQ876024.1, HQ876022.1) can be obtained from GenBank. However, as noted herein before, the sequence of the gene encoding such enzymes and the amino acid sequence of the enzymes may vary from one microorganism to another.

In certain embodiments, a parental microorganism may contain more than one enzyme which is capable of converting pyruvate to acetolactate. Where a parental microorganism contains more than one enzyme which is capable of converting pyruvate to acetolactate, one or more genetic modification may be introduced such that expression and/or activity of two or more of the enzymes is disrupted. Where more than one enzyme is present in a parental microorganism, disrupting more than one such enzyme may have the effect of increasing the production of succinate, one or more TCA cycle intermediates and/or ethanol above the level that may be achieved if only a single enzyme is disrupted. Production levels may be further increased with the disruption of each additional enzyme present in the parental microorganism. While disrupting expression and/or activity of all such enzymes activity may provide some advantage in terms of production of desired products, the inventors do not contemplate it to be necessary to disrupt expression and/or activity of all such enzymes in order to gain the benefits of the invention.

In one embodiment, at least two, three, four or five enzymes capable of converting pyruvate to acetolactate are disrupted.

In embodiments of the invention where the conversion of pyruvate to acetolactate is substantially or completely blocked, growth of and fermentation by the microorganism may require supplementation with one or more amino acids, including, for example, valine, leucine and isoleucine. This can be achieved by any means which makes the amino acid(s) available to the microorganism. By way of example, one or more amino acid may be added to a culture, growth or fermentation media, to a culture of the microorganisms, and/or to a fermentation broth. In certain embodiments, the amino acid(s) may be added directly to the media or broth or added in the form of an extract, for example yeast extract.

In one embodiment, the one or more enzymes capable of converting acetolactate to acetoin is an acetolactate decarboxylase (budA).

Acetolactate, decarboxylase activity is capable of converting acetolactate, to acetoin FIGS. 1*a* and 1*b*. One or more enzyme having acetolactate decarboxylase activity may be expressed in a parental microorganism. Exemplary amino acid (AEI90717.1, ADK.13906.1, AEI90718.1) and nucleic acid (HQ876011.1, CP001666.1-CLJU_c08380, HQ876012.1) sequence information for acetolactate decarboxylase from *C. autoethanogenum, C. ljungdahlii* and *C. ragsdalei* can be obtained from GenBank. However, as noted herein before, the sequence of the gene encoding such enzymes and the amino acid sequence of the enzymes may vary from one microorganism to another.

In certain embodiments, a parental microorganism may contain more than one enzyme which is capable of converting acetolactate to acetoin. Where a parental microorganism contains more than one such enzyme, one or more genetic modification may be introduced such that expression and/or activity of two or more of the enzymes is disrupted. Were more than one such enzyme is present in a parental microorganism, disrupting more than one enzyme may have the effect of increasing the production of valine, leucine, isoleucine, ethanol, lactate, formate and succinate, andlor one or more TCA cycle intermediates above the level that may be achieved if only a single enzyme is disrupted. Production levels may be further increased with the disruption of each additional enzyme present in the parental microorganism. While disrupting expression and/or activity of all such enzymes may provide some advantage in terms of production of desired products, the inventors do not contemplate it to be necessary to disrupt expression and/or activity of all such enzymes in order to gain the benefits of the invention.

In one embodiment, the one or more enzyme capable of converting acetoin to 2,3-butanediol is chosen from the group comprising a 2,3-Butanediol dehydrogenase (2,3bdh) and an acetoin reductase.

2,3-butanediol dehydrogenase activity is capable of converting acetoin to 2,3-butanediol FIGS. 1*a* and 1*b*. Exemplary amino acid (AEI90715.1, ADK15380.1, AEI90716.1) and nucleic acid sequence (HQ876009.1, CP001666.1-CLJU_c23220, HQ876010.1) information for 2,3-butanediol dehydrogenase from *C. autoethanogenum, C. ljungdahlii* and *C. ragsdalei* can be obtained from GenBank. One or more enzyme having acetolactate synthase activity may be expressed in a parental microorganism. By way of example, the inventors have identified that *C. autoethanogenum, C. ragsdalei* and *C. ljungdahiii* include an additional primary-secondary alcohol dehydrogenase capable of converting acetoin to 2,3-butanediol. Exemplary sequence information for this enzyme is provided in SEQ ID nos 34, 35, 36, and 37. However, as noted herein before, the sequence of the gene encoding such enzymes and the amino acid sequence of the enzymes may vary from one microorganism to another.

In certain embodiments, a parental microorganism may contain more than one enzyme which is capable of converting acetoin to 2,3-butanediol. Where a parental microorganism contains more than one such enzyme, one or more genetic modification may be introduced such that expression and/or activity of two or more of the enzymes is disrupted. Where more than one such enzyme is present in a parental microorganism, disrupting more than one such enzyme may have the effect of increasing the production of leucine, isoleucine, ethanol, lactate, formate and succinate, and/or one or more TCA cycle intermediates above the level that may be achieved if only a single enzyme is disrupted. Production levels may be further increased with the disruption of each additional enzyme present in the parental microorganism. While disrupting expression and/or activity of all such enzymes may provide some advantage in terms of production of desired products, the inventors do not contemplate it to be necessary to disrupt expression and/or activity of all such enzymes in order to gain the benefits of the invention.

In one embodiment, at least two or three enzymes capable of converting acetoin to 2,3-butanediol are disrupted.

In one embodiment, the microorganism is selected from the group of acetogenic carboxydotrophic organisms comprising the species *Clostridium autoethanogenum, Clostridium ljungdahlii, Clostridium ragsdalei, Clostridium carboxidivorans, Clostridium drakei, Clostridium scatologenes, Clostridium aceticum, Clostridium formicoaceticum, Clostridium magnum, Acetobacterium woodii, Alkalibaculum bacchii, Moorella thermoacetica, Sporomusa ovate, Butyribacterium methylotrophicum, Blautia producta, Eubacterium limosum, Thermoanaerobacter kiuvi.*

These carboxydotrophic acetogens are defined by their ability to utilize and grow chemoautotrophically on gaseous one-carbon (C1) sources such as carbon monoxide (CO) and carbon dioxide (CO2) with carbon monoxide (CO) and/or hydrogen (H2) as energy source under anaerobic conditions forming acetyl-CoA, acetate and other products. They share the same mode of fermentation, the Wood-Ljungdahl or reductive acetyl-CoA pathway, and are defined by the presence of the enzyme set consisting of Carbon monoxide dehydrogenase (CODH), Hydrogenase, Formate dehydrogenase, Formyl-tetrahydrofolate synthetase, Methylene-tetrahydrofolate dehydrogenase, Formyl-tetrahydrofolate cyclohydrolase, Methylene-tetrahydrofotate reductase, and Carbon monoxide dehydrogenase/Acetyl-CoA synthase (CODH/ACS), which combination is characteristic and unique to this type of bacteria (Drake, Küset, Matthies, Wood, & Ljungdahl, 2006). In contrast to chemoheterotrophic growth of sugar-fermenting bacteria that convert the substrate into biomass, secondary metabolites and pyruvate from which products are formed (either via acetyl-CoA or directly), in acetogens the substrate is channelled directly into acetyl-CoA, from which products, biomass, and secondary metabolites are formed.

In a one embodiment, the microorganism is selected from a cluster of carboxydotrophic Clostridia comprising the species *C. autoethanogenum, C. ljungdahlii*, and "*C. ragsdalei*" and related isolates. These include but are not limited to strains *C. autoethanogenum* JAI-1$^T$ (DSM10061) (Abrini, Naveau, & Nyns, 1994), *C. autoethanogenum* LBS1560 (DSM19630) (WO/2009/064200), *C. autoethanogenum* LBS1561 (DSM23693), *C. ljungdahlii* PETC$^T$ (DSM13528=ATCC 55383) (Tanner, Miller, & Yang, 1993), *C. ljungdahlii* ERI-2 (ATCC 55380) (U.S. Pat. No. 5,593, 886), *C. ljungdahlii* C-01 (ATCC 55988) (U.S. Pat. No.

6,368,819), *C. ljungdahlii* O-52 (ATCC 55989) (U.S. Pat. No. 6,368,819), or "*C. ragsdalei* P11$^{T}$" (ATCC BAA-622) (WO 2008/028055), and related isolates such as "*C. coskatii*" (US patent 2011/0229947), and mutant strains thereof such as *C. ljungdahlii* OTA-1 (Tirado-Acevedo O. Production of Bioethanol from Synthesis Gas Using *Clostridium ljungdahlii*. PhD thesis, North Carolina State University, 2010).

These strains form a suhcluster within the Clostridial rRNA cluster I (Collins et al., 1994), having at least 99% identity on 16S rRNA gene level, although being distinct species as determined by DNA-DNA reassociation and DNA fingerprinting experiments (WO 2008/028055, US patent 2011/0229947).

The strains of this cluster are defined by common characteristics, having both a similar genotype and phenotype, and they all share the same mode of energy conservation and fermentative metabolism. The strains of this cluster lack cytochromes and conserve energy via an Rnf complex.

All strains of this cluster have a genome size of around 4.2 MBp (Köpke et al., 2010) and a CC composition of around 32 % mol (Abrini et al., 1994; Köpke et al., 2010; Tanner et al., 1993) (WO 2008/028055; US patent 2011/0229947), and conserved essential key gene operons encoding for enzymes of Wood-Ljungdahl pathway (Carbon monoxide dehydrogenase, Formyl-tetrahydrofolate synthetase, Methylene-tetrahydrofolate dehydrogenase, Formyl-tetrahydrofolate cyclohydrolase, Methylene-tetrahydrofolate reductase, and Carbon monoxide dehydrogenase/Acetyl-CoA synthase), hydrogenase, formate dehydrogenase, Rnf complex (rnfCDGEAB), pyruvate:ferredoxin oxidoreductase, aldehyde: ferredoxin oxidoreductase (Köpke et al., 2010, 2011). The organization and number of Wood-Ljungdahl pathway genes, responsible for gas uptake, has been found to be the same in all species, despite differences in nucleic and amino acid sequences (Köpke et al., 2011).

The strains all have a similar morphology and size (logarithmic growing cells are between 0.5-0.7×3-5 μm), are mesophilic (optimal growth temperature between 30-37° C.) and strictly anaerobe (Abrini et al., 1994; Tanner et al., 1993) (WO 2008/028055). Moreover, they all share the same major phylogenetic traits, such as same pH range (pH 4-7.5, with an optimal initial pH of 5.5-6), strong autotrophic growth on CO containing gases with similar growth rates, and a metabolic profile with ethanol and acetic acid as main fermentation end product, with small amounts of 2,3-butanediol and lactic acid formed under certain conditions (Abrini et at, 1994; Köpke et al., 2011; Tanner et at, 1993)(WO 2008/028055). Indole production has been observed with all species. However, the species differentiate in substrate utilization of various sugars (e.g. rhamnose, arabinose), acids (e.g. gluconate, citrate), amino acids (e.g. arginine, histidine), or other substrates (e.g. betaine, butanol). Some of the species were found to be auxotroph to certain vitamins (e.g. thiamine, biotin) while others were not. Reduction of carboxylic acids into their corresponding alcohols has been shown in a range of these organisms (Perez, Richter, Loftus, & Angenent, 2012).

The traits described are therefore not specific to one organism like *C. autoethanogenum* or *C. ljungdahlii*, but rather general traits for carboxydotrophic, ethanol-synthesizing Clostridia. Thus, the invention can be anticipated to work across these strains, although there may be differences in performance.

In certain embodiments, the parental microorganism is selected from the group comprising *Clostridium autoethanogenum, Clostridium ljungdahlii*, and *Clostridium ragsdalei*. In one embodiment, the group also comprises *Clostridium coskatii*. In one particular embodiment, the parental microorganism is *Clostridium autoethanogenum* DSM23693.

Parental microorganisms may be modified to arrive at the microorganisms of the invention using any number of known transformation and recombinant nucleic acid techniques. Such techniques are described for example in Sambrook et al, (Molecular Cloning: A laboratory manual, Cold Spring Harbor Laboratory Press, Cold Spring Harbor, N.Y., 1989). By way of further example, the methodology described in the examples section hereinafter can be used.

By way of general example, in the case of introducing a mutation into a gene, or otherwise disrupting or knocking out a gene, an appropriate nucleic acid construct or vector can be designed to integrate into the genome of the parental microorganism to disrupt the gene. Such constructs will typically include nucleic acid sequences (arms) homologous to a region within or flanking the gene to be disrupted, which allow for homologous recombination to occur, and the introduction of a mutation, the excision of a region of nucleic acid from the gene, or the substitution of a region of the gene with a nucleic acid on the contrast, to occur. While it is preferred that the arms on the constructs have 100% complementarity to the region in the genome which they are targeted to, this is not necessary, provided that the sequence is sufficiently complementary to allow for targeted recombination with the genetic region of interest. Typically, the arms will have a level of homology which would allow for hybridisation to a target region under stringent conditions, as defined in Sambrook et al 1989.

Skilled persons will appreciate nucleic acid sequences sufficient to allow for targeted homologous recombination and integration of an exogenous nucleic acid into the genome of a parental microorganism having regard to the available sequence information for the enzymes involved in the 2,3-hutanediol biosynthesis pathway. However, by way of example, in the case of budA, the flanking homology arms described herein may be used (for example, Seq ID 3, 4 and 78-81), or in the case of *C. ljungdahlii*, designed from the nucleic acid sequence information on Genbank (CP001666, 1). "By way of further example, the flanking sequences of genes encoding enzymes to be disrupted in accordance with the invention may he determined from genomic sequence information from relevant microorganisms. By way of particular example, flanking sequences in *C. ljundahlii* can be determined from the information on GenBank CP001666.1

By way of further general example, where a nucleic acid is introduced into a parental microorganism to express a protein or nucleic acid which inhibits the expression or activity of an enzyme in the 2,3-butanediol biosynthesis pathway, or to express a protein which increases the expression of a compound which inhibits the expression or activity of an enzyme in the 2,3-butanediol biosynthesis pathway, the construct will be designed to allow for expression of the protein in the microorganism. Typically it will include appropriate regulatory elements, including a promoter. Constitutive or inducible promoters may be used.

Where the invention employs the direct disruption of a gene by introducing a mutation or the like, the construct or vector used to transfbrm the parental microorganism will be adapted to integrate into the genome of microorganism, as mentioned above. in the case of expression of a protein or nucleic acid that is adapted to disrupt the expression or activity of an enzyme in the 2,3-butanediol biosynthesis pathway, or increase the expression or activity of an inhibitor of an enzyme involved in the pathway, the constructs may remain extra-chromosomal upon transformation of a parental microorganism or may be adapted for intergration into the genome of the microorganism. Accordingly, constructs of use in the invention may include nucleotide sequences adapted to assist integration (for example, a region which allows for homologous recombination and targeted integration into the host genome) or expression and replication of an extrachromosomal construct (for example, origin of replication, promoter and other regulatory sequences).

Nucleic acid constructs of use in the invention may be constructed using any number of techniques standard in the art. For example, chemical synthesis or recombinant techniques may be used. Such techniques are described, for example, in Sambrook et at (Molecular Cloning: A laboratory manual, Cold Spring Harbor Laboratory Press, Cold Spring Harbor, N.Y., 1989). Further exemplary techniques are described in the Examples section herein after. Essentially, the individual genes, regulatory elements, homology arms and the like will be operably linked to one another so that they can perform their desired function. Suitable vectors for use in the invention will be appreciated by those of ordinary skill in the art. However, by way of example, the following vectors may be suitable: pMTL, pIMP, pJIR and the plasmids exemplified in the Examples section herein after.

It should be appreciated that nucleic acids of use in generating the microorganisms of the invention may be in any appropriate form, including RNA, DNA, or cDNA, including double-stranded and single-stranded nucleic acids.

The one or more exogenous nucleic acids may be delivered to a parental microorganism as naked nucleic acids or may be formulated with one or more agents to facilitate the tranformation process (for example, liposome-conjugated nucleic acid, an organism in which the nucleic acid is contained). The one or more nucleic acids may be DNA, RNA, or combinations thereof, as is appropriate.

The microorganisms of the invention may be prepared from a parental microorganism and one or more exogenous nucleic acids using any number of techniques known in the art for producing recombinant microorganisms. By way of example only, transformation (including transduction or transfection) may be achieved by electroporation, conjugation, prophage induction, or chemical and natural competence. Suitable transformation techniques are described for example in Sambrook J, Fritsch E F, Maniatis T: Molecular Cloning: A laboratory Manual, Cold Spring Harbour Labrotary Press, Cold Spring Harbour, 1989.

By way of further example, the electroporation techniques described in: Koepke et al. 2010, *Poc. Nat. Acad. Sci. U.S.A.* 107: 13087-92; PCT/NZ2011/000203; WO2012/053905; Straetz et al., 1994, *Appl. Environ. Microbiol.* 60:1033-37; Mermelstein et al., 1992, *Biotechnology,* 10, 190-195; Jennert et al., 2000, *Microbiology,* 146: 3071-3080; Tyurin et al., 2004, *Appl. Environ. Microbiol.* 70: 883-890; may be used. By way of further example, prophage induction techniques as described in Prasanna Tamarapu Parthasarathy, 2010, Development of a Genetic Modification System in *Clostridium scatologenes* ATCC 25775 for Generation of Mutants, Masters Project Western Kentucky University, could be used. By way of further example, the conjugation methods described in Herbert et al., 2003, *FEMS Microhiol. Lett.* 229: 103-110 or Williams et al., 1990, *J Gen. Microbiol.* 136: 819-826 could be employed.

In certain embodiments, due to the restriction systems which are active in the microorganism to be transformed, it is necessary to methylate the nucleic acid to be introduced into the microorganism. This can be done using a variety of techniques, including those described below, and further exemplified in the Examples section herein after.

By way of example, in one embodiment, a recombinant microorganism of the invention is produced by a method comprises the following steps:

introduction into a shuttle microorganism of (i) a construct/vector to be introduced to the parental microorganism as described herein and (ii) a methylation construct/vector comprising a methyltransferase gene;

expression of the methyltransferase gene;

isolation of one or more constructs/vectors from the shuttle microorganism; and, introduction of the one or more construct/vector into a destination microorganism.

In one embodiment, the methyltransferase gene of step B is expressed consitutively. In another embodiment, expression of the methyltransferase gene of step B is induced.

The shuttle microorganism is a microorganism, preferably a restriction negative microorganism, that facilitates the methylation of the nucleic acid sequences that make up the expression constructivector. In a particular embodiment, the shuttle microorganism is a restriction negative *E. coli, Bacillus subiillis*, or *Lactococcus lactis.*

The methylation construct/vector comprises a nucleic acid sequence encoding a methyltransferase.

Once the expression construct/vector and the methylation construct/vector are introduced into the shuttle microorganism, the methyltransferase gene present on the methylation construct/vector is induced. Induction may be by any suitable promoter system although in one particular embodiment of the invention, the methylation construct/vector comprises an inducible lac promoter (for example, as in SEQ_ID NO 31) and is induced by addition of lactose or an analogue thereof, more preferably isopropyl-β-D-thio-galactoside (IPTG). Other suitable promoters include the ara, tet, or T7 system. In a further embodiment of the invention, the methylation constructivector promoter is a constitutive promoter.

In a particular embodiment, the methylation constructivector has an origin of replication specific to the identity of the shuttle microorganism so that any genes present on the methylation construct/vector are expressed in the shuttle microorganism. Preferably, the construct/vector to be introduced into the parental microorganism has an origin of replication specific to the identity of the microorganism.

Expression of the methyltransferase enzyme results in methylation of the genes present on the construct/vector to be introduced to a parental microorganism. The constmctivector may then be isolated from the shuttle microorganism according to any one of a number of known methods. By way of example only, the methodology described in the Examples section described hereinafter may be used to isolate the construct/vector.

In one particular embodiment, both constructivector are concurrently isolated.

The construct/vector destined for the parental microorganism may be introduced into the microorganism using any number of known methods. However, by way of example, the methodology described in the Examples section hereinafter may be used.

It is envisaged that a methyltransferase gene may be introduced into a shuttle microorganism and over-expressed. Thus, in one embodiment, the resulting methyltransferase enzyme may be collected using known methods and used in vitro to methylate the construct to be introduced into the parental microorganism. The construct/vector may then be introduced into the destination (parental) microorganism. In another embodiment, the methyltransferase gene is introduced into the genome of the shuttle microorganism followed by introduction of the construct destined for the parental microorganism into the shuttle microorganism, isolation of one or more constructs/vectors from the shuttle microorganism and then introduction of the construct/vector into the destination arental) microorganism.

It is envisaged that the construct/vector destined for the parental microorganism and the methylation construct/vector as defined above may be combined to provide a composition of matter. Such a composition has particular utility in circumventing restriction barrier mechanisms to produce the recombinant microorganisms of the invention.

In one particular embodiment, the construct/vectors described herein before are plasmids.

Skilled person will appreciate a number of suitable methyltransferases of use in producing the microorganisms of the invention. However, by way of example the *Bacillus subtilis* phage ΦT1 methyltransferase and the methyltransferase described in the Examples herein after may be used. Nucleic acids encoding suitable methyltransferases will be readily appreciated having regard to the sequence of the desired methyltransferase and the genetic code. In one embodiment, the nucleic acid encoding a methyltransferase is described in the Examples herein after (for example the nucleic acid of SEQ_ID NO. 31).

Any number of constructs/vectors adapted to allow expression of a methyltransferase gene may be used to generate the methylation construct/vector. However, by way of example, the plasmid described in the Examples section hereinafter may be used.

From the information contained herein, it will be appreciated that one may tailor the genetic modification of a parental microorganism to favour the production of one or more products over one or more other products. For example, disrupting the conversion of pyruvate to acetolactate favours the production of lactate, formate, malate, fumarate, citrate, succinate and 2-oxogluterate over the production of valine, leucine and isoleucine.

Production Method

The invention provides a method for producing one or more product by microbial fermentation comprising fermenting a substrate comprising CO using a microorganism of the invention. In one particular embodiment, the method is for producing ethanol or one or more other products by microbial fermentation comprising fermenting a substrate comprising CO using a microorganism of the invention. The methods of the invention may be used to reduce the total atmospheric carbon emissions from an industrial process.

Preferably, the fermentation comprises the steps of anaerobically fermenting a substrate in a bioreactor to produce the one or more products (in one particular embodiment, ethanol, or ethanol and one or more other products) using a recombinant microorganism of the invention.

In one embodiment the method comprises the steps of:

(a) providing a substrate comprising CO to a bioreactor containing a culture of one or more microorganism of the first aspect of the invention; and
(b) anaerobically fermenting the culture in the bioreactor to produce one or more products (in one embodiment including ethanol).

In one embodiment the method comprises the steps of:

i. capturing CO-containing gas produced as a result of the industrial process, before the gas is released into the atmosphere;
ii. the anaerobic fermentation of the CO-containing gas to produce one or more products (in one embodiment including ethano)1 by a culture containing one or more microorganism of the first aspect of the invention.

In an embodiment of the invention, the gaseous substrate fermented by the microorganism is a gaseous substrate containing CO. The gaseous substrate may be a CO-containing waste gas obtained as a by-product of an industrial process, or from some other source such as from automobile exhaust fumes. In certain embodiments, the industrial process is selected from the group consisting of ferrous metal products manufacturing, such as a steel mill, non-ferrous products manufacturing, petroleum refining processes, gasification of coal., electric power production, carbon black production, ammonia production, natural gas refining, methanol production and coke manufacturing. In these embodiments, the CO-containing gas may be captured from the industrial process before it is emitted into the atmosphere, using any convenient method. The CO may be a component of syngas (gas comprising carbon monoxide and hydrogen). The CO produced from industrial processes is normally flared off to produce $CO_2$ and therefore the invention has particular utility in reducing $CO_2$ greenhouse gas emissions and producing butanol for use as a biofuel. Depending on the composition of the gaseous CO-containing substrate, it may also be desirable to treat it to remove any undesired impurities, such as dust particles before introducing it to the fermentation. For example, the gaseous substrate may be filtered or scrubbed using known methods.

It will be appreciated that for growth of the bacteria and CO-to-ethanol (and/or other product(s)) to occur, in addition to the CO-containing substrate gas, a suitable liquid nutrient medium will need to be fed to the bioreactor. The substrate and media may be fed to the bioreactor in a continuous, batch or batch fed fashion. A nutrient medium will contain vitamins and minerals sufficient to permit growth of the micro-organism used. Anaerobic media suitable for fermentation to produce ethanol (and optionally one or more other products) using CO are known in the art. For example, suitable media are described in Biebel (Journal of Industrial Microbiology & Biotechnology (2001) 27, 18-26). The substrate and media may be fed to the bioreactor in a continuous, hatch or batch fed fashion. In one embodiment of the invention the media is as described in the Examples section herein after.

The fermentation should desirably be carried out under appropriate conditions for the CO-to-ethanol (and/or other product(s)) fermentation to occur. Reaction conditions that should be considered include pressure, temperature, gas flow rate, liquid flow rate, media pH, media redox potential, agitation rate (if using a continuous stirred tank reactor), inoculum level, maximum gas substrate concentrations to ensure that CO in the liquid phase does not become limiting, and maximum product concentrations to avoid product inhibition.

In addition, it is often desirable to increase the CO concentration of a substrate stream (or CO partial pressure in a gaseous substrate) and thus increase the efficiency of fermentation reactions where CO is a substrate. Operating at increased pressures allows a significant increase in the rate of CO transfer from the gas phase to the liquid phase where it can be taken up by the micro-organism as a carbon source for the production of ethanol (and/or other product(s)). This in turn means that the retention time (defined as the liquid volume in the bioreactor divided by the input gas flow rate) can be reduced when bioreactors are maintained at elevated pressure rather than atmospheric pressure. The optimum reaction conditions will depend partly on the particular micro-organism of the invention used. However, in general, it is preferred that the fermentation be performed at pressure higher than ambient pressure. Also since a given CO-to-ethanol (and/or other product(s)) conversion rate is in part a function of the substrate retention time, and achieving a desired retention time in turn dictates the required volume of a bioreactor, the use of pressurized systems can greatly reduce the volume of the bioreactor required, and consequently the capital cost of the fermentation equipment. According to examples given in U.S. Pat. No. 5,593,886, reactor volume can be reduced in linear proportion to increases in reactor operating pressure, i.e. bioreactors operated at 10 atmospheres of pressure need only be one tenth the volume of those operated at 1 atmosphere of pressure.

The benefits of conducting a gas-to-ethanol fermentation at elevated pressures has been described elsewhere. For example, WO 02/08438 describes gas-to-ethanol fermentations performed under pressures of 30 psig and 75 psig, giving ethanol productivities of 150 g/l/day and 369 g/l/day respectively. However, example fermentations performed using similar media and input gas compositions at atmospheric pressure were found to produce between 10 and 20 times less ethanol per litre per day.

It is also desirable that the rate of introduction of the CO-containing gaseous substrate is such as to ensure that the concentration of CO in the liquid phase does not become limiting. This is because a consequence of CO-limited conditions may be that the ethanol product is consumed by the culture.

The composition of gas streams used to feed a fimmentation reaction can have a significant impact on the efficiency and/or costs of that reaction. For example, O2 may reduce the efficiency of an anaerobic fermentation process. Processing of unwanted or unnecessary gases in stages of a fermentation process before or after fermentation can increase the burden on such stages (e.g. where the gas stream is compressed before entering a bioreactor, unnecessary energy may be used to compress gases that are not needed in the fermentation). Accordingly, it may be desirable to treat substrate streams, particularly substrate streams derived from industrial sources, to remove unwanted components and increase the concentration of desirable components.

In certain embodiments a culture of a bacterium of the invention is maintained in an aqueous culture medium. Preferably the aqueous culture medium is a minimal anaerobic microbial growth medium. Suitable media are known in the art and described for example in U.S. Pat. Nos. 5,173,429 and 5,593,886 and WO 02/08438, and as described in the Examples section herein after.

The one or more products produced by a method of the invention (in one embodiment ethanol, or a mixed alcohol stream containing ethanol and/or one or more other products) may be recovered from the fermentation broth by methods known in the art, such as fractional distillation or evaporation, pervaporation, and extractive fermentation, including for example, liquid-liquid extraction. By-products such as acids including acetate may also be recovered from the fermentation broth using methods known in the art. For example, an adsorption system involving an activated charcoal filter or electrodialysis may be used. Alternatively, continuous gas stripping may also be used.

In certain preferred embodiments of the invention, ethanol and/or one or more other products are recovered from the fermentation broth by continuously removing a portion of the broth from the bioreactor, separating microbial cells from the broth (conveniently by filtration), and recovering one or more products from the broth. Alcohols may conveniently be recovered for example by distillation, and acids may be recovered for example by adsorption on activated charcoal. The separated microbial cells are preferably returned to the fermentation bioreactor. The cell free permeate remaining after any alcohol(s) and acid(s) have been removed is also preferably returned to the fermentation bioreactor. Additional nutrients (such as B vitamins) may be added to the cell free permeate to replenish the nutrient medium before it is returned to the bioreactor.

Also, if the pH of the broth was adjusted as described above to enhance adsorption of acetic acid to the activated charcoal, the pH should be re-adjusted to a similar pH to that of the broth in the fermentation bioreactor, before being returned to the bioreactor.

Succinate can be recovered from the fermentation broth using a number of techniques such as acidification, electrodialysis coupled with ion-exchange chromatography (Song and Lee, 2006, *Enzyme Microb Technol* 39, 352-361), precipitation with Ca(OH) coupled with filtration and addition of sulfuric acid (Lee et al 2008, *Appl Microbiol Biotechnol* 79, 11-22) or reactive extraction with amine-based extractants such as tri-n-octylamine (Huhet al, 2006, *Proc Biochem* 41, 1461-1465). For all methods it is crucial to have the free acid form, and not the salt. Most biotechnological production processes for succinic acid however operate at neutral or slightly acidic range of pH 6-7. Given the pKa of succinic acid (pKa=4.16 and 5.61), the majority is present as salt and not as free acid under these conditions. *C. autoethanogenum* and carboxydotrophic acetogenas however are known to tolerate and grow at a desirable low pH range of pH 4-6.

Branched-chain amino acids valine, leucine, and isoleucine can be relatively easily recovered from the fermentation broth by concentration (e.g. reverse osmosis) and crystallization or removal of the biomass (e.g. ultrafiltration or centrifugation) and ion exchange chromatography (Ikeda, A., 2003, Amino Acid Production Processes, in R. Fauric and J. Thommel (eds.) Microbial production of L-amin acids, 1-35).

Lactate, formate, 2-oxogluterate and other products can be recovered from the fermentation broth by any known method. However, by way of example, in the case of lactate, conventional fermentation process produces calcium lactate precipitate, which can be collect and re-acidified. Alternatively, membrane techniques, such as electrodialysis can be sued to separate lactate. Low concentrations of lactate can be separated from a fermentation broth by applying a suitable potential across a selective ion permeable membrane. Other suitable techniques include nanofiltration, wherein monovalent ions can selectively pass through a membrane under pressure.

It would be appreciated that in some situations, the method may be performed to produce and recover products other than ethanol (for example, one or more products comprising valine, leucine, succinate, pyruvate, lactate and formate). Accordingly, the invention should be understood to include methods for the production of one or more of these products.

EXAMPLES

The invention will now be described in more detail with reference to the following non-limiting examples.

Example 1

Deletion of *C. autoethanogenum* budA Gene by Homologous Recombination

Figure 2:
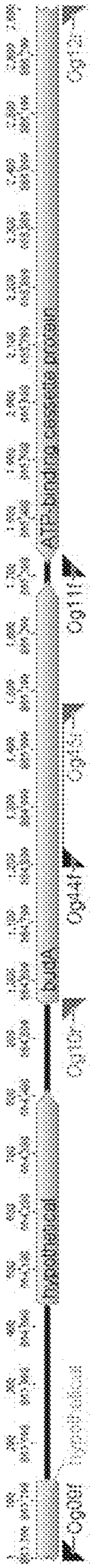
FIG. 2 shows the budA gene and its 5' and 3' flanking regions on *C. autoethanogenum* DSM23693 genome. Also indicated are the primers used for PCR amplification and subsequent cloning of the flanking fragments in pMTL85141 plasmid.
Figure 3:
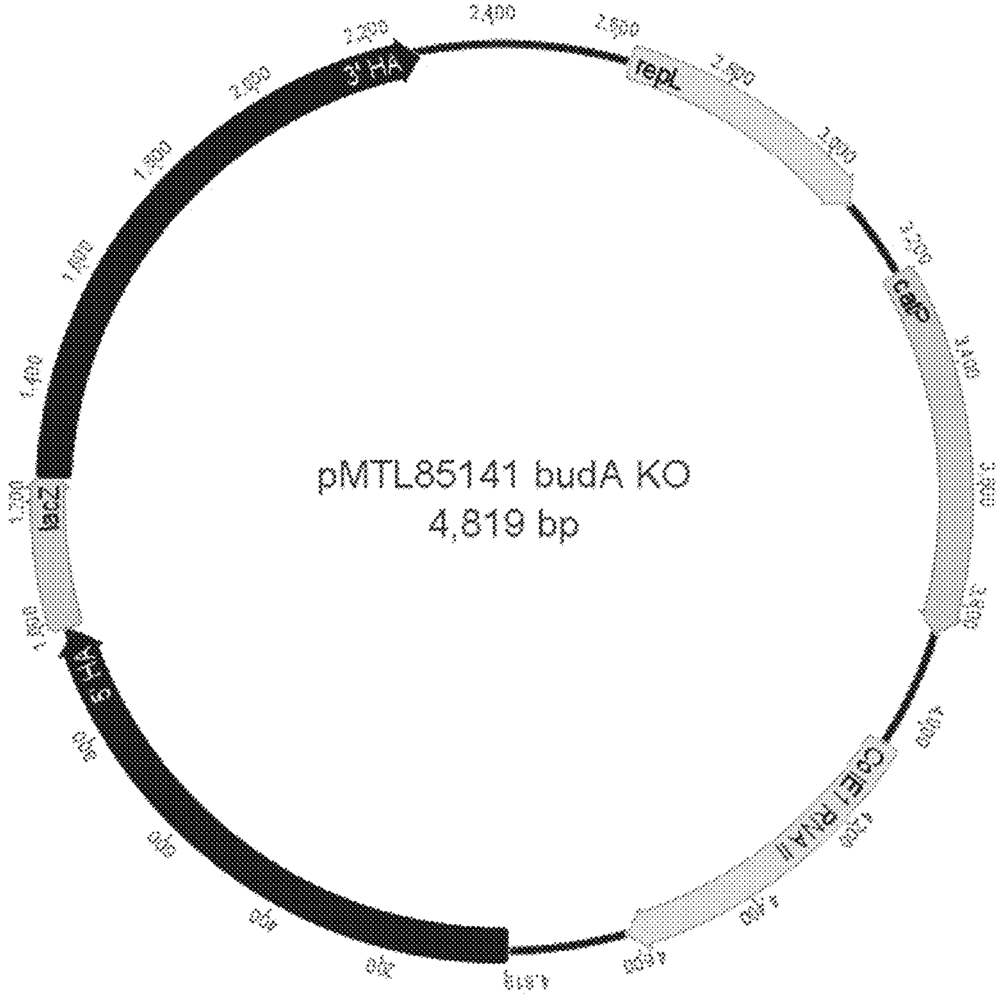
FIG. 3 shows an exemplanary pMTL85141-budA-ko plasmid harbouring the 5' and 3' budA gene flanking DNA fragments separated by a lacZ gene for budA gene knockout in *C. autoethanogenum* DSM23693.
Figure 4:
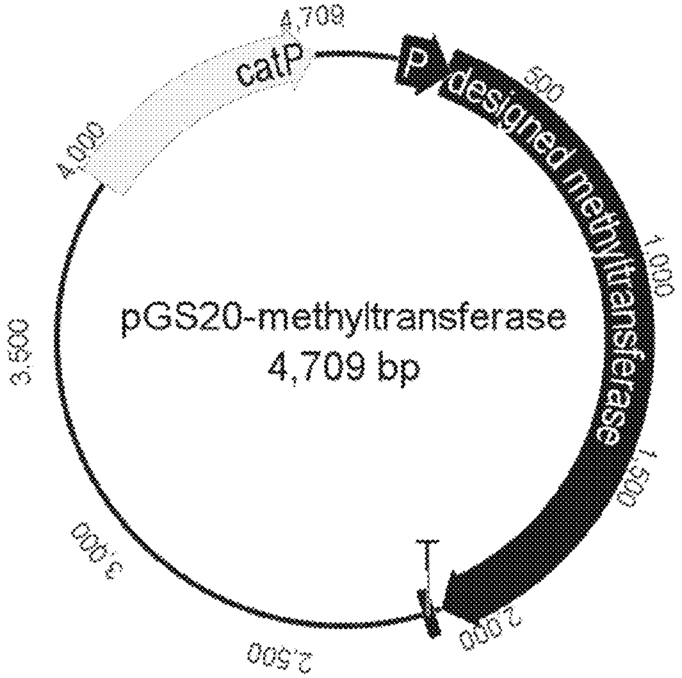
FIG. 4 shows an exemplary methylation plasmid of use in the invention
Figure 5:
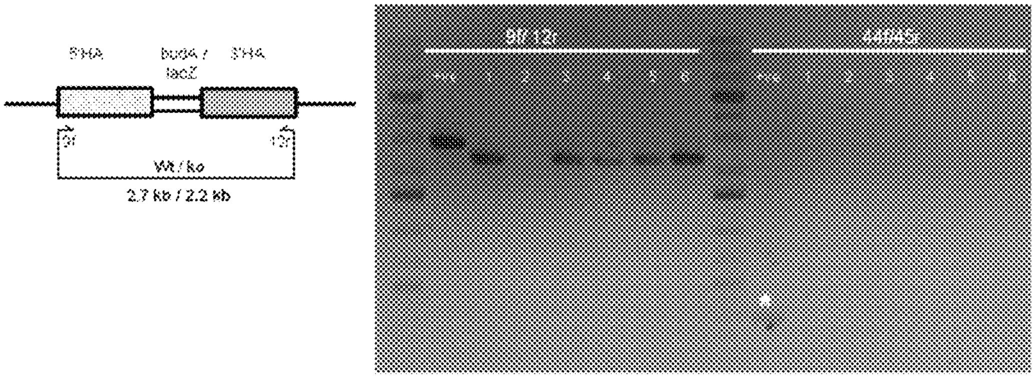
FIG. 5 shows a graphical presentation of genomic region of *C. autoethanogenum* DSM23693 following budA gene knockout and also indicates the position of primers used for screening *C. autoethanogenum* DSM23693 budA gene knockouts and the expected size of PCR products from wild-type *C. autoethanogenum* DSM23693 and its corresponding budA gene knockout.

Genetic modifications were carried out using a plasmid containing the 5' and 3' homology arms of budA gene of *C. autoethanogenum* DSM23693 (FIG. 1*a*, FIG. 1*b*, and FIG. 2). This plasmid was methylated in vivo using a novel methyltransferase and then transformed into *C. autoethanogenum* DSM23693 (DSMZ, Germany). The budA gene knockout has been shown by PCR and by the inhibition of 2,3-butanediol production in *C. autoethanogenum* DSM23693 ΔbudA strains.

Conjstruction of Expression Plasmid:

Standard Recombinant DNA and molecular cloning techniques were used in this invention and are described by Sambrook et al, 1989 and Ausubel et al, 1987. DNA sequences of 5' upstream flanking homology arm (Seq. ID 3) and 3' downstream flanking homology arm (Seq. ID 4) of *Clostridum autoethanogenum* DSM23693 budA gene were obtained from NCBI.

Genomic DNA from *Clostridum autoethanogenum* DSM23693 was isolated using Purelink Genomic DNA mini kit from Invitrogen, according to the manufacturer's instruction.

The 5' (Seq. ID. 3) and 3' (Seq. ID. 4) flanking homology arms were amplified by PCP with oligonucleotides in Table 1 using *Clostridum autoethanogenum* DSM23693 genomic DNA as template, iProof High Fidelity DNA Polymerase (Bio-Rad Labratories) and the following program: initial denaturation at 98° C. for 30 seconds, followed by 25 cycles of denaturation (98° C. for 10 seconds), annealing (60° C. for 15 seconds) and elongation (7° C. for 30 seconds), before a final extension step (72° C. for 7 minutes).

TABLE 1

Oligonucleotides for cloning

| Target | Oligonucleotide Name | DNA Sequence (5' to 3') | SEQ_ID NO. |
|---|---|---|---|
| 5' Homology arm | Og09f | attcat**cctgcagg**TTTCTTCACAGGAAAATATACTTCAG | 5 |
| 5' Homology arm | Og10r | gact**gcggccgc**ATTACATTCACCTCTATGTCATTATAAC | 6 |
| 3' Homology arm | Og11f | attt**gctagc**ACTAGACAGTGCTAATAACAATGTCTAG | 7 |
| 3' Homology arm | Og12r | atat**ggcgcgcc**TCATAAACCTGGATAACATAAGC | 8 |
| Plasmid | M13f | GTAAAACGACGGCCAG | 10 |
| Plasmid | M13r | CAGGAAACAGCTATGACC | 11 |

The amplified 964 bp 5' flanking homology arm (5'HA) of budA gene was cut with SbfI and NotI resitriction enzymes and cloned into the *E. coli-Clostridium* shuttle vector pMTL 85141 (Seq. ID 9; FJ797651. 1; Nigel Minton, University of Nottingham; Heap et al., 2009) using SbfI and NotI restriction sites and strain *E. coli* XLI-Blue MRF' Kan (Stratagene). The created plasmid pMTL85141-budA-5'HA and the 977 bp PCR product of the 3' homology arm of budA gene were both cut with NheI and AscI. A ligation of these digested DNA fragments was transformed into *E. coli* XL1-Blue MRF' Kan (Stratagene) resulting in the plasmid pMTL85141-budA-ko. The insert in the resulting plasmid pMTL85141-budA-ko (SEQ_ID No. 12) was completely sequenced using oligonucleotides given in Table 1 and sequencing results confirmed that both 5' and 3' homology arms were free of mutations.

Methylation of DNA:

A hybrid methyltransferase gene fused to an inducible lac promoter (SEQ ID No. 31) was designed, by alignment of methyltransferase genes from *C. autothanegenum, C. ljungdahlii*, and *C. ragsdalei*, as described in U.S. patent application Ser. No. 13/049,263. Expression of the methyltransferase results in a protein having the sequence of SEQ ID No. 32). The hybrid methyltransferase gene was chemically synthesized and cloned into vector pGS20 (ATG:biosynthetics GmbH, Merzhausen, Germany—SEQ ID No. 33) using EcoRI. The resulting methylation plasmid pGS20-methyltransferase was double transformed with the plasmid pMTL85141-budA-ko into the restriction negative *E. coli* XL1-Blue MRF' Kan (Stratagene). In vivo methylation was induced by addition of 1 mM IPTG, and methylated plasmids were isolated using the Zymo mini prep Kit (Zymo). The resulting methylated plasmid composition was used for transformation of *C. autoethanogenum* DSM23693.

Transformation:

During the complete transformation experiment, *C. autoethanogenum* DSM23693 was grown in YTF media (Tab. 2) in the presence of reducing agents and with 30 psi steel mill waste gas (collected from New Zealand Steel site in Glenbrook, NZ; composition: 44% CO, 32% $N_2$, 22% $CO_2$, 2% $H_2$) at 37° C. using standard anaerobic techniques described by Hungate (1969) and Wolfe (1971).

TABLE 2

YTF media

| Media component | per L of Stock |
|---|---|
| Yeast Extract | 10 g |
| Tryptone | 16 g |
| Sodium chloride | 0.2 g |
| Fructose | 10 g |
| Distilled water | To 1 L |
| **Reducing agent stock** | **per 100 mL of stock** |
| NaOH | 0.9 g |
| Cystein•HCl | 4 g |
| Na2S | 4 g |
| Distilled water | To 100 mL |

To make competent cells, a 50 ml culture of *C. autoethanogenum* DSM23693 was subcultured to fresh YTF media for 5 consecutive days. These cells were used to inoculate 50 ml YTF media containing 40 mM DL-threortine at an $OD_{600\ nm}$ of 0.05. When the culture reached an $OD_{600\ nm}$ of 0.5, the cells were incubated on ice for 30 minutes and then transferred into an anaerobic chamber and harvested at 4,700×g and 4° C. The culture was twice washed with ice-cold electroporation buffer (270 mM sucrose, 1 mM MgCl2, 7 mM sodium phosphate, pH 7.4) and finally suspended in a volume of 600 μl fresh electroporation buffer. This mixture was transferred into a pre-cooled electroporation cuvette with a 0.4 cm electrode gap containing 2 μg of the methylated plasmid mix and 1 μl Type 1 restriction inhibitor (Epicentre Biotechnologies) and immediately pulsed using the Gene pulser Xcell electroporation system (Bio-Rad) with the following settings: 2.5 kV, 600 Ω, and 25 μF. Time constants of 3.7-4.0 ms were achieved. The culture was transferred into 5 ml fresh YTF media. Regeneration of the cells was monitored at a wavelength of 600 nm using a Spectronic Helios Epsilon Spectrophotometer (Thermo) equipped with a tube holder. After an initial drop in biomass, the cells started growing again. Once the biomass doubled from that point about 200 μl of culture was spread on YTF-agar plates and PETC agar plates containing 5 g/l fructose (Table 3) (both containing 1.2% Bacto™ Agar (BD) and 15 μg/ml Thiamphenicol). After 3-4 days of incubation with 30 psi steel mill gas at 37° C., 500 colonies per plate were clearly visible.

TABLE 3

PETC media (ATCC media 1754; atcc.org/Attachments/2940.pdf)

| Media component | Concentration per 1.0 L of media |
|---|---|
| $NH_4Cl$ | 1 g |
| KCl | 0.1 g |
| $MgSO_4 \cdot 7H_2O$ | 0.2 g |
| NaCl | 0.8 g |
| $KH_2PO_4$ | 0.1 g |
| $CaCl_2$ | 0.02 g |
| Trace metal solution | 10 ml |
| Wolfe's vitamin solution | 10 ml |
| Yeast Extract | 1 g |
| Resazurin (2 g/L stock) | 0.5 ml |
| MES | 2 g |
| Reducing agent | 0.006-0.008% (v/v) |
| Distilled water | Up to 1 L, pH 5.5 (adjusted with HCl) |
| | per L of Stock |
| Wolfe's vitamin solution | |
| Biotin | 2 mg |
| Folic acid | 2 mg |
| Pyridoxine hydrochloride | 10 mg |
| Thiamine•HCl | 5 mg |
| Riboflavin | 5 mg |
| Nicotinic acid | 5 mg |
| Calcium D-(+)-pantothenate | 5 mg |
| Vitamin $B_{12}$ | 0.1 mg |
| p-Aminobenzoic acid | 5 mg |
| Thioctic acid | 5 mg |
| Distilled water | To 1 L |
| Trace metal solution | |
| Nitrilotriacetic Acid | 2 g |
| $MnSO_4 \cdot H_2O$ | 1 g |

TABLE 3-continued

PETC media (ATCC media 1754; atcc.org/Attachments/2940.pdf)

| | |
|---|---|
| $Fe(SO_4)_2(NH_4)_2 \cdot 6H_2O$ | 0.8 g |
| $CoCl_2 \cdot 6H_2O$ | 0.2 g |
| $ZnSO_4 \cdot 7H_2O$ | 0.2 mg |
| $CuCl_2 \cdot 2H_2O$ | 0.02 g |
| $NaMoO_4 \cdot 2H_2O$ | 0.02 g |
| $Na_2SeO_3$ | 0.02 g |
| $NiCl_2 \cdot 6H_2O$ | 0.02 g |
| $Na_2WO_4 \cdot 2H_2O$ | 0.02 g |
| Distilled water | To 1 L |
| Reducing agent stock | per 100 mL of stock |
| NaOH | 0.9 g |
| Cystein•HCl | 4 g |
| Na2S | 4 g |
| Distilled water | To 100 mL |

The colonies were streaked on fresh PETC agar plates also containing 5 g/L fructose and 15 μg/ml Thiamphenicol. After 2 days of incubation with 30 psi steel mill gas at 37° C. single colonies from these plates were restreaked on fresh non-selective PETC agar plates containing 5 g/l fructose only. The resreaking on PETC agar plates with 5 g/l fructose was repeated once again and plates incubated with 30 psi steel mill gas at 37° C. After 3 days 6 single colonies growing on non-slective media were inoculated in 2 ml PETC liquid media containing 5 g/l fructose. When growth occurred, the culture was sequentially upscaled to 5 ml, 25 ml and then to 50 ml PETC media containing 5 g/l fructose and 30 psi steel mill gas as carbon source.

Coryformation of the Successful Transformation:

*C. autoethanogenum:* To verify the identity of the six clones and the DNA transfer, genomic DNA was isolated from all 6 colonies/clones in PETC liquid media using Purelink™ Genomic DNA mini kit (Invitrogen) according to manufacturer's instruction. These genomic DNA along with that of *C. autoethanogenum* DSM23693 wildtype were used as template in PCR. The PCR was performed with iproof High Fidelity DNA Polymerase (Bio-Rad Laboratories), primers as listed in Table 4 and the following program: initial denaturation at 98° C. for 2 minutes, followed by 25 cycles of denaturation (98° C. for 10 seconds), annealing (61° C. for 15 seconds) and elongation (72° C/ for 90 seconds), before a final extension step (72° C. for 7 minutes). The genomic DNA from wildtype *C. autoethanogenum* DSM23693 was used as template in control PCR.

TABLE 4

Oligonucleotides for PCR confirmation of plasmid and species

| Target region | Oligonucleotide Name | DNA Sequence (5' to 3') | Seq ID No. |
|---|---|---|---|
| 16s rRNA gene | FD1 | CCGAATTCGTCGACAACAGAGTTTGATCCTGGCTCAG | 27 |
| 16s rRNA gene | rP2 | CCCGGGATCCAAGCTTACGGCTACCTTGTTACGACTT | 28 |
| Homology arm | og09f | attcat**cctgcagg**TTTCTTCACAGGAAAATATACTTCAG | 5 |
| Homology arm | Og12r | atat**ggcgcc**TCATAAACCTGGATAACATAAGC | 8 |
| budA gene | Og44f | TTGCTGTAGTCACTGAACTGGAAAA | 29 |
| budA gene | Og45r | AATCAGGACACCTAAATCCAACCAC | 30 |

To confirm the identity of the 6 clones, PCR was performed against the 16s rRNA gene using, primers fD1 (Seq. ID. 27) and rP2 (Seq. ID 28) and using PCR conditions as described above. The PCR products were purified using Zymo Clean and Concentrator™ kit and sequenced using primer rP2 (Seq. ID 28). Sequences of all 6 clones (Seq. ID. 13-19) showed at least 90% identity against the 16S rRNA gene of *C. autoethanogenum* (Seq. ID 15; Y18178, GI:7271109).

PCR of 6 analyzed clones with primers specific to the budA target region using primers Og09f (Seq. ID. 5) and Og12r (Seq. ID. 8) resulted in amplification of 2.2 kb DNA fragment from 5 out of 6 clones. PCR product of 2.7 kb was amplified with wildtype *C. autoethanogenum* DSM23693 genomic DNA. The identity of the 2.2 kb PCR products from potential budA knockout clones was confirmed by sequencing (Seq ID 20-26) with primers listed in Table 5 and no sequence of budA gene was detected in these fragments. The lacZ DNA fragment had replaced the budA gene. The absence of budA gene in these 6 clones was confirmed again by PCR with primers, Og44f (Seq. ID. 29) and Og45r (Seq. ID. 30) specific to the 275 bp internal region of *C. autoethanogenum* DSM23693 budA gene which was amplified only from wild type *C. autoethanogenum* DSM23693.

Absence of 2,3 Butanediol Production and Increase in Ethanol Yield:

To demonstrate the lack of acetoin and subsequently 2,3-butanediol production, serum bottle experiments were carried out with clone 1 in triplicates with steel mill waste gas (composition, 44% CO, 12% N2, 22% CO2, and 2% H2; collected from a steel site in Glenbrook, New Zealand) and PETC media as described above. Unmodified wild type strain of *C. autoethanogenum* DSM23693 was grown under the same conditions as control.

Analysis of metabolites was performed by HPLC using an Agilent 1100 Series HPLC system equipped with a RID operated at 35° C. (Refractive Index Detector) and an Alltech IOA-2000 Organic acid column (150×6.5 mm, particle size 5 μm) kept at 32° C. Slightly acidified water was used (0.005 M $H_2SO_4$) as mobile phase with a flow rate of 0.25 ml/min. To remove proteins and other cell residues, 400 μl samples were mixed with 100 μl of a 2%) (w/v) 5-Sulfosalicylic acid and centrifuged at 14,000×g for 3 min to separate precipitated residues. 10 μl of the supernatant were then injected into the HPLC for analyses.

The results of serum bottle experiments with ΔbudA *C. autoethanogenum* DSM23693 clone 1 and unmodified wild type *C. autoethanogenum* DSM23693 are shown in Table 5. Maximum biomass of strain ΔbudA *C. autoethanogenum* DSM23693 was with an $OD_{600\ nm}$ of 0.32 relatively lower than the unmodified wild-type, which grew to an OD600 nm of 0.58. Compared to the wild type, no 2,3-butanediol was detected in the culture of the ΔbudA *C. autoethanogenum* DSM23693 clone 1, and the ethanol yield was significantly higher in ΔbudA *C. autoethanogenum* DSM23693 clone 1 than in the unmodified *C. autoethanogenum* DSM23693 (Table 5).

TABLE 5

Metabolites produced by ΔbudA *C. autoethanogenum* DSM23693 clone 1 and unmodified wildtype *C. autoethanogenum* DSM23693 relative to the biomass

| Metabolite (g/l) | Media | Wildtype | ΔbudA Clone 1 |
|---|---|---|---|
| Ethanol | 1.395 | 2.500 | |
| Acetic acid | 2.296 | 0.180 | |

TABLE 5-continued

Metabolites produced by ΔbudA *C. autoethanogenum* DSM23693 clone 1 and unmodified wildtype *C. autoethanogenum* DSM23693 relative to the biomass

| Metabolite (g/l) | Media | Wildtype | ΔbudA Clone 1 |
|---|---|---|---|
| 2,3-butanediol | 0.085 | 0.000 | |
| Lactic acid | 0.020 | 0.197 | |
| Formic acid | 0.002 | 1.647 | |
| Succinic acid | 0.002 | 0.344 | |

Production of Other Metabolites—Lactate, Formate, Succinate, 2-oxogluterate Valine, Leucine, Isoleucine:

At the same time, interestingly, while the unmodified *C. autoethanogenum* DSM23693 produced only 0.02 g/l lactic acid as other by-product, ΔbudA *C. autoethanogenum* DSM23693 produced a significantly higher amount of lactic acid 0.07 g/l (0.197 g/l normalized to biomass) as well as 0.53 g/l (1.647 normalized to biomass) formic acid and 0.13 g/l (0.344 g/l normalized to biomass) succinic acid (Table 5). This increase is likely from the pyruvate, early precursor of 2,3-butanediol FIGS. 1*a* and 1*b*, accumulation because of knockout of budA gene which has blocked the production of 2,3-butanediol.

The production of succinate and lactate by ΔbudA *C. autoethanogenum* DSM23693 was also confirmed by Gas Chromatography-Mass spectrometry (GC-MS). For this, about 2.5 ml culture of ΔbudA *C. autoethanogenum* DSM23693 clone 1 grown with steel mill waste gas (composition, 44% CO, 32% N2, 22% CO2, and 2% H2; collected from a steel site in Glenbrook, New Zealand) at an optical density of 0.32 was centrifuged and supernatant was filtered through 0.2 uM filter (Smart K F, Aggio R B, Van Houtte J R, Villas-Bôas S G, Analytical platform for metabotome analysis of microbial cells using methyl chlorothrmate derivatization followed by gas chromatography-mass spectrometry, Nat Protoc. 2010 September; 5(10):1709-29. 2010). About 0.65 ml culture of wild type *C. autoethanogenum* DSM23693 and 2.5 ml of media blank were processed similarly. The samples were freeze-dried and analyzed by GC-MS in triplicates at the University of Auckland. As seen in Table 6 the peak intensity of the succinate and lactate signal was stronger in ΔbudA *C. autoethanogenum* DSM23693 clone 1 compared to unmodified *C. autoethanogenum* DSM23693 and the control media blank. The GC-MS results for succinate and lactate are consistent with HPLC results.

GC-MS results (Table 6) not only confirmed production of lactate and succinate with ΔbudA *C. autoethanogenum* DSM23693 clone 1, but also show production of 2-oxogluterate, the other incomplete TCA cycle endproduct besides succinate, and branched-chain amino acids valine, leucine, isoleucine, which are produced from pyruvate and acetolactate, the precursors of 2,3-butanediol which are likely to be present at elevated levels in the ΔbudA *C. autoethanogenum* strain. TCA cycle intermediates such as malate, fumerate, citrate, cis-Aconitate, iso-Citrate haven't been tested, but are likely to be elevated, as end-products succinate and 2-oxogluterate have been found to be produced (FIG. 1*b*).

TABLE 6

Metabolite analysis of ΔbudA *C. autoethanogenum* DSM23693 clone 1 (ΔbudA) and unmodified wild type *C. autoethanogenum* DSM23693 (Wild type) by GC-MS, Media was included in the analyses as a control. The values given in table correspond to the normalized peak intensity obtained for each replicate (R).

| Metabolite | Media | | | Average |
|---|---|---|---|---|
| Lactate | 0.547053273 | 0.474988 | 0.431645 | 0.48 |
| Succinate | 1.036264929 | 0.960478 | 1.243932 | 1.08 |
| 2-Oxogluterate | ND | ND | ND | 0.00 |
| Valine | 5.970408365 | 5.446962 | 5.937764 | 5.79 |
| Leucine | 3.418425725 | 3.154261 | 3.237803 | 3.27 |
| Isoleucine | ND | ND | 0.607184 | 0.20 |

| Metabolite | Wild type | | | Average |
|---|---|---|---|---|
| Lactate | 0.801302932 | 0.691344 | 0.853559 | 0.78 |
| Succinate | 0.547053273 | 0.474988 | 0.431645 | 0.48 |
| 2-Oxogluterate | ND | 0.003092 | 0.0028 | 0.00 |
| Valine | 0.018545724 | 0.011764 | 0.014182 | 0.01 |
| Leucine | 0.0307755 | 0.024291 | 0.023099 | 0.03 |
| Isoleucine | 0.008136206 | 0.005305 | 0.00643 | 0.01 |

| Metabolite | ΔbudA Clone 1 (Sample 1) | | | ΔbudA Clone 1 (Sample 2) | | | Average |
|---|---|---|---|---|---|---|---|
| Lactate | 5.017350825 | 5.672474 | 5.237064 | 5.987887 | 5.138095 | 4.39521 | 5.24 |
| Succinate | 2.535447097 | 2.984226 | 2.516218 | 5.017351 | 5.672474 | 5.237064 | 3.99 |
| 2-Oxogluterate | 0.522265764 | 0.462277 | ND | 1.22281 | 0.021205 | ND | 0.37 |
| Valine | 11.13216958 | 9.419048 | 7.824351 | 10.08887 | 10.66202 | 9.192138 | 9.72 |
| Leucine | 10.92981831 | 5.478571 | 4.497006 | 4.70419 | 11.36585 | 4.441235 | 6.90 |
| Isoleucine | 6.087638048 | 9.397619 | 0.895459 | 10.59162 | 2.912456 | 9.976735 | 6.64 |

ND = not detected.

Production of acetoin and 2,3-butanediol is usually associated with deacidification of strong pyruvic acid (Xiao, Z., and P. Xu. 2007. Acetoin metabolism in bacteria. Crit. Rev. Biochem. Microbiol, 33:127-140), which can pose a serious threat to the cell by destroying the internal pH and proton gradient needed for energy conservation. Both acetoin and 2,3-butanediol are pH neutral compounds. Production of 2,3-butanediol also serves as electron sink to offload surplus reducing equivalents produced during the fermentation process.

While not wishing to be bound by any particular theory, the inventors believe that by knocking-out production of acetoin and 2,3-butanediol, the cell needs to find other ways to deacidify pyruvic acid (pKa=2.50) and offload reducing equivalents and thus is shifting it's metabolism to production of other (novel) products such as branched-chain amino acids valine, leucine or isoleucine, succinate (pKa1=4.20, pKa2=5.60), lactic acid (pKa=3.86), and formic acid (pka=3.77). Production of succinic acid also gives the chance to offload 4 reducing equivalents, while 2 reducing equivalents can be offloaded by production of lactic acid.

Example 2

Succinate Pathway

The pathway for production of succinate is described in FIG. 1b. Respective genes were identified in *Clostridium autoethanogenum* and enzyme activity was demonstrated.

In a first step, pyruvate is converted to malate, either directly catalyzed by a malic enzyme or via oxaloacetate catalyzed by a malate dehydrogenase. Oxaloacetate (OAA) can be produced from pyruvate by action of a Pyruvate carboxylase, or via Phosphoenolpyruvate (PEP) in a two step conversion catalyzed by Pyruvate phosphate dikinase (PPDK) and PEP carboxykinase (PCK). Malate is subsequently converted to succinate in a two-step process catalysed by Fumarate hydratase and fumarate reductase. Respective genes were identified in *C. autoethanogenum* and homologous genes are present in other carboxydotrophic acetogens as *C. ljungdahlii* and *C. ragsdalei* (Table 7).

TABLE 7

Genes and Enzymes identified to be involved in Succinate production

| | *C. autoethanogenum* | *C. ljungdahlii* | *C. ragsdalei* |
|---|---|---|---|
| Malic enzyme 1 | Seq. ID 38-39 | CP001666.1 CLJU_c04160; ADK13498.1 | Seq. ID 60-61 |
| Malic enzyme 2 | Seq. ID 40-41 | CP001666.1 CLJU_c38460; ADK16871.1 | — |
| Malate dehydrogenase | Seq. ID 42-43 | CP001666.1 CLJU_c05920; ADK13674.1 | Seq. ID 62-63 |
| Pyruvate phosphate dikinase (PPDK) | Seq. ID 44-45 | CP001666.1 CLJU_c08140; ADK13882.1 | Seq. ID 64-65 |
| Pyruvate carboxylase (PYC) | Seq. ID 46-47 | CP001666.1 CLJU_c37390; ADK16765.1 | Seq. ID 66-67 |
| PEP carboxykinase (PCK) | Seq. ID 48-49 | CP001666.1 CLJU_c06210; ADK13703.1 | Seq. ID 68-69 |
| Fumarate hydratase subunit A | Seq. ID 50-51 | CP001666.1 CLJU_c40600; ADK17084.1 | Seq. ID 70-71 |
| Fumarate hydratase subunit B | Seq. ID 52-53 | CP001666.1 CLJU_c40590; ADK17083.1 | Seq. ID 72-73 |
| Fumarate reductase 1, flavoprotein | Seq. ID 54-55 | CP001666.1 CLJU_c22800; ADK15338.1 | Seq. ID 74-75 |
| Fumarate reductase 2, flavoprotein | Seq. ID 56-57 | CP001666.1 CLJU_c30250; ADK16073.1 | — |

TABLE 7-continued

| Genes and Enzymes identified to be involved in Succinate production | | | |
|---|---|---|---|
| | *C. autoethanogenum* | *C. ljungdahlii* | *C. ragsdalei* |
| Fumarate reductase 3, flavoprotein | Seq. ID 58-59 | CP001666.1 CLJU_c08670; ADK13935.1 | Seq. ID 76-77 |

Assay of Enzyme Activities:

Cells (*Clostridium autoethanogenum*) were harvested in the exponential phase of anaerobic growth. Cultures ($A_{600}$~0.45), and pelleted at 8000×q, 4° C. for 10 min. The supernatant was discarded, and the pellet was washed twice in wash buffer (0.1 M Tris-HCl, 10 mM dithiothreitol (DTT), pH 6.5, 4° C.). Finally, the pellet was resuspended in wash buffer containing protease inhibitor and mixed with 1.44 g of zirconia beads (Ambion RiboPure Bacteria Kit). Tubes were chilled on ice for 5 mins prior to disruption in a Vortex Mixer with a vortex adapter (Vortex Genie 2, Scientific Industries, Inc.) through 5 cycles of 1 min beating at 3200 rpm followed by 1 min on ice between cycles. After lysis, the sample was centrifuged (13,000×g, 4° C. for 10 min), and the supernatant was atiquoted and stored at −80° C. until analysis.

All assays were based on the oxidation of NADH to NAD ($\epsilon$=6.2 $mM^{-1}$ $cm^{-1}$) under aerobic conditions in a cuvette with a path length of 1 cm. Enzyme activities were obtained from three replicates of at least two independent cell extractions. Protein content of the extracts was determined using a commercial kit (Pierce® Microplate BCA Protein Assay Kit-Reducing Agent Compatible, Thermo Scientific). One unit of enzyme activity was defined as the amount of enzyme that could convert a nanomole of substrate into product per minute per mg of total protein.

The activity of malate dehydrogenase was measured spectrophotometrically by following the oxidation of reduced pyridine nucleotides with oxaloacetate (OAA) (Sridhar J. et al, 2000, Elucidation of enzymes in fermentation pathways used by *Clostridium thermosuccinogenes* growing on inulin. *Appl. Environ. Microbiol.* 66, 246-51). The reaction mixture contained the following: 0.1M Tris-Cl pH 6.5, 10 mM DTT, 0.15 mM NADH, 5 mM fumarate, 0.3 mM NADH and cell-free extract. The reaction was initiated by the addition of OAA and was monitored at room temperature. The specific activity of this enzyme in cell-free extracts of *Clostridium autoethanogenum* was measured as 160±17 nmol $min^{-1}$ mg $protein^{-1}$. This activity was comparable with the malate dehydrogenase found in *Clostridium thermosuccinogenes* measured at 3° C. (Sridhar J. et al, 2000, Elucidation of enzymes in fermentation pathways used by *Clostridium thermosuccinogenes* growing on inulin. *Appl. Environ. Microbiol.* 66, 246-51).

The activity of fumarate reductase was measured based on the conversion of fumarate to succinate (Sridhar J. et al, 2000. Elucidation of enzymes in fermentation pathways used by *Clostridium thermosuccinogenes* growing on inulin. *Appl. Environ. Microbiol.* 66, 246-51). The reaction mixture contained the following: 0.1M Tris-Cl pH 6.5, 10 mM DTT, 0.15 mM NADH, 5 mM fumarate and cell-free extract. The reaction was initiated by the addition of fumarate and was monitored at room temperature. The specific activity of this enzyme in cell-free extracts of *Clostridium autoethanogenum* was measured as 17.3±1.3 nmol $min^{-1}$ mg $protein^{-1}$.

The assays confirmed that *Clostridium autoethanogenum* posseses malate dehydrogenase activity, fumarate reductase/succinate dehydrogenase As described herein, the invention provides microorganisms and methods which allow for increased production of ethanol by microbial fermentation of substrates comprising carbon monoxide. It also provides for the production of succinate. There have been no previous reports of the production of succinate by acetogens, let alone carboxydotrophic acetogens. The potential to produce succinate by microbial fermentation may have a number of advantages over the current petrochemical production methods. The microorganisms also produce formate and branched chain amino acids which have not (previously been described as products of fermentation by acetogenic microorganisms, Succinate is used as a bulk platform chemical for the production of a number of industrial chemicals including 1,4-butanediol, tetrahydrofuran, gamma-butyrolactone, ethylene diamine disuccinate, diethyl succinate, and adipic acid. Formate is used in preservation of animal food and in leather tanning processes, as well as a bleaching solution in the pulp and paper industry. Branched chain amino acids have a number of uses in industrial biotechnology.

The microorganisms of the invention also produce one or more other products. The use of these products has been described elsewhere herein.

Example 3

Group II Intron Based Insertional Inactivation of Genes Involved in 2,3-BDO Biosynthesis in *C. autoethanogenum* DSM23693

Design and Construction of ClosTron Constructs Targeting budA and 2,3bdh Gene:

The acetolactate decarboxylase (budA) and 2,3-butanediol dehydrogenase (2,3-bdh) genes involved in 2,3-Butanediol. production in *C. autoethanogenum* DSM23693 were inactivated using ClosTron group II intron mediated gene disruption tool (Heap et al., 2010). The Perutka algorithm hosted at ClosTron.com was used to identify the group II intron target site between bases 450/451 and 468/469 on the sense strand of budA and 2,3-bdh genes, respectively. The same algorithm was used to design the intron targeting regions (Seq. ID. 82 and 83) which was commercially synthesized by DNA2.0 and delivered in pMTL007C-E5 vector. The final vectors, pMTL007C-E5-budA-450!451s and pMTL007C-E5-2,3bdh-468!469s, contain a Retro-tranposition-Activated ermB Marker (RAM) which confers resistance to antibiotic Clarithromycin upon insertion into the target site.

The pMTL007C-E5-budA-450!451s and pMTL007C-E5-2,3bdh-468!469s plasmids were introduced into *C. autoethanogenum* DSM23693 by conjugating with donor *E. coli* strain CA434 as donor. Briefly, the donor strain was grown overnight in LB media supplemented with 25 μg/ml chloramphenicol and 100 μg/ml spectinomycin. Cells from 1.5 ml culture were harvested and washed in phosphate buffered saline. The donor cells pellet was resuspended in 200 μl culture of exponentially growing recipient *C. autoethanogenum* DSM23693. The mixture was spotted on PETC agar media supplemented with fructose and incubated at 37° C. in pressurized gas jar. After 24 hours the cells were scrapped and resuspended in 500 μl PETC broth and spread on PETC agar media supplemented with 15 μg/ml thiamphenicol (Sigma) and 10 μg/ml trimethoprim (Sigma). *C. autoethanogenum* transconjugants were selected using 15 μg/ml thiamphenicol and *E. coli* CA434 strain was counter selected using 10 μg/ml trimethoprim. Colonies were observed after 3 days of incubation at 37° C. in pressurized gas jars.

Streaks of single colonies were made sequentially first on PETC-MES media containing 15 μg/ml thiamphenicol and 10 μg/ml trimethoprim followed by on agar plates with PETC media containing 5 μg/ml Clarithromycin. 4 colonies per plasmid were randomly screened for group II intron insertion by PCR using primers Og44f (Seq. ID. 29) and Og45r (Seq. ID. 30), flanking the group II intron insertion site in budA gene, and primers Og42f (Seq. ID. 84) and Og43r (Seq. ID. 85), flanking the group II intron insertion site in 2,3-bdh gene. The Maxime PCR PreMix Kit was used for PCR. 16s rDNA was also PCR amplified using primers fD1 (Seq. ID. 27) and rP2 (Seq. ID.28) and Maxime PCR PreMix Kit.

Figure 6:
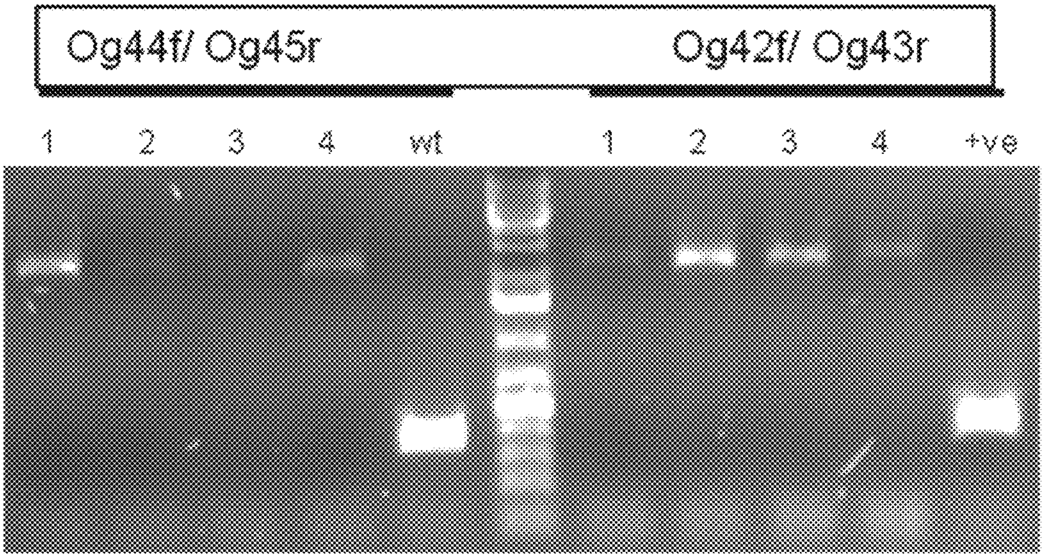
FIG. 6: PCR confirmation of RAM insertion in *C. autoethanogenum* DSM23693 budA and 2,3bdh genes using primers Og44f/Og45r and Og42f/Og43r.

Confirmation of budA and 2,3bdh Gene Disruption Using ClosTron Group II Insertional Inactivation Tool:

Amplification of PCR products of 273 and 375 bp with primers Og44f/Og45r and Og42f/Of43r indicates the unmodified wild type budA and 2.3-bdh genes, respectively. Amplification of PCR products of ~2 kb using the same set of primers indicates insertion of ClosTron group II intron in the target genes. In case of clones targeting budA gene, clones 1 and 3 had bands of expected size. Clone 4 appears to be a mix with both the wild type and disrupted gene (FIG. 6). All 4 clones which were targeted for 2,3-bdh gene appear positive for gene disruption as seen by the amplification of 2 kb PCR product (FIG. 6). These results confirm the disruption of budA and 2,3-bdh genes in *C. autoethanogenum* DSM23693.

The 16s rDNA PCR product of Δ2,3bdh ClosTron clones 2 (Seq ID. 86, and 87) and 4 (Seq ID. 88 and 89) and ΔbudA ClosTron clones 1 (Seq ID. 90 and 91) and 3 (Seq ID. 92 and 93) were sequence confirmed to be of *C. autoethanogenum* DSM23693.

Thus the inventors have demonstrated targeted gene disruption in acetogenic *C. autoethanogenum* DSM23693 using two different approaches—(i) gene knockout by homologous recombination and (ii) by gene disruption using group II intron based insertional inactivation tool.

Study of ΔbudA and Δ2,3bdhClosTron Mutants for 2,3BDO Production:

The metabolites from ΔbudA and Δ2,3bdh mutants growing in serum bottles were analysed by HPLC (as explained earlier). The ΔbudA Clostron mutant like the ΔbudA knockout mutant did not produce 2,3-BDO (Table 8). The disruption of budA gene by two different methods in *C. autoethanogenum* confirms the role of budA gene in 2,3-BDO biosynthesis.

TABLE 8

Metabolites production by ΔbudA and Δ2,3 bdh ClosTron *C. autoethanogenum* DSM23693 mutants

| | ΔbudA | | Δ2,3 bdh | |
|---|---|---|---|---|
| Metabolites | Clone 1 | Clone 3 | Clone 2 | Clone 4 |
| Ethanol | 0.09 | 0.08 | 0.37 | 0.23 |
| Acetic Acid | 2.56 | 2.63 | 3.78 | 3.34 |
| 2-3-Butanediol | 0.0 | 0.0 | 0.01 | 0.01 |
| Lactic Acid | 0.0 | 0.0 | 0.0 | 0.0 |

The Δ2,3bdh ClosTron mutant still produced 2,3-BDO (Table 8) indicating the participation of a second gene in converting acetoin to 2,3-BDO.

Yan et al have shown that a secondary alcohol dehydrogenase from *C. beijerinckii* and three other organisms can also convert acetoin to 2,3-BDO (Yan. Lee & Liao, 2009). A similar secondary alcohol dehydrogenase (SecAdh) gene is found in *C. autothenogenum* DSM23693 (Seq ID 34 and 35), *C. ljungdahlii* (Seq ID 36) and *C. ragsdalei* (Seq ID 37).

In the absence of 2,3-bdh gene in *C. autoethanogenum* DSM23693, the SecAdh would most likely convert acetoin to 2,-3BDO.

Role of a Second Dehydrogenase in Converting Acetoin to 2,3-BDO:

To test the role of a second gene in converting acetoin to 2,3-BDO, wild type *C. autoethanogenum* DSM23693 and Δ2,3bdh ClosTron mutant were fed with 10 g/L acetoin in fermentation experiments.

Fermentation with Wild Type and Δ2,3bdh ClosTron Mutant:

Fermentations were carried out in 1.5 L bioreactors at 37° C. and CO-containing steel mill gas as sole energy and carbon source as described below. A defined medium containing per litre: MgCl, $CaCl_2$ (0.5 mM), KCl (2 mM), $H_3PO_4$ (5 mM), Fe (100 μM), Ni, Zn (5 μM), Mn, B, W, Mo, Se(2 μM) was used for culture growth. The media was transferred into the bioreactor and autoclaved at 121° C. for 45 minutes. After autoclaving, the medium was supplemented. with Thiamine, Pantothenate (0.05 mg), Biotin (0.02 mg) and reduced with 3 mM Cysteine-HCl. To achieve anacrobicity the reactor vessel was sparged with nitrogen through a 0.2 μm filter. Prior to inoculation, the gas was switched to CO-containing steel mill gas, feeding continuously to the reactor. The feed gas composition was 2% $H_2$ 42% CO 20% $CO_2$ 36% $N_2$. The pH of the culture was maintained between 5 and 5.2. The gas flow was initially set at 80 ml/min, increasing to 200 ml/min during mid-exponential phase, while the agitation was increased from 200 rpm to 350. $Na_2S$ was dosed into the bioreactor at 0.25 ml/hr. Once the OD600 reached 0.5, the bioreactor was switched to a continuous mode at a rate of 1.0 ml/min (Dilution rate 0.96 $d^{-1}$). When the growth was stable, the reactor was spiked with 10 g/L racemic mix of acetoin. Media samples were taken to measure the biomass and metabolites by HPLC.

Figure 7:
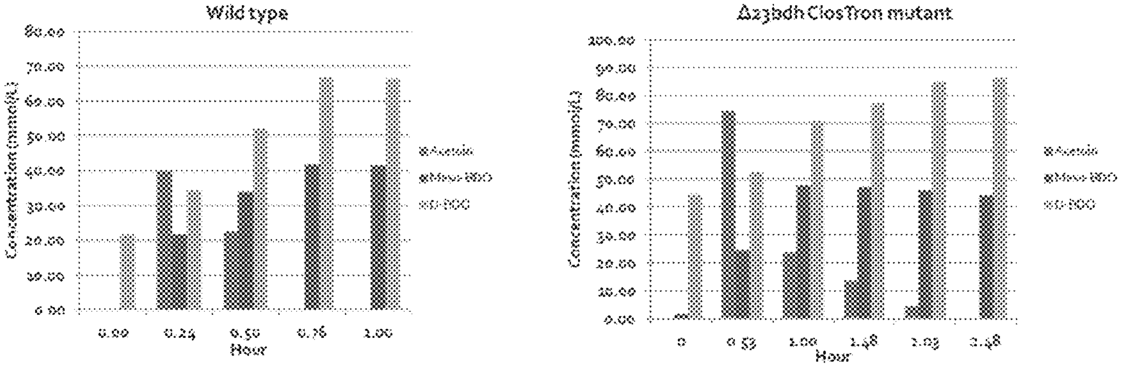
FIG. 7 shows the rate of conversion of acetoin to butanediol by *C. autoethanogenum* DSM23693 and Δ2,3bdh ClosTron mutant in fermentation.

The metabolites were analysed by HPLC regularly until the disappearance of acetoin. The wild type *C. autoethanogenum* DSM23693 converted all acetoin to meso-BDO and 2,3-BDO in less than 1 h (FIG. 7). The rate of conversion of acetoin to meso-BDO and 2,3-BDO was relatively slow in Δ2,3bdh ClosTron mutant. The Δ2,3bdh ClosTron mutant reduced 10 g/L acetoin in more than 2 h. These results indicate the role of a second dehydrogenase in complementing for the disruption of 2,3bdh gene, albeit at slower rate.

Example 4

Modified *C. autoethanogenum* DSM23693 Strain Producing Only Acetoin

Industrial separation of acetoin from ethanol is technically more feasible compared to its downstream product 2,3-BDO. It is thus desirable to have a *C. autoethanogenum* strain producing acetoin and not its reduced form, 2,3-BDO. As Δ2,3bdh ClosTron mutant still produces 2,3-BDO, it is desirable to have a *C. autoethanogenum* DSM23693 strain in which both the 2,3bdh and SecAdh genes are disrupted. This can be achieved by two ways (a) homologous recombination and (b) marker less gene disruption using ClosTron tool as explained in Example 1 and Example 3.

(a) Δ2,3bdh ΔSecAdh Double Knockout *C. autoethanogenum* DSM23693 Strain by Homologous Recombination:

The ~1 kb 5' (Seq. ID. 94) and 3' (Seq. ID. 95) homology arms of 2,3bdh genes are PCR amplified using *C. autoethanogenum* DSM23693 genomic DNA. Primers Og13f (Seq. ID. 96)/Og14r (Seq. ID. 97) and Og15f (Seq. ID. 98)/Og16r (Seq. ID. 99) are used to amplify the 5' and 3' homology arms, respectively. The two PCR products are cloned into pMTL85151. plasmids between the Sbfl/Notl. and Nhel/Ascl sites to get pMTL85151-2,3bdh-KO. This plasmid is introduced into *C. autoethanogenum* DSM23693 either by conjugation or by electroporation as described in the above examples. Following selection on thiamphenicol plates the transformants are screened for 2,3bdh knockout using the primers Og33f (Seq. ID.100) and Og34r (Seq. ID.101) that flank the homology arms of 2,3bdh for PCR and sequencing of this PCR product.

The plasmid for SecAdh gene knockout is similarly constructed. The ~1 kb 5' (Seq. ID. 102) and 3' (Seq. ID. 103) homology arms of SecAdh genes are PCR amplified using *C. autoethanogenum* DSM23693 genomic DNA. Primers Sec5f (Seq. ID. 104)/Sec5r (Seq. ID. 105) and Sec3f (Seq. ID. 106)/Sec3r (Seq. ID. 107) are used to amplify the 5' and 3' homology arms, respectively. The two PCR products are cloned into pMTL85151 plasmids between the Sbfl/Notl and Nhel/Ascl sites to get pMTL85151-SecAdh-KO. Following selection on thiamphenicol plates the transformants are screened for SecAdh knockout using the primers SecOf (Seq. ID.108) and SecOr (Seq. ID.109) that flank the homology arms of SecAdh gene for PCR.

Once having achieved the knockout of either 2,3bdh or the SecAdh genes in *C. autoethanogenum* DSM23693, the second gene in these single mutants is targeted using either pMTL85151-2,3bdh-KO or pMTL85151-SecAdh-KO plasmids. The plasmid is introduced into the single gene knockout mutant either by electroporation or by conjugation as already described in Example 1 and 3. The transformants are screened for the knockout of the second gene using the primers flanking the homology arms of the corresponding genes.

(b) Δ2,3bdh ΔSecAdh Double Gene Disruption Using ClosTron:

The RAM ermB cassette in the ClosTron group II intron construct is flanked by Flippase Recombination sites (Frt). By introducing flippase recombinase into Δ2,3bdh ClosTron mutant either by conjugation or by electroporation, the RAM ermB marker of ~1.3 kb is removed from the genome of the mutant and thus the ermB marker is recycled. A ~0.8 kb fragment of group II intron will be left on the genome. This is confirmed by (i) testing its susceptibility to clarithromycin and (ii) by PCR with the primers flanking the group II intron insertion site with the primers Og42f (Seq. ID. 84) and Og43r (Seq. ID. 85) and sequencing of the PCR product. Once obtaining the Δ2,3bdh ClosTron mutant without RAM ermB marker (Δ2,3bdh-ermB ClosTron), the SecAdh gene in the mutant is targeted in a similar way using ClosTron group II intron insertional inactivation tool. The intron insertion site between bases 399 and 400 on the sense strand is identified in the SecAdh gene using Perutka algorithm hosted at ClosTron.com and the intron targeting cassette has been designed (Seq. ID. 110). The intron targeting cassette is commercially synthesized by DNA2.0 and delivered in pMTL007C-E2 vector as pMTL007C-E5-SecAdh-399!400s which is introduced into Δ2,3bdh-ermB ClosTron mutant by either conjugation or electroporation. The transformants are sequentially selected on thiamphenicol and clarithromycin agar plates and screened by PCR with primers SecCTf (Seq. ID. 111) and SecCTr (Seq. ID. 112) as explained earlier in Example 3.

The Δ2,3bdh ΔSecAdh double gene disrupted *C. autoethanogenum* DSM23693 mutant is created by using either homologous recombination technique or by ClosTron group II intron insertional inactivation tool as explained in the above paragraphs.

The disruption of 2,3bdh and SecAdh genes and the production of acetoin, other metabolites and 2,3-BDO is confirmed by performing enzyme activity assays for the conversion of acetoin to 2,3-BDO and also by analysing the products produced by the mutant by HPLC, as previously described.

Example 5

Modified *C. autoethanogenum* DSM23693 Strain Producing Reduced or No 2,3-BDO As shown in FIGS. 1*a* and 1*b*, acetolactate is one of the intermediates in 2,3-BDO biosynthesis and is also the precursor for the synthesis of branched chain amino acids. The enzyme acetolactate synthase catalyses the reaction leading to acetolactate from 2 molecules of pyruvate as substrates. The enzyme acetolactate synthase is broadly classified into two groups; (i) anabolic acetolactate synthase is associated with the genes involved in the synthesis of branched amino acids like valine, isoleucine and leucine and (ii) catabolic acetolactate synthase is associated with 2,3-BDO synthesis (alsS; amino acid—AE190719.1 and nucleic acid—HQ876013.1).

The genome of *C. autoethanogenum* DSM23693 has 3 putative anabolic acetolactate synthase genes, ilvC, ilvl and ilvB. Exemplary amino acid sequence from *C. autoethanogenum* (AEI90719.1AE190730.1, AEI90731.1, AEI90713.1, AEI90714,1), *C. ljungdahlii* (ADK15104.1, ADK15104.1 ADK15105.1ADK15400.1, ADK15400.1), and *C. ragsdalei* (AEI90734.1, AEI90734.1, AEI90735.1, AEI90727.1, AEI90727.1) and respective nucleic acid sequences from *C. autoethanogenum* (HQ876013.1, HQ876023.1, HQ876021.1), *C. Ijungdahiii* (CP001666.1—CLJU_c38920, CLJU_c32420, CLJU_c20420-30), and *C. ragsdalei* (HQ876014.1, HQ876024.1, HQ876022.1) are obtained from GenBank.

The disruption of all 4 acetolactate synthase genes or any combination of these 4 genes should lead to a decrease in acetoin and 2,3-BDO production. In order to ensure the growth of these mutants the media is supplemented with the three branched chain amino acids valine, leucine and isoleucine.

As described in Examples 1, 3 and 4 single mutants of *C. autoethanogenum* DSM23693 alsS, ilvC, ilvl and ilvB mutants can be created by either homologous recombination or using ClosTron group II intron mutagenesis tool.

Design of alsS, ilvC, ilvi and ilvB Knockout Cassettes:

The knockout constructs for alsS, ilvC, livl and ilvB genes are designed as explained above. The ~1 kb 5' (Seq. ID. 113) and 3' (Seq. ID. 114) homology arms of alsS gene are PCR amplified using *C. autoethanogenum* DSM23693 genomic DNA. Primers alsS5f (Seq. ID. 115)/alsS5r (Seq. ID. 116) and alsS3f (Seq. ID. 117)/alsS3r (Seq. ID. 118) are used to amplify the 5' and 3' homology arms, respectively. The two PCR products are cloned into pMTL85151 plasmids between the Sbfl/Notl and Nhel/Ascl sites to get pMTL85151-alsS-KO. This plasmid is introduced into *C. autoethanogenum* DSM23693 either by conjugation or by electroporation as described in the above examples. Following selection on thiamphenicol plates the transformants are screened for alsS knockout using the primers alsSOf (Seq. ID.119) and alsSOr (Seq. ID.120) that flank the homology arms of alsS for PCR and sequencing of this PCR product.

For knockout of ilvC gene, the ~1 kb 5' (Seq. ID. 121) and 3' (Seq. ID. 122) homology arms of ilvC gene are PCR amplified using *C. autoethanogenum* DSM23693 genomic DNA.

Primers ilvC5f (Seq. ID. 123)/ilvC5r (Seq. ID. 124) and ilvC3f (Seq. ID. 125)/ilvC3r (Seq. ID. 126) are used to amplify the 5' and 3' homology arms, respectively. The two PCR products are cloned into pMTL85151 plasmids between the Sbfl/Notl and Nhel/Ascl sites to get pMTL85151-ilvC-KO. This plasmid is introduced into *C. autoethanogenum* DSM23693 either by conjugation or by electroporation as described in the above examples. Following selection on thiamphenicol plates the transformants are screened for ilvC knockout using the primers ilvCOf (Seq. ID. 127) and ilvCOr (Seq. ID. 128) that flank the homology arms of ilvC gene for PCR and sequencing of this PCR product.

For knockout of ilvl gene, the~1 kb 5' (Seq. ID. 129) and 3' (Seq. ID. 130) homology arms of ilvl gene are PCR amplified using *C. autoethanogenum* DSM23693 genomic DNA. Primers ilvi5f (Seq. ID. 131)/ilvl5r (Seq. ID, 132) and ilvl3f (Seq. ID. 133)/ilvI3r (Seq. ID. 134) are used to amplify the 5' and 3' homology arms, respectively. The two PCR products are cloned into pMTL85151 plasmids between the Sbfl/Notl and Nhel/Ascl sites to get pMTL85151-ilvl-KO. This plasmid is introduced into *C. autoethanogenum* DSM23693 either by conjugation or by electroporation as described in the above examples. Following selection on thiamphenicol plates the transthrmants can be screened for ilvl knockout using the primers ilvlOf (Seq. ID.135) and ilvIOr (Seq. ID. 136) that flank the homology arms of ilvI gene for PCR and sequencing of this PCR product.

For knockout of ilvB gene, the ~1 kb 5' (Seq. ID. 137) and 3' (Seq. ID. 138) homology arms of ilvB gene are PCR amplified using *C. autoethanogenum* DSM23693 genomic DNA. Primers ilvB5f (Seq. ID. 139)/ilvB5r (Seq. ID. 140) and ilvB3f (Seq. ID. 141)/ilvB3r (Seq. ID. 142) are used to amplify the 5' and 3' homology aims, respectively. The two PCR products are cloned into pMTL85151 plasmids between the Sbfl/Notl and Nhel/Ascl sites to get pMTL85151-ilvB-KO. This plasmid are introduced into *C. autoethanogenum* DSM23693 either by conjugation or by electroporation as described in the above examples. Following selection on thiamphenicol plates the transformants are screened for ilvB knockout using the primers ilvBOf (Seq. ID.143) and ilvBOr (Seq. ID.144) that flank the homology arms of ilvB gene for PCR and sequencing of this PCR product.

Once the single gene knockout mutants are obtained the other 3 acetolactate synthase genes are sequentially targeted to create a mutant having all 4 acetolactate synthase genes deleted. The growth of these mutants may be auxotrophic to branched chain amino acids. The production or lack of production of acetoin, 2,3-BDO and other metabolites in these mutants can be analysed by HPLC, as described for the previous examples. The enzyme activity assays with pyruvate as substrate and thiamine diphosphate and flavin adenine dinucleotide as cofactors can be performed to confirm for the loss of acetolactate synthase activity in these mutants (rittinann, Vyazmensky, Hubner, Barak & Chipman, 2005; Vinogradov et al, 2006).

Design of ClosTron Group II Intron Targeting Cassettes for alsS, ilvC, ilvl and Genes:

*C. autoethanogenum* DSM23693 alsS, ilvC, ilvl and ilvB genes can also be disrupted or inactivated using ClosTron group II intron mediated gene disruption tool (Heap et al., 2010). The Perutka algorithm hosted at ClosTron.com is used to identify the group II intron target site between bases 303/304, 228/229, 975/976 and 157/158 on the sense strand of alsS, ilvC, ilvl and on the antisense strand of ilvB genes, respectively. Other sites identified by the algorithm can also be targeted. The same algorithm has been used to design the intron targeting regions (alsS—Seq. ID.145; ilvC—Seq. ID.146; ilvl—Seq. ID.147 and ilvB—Seq. ID.148) which can be commercially synthesized by DNA2.0 and delivered in pMTL007C-E2 vector. The final vectors, pMTL007C-E2-alsS-303!304s, pMTL007C-E2-ilvC-228!229s, pMTL007C-E2-livl-975!976s and pMTL007C-E2-ilvB-157!158a, contain a Retro-tranposition-Activated ermB Marker (RAM) which confers resistance to antibiotic Clarithromycin upon insertion into the target site. These plasmids are introduced into *C. autoethanogenum* DSM23693 by either conjugation or electroporation. The transformants are sequentially selected on thiamphenicol and clarithromycin agar plates and screened by PCR with primers alsSCTf (Seq. ID. 149) and alsSCTr (Seq. ID. 150), ilvCCTf (Seq. ID. 151) and ilvCCTr (Seq. ID. 152), ilvICTf (Seq. ID. 153) and ilvICTr (Seq. ID. 154) and ilvBCTf (Seq. ID. 155) and ilvBCTr (Seq. ID. 156) for inactivation of alsS, ilvC, ilvl and ilvB genes, respectively.

Once ClosTron mutants with single gene disrupted are obtained, the RAM ermB cassette is removed from the genome of these mutants using pMTL plasmids carrying a flippase gene which is introduced into the mutant by either electroporation or by conjugation. The resulting transformants are screened for the toss of ermB cassette by testing its susceptibility to clarithromycin and (ii) by PCR with the primers flanking the group II intron insertion site with alsS-CTf (Seq. ID. 149) and alsSCTr (Seq. ID. 150), ilvCCTf (Seq. ID. 151) and ilvCCTr (Seq. ID. 152), iivICTf (Seq. ID. 153) and ilvBICTr (Seq. ID. 154) and ilvBCTf (Seq. ID. 155) and ilvBCTr (Seq. ID. 156) in alsS, ilviC, and ilvB2 genes, respectively, and by further sequencing of these PCR product.

After confirming the loss of ermB cassette, the ClosTron mutants like the knockout mutants are sequentially targeted for the inactivation of other acetolactate synthase genes. In one embodiment, these ClosTron mutants are grown in the presence of branched chain amino acids. The production or lack of production of acetoin, 2,3-BDO and other metabolites in these mutants can be analysed by HPLC as described in previous examples. The enzyme activity assays with pyruvate as substrate and thiamine diphosphate and flavin adenine dinucleotide as cofactors can be performed to confirm for the loss of acetolactate synthase activity in these mutants (Tittman et al, 2005; Vinogradov et al, 2006).

Example 6

Disruption of 2,3-BDO Pathway Genes in *C. ljungdhalii* and *C. ragsdalei*

The pathway for 2,3-BDO production is conserved across acetogens including *C. autoethanogenum, C. ljungdahlii* and *C. ragsdalei*. The alsS, ilvC, ivvI, ilvB, budA, 2,3bdh and SecAdh genes in the three acetogens share high degree of sequence homology. Hence these genes can be genetically modified to increase or decrease the 2,3-BDO production in the three acetogens. Method to genetically modify *C. ljungdahlii* by electroporation have been described (Kapke et al., 2010) (PCT/NZ2011/000203). Electroporation and conjugation methods that have been described above for *C. autoethanogenum* can be applied to *C. ragsdalei* by any skilled person.

The amino acid and nucleic acid sequences for *C. ljungdahlii* and *C. ragsdalei* alsS, ilvC, ilvB1, ilvB2, budA, and 2,3bdh genes can be obtained from GenBank. The *C. ljungdahlii* (Seq. ID. 36) and *C. ragsdalei* (Seq. ID. 37) SecAdh nucleotide sequences are provided.

The knockout and ClosTron plasmids that were used to disrupt alsS, ilvC, ilvB1 ilvB2, budA, 2,3bdh and SecAdh genes by homologous recombination and ClosTron group II intron based insertional inactivation in *C. autoethanogenum* can also be used to disrupt the same genes *C. ljungdahlii* and *C. ragsdalei*. For example pMTL85141-budA-ko, pMTL007C-E5-budA-450!451 s and pMTL007C-E5-2,3bdh-468!469s can be introduced into *C. ljungdahlii* (explained below in Example 6a) and *C. ragsdalei* (explained below in Example 6b) by either electroporation or conjugation as described above for *C. autoethanogenum* in Examples 1 and 3. Similar mutant screening and characterization methods can be applied in *C. ljungdahlii* and *C. ragsdalei.*

Example 6a

Disruption of budA and 2,3bdh Genes in *C. ljungdahlii* by Homologous Recombination and Group II Intron Based Insertional Inactivation Tool for No and Reduced 2,3-BDO Production Plasmids pMTL85141-budA-ko is introduced into *C. ljungdahlii* by electroporation (Koepke et al 2010). The transformants are selected on PETC-agar plates containing 15 μg/ml thiamphenicol and screened for budA knockout using primers Og44f (Seq. ID. 29) and Og45r (Seq. ID. 30)

For budA and 2,3bdh gene disruptions in *C. ljungdahlii* using ClosTron group II intron based insertional inactivation tool, plasmids pMTL007C-E5-budA-450!451s and pMTL007C-E5-2,3bdh-468!469s are introduced into *C. ljungdahlii* by conjugation. Streaks of single colonies following conjugation are made sequentially first on PETC agar media containing 15 μg/ml thiamphenicol and 10 μg/ml trimethoprim followed by on agar plates with PETC media containing 5 μg/ml Clarithromycin. Colonies per plasmid are randomly screened for group II intron insertion by PCR using primers Og44f (Seq. ID. 29) and Og45r (Seq. ID. 30), flanking the group II intron insertion site in budA gene, and primers Og42f (Seq. ID. 84) and Og43r (Seq. ID. 85), flanking the group II intron insertion site in 2,3-bdh gene.

The budA and 2,3bdh knockout and ClosTron *C. ljungdahlii* mutants generated above are analyzed for 2,3-BDO and acetoin production by HPLC and fermentation in bioreactors as explained in Examples 1 and 3.

Example 6b

Disruption of budA and 2,3bdh Genes in *C. ragsdalei* by Homologous Recombination and Group II Intron Based Insertional Inactivation Tool for No and Reduced 2,3-BDO Production Plasmids pMTL85141-budA-ko is introduced into *C. ragsdalei* by electroporation as described above for *C. autoethaogenum* or *C. ljungdahlii*, either by electroporation or conjugation. The transformants are selected on PETC-agar plates containing 15 μg/ml thiamphenicol and screened for budA knockout using primers Og44f (Seq. ID. 29) and Og45r (Seq. ID. 30)

For budA and 2,3bdh gene disruptions in *C. ragsdalei* using ClosTron group II intron based insertional inactivation tool, plasmids pNITL007C-E5-budA-450!45 is and pMIL007C-E5-2,3bdh-468!469s are introduced into *C. ragsdalei* by conjugation. Streaks of single colonies following conjugation are made sequentially first on PETC agar media containing 15 μg/ml thiamphenicol and 10 μg/ml trimethoprim followed by on agar plates with PETC media containing 5 μg/ml Clarithromycin. Colonies per plasmid are randomly screened for group II intron insertion by PCR using primers Og44f (Seq. ID. 29) and Og45r (Seq. ID. 30), flanking the group II intron insertion site in budA gene, and primers Og42f (Seq. ID. 84) and Og43r (Seq, ID. 85), flanking the group II intron insertion site in 2,3-bdh gene.

The budA and 2,3bdh knockout and ClosTron *C. ragsdalei* mutants generated above are anlyzed for 2,3-BDO and acetoin production by HPLC and fermentation in bioreactors as explained in Examples 1 and 3.

Example 7

Modified *C. ljungdahlii* Producing Only Acetoin

As explained earlier, separation of acetoin from ethanol is technically more feasible compared to 2,3-BDO. It is thus desirable to have a *C. ljungdahlii* strain producing acetoin and not 2,3-BDO. This will be achieved by deleting or disrupting both 2,3bdh and SecAdh genes in two ways as explained in Example 6a.: (a) homologous recombination and (b) marker less gene disruption using ClosTron tool.

(a) Δ2,3bdh ΔSecAdh Double Knockout *C. ljungdahlii* Strain by Homologous Recombination:

The ~1 kb 5' (Seq. ID. 94) and 3' (Seq. ID. 95) homology arms of 2,3bdh genes are PCR amplified using *C. ljungdahlii* genomic DNA. Primers Og13f (Seq, ID. 96)/Og14r (Seq. ID. 97) and Og15f (Seq. ID. 98)/Og16r (Seq. ID. 99) are used to amplify the 5' and 3' homology arms, respectively. The two PCR products are cloned into pMTL85151 plasmids between the Sbfl/Notl and Nhel/Ascl sites to get pMTL85151-2,3bdh-KO. This plastaid is introduced into *C. ljungdahlii* either by conjugation or by electroporation as described in the above Example 6a. Following selection on thiamphenicol plates the transformants are screened for 2,3bdh knockout using the primers Og33f (Seq. ID.100) and Og34r (Seq. ID.101) that flank the homology arms of 2,3bdh for PCR and sequencing of this PCR product.

The plasmid for SecAdh gene knockout is similarly constructed. The ~1 kb 5' (Seq. ID. 102) and 3' (Seq. ID. 103) homology arms of SecAdh genes are PCR amplified using *C. ljungdahlii* genomic DNA. Primers Sec5f (Seq. ID. 104)/Sec5r (Seq. ID. 105) and Sec3f (Seq. ID. 106)/Sec3r (Seq. ID. 107) are used to amplify the 5' and 3' homology arms, respectively. The two PCR products are cloned into pMTL85151 plasmids between the Sbfl/Notl and Nhel/Ascl sites to get pMTL85151-SecAdh-KO. Following selection on thiamphenicol plates the transformants are screened for SecAdh knockout using the primers SecOf (Seq. ID.108) and SecOr (Seq. ID.109) that flank the homology arms of SecAdh gene for PCR.

Once having achieved the knockout of either 2,3bdh or the SecAdh genes in *C. ljungdahlii*, the second gene in these single mutants is targeted using either pMTL85151-2,3bdh-KO or 'pMTL85151-SecAdh-KO plasmids. The plasmid is introduced into the single gene knockout mutant either by electroporation or by conjugation as already described in Example 6a. The transformants are screened for the knockout of the second gene using the primers flanking the homology arms of the corresponding genes.

(b) Δ2,3bdh ΔSecAdh Double Gene Disruption Using ClosTron in *C. ljungdahlii:*

The RAM ermB cassette in the ClosTron group II intron construct is flanked by Flippase Recombination sites (Frt). By introducing flippase recombinase into Δ2,3bdh ClosTron mutant either by conjugation or by electroporation, the RAM ermB marker of ~1.3 kb is removed from the genome of the mutant and thus the ermB marker can be recycled. A ~0.8 kb fragment of group II intron will be left on the genome. This is confirmed by (i) testing its susceptibility to clarithromycin and (ii) by PCR with the primers flanking the group II intron insertion site with the primers Og42f (Seq. ID. 84) and Og43r (Seq. ID. 85) and sequencing of the PCR product. Once obtaining the Δ2,3bdh ClosTron mutant without RAM ermB marker (Δ2,3bdh-ermB ClosTron), the SecAdh gene in the mutant is targeted in a similar way using ClosTron group II intron insertional inactivation tool. The intron insertion site between bases 399 and 400 on the sense strand is identified in the SecAdh gene using Perutka algorithm hosted at ClosTron.com and the intron targeting cassette is designed (Seq. ID. 110). The intron targeting cassette is commercially synthesized by DNA2.0 and delivered in pMTL007C-E2 vector as pMTL007C-E5-SecAdh-399!400s which is introduced into Δ2,3bdh-ermB ClosTron mutant by either conjugation or electroporation. The transformants are sequentially selected on thiamphenicol and clarithromycin agar plates and screened by PCR with primers SecCTf (Seq. ID. 111) and SecCTr (Seq. ID. 112) as explained earlier in Example 6a.

The Δ2,3bdh ΔSecAdh double gene disruption *C. ljungdahlii* mutant is created by using either homologous recombination technique or by ClosTron group II intron insertional inactivation tool as explained in the above paragraphs.

The disruption of 2,3bdh and SecAdh genes and the production of metabolites and 2,3-BDO is confirmed by performing enzyme activity assays for the conversion of acetoin to 2,3-BDO and also by analysing the products produced by the mutant by HPLC, as previously described.

Example 8

Modified *C. ljungdahlii* Strain Producing Reduced or No 2,3-BDO

As shown in FIGS. 1*a* and 1*b*, acetolactate is one of the intermediates in 2,3-BDO biosynthesis and is also the precursor for the synthesis of branched chain amino acids. The enzyme acetolactate synthase catalyses the reaction leading to acetolactate from 2 molecules of pyruvate as substrates. The enzyme acetolactate synthase is broadly classified into two groups; (i) anabolic acetolactate synthase is associated with the genes involved in the synthesis of branched amino acids like valine, isoleucine and leucine and (ii) catabolic acetolactate synthase is associated with 2,3-BDO synthesis.

The genome of *C. ljungdahlii* has 3 putative anabolic acetolactate synthase genes, ilvC, ilvl and ilvB and 1 catabolic acetolactate synthase, alsS. Exemplary amino acid sequence from *C. ijungdahlii* (ADK15104.1, ADK15104.1, ADK15105.1, ADK15400.1, ADK15400.1) and respective nucleic acid sequences from *C. ljungdahlii* (CP001666.1, (CLJU_c38920, CLJU_c32420, CLJU_c20420-30) are obtained from GenBank.

The disruption of all 4 acetolactate synthase genes or any combination of these 4 genes should lead to a decrease in acetoin and 2,3-BDO production. In order to ensure the growth of these mutants the media is supplemented with the three branched chain amino acids valine, leucine and isoleucine.

As described in Examples 6a, and 7 single mutants of *C. ljungdahlii* alsS, ilvC, ilvI and ilvB mutants can be created by either homologous recombination or using ClosTron group II intron mutagenesis tool.

Design of alsS, IlvC, ilvl and ilvB Knockout Cassettes:

The knockout constructs for alsS, ilvC, ilvl and ilvB genes are designed as explained above.

The ~1 kb 5' (Seq. ID. 113) and 3' (Seq. ID. 114) homology arms of alsS gene are PCR amplified using *C. ljungdahlii* genomic DNA. Primers alsS5f (Seq. ID. 115)/alsSr (Seq. ID. 116) and alsS3f (Seq. ID. 117) / alsS3r (Seq. ID. 118) are used to amplify the 5' and 3' homology arms, respectively. The two PCR products are cloned into pMTL85151 plasmids between the Sbfl/Notl and Nhel/Ascl sites to get pMTL85151-alsS-KO. This plasmid is introduced into *C. ljungdahlii* either by conjugation or by electroporation as described in the above examples. Following selection on thiamphenicol plates the transformants are screened for alsS knockout using the primers alsSOf (Seq. ID.119) and alsSOr (Seq. ID.120) that flank the homology arms of alsS for PCR and sequencing of this PCR product.

For knockout of ilvC gene, the ~1 kb 5' (Seq. ID. 121) and 3' (Seq. ID. 122) homology arms of ilvC gene are PCR amplified using *C. ljungdahlii* genomic DNA. Primers ilvC5f (Seq. ID. 123)/ilvC5r (Seq. ID. 124) and ilvC3f (Seq. ID. 125)/ ilvC3r (Seq. ID. 126) are used to amplify the 5' and 3' homology arms, respectively. The two PCR products are cloned into pMTL85151 plasmids between the Sbfl/Notl and Nhel/Ascl sites to get pMTL85151-ilvC-KO. This plasmid is introduced into *C. ijungdahlii* either by conjugation or by electroporation as described in the above examples. Following selection on thiamphenicol plates the transformants are screened for ilvC knockout using the primers iivCOf (Seq. ID. 127) and ilvCOr (Seq. ID. 128) that flank the homology arms of ilvC gene for PCR and sequencing of this PCR product.

For knockout of ilvl gene, the ~1 kb 5' (Seq. ID. 129) and 3' (Seq. ID. 130) homology arms of ilvl gene are PCR amplified using *C. ljungdahlii* genomic DNA. Primers ilvl5f (Seq. ID. 131)/ilvI5r (Seq. ID. 132) and ilvI3f (Seq. ID. 133)/ilvI3r (Seq. ID. 134) are used to amplify the 5' and 3' homology arms, respectively. The two PCR products are cloned into pMTL85151 plasmids between the Sbfl/Notl and Nhel/Ascl sites to get pMTL85151-ilvl-KO. This plasmid is introduced into *C. ljungdahlii* either by conjugation or by electroporation as described in the above examples. Following selection on thiamphenicol plates the transforrnants are screened for ilvI knockout using the primers ilvIOf (Seq. ID.135) and ilvIOr (Seq. ID. 136) that flank the homology arms of ilvi gene for PCR and sequencing of this PCR product.

For knockout of ilvB gene, the ~1 kb 5' (Seq. ID. 137) and 3' (Seq. ID. 138) homology arms of ilvB gene are PCR amplified using *C. ljungdahlii* genomic DNA. Primers ilvB5f (Seq. ID. 139)/ilvB5r (Seq. ID. 140) and ilvB3f (Seq. ID. 141)/ ilvB3r (Seq. ID. 142) are used to amplify the 5' and 3' homology arms, respectively. The two PCR products are cloned into pMTL85151 plasmids between the Sbfl/Notl and Nhel/Ascl sites to get pMTL85151-ilvB-KO. This plasmid is introduced into *C. ljungdahlii* either by conjugation or by electroporation as described in the above examples. Following selection on thiamphenicol plates the transformants are screened for ilvB knockout using the primers ilvBOf (Seq. ID.143) and ilvBOr (Seq. ID.144) that flank the homology arms of ilvB gene for PCR and sequencing of this PCR product.

Once the single gene knockout mutants are obtained the other 3 acetolactate synthase genes are sequentially targeted to create a mutant having all 4 acetolactate synthase genes deleted. The growth of these mutants may be auxotrophic to branched chain amino acids. The production or lack of production of acetoin, 2,3-BDO and other metabolites in these mutants can be analysed by HPLC, as described for the previous examples. The enzyme activity assays with pyruvate as substrate and thiamine diphosphate and flavin adenine dinucleotide as cofactors can be performed to confirm for the loss of acetolactate synthase activity in these mutants (Tittmann, Vyazmensky, Hubner, Barak, & Chipman, 2005; Vinogradov et al., 2006).

Design of ClosTron Group II Intron Targeting Cassettes for alsS, ilvC, ilvI and ilvB Genes:

*C. ljungdahlii* alsS, ilvC, ilvI and ilvB genes can also be disrupted or inactivated using ClosTron group II intron mediated gene disruption tool (Heap et al., 2010). The Perutka algorithm hosted at ClosTron.com is used to identify the group II intron target site between bases 303/304, 228/229, 975/976 and 157/158 on the sense strand of alsS, ilvC, ilvI and antisense strand of ilvB genes, respectively. Other sites identified by the algorithm can also be targeted. The same algorithm is used to design the intron targeting regions (alsS—Seq. ID.145; ilvC—Seq. ID.1.46; ilvI—Seq. ID.147 and ilvB—Seq. ID.148) which is commercially synthesized by DNA2.0 and delivered in pMTL007C-E2 vector. The final vectors, pMTL007C-E2-alsS-303!304s, pMTL007C-E2-ilvC-228!229s, pMTL007C-E2-ilvI-975!976s and pMTL007C-E2-ilvB-157!158a, contain a Retro-tranposition-Activated ermB Marker (RAM) which confers resistance to antibiotic Clarithromycin upon insertion into the target site. These plasmids are introduced into *C. ljungdahlii* by either conjugation or electroporation. The transformants are sequentially selected on thiamphenicol and clarithromycin agar plates and screened by PCR with primers alsSCTf (Seq. ID. 149) and alsSCTr (Seq. ID. 150), ilvCCTf (Seq. ID. 151) and ilvCCTr (Seq. ID. 152), ilvICTf (Seq. ID. 153) and ilvICTr (Seq. ID. 154) and ilvBCTf (Seq. ID. 155) and ilvBCTr (Seq. ID. 156) for inactivation of alsS, ilvC, ilvI and ilvB genes, respectively.

Once ClosTron mutants with single gene disrupted are obtained, the RAM ermB cassette is removed from the genome of these mutants using pMTL plasmids carrying a flippase gene which is introduced into the mutant by either electroporation or by conjugation. The resulting transformants are screened for the loss of ermB cassette by testing its susceptibility to clarithromycin and (ii) by PCR with the primers flanking the group II intron insertion site with alsSCTf (Seq. ID. 149) and alsSCTr (Seq. ID. 150), ilvCCTf (Seq. ID. 151) and ilvCCTr (Seq. ID. 152), ilvICTf (Seq. ID. 153) and ilvICTr (Seq. ID. 154) and ilvBCTf (Seq. ID. 155) and ilvBCTr (Seq. ID. 156) in alsS, ilvC, ilvB1 and ilvB2 genes, respectively, and by further sequencing of these PCR product.

After confirming the loss of ermB cassette, the ClosTron mutants like the knockout mutants are sequentially targeted for the inactivation of other acetolactate synthase genes. In one embodiment, these ClosTron mutants are grown in the presence of branched chain amino acids. The production or lack of production of acetoin, 2,3-BDO and other metabolites in these mutants is analysed by HPLC as described in previous examples and studied by performing enzyme activity assays with pyruvate as substrate and thiamine diphosphate and flavin adenine dinucleotide as cofactors can be performed to confirm for the loss of acetolactate synthase activity in these mutants (Tittmann et al., 2005; Vinogradov et al., 2006).

Example 9

Modified *C. ragsdalei* Producing Only Acetoin

As explained earlier, separation of acetoin from ethanol is technically more feasible compared to 2,3-BDO. It is thus desirable to have a *C. ragsdalei* strain producing acetoin and not 2,3-BDO. This will be achieved by deleting or disrupting both 2,3bdh and SecAdh genes in two ways as explained in Example 6b,: (a) homologous recombination and (b) marker less gene disruption using ClosTron tool.

(a) Δ2,3bdh ΔSecAdh Double Knockout *C. ragsdalei* Strain by Homologous Recombination:

The ~1 kb 5' (Seq. ID. 94) and 3' (Seq. ID. 95) homology arms of 2,3bdh genes are PCR amplified using *C. ragsdalei* genomic DNA. Primers Og13f (Seq. ID. 96)/Og14r (Seq. ID. 97) and Og15f (Seq. ID. 98)/Og16r (Seq. ID. 99) are used to amplify the 5' and 3' homology arms, respectively. The two PCR products are cloned into pMTL85151 plasmids between the Sbfl/Notl and Nhel/Ascl sites to get pMTL85151-2,3bdh-KO. This plasmid is introduced into *C. ragsdalei* either by conjugation or by electroporation as described in the above Example 6b. Following selection on thiamphenicol plates the transformants are screened for 2,3bdh knockout using the primers Og33f (Seq. ID.100) and Og34r (Seq. ID.101) that flank the homology arms of 2,3bdh for PCR and sequencing of this PCR product.

The plasmid for SecAdh gene knockout is similarly constructed. The ~1 kb 5' (Seq. ID. 102) and 3' (Seq. ID. 103) homology arms of SecAdh genes are PCR amplified using *C. ragsdalei* genomic DNA. Primers Sec5f (Seq. ID. 104)/Sec5r (Seq. ID. 105) and Sec3f (Seq. ID. 106) Sec3r (Seq. ID. 107) are used to amplify the 5' and 3' homology arms, respectively. The two PCR products are cloned into pMTL85151 plasmids between the Sbfl/Notl and Nhel/Ascl sites to get pMTL85151-SecAdh-KO. Following selection on thiamphenicol plates the transformants are screened for SecAdh knockout using the primers SecOf (Seq. ID.108) and SecOr (Seq. ID.109) that flank the homology arms of SecAdh gene for PCR.

Once having achieved the knockout of either 2,3bdh or the SecAdh genes in *C. ragsdalei*, the second gene in these single mutants is targeted using either pMTL85151-2,3bdh-KO or pMTL85151-SecAdh-KO plasmids. The plasmid is introduced into the single gene knockout mutant either by electroporation or by conjugation as already described in Example 6b. The transformants are screened for the knockout of the second gene using the primers flanking the homology arms of the corresponding genes.

(b) Δ2,3bdh ΔSecAdh Double Gene Disruption Using ClosTron in *C. ragsdalei:*

The RAM ermB cassette in the ClosTron group II intron construct is flanked by Flippase Recombination sites (Frt). By introducing flippase recombinase into Δ2,3bdh ClosTron mutant either by conjugation or by electroporation, the RAM ermB marker of ~1.3 kb is removed from the genome of the mutant and thus the ermB marker can be recycled. A ~0.8 kb fragment of group II intron will be left on the genome. This is confirmed by (i) testing its susceptibility to clarithromycin and (ii) by PCR with the primers flanking the group II intron insertion site with the primers Og42f (Seq. ID. 84) and Og43r (Seq. ID. 85) and sequencing of the PCR product. Once obtaining the Δ2,3bdh ClosTron mutant without RAM ermB marker (Δ2,3bdh-ermB ClosTron), the SecAdh gene in the mutant is targeted in a similar way using ClosTron group II intron insertional inactivation tool. The intron insertion site between bases 399 and 400 on the sense strand is identified in the SecAdh gene using Perutka algorithm hosted at ClosTron.com and the intron targeting cassette has been designed (Seq. ID. 110). The intron targeting cassette is commercially synthesized by DNA2.0 and delivered in pMTL007C-E2 vector as pMTL007C-E5-SecAdh-399!400s which is introduced into Δ2,3bdh-ermB ClosTron mutant by either conjugation or electroporation. The transformants can be sequentially selected on thiamphenicol and clarithromycin agar plates and screened by PCR with primers SecCTf (Seq. ID. 111) and SecCTr (Seq. ID. 112) as explained earlier in Example 6b.

The Δ2,3bdh ΔSecAdh double gene disruption *C. ragsdalei* mutant is created by using either homologous recombination technique or by ClosTron group II intron insertional inactivation tool as explained in the above paragraphs.

The disruption of 2,3bdh and SecAdh genes is confirmed by performing enzyme activity assays for the conversion of acetoin to 2,3-BDO and also by analysing the metabolites and 2,3-BDO produced by the mutant by HPLC, as previously described.

Example 10

Modified *C. ragsdalei* Strain Producing Reduced or No 3-BDO

As shown in FIG. 1 acetolactate is one of the intermediates in 2,3-BDO biosynthesis and is also the precursor for the synthesis of branched chain amino acids. The enzyme acetolactate synthase catalyses the reaction leading to acetolactate from 2 molecules of pyruvate as substrates. The enzyme acetolactate synthase is broadly classified into two groups; (i) anabolic acetolactate synthase is associated with the genes involved in the synthesis of branched amino acids like valine, isoleucine and leucine and (ii) catabolic acetolactate synthase is associated with 2,3-BDO synthesis).

The genome of *C. ragsdalei* has 3 putative anabolic acetolactate synthase genes, ilvC, ilvI and ilvB and 1 catabolic acetolactate synthase, alsS. Exemplary amino acid sequence from *C. ragsdalei* (AEI90734.1, AEI90734.1, AEI90735.1, AE190727.1, AE190727.1) and respective nucleic acid sequences HQ876014.1, HQ876024.1, HQ876022.1) are obtained from GenBank.

The disruption of all 4 acetolactate synthase genes or any combination of these 4 genes should lead to a decrease in acetoin and 2,3-BDO production. In order to ensure the growth of these mutants the media is supplemented with the three branched chain amino acids valine, leucine and isoleucine.

As described in Examples 6b, and 9 single mutants of *C. ragsdalei* alsS, ilvC, ilvl and ilvB mutants can be created by either homologous recombination or using ClosTron group II intron mutagenesis tool.

Design of alsS, ilvC, ilvI and ilvB Knockout Cassettes:

The knockout constructs for alsS, ilvC, ilvI and ilvB Genes are Designed as Explained Above.

The ~1 kb 5' (Seq. ID. 113) and 3' (Seq. ID. 114) homology arms of alsS gene are PCR amplified using *C. ragsdalei* genomic DNA. Primers alsS5f (Seq. ID. 115)/alsSr (Seq. ID. 116) and alsS3f (Seq. ID. 117)/alsS3r (Seq. ID. 118) are used to amplify the 5' and 3' homology arms, respectively. The two PCR products are cloned into pMTL85151 plasmids between the Sbfl/Notl and Nhel/Ascl sites to get pMTL85151-alsS-KO. This plasmic is introduced into *C. ragsdalei* either by conjugation or by electroporation as described in the above examples. Following selection on thiamphenicol plates the transformants are screened for alsS knockout using the primers alsSOf (Seq. ID.119) and alsSOr (Seq. ID.120) that flank the homology arms of alsS for PCR and sequencing of this PCR product.

For knockout of ilvC gene, the ~1 kb 5' (Seq. ID. 121) and 3' (Seq. ID. 122) homology arms of ilvC gene are PCR amplified using *C. ragsdalei* genomic DNA. Primers ilvCSf (Seq. ID. 123)/ilvC5r (Seq. ID. 124) and ilvC3f (Seq. ID. 125)/ilvC3r (Seq. ID. 126) are used to amplify the 5' and 3' homology arms, respectively. The two PCR products are cloned into pMTL85151 plasmids between the Sbfl/Notl and Nhel/Ascl sites to get pMTL85151-ilvC-KO. This plasmid is introduced into *C. ragsdalei* either by conjugation or by electroporation as described in the above examples. Following selection on thiamphenicol plates the transformants are screened for ilvC knockout using the primers ilvCOf (Seq. ID. 127) and ilvCOr (Seq. ID. 128) that flank the homology arms of ilvC gene for PCR and sequencing of this PCR product.

For knockout of ilvI gene, the ~1 kb 5' (Seq. ID. 129) and 3' (Seq. ID. 130) homology arms of ilvI gene are PCR amplified using *C. ragsdalei* genomic DNA. Primers ilvI5f (Seq. ID. 131)/ilvI5r (Seq. ID. 132) and ilvI3f (Seq. ID. 133)/ilvI3r (Seq. ID. 134) are used to amplify the 5' and 3' homology arms, respectively. The two PCR products are cloned into pMTL85151 plasmids between the Sbfl/Notl and Nhel/Ascl sites to get pMTL85151-ilvI-KO. This plasmid is introduced into *C. ragsdalei* either by conjugation or by electroporation as described in the above examples. Following selection on thiamphenicol plates the transformants are screened for ilvI knockout using the (primers ilvIOf (Seq. ID. 135) and ilvIOr (Seq. ID. 136) that flank the homology arms of ilvI gene for PCR and sequencing of this PCR product.

For knockout of ilvB gene, the ~1 kb 5' (Seq. ID. 137) and 3' (Seq. ID. 138) homology arms of ilvB gene are PCR amplified using *C. ragsdalei* genomic DNA. Primers ilvB5f (Seq. ID. 139)/ilvB5r (Seq. ID. 140) and ilvB3f (Seq. ID. 141)/ilvB3r (Seq. ID. 142) are used to amplify the 5' and 3' homology arms, respectively. The two PCR products are cloned into pMTL85151 plasmids between the Sbfl/Notl and Nhel/Ascl sites to get pMTL85151-ilvB-KO. This plasmid is introduced into *C. ragsdalei* either by conjugation or by electroporation as described in the above examples. Following selection on thiamphenicol plates the transformants are screened for ilvB knockout using the primers ilvBOf (Seq. ID.143) and ilvIBOr (Seq. ID.144) that flank the homology arms of ilvB gene for PCR and sequencing of this PCR product.

Once the single gene knockout mutants are obtained the other 3 acetolactate synthase genes are sequentially targeted to create a mutant having all 4 acetolactate synthase genes deleted. The growth of these mutants may be auxotrophic to branched chain amino acids. The production or lack of production of acetoin, 2,3-BDO and other metabolites in these mutants can be analysed by HPLC, as described for the previous examples. The enzyme activity assays with pyruvate as substrate and thiamine diphosphate and flavin adenine dinucleotide as cofactors can be performed to confirm for the loss of acetolactate synthase activity in these mutants (Tittmann, Vyazmensky, Hübner, Barak, & Chipman, 2005; Vinogradov et al., 2006).

Design of ClosTron Group II Intron Targeting Cassettes for alsS, ilvC, ilvl and ilvB Genes:

*C. ragsdalei* alsS, ilvC, ilvl and ilvB genes can also be disrupted or inactivated using ClosTron group II intron mediated gene disruption tool (Heap et al., 2010). The Perutka algorithm hosted at ClosTron.com is used to identify the group II intron target site between bases 303/304, 228/229, 975/976 and 157/158 on the sense strand of alsS, ilvC, ilvl and antisense strand of ilvB genes, respectively. Other sites identified by the algorithm can also be targeted. The same algorithm is used to design the intron targeting regions (alsS—Seq. ID.145; ilvC—Seq. ID.146; ilvI—Seq. ID.147 and ilvB—Seq. ID.148) which is commercially synthesized by DNA2.0 and delivered in pMTL007C-E2 vector. The final vectors, pMTL007C-E2-alsS-303!304s, pMTL007C-E2-ilvC-228!229s, pMTL007C-E2-ilvl-975!976s and pMTL007C-E2-ilvB-157!158a, contain a Retro-tranposition-Activated ermB Marker (RAM) which confers resistance to antibiotic Clarithromycin upon insertion into the target site. These plasmids are introduced into *C. ragsdalei* by either conjugation or electroporation. The transformants are sequentially selected on thiamphenicol and clarithromycin agar plates and screened by PCR with primers alsSCTf (Seq. ID. 149) and alsSCTr (Seq. ID. 150), ilvCCTf (Seq. ID. 151) and ilvCCTr (Seq. ID. 152), ilvICTf (Seq. ID. 153) and ilvICTr (Seq. ID. 154) and ilvBCIf (Seq. ID. 155) and ilvBCTr (Seq. ID. 156) for inactivation of alsS, ilvC, ilvI and ilvB genes, respectively.

Once ClosTron mutants with single gene disrupted are obtained, the RAM ermB cassette is removed from the genome of these mutants using pMTL plasmids carrying a flippase gene which is introduced into the mutant by either electroporation or by conjugation. The resulting transformants are screened for the loss of ermB cassette by testing its susceptibility to clarithromycin and (ii) by PCR with the primers flanking the group II intron insertion site with alsSCTf (Seq. ID. 149) and alsSCTr (Seq. ID. 150), ilvCCTf (Seq. ID. 151) and ilvCCTr (Seq. ID. 152), ilvICTf (Seq. ID. 153) and ilvICTr (Seq. ID. 154) and ilvBCTf (Seq. ID. 155) and ilvBCTr (Seq. ID. 156) in alsS, ilvC, ilvB1 and ilvB2 genes, respectively, and by further sequencing of these PCR product.

After confirming the loss of ermB cassette, the ClosTron mutants like the knockout mutants are sequentially targeted for the inactivation of other acetolactate synthase genes. In one embodiment, these ClosTron mutants are grown in the presence of branched chain amino acids. The production or lack of production of acetoin, 2,3-BDO and other metabolites in these mutants is analysed by HPLC as described in previous examples and studied by performing enzyme activity assays with pyruvate as substrate and thiamine diphosphate and flavin adenine dinucleotide as cofactors can be performed to confirm for the loss of acetolactate synthase activity in these mutants (Tittmann et al., 2005; Vinogradov et al., 2006).

The invention has been described herein, with reference to certain preferred embodiments, in order to enable the reader to practice the invention without undue experimentation. However, a person having ordinary skill in the art will readily recognise that many of the components and parameters may be varied or modified to a certain extent or substituted for known equivalents without departing from the scope of the invention. It should be appreciated that such modifications and equivalents are herein incorporated as if individually set forth. Titles, headings, or the like are provided to enhance the reader's comprehension of this document, and should not be read as limiting the scope of the present invention.

The entire disclosures of all applications, patents and publications, cited above and below, if any, are hereby incorporated by reference. However, the reference to any applications, patents and publications in this specification is not, and should not be taken as an acknowledgment or any form of suggestion that they constitute valid prior art or form part of the common general knowledge in any country in the world.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

References

Abrini, J. Naveau, H. & Nyns, E. J., 1994. *Clostridium autoethanogenum*, sp. nov., an anaerobic bacterium that produces ethanol from carbon monoxide. *Archives of microbiology,* 161(4), pp. 345-351. Available at: http://www.springerlink.com/index/v143151w30423660.pdf [Accessed September 4, 2011].

Collins, M. D., Lawson, P. A., Willems, A., Cordoba, J. J., Fernandez-Garayzabal, J., Garcia, P., Cai, J., et al. (1994). The phylogeny of the genus *Clostridium:* proposal of five new genera and eleven new species combinations. *International journal of systematic bacteriology,* 44(4), 812-26. Retrieved from http://www.ncbi.nlm.nih.gov/pubmed/7981107

Drake, H. L., Küsel, K., Matthies, C., Wood, H. G., & Ljungdahl, L. G. (2006). Acetogenic Prokaryotes. In M. Dworkin, S. Falkow, E. Rosenberg, Schleifer, & E. Stackebrandt (Eds.), *The Prokaryotes* (3rd Editio., pp. 354-420). New York, N.Y.: Springer. doi:10.1007/0-387-30742-7

Köpke, M, Mihalcea, C., Liew, F., Tizard, J. H. Ali, M. S., Conolly, J. J., Al-Sinawi, B., et al. (2011). 2,3-Butanediol Production By Acetogenic Bacteria, an Alternative Route To Chemical Synthesis, Using Industrial Waste Gas. *Applied and environmental microbiology,* 77(15), 5467-75. doi:10.1128/AEM.00355-11

Perez, J. M., Richter, H., Loftus, S. E., & Angenent, L. T. (2012). Biocatalytic reduction of short-chain carboxylic acids into their corresponding alcohols with syngas fermentation. *Biotechnology and bioengineering,* 1-30. doi:10.1002/bit.24786

Smart K F, Aggio R B, Van Houtte J R, Villas-Boas S G, Analytical platform for metabolome analysis of microbial cells using methyl chloroformate derivatization followed by gas chromatography-mass spectrometry, Nat Protoc. 2010 September; 5(10):1709-29. 2010

Tanner, R. S., Miller, L, M., & Yang, D. (1993), *Clostridium ljungdahlii* sp. nov., an acetogenic species in clostridial rRNA homology group I. *International journal of systematic bacteriology,* 43(2), 232. Retrieved from http://ijs.sgmjournals.org/content/43/2/232.short Heap, J. T., Kuehne, S. a, Ehsaan, M., Cadman, S. T., Cooksley, C. M., Scott, J. C., & Minton, N. P. (2010). The ClosTron: Mutagenesis in *Clostridium* refined and streamlined. *Journal of microbiological methods,* 80(1), 49-55. doi:10.1016/j.mimet.2009.10.018

Köpke, M., Held, C., Hujer, S., Liesegang, H., Wiezer, A., Wollherr A., Ehenreich, A., et al. (2010). *Clostridium ljungdahlii* represents a microbial production platform based on syngas. *Proceedings of the National Academy of Sciences of the United States of America,* 107(29), 13087-92. doi:10.1073/pnas.1004716107

Tittmann, K., Vyazmensky, M., Hubner, O., Barak, Z., & Chipman, D. M. (2005). The carbotigation reaction of acetohydroxyacid synthase II: steady-state intermediate distributions in wild type and mutants by NMR, *Proceedings of the National Academy Sciences of the United States of America,* 102(3), 553-8. doi:10.1073/pnas.0408210101

Vinogradov, V., Vyazmensky, M., Engel, S., Belenky, I., Kaplun, A., Kryukov, O., Barak, Z., et al. (2006). Acetohydroxyacid synthase isozyme I from *Escherichia coli* has unique catalytic and regulatory properties. *Biochimica et biophysica acta,* 1760(3), 356-63. doi :10.1016/j.bbagen ,2005.10.008

Yan, Y., Lee, C.-C, & Liao, J. C. (2009). Enantioselective synthesis of pure (R,R)-2,3-butanediol in *Escherichia coli* with stereospecific secondary alcohol dehydrogenases. *Organic & biomolecular chemistry,* 7(19), 3914-7. doi:10.1039/b913501d

The invention claimed is:

1. A method of producing a product comprising culturing a recombinant carboxydotrophic acetogenic microorganism in the presence of a gaseous substrate to produce at least one product, wherein the microorganism comprises at least one genetic modification that disrupts the expression and/or activity of an enzyme in the 2,3-butanediol biosynthesis pathway selected from the group consisting of (i) an enzyme capable of converting pyruvate to acetolactate, (ii) an enzyme capable of converting acetolactate to acetoin, and (iii) an enzyme capable of converting acetoin to 2,3-butanediol.

2. The method of claim 1, wherein the product is selected from the group consisting of ethanol, formate, lactate, pyruvate, succinate, valine, leucine, isoleucine, acetolactate, malate, fumarate, 2-oxogluterate, and citrate.

3. The method of claim 2, wherein the product is ethanol.

4. The method of claim 1, wherein the microorganism comprises at least one genetic modification that disrupts the expression and/or activity of at least two enzymes in the 2,3-butanediol biosynthesis pathway selected from the group consisting of (i) an enzyme capable of converting pyruvate to acetolactate, (ii) an enzyme capable of converting acetolactate to acetoin, and (iii) an enzyme capable of converting acetoin to 2,3-butanediol.

5. The method of claim 1, wherein the enzyme capable of converting pyruvate to acetolactate is acetolactate synthase.

6. The method of claim 5, wherein the acetolactate synthase is AlsS.

7. The method of claim 1, wherein the enzyme capable of converting acetolactate to acetoin is acetolactate decarboxylase.

8. The method of claim 7, wherein the acetolactate decarboxylase is BudA.

9. The method of claim 1, wherein the enzyme capable of converting acetoin to 2,3-butanediol is 2,3-butanediol dehydrogenase, acetoin reductase, or primary:secondary alcohol dehydrogenase.

10. The method of claim 9, wherein the 2,3-butanediol dehydrogenase is 2,3-Bdh.

11. The method of claim 1, wherein the microorganism produces an increased amount of the product compared to a parental microorganism and/or a reduced amount of 2,3-butanediol or a precursor thereof compared to a parental microorganism.

12. The method of claim 11, wherein the parental microorganism is *Clostridium autoethanogenum, Clostridium ljungdahlii, Clostridium ragsdalei*, or *Clostridium coskatii.*

13. The method of claim 11, wherein the parental microorganism is *Clostridium Autoethanogenum* DSM23693.

14. The method of claim 1, wherein the gaseous substrate is an industrial waste gas or an industrial off gas.

15. The method of claim 1, wherein the gaseous substrate is syngas.

16. The method of claim 1, wherein the gaseous substrate comprises CO.

17. The method of claim 16, wherein the gaseous substrate comprises at least 20% CO by volume.

* * * * *

SEQUENCE LISTING

<160> NUMBER OF SEQ ID NOS: 156

<210> SEQ ID NO 1
<211> LENGTH: 719
<212> TYPE: DNA
<213> ORGANISM: Clostridia autoethanogenum

<400> SEQUENCE: 1
atggatgatg aggtgaaagt cccaaaccat atatatcaaa tgtctacaat aaatgcactt 60
gtttcggggc tgtatgatgg ctgtgtttca ttatctaaac ttcttaaaaa aggaaacttt 120
ggtataggta cttttaaagg tctagatggt gaactaactc ttttaaatgg aactttttat 180
aggactaaac ctgatggcag cgtatacgta tgttccaaaa acgtatccgt tccttttgct 240
gtagtcactg aactggaaaa ttataatact tataatattc aaaatcgtac ttcttatgaa 300
gatataagaa aagaattgga cagctttata gaaagcaaaa atatatttta tgctttctat 360
atggaaggta aatttaatta tgtaaaaaca cgtactgttg taaaacagaa tatgccttat 420
aagcctatgg ctgaagttgt taaagatcag cctatgtttg aatataacgg tgttgatgga 480
tatgtggttg gatttaggtg tcctgattat gttgaaggcc ttaatgtccc tggatatcat 540
tttcatttca taaataaaga taagaaattt ggtggacata taagtgaatt ttccattgaa 600
aatgcgaagg tttatgtaca gaactgttct tgctttagga tggaacttcc taaaaagaaa 660
gtttttataa tatggaagta caagatagaa acgatgagat aacaagtgtt gaaaaataa 719

<210> SEQ ID NO 2
<211> LENGTH: 239
<212> TYPE: PRT
<213> ORGANISM: Clostridium autoethanogenum

<400> SEQUENCE: 2

Met Asp Asp Glu Val Lys Val Pro Asn His Ile Tyr Gln Met Ser Thr
1 5 10 15

Ile Asn Ala Leu Val Ser Gly Leu Tyr Asp Gly Cys Val Ser Leu Ser
20 25 30

Lys Leu Leu Lys Lys Gly Asn Phe Gly Ile Gly Thr Phe Lys Gly Leu
35 40 45

Asp Gly Glu Leu Thr Leu Leu Asn Gly Thr Phe Tyr Arg Thr Lys Pro
50 55 60

Asp Gly Ser Val Tyr Val Cys Ser Lys Asn Val Ser Val Pro Phe Ala
65 70 75 80

Val Val Thr Glu Leu Glu Asn Tyr Asn Thr Tyr Asn Ile Gln Asn Arg
85 90 95

Thr Ser Tyr Glu Asp Ile Arg Lys Glu Leu Asp Ser Phe Ile Glu Ser
100 105 110

Lys Asn Ile Phe Tyr Ala Phe Tyr Met Glu Gly Lys Phe Asn Tyr Val
115 120 125

Lys Thr Arg Thr Val Val Lys Gln Asn Met Pro Tyr Lys Pro Met Ala
130 135 140

Glu Val Val Lys Asp Gln Pro Met Phe Glu Tyr Asn Gly Val Asp Gly
145 150 155 160

Tyr Val Val Gly Phe Arg Cys Pro Asp Tyr Val Glu Gly Leu Asn Val
165 170 175

Pro Gly Tyr His Phe His Phe Ile Asn Lys Asp Lys Lys Phe Gly Gly
180 185 190

His Ile Ser Glu Phe Ser Ile Glu Asn Ala Lys Val Tyr Val Gln Asn

-continued

```
        195                 200                 205

Cys Ser Cys Phe Arg Met Glu Leu Pro Lys Asn Glu Ser Phe Tyr Asn
    210                 215                 220

Met Glu Val Gln Asp Arg Asn Asp Glu Ile Thr Ser Val Glu Lys
225                 230                 235


<210> SEQ ID NO 3
<211> LENGTH: 964
<212> TYPE: DNA
<213> ORGANISM: Clostridium autoethanogenum

<400> SEQUENCE: 3

tttcttcaca ggaaaatata cttcagtaac aagatcttta ggaatggtga cttggtgggg      60

gtcagttaca tatacttcat atggtgggtt tgtaagttta tatccttcat tttctaccca     120

ttccctcaac ttagcatata cagagatgtt aattctgaat atgagcccct taaaacagac     180

ttcgcacaaa ggactccagg caagtatctt gttcccttta caatctcctt tatcggaatg     240

gcaagttctg tatcattgcc agaaggattg tattcagcgc tgtgataaat agttattggc     300

ttaccaagaa agtcaattac aaaaatatat ataaagaaag caaagctaca tatattaaag     360

catttaaggt aaaactaaaa atattataaa aatgaaatta ttttttctca tagctaaagt     420

tacataatac gaggaggatt tataatgaaa aaagtaatag gaattataag tattgtacta     480

tttgtactcg tagcacttca atcctgtgct gcaggagtag gaaatgcatt aagtaataac     540

aaagaagcta gtggatctgc tggattattt ttatctgtat gtatgcttat tgctggaata     600

atagcaataa tatcaaaata tagtaaaggt atgactataa cagctatagt attttatttg     660

ttagcttttg ttgtagggat tgctaatgtt gggcattttt cagatttgca aatttggtca     720

atcattaact tgatatttgc tggactattg atatttcatt tgcttaaaaa taagcaatta     780

tataatagca gtgggaaaaa gtagaatcat atattgtaat tatttttaat tatgttggca     840

aaattgaaat tgtcactgaa acacctctaa atgttttaaa tacatatgtt taattattgt     900

gacagattct aatagtagaa agtagaaatt tgctatgtta taatgacata gaggtgaatg     960

taat                                                                  964


<210> SEQ ID NO 4
<211> LENGTH: 977
<212> TYPE: DNA
<213> ORGANISM: Clostridium autoethanogenum

<400> SEQUENCE: 4

actagacagt gctaataaca atgtctagtg ctttttatct tgctcaattt tttcattgag      60

ttcatttaag taagtccacc tgtccatctt ttcgtctagc tctttttcca gtgaattctt     120

ttcggataag agatcttcaa gaagtgcata atcagatgaa gcagcttcca tttctatttt     180

cttttcagat atagattttt ctagatgttc aattacctca tctattttgt caaactccat     240

ttgttctgca taggtaaatt ttagaggctt ttctttttgc aacttatagt tgtttttagc     300

tgtatttttc ttagagctta ttttttcctc tgatattttt gcagttttgt gaaaatagga     360

atagtttcct gtatattgag tgattttacc gtttccttca aaagaaaata ttttatcaac     420

tgttttgtca aggaagtacc tgtcatgaga tacagctata acagctcctt caaaatcgtt     480

aatataatct tctaggattg taagtgtttc tatatccaga tcatttgttg gttcgtccag     540

caaaagtaca ttagggtaat tcatcagtat ttttagaaga tataatcttc ttcgttctcc     600

tcctgaaagt tttccaaggg gagtccattg aactgaaggt tcaaataaaa aattttcaag     660
```

-continued tacagcagaa gcacttattt tttcacccga tgaagttgac gcatattctg atgtcccacg 720
tatgtattca attacccttt cgttcatatc catatcagaa attccctgag aatagtatcc 780
tatctttact gtttcaccta tatctatagt gccgctgtcc ggcagaattt tttgaactaa 840
aatattcata agagtggatt taccacttcc attaggtcca ataataccta ttctgtcatt 900
atttagtatg ttataagtga aatttttaat taatgtcttt tcaccaaaac ttttgcttat 960
gttatccagg tttatga 977

<210> SEQ ID NO 5
<211> LENGTH: 40
<212> TYPE: DNA
<213> ORGANISM: Artificial sequence
<220> FEATURE:
<223> OTHER INFORMATION: Synthetic primer

<400> SEQUENCE: 5
attcatcctg caggtttctt cacaggaaaa tatacttcag 40

<210> SEQ ID NO 6
<211> LENGTH: 40
<212> TYPE: DNA
<213> ORGANISM: Artificial sequence
<220> FEATURE:
<223> OTHER INFORMATION: Synthetic primer

<400> SEQUENCE: 6
gactgcggcc gcattacatt cacctctatg tcattataac 40

<210> SEQ ID NO 7
<211> LENGTH: 38
<212> TYPE: DNA
<213> ORGANISM: Artificial sequence
<220> FEATURE:
<223> OTHER INFORMATION: Synthetic primer

<400> SEQUENCE: 7
atttgctagc actagacagt gctaataaca atgtctag 38

<210> SEQ ID NO 8
<211> LENGTH: 35
<212> TYPE: DNA
<213> ORGANISM: Artificial sequence
<220> FEATURE:
<223> OTHER INFORMATION: Synthetic primer

<400> SEQUENCE: 8
atatggcgcg cctcataaac ctggataaca taagc 35

<210> SEQ ID NO 9
<211> LENGTH: 2963
<212> TYPE: DNA
<213> ORGANISM: Escherichia coli

<400> SEQUENCE: 9
cctgcaggat aaaaaaattg tagataaatt ttataaaata gttttatcta caattttttt 60
atcaggaaac agctatgacc gcggccgctg tatccatatg accatgatta cgaattcgag 120
ctcggtaccc ggggatcctc tagagtcgac gtcacgcgtc catggagatc tcgaggcctg 180
cagacatgca agcttggcac tggccgtcgt tttacaacgt cgtgactggg aaaaccctgg 240
cgttacccaa cttaatcgcc ttgcagcaca tccccctttc gccagctggc gtaatagcga 300

-continued

```
agaggcccgc accgatcgcc cttcccaaca gttgcgcagc ctgaatggcg aatggcgcta    360
gcataaaaat aagaagcctg catttgcagg cttcttattt ttatggcgcg ccgcattcac    420
ttcttttcta tataaatatg agcgaagcga ataagcgtcg gaaaagcagc aaaaagtttc    480
ctttttgctg ttggagcatg gggttcagg gggtgcagta tctgacgtca atgccgagcg     540
aaagcgagcc gaagggtagc atttacgtta gataaccccc tgatatgctc cgacgcttta    600
tatagaaaag aagattcaac taggtaaaat cttaatatag gttgagatga taaggtttat    660
aaggaatttg tttgttctaa tttttcactc attttgttct aatttctttt aacaaatgtt    720
cttttttttt tagaacagtt atgatatagt tagaatagtt taaaataagg agtgagaaaa    780
agatgaaaga aagatatgga acagtctata aaggctctca gaggctcata gacgaagaaa    840
gtggagaagt catagaggta gacaagttat accgtaaaca aacgtctggt aacttcgtaa    900
aggcatatat agtgcaatta ataagtatgt tagatatgat tggcggaaaa aaacttaaaa    960
tcgttaacta tatcctagat aatgtccact taagtaacaa tacaatgata gctacaacaa   1020
gagaaatagc aaaagctaca ggaacaagtc tacaaacagt aataacaaca cttaaaatct   1080
tagaagaagg aaatattata aaaagaaaaa ctggagtatt aatgttaaac cctgaactac   1140
taatgagagg cgacgaccaa aaacaaaaat acctcttact cgaatttggg aactttgagc   1200
aagaggcaaa tgaaatagat tgacctccca ataacaccac gtagttattg ggaggtcaat   1260
ctatgaaatg cgattaaggg ccggccagtg ggcaagttga aaaattcaca aaaatgtggt   1320
ataatatctt tgttcattag agcgataaac ttgaatttga gagggaactt agatggtatt   1380
tgaaaaaatt gataaaaata gttggaacag aaaagagtat tttgaccact actttgcaag   1440
tgtaccttgt acctacagca tgaccgttaa agtggatatc acacaaataa aggaaaaggg   1500
aatgaaacta tatcctgcaa tgctttatta tattgcaatg attgtaaacc gccattcaga   1560
gtttaggacg gcaatcaatc aagatggtga attggggata tatgatgaga tgataccaag   1620
ctatacaata tttcacaatg atactgaaac attttccagc ctttggactg agtgtaagtc   1680
tgactttaaa tcatttttag cagattatga aagtgatacg caacggtatg gaaacaatca   1740
tagaatggaa ggaaagccaa atgctccgga aaacattttt aatgtatcta tgataccgtg   1800
gtcaaccttc gatggcttta atctgaattt gcagaaagga tatgattatt tgattcctat   1860
ttttactatg ggaaatattt ataaagaaga taacaaaatt atacttcctt tggcaattca   1920
agttcatcac gcagtatgtg acggatttca catttgccgt tttgtaaacg aattgcagga   1980
attgataaat agttaacttc aggtttgtct gtaactaaaa acaagtattt aagcaaaaac   2040
atcgtagaaa tacggtgttt tttgttaccc taagtttaaa ctccttttttg ataatctcat  2100
gaccaaaatc ccttaacgtg agttttcgtt ccactgagcg tcagaccccg tagaaaagat   2160
caaaggatct tcttgagatc cttttttttct gcgcgtaatc tgctgcttgc aaacaaaaaa  2220
accaccgcta ccagcggtgg tttgtttgcc ggatcaagag ctaccaactc tttttccgaa   2280
ggtaactggc ttcagcagag cgcagatacc aaatactgtt cttctagtgt agccgtagtt   2340
aggccaccac ttcaagaact ctgtagcacc gcctacatac ctcgctctgc taatcctgtt   2400
accagtggct gctgccagtg gcgataagtc gtgtcttacc gggttggact caagacgata   2460
gttaccggat aaggcgcagc ggtcgggctg aacggggggt tcgtgcacac agcccagctt   2520
ggagcgaacg acctacaccg aactgagata cctacagcgt gagctatgag aaagcgccac   2580
gcttcccgaa gggagaaagg cggacaggta tccggtaagc ggcagggtcg gaacaggaga   2640
gcgcacgagg gagcttccag ggggaaacgc ctggtatctt tatagtcctg tcgggtttcg   2700
```

ccacctctga cttgagcgtc gatttttgtg atgctcgtca ggggggcgga gcctatggaa 2760
aaacgccagc aacgcggcct ttttacggtt cctggccttt tgctggcctt ttgctcacat 2820
gttctttcct gcgttatccc ctgattctgt ggataaccgt attaccgcct ttgagtgagc 2880
tgataccgct cgccgcagcc gaacgaccga gcgcagcgag tcagtgagcg aggaagcgga 2940
agagcgccca atacgcaggg ccc 2963

<210> SEQ ID NO 10
<211> LENGTH: 16
<212> TYPE: DNA
<213> ORGANISM: Artificial sequence
<220> FEATURE:
<223> OTHER INFORMATION: Synthetic primer

<400> SEQUENCE: 10
gtaaaacgac ggccag 16

<210> SEQ ID NO 11
<211> LENGTH: 18
<212> TYPE: DNA
<213> ORGANISM: Artificial sequence
<220> FEATURE:
<223> OTHER INFORMATION: Synthetic primer

<400> SEQUENCE: 11
caggaaacag ctatgacc 18

<210> SEQ ID NO 12
<211> LENGTH: 4819
<212> TYPE: DNA
<213> ORGANISM: Artificial sequence
<220> FEATURE:
<223> OTHER INFORMATION: budA gene knockout plasmid pMTL85141-budA-ko

<400> SEQUENCE: 12
cctgcaggtt tcttcacagg aaaatatact tcagtaacaa gatctttagg aatggtgact 60
tggtgggggt cagttacata tacttcatat ggtgggtttg taagtttata tccttcattt 120
tctacccatt ccctcaactt agcatataca gagatgttaa ttctgaatat gagcccctta 180
aaacagactt cgcacaaagg actccaggca agtatcttgt tccctttaca atctccttta 240
tcggaatggc aagttctgta tcattgccag aaggattgta ttcagcgctg tgataaatag 300
ttattggctt accaagaaag tcaattacaa aaatatatat aaagaaagca aagctacata 360
tattaaagca tttaaggtaa aactaaaaat attataaaaa tgaaattatt ttttctcata 420
gctaaagtta cataatacga ggaggattta taatgaaaaa agtaatagga attataagta 480
ttgtactatt tgtactcgta gcacttcaat cctgtgctgc aggagtagga aatgcattaa 540
gtaataacaa agaagctagt ggatctgctg gattattttt atctgtatgt atgcttattg 600
ctggaataat agcaataata tcaaaatata gtaaaggtat gactataaca gctatagtat 660
tttatttgtt agcttttgtt gtagggattg ctaatgttgg gcatttttca gatttgcaaa 720
tttggtcaat cattaacttg atatttgctg gactattgat atttcatttg cttaaaaata 780
agcaattata taatagcagt gggaaaaagt agaatcatat attgtaatta tttttaatta 840
tgttggcaaa attgaaattg tcactgaaac acctctaaat gttttaaata catatgttta 900
attattgtga cagattctaa tagtagaaag tagaaatttg ctatgttata atgacataga 960
ggtgaatgta atgcggccgc tgtatccata tgaccatgat tacgaattcg agctcggtac 1020

-continued

```
ccggggatcc tctagagtcg acgtcacgcg tccatggaga tctcgaggcc tgcagacatg   1080
caagcttggc actggccgtc gttttacaac gtcgtgactg ggaaaaccct ggcgttaccc   1140
aacttaatcg ccttgcagca catccccctt tcgccagctg gcgtaatagc gaagaggccc   1200
gcaccgatcg cccttcccaa cagttgcgca gcctgaatgg cgaatggcgc tagcagtatt   1260
gatagaaaaa aacactagac agtgctaata acaatgtcta gtgcttttta tcttgctcaa   1320
tttttcatt gagttcattt aagtaagtcc acctgtccat cttttcgtct agctcttttt   1380
ccagtgaatt cttttcggat aagagatctt caagaagtgc ataatcagat gaagcagctt   1440
ccatttctat tttcttttca gatatagatt tttctagatg ttcaattacc tcatctattt   1500
tgtcaaactc catttgttct gcataggtaa attttagagg cttttctttt tgcaacttat   1560
agttgttttt agctgtattt ttcttagagc ttattttttc ctctgatatt tttgcagttt   1620
tgtgaaaata ggaatagttt cctgtatatt gagtgatttt accgtttcct tcaaaagaaa   1680
atattttatc aactgttttg tcaaggaagt acctgtcatg agatacagct ataacagctc   1740
cttcaaaatc gttaatataa tcttctagga ttgtaagtgt ttctatatcc agatcatttg   1800
ttggttcgtc cagcaaaagt acattagggt aattcatcag tatttttaga agatataatc   1860
ttcttcgttc tcctcctgaa agttttccaa ggggagtcca ttgaactgaa ggttcaaata   1920
aaaaattttc aagtacagca gaagcactta tttttcacc cgatgaagtt gacgcatatt   1980
ctgatgtccc acgtatgtat tcaattaccc tttcgttcat atccatatca gaaattccct   2040
gagaatagta tcctatcttt actgtttcac ctatatctat agtgccgctg tccggcagaa   2100
tttttgaac taaaatattc ataagagtgg atttaccact tccattaggt ccaataatac   2160
ctattctgtc attatttagt atgttataag tgaaattttt aattaatgtc ttttcaccaa   2220
aacttttgct tatgttatcc aggtttatga ctttttacc ggcgcgccgc attcacttct   2280
tttctatata aatatgagcg aagcgaataa gcgtcggaaa agcagcaaaa agtttccttt   2340
ttgctgttgg agcatggggg ttcagggggt gcagtatctg acgtcaatgc cgagcgaaag   2400
cgagccgaag ggtagcattt acgttagata accccctgat atgctccgac gctttatata   2460
gaaaagaaga ttcaactagg taaaatctta atataggttg agatgataag gtttataagg   2520
aatttgtttg ttctaatttt tcactcattt tgttctaatt tcttttaaca aatgttcttt   2580
ttttttaga acagttatga tatagttaga atagtttaaa ataaggagtg agaaaaagat   2640
gaaagaaaga tatggaacag tctataaagg ctctcagagg ctcatagacg aagaaagtgg   2700
agaagtcata gaggtagaca agttataccg taaacaaacg tctggtaact tcgtaaaggc   2760
atatatagtg caattaataa gtatgttaga tatgattggc ggaaaaaaac ttaaaatcgt   2820
taactatatc ctagataatg tccacttaag taacaataca atgatagcta caacaagaga   2880
aatagcaaaa gctacaggaa caagtctaca aacagtaata acaacactta aaatcttaga   2940
agaaggaaat attataaaaa gaaaaactgg agtattaatg ttaaaccctg aactactaat   3000
gagaggcgac gaccaaaaac aaaaatacct cttactcgaa tttgggaact ttgagcaaga   3060
ggcaaatgaa atagattgac ctcccaataa caccacgtag ttattgggag gtcaatctat   3120
gaaatgcgat taagggccgg ccagtgggca agttgaaaaa ttcacaaaaa tgtggtataa   3180
tatctttgtt cattagagcg ataaacttga atttgagagg gaacttagat ggtatttgaa   3240
aaaattgata aaaatagttg gaacagaaaa gagtattttg accactactt tgcaagtgta   3300
ccttgtacct acagcatgac cgttaaagtg gatatcacac aaataaagga aaagggaatg   3360
aaactatatc ctgcaatgct ttattatatt gcaatgattg taaaccgcca ttcagagttt   3420
```

-continued aggacggcaa tcaatcaaga tggtgaattg ggatatatg atgagatgat accaagctat 3480
acaatatttc acaatgatac tgaaacattt tccagccttt ggactgagtg taagtctgac 3540
tttaaatcat ttttagcaga ttatgaaagt gatacgcaac ggtatggaaa caatcataga 3600
atggaaggaa agccaaatgc tccggaaaac atttttaatg tatctatgat accgtggtca 3660
accttcgatg gctttaatct gaatttgcag aaaggatatg attatttgat tcctattttt 3720
actatgggga aatattataa agaagataac aaaattatac ttcctttggc aattcaagtt 3780
catcacgcag tatgtgacgg atttcacatt tgccgttttg taaacgaatt gcaggaattg 3840
ataaatagtt aacttcaggt ttgtctgtaa ctaaaaacaa gtatttaagc aaaaacatcg 3900
tagaaatacg gtgtttttg ttaccctaag tttaaactcc tttttgataa tctcatgacc 3960
aaaatccctt aacgtgagtt ttcgttccac tgagcgtcag accccgtaga aaagatcaaa 4020
ggatcttctt gagatccttt ttttctgcgc gtaatctgct gcttgcaaac aaaaaaacca 4080
ccgctaccag cggtggtttg tttgccggat caagagctac caactctttt tccgaaggta 4140
actggcttca gcagagcgca gataccaaat actgttcttc tagtgtagcc gtagttaggc 4200
caccacttca agaactctgt agcaccgcct acatacctcg ctctgctaat cctgttacca 4260
gtggctgctg ccagtggcga taagtcgtgt cttaccgggt tggactcaag acgatagtta 4320
ccggataagg cgcagcggtc gggctgaacg gggggttcgt gcacacagcc cagcttggag 4380
cgaacgacct acaccgaact gagataccta cagcgtgagc tatgagaaag cgccacgctt 4440
cccgaaggga gaaaggcgga caggtatccg gtaagcggca gggtcggaac aggagagcgc 4500
acgagggagc ttccaggggg aaacgcctgg tatctttata gtcctgtcgg gtttcgccac 4560
ctctgacttg agcgtcgatt tttgtgatgc tcgtcagggg ggcggagcct atggaaaaac 4620
gccagcaacg cggccttttt acggttcctg gccttttgct ggccttttgc tcacatgttc 4680
tttcctgcgt tatcccctga ttctgtggat aaccgtatta ccgcctttga gtgagctgat 4740
accgctcgcc gcagccgaac gaccgagcgc agcgagtcag tgagcgagga agcggaagag 4800
cgcccaatac gcagggccc 4819

<210> SEQ ID NO 13
<211> LENGTH: 1460
<212> TYPE: DNA
<213> ORGANISM: Clostridium autoethanogenum

<400> SEQUENCE: 13
ggctcaggac gaacgctggc ggcgtgctta acacatgcaa gtcgagcgat gaagctcctt 60
cgggagtgga ttagcggcgg acgggtgagt aacacgtggg taacctacct caaagagggg 120
gatagcctcc cgaaagggag attaataccg cataataatc agttttcaca tggagactga 180
tttaaaggag taatccgctt tgagatggac ccgcggcgca ttagctagtt ggtagggtaa 240
cggcctacca aggcgacgat gcgtagccga cctgagaggg tgatcggcca cattggaact 300
gagagacggt ccagactcct acgggaggca gcagtgggga atattgcaca atgggcgaaa 360
gcctgatgca gcaacgccgc gtgagtgaag aaggttttcg gattgtaaag ctctgtcttt 420
ggggacgata atgacggtac ccaaggagga agccacggct aactacgtgc cagcagccgc 480
ggtaatacgt aggtggcgag cgttgtccgg aattactggg cgtaaagagt gcgtaggcgg 540
atatttaagt gagatgtgaa atacccgggc ttaacccggg cactgcattt caaactggat 600
atctagagtg cgggagagga gaatggaatt cctagtgtag cggtgaaatg cgtagagatt 660

-continued

```
aggaagaaca ccagtggcga aggcgattct ctggaccgta actgacgctg aggcacgaaa    720

gcgtgggtag caaacaggat tagataccct ggtagtccac gccgtaaacg atgagtacta    780

ggtgtaggag gtatcgaccc cttctgtgcc gcagtaaaca caataagtac tccgcctggg    840

aagtacgatc gcaagattaa aactcaaagg aattgacggg ggcccgcaca agcagcggag    900

catgtggttt aattcgaagc aacgcgaaga accttacctg gacttgacat accctgaata    960

tcttagagat aagagaagcc cttcggggca gggatacagg tggtgcatgg ttgtcgtcag   1020

ctcgtgtcgt gagatgttag gttaagtcct gcaacgagcg caacccctgt tgttagttgc   1080

taacatttag ttgagcactc tagcaagact gccgcggtta acgcggagga aggtggggat   1140

gacgtcaaat catcatgccc cttatgtcca gggcaacaca cgtgctacaa tgggcagtac   1200

agagagaagc aagaccgcaa ggtggagcaa acctcaaaaa ctgcccccag ttcggattgc   1260

aggctgaaac tcgcctacat gaagttggag ttgctagtaa tcgcgaatca gaatgtcgcg   1320

gtgaatacgt tcccgggcct tgtacacacc gcccgtcaca ccatgagagc tggcaacacc   1380

cgaagtccgt agtctaactt aggaggacgc ggccgaaggt ggggttagta attggggtga   1440

agtcgtaaca aggtagccgt                                               1460
```

<210> SEQ ID NO 14
<211> LENGTH: 677
<212> TYPE: DNA
<213> ORGANISM: Clostridium autoethanogenum

<400> SEQUENCE: 14

```
aagaacmttg saaaktccst racsatggwg asycstwmgc kkagkrrmyy mgcrrysgac     60

gggtgagtma cacgtgggta acctaccycr rrgaggggga tagcctcccs aaagggagat    120

taataccgca taataatcag ttttcacatg gagaytgwtt taaaggagta atccgctttg    180

agatggaccc gcggcgcatt agctagttgg tagggtaacg gcctaccaag gcgackatgc    240

gtagccgacc tgagagggtg atcggccaca ttggaactga sagacggtcc asactcctac    300

gggaggcagc agtggggaat attgcacaat gggcgaaagc ctgatgcagc aacgccgcgt    360

gagtgaagaa ggttttcgga ttgtaaagct ctgtctttgg ggacgataat gacggtaccc    420

aaggaggaag ccacggstaa ctacgkgcca scakccgcgg taatacgtas gtggcgagcg    480

ttgtccggaa ttactgggcg taaakastgc gtakgcggat atttaaktga satgtgaaat    540

asccgggctt aaccygggyw ctgywtttca mactggatat ctakagtgcg ggagaggasa    600

atgkaattcy taktgtascg gtgaartgcs takasattak gaasaacacc mktggcgaak    660

gcgattckct ggaccgt                                                   677
```

<210> SEQ ID NO 15
<211> LENGTH: 720
<212> TYPE: DNA
<213> ORGANISM: Clostridium autoethanogenum

<400> SEQUENCE: 15

```
trarakkgak cyysgrtccc kkgrmswcst ggyarggtaa csgymwrcyw rgrysacgak     60

gcgtmgycra cctgaraggg tgatcggcca cmttggaact gagagacggt ccaractcct    120

acgggaggca gcagtgggga atattgcaca atgggcgaaa gcctgatgca gcaacgccgc    180

gtgagtgaag aaggttttcg gattgtaaag ctctgtcttt ggggacgata atgacggtmc    240

ccaaggagga agccacggct aactacgtgc cascagccgc ggtaatacgt aggtggcrag    300

cgttgtccgg aattactggg cgtaaagagt gcgtaggcgg atatttaagt gagatgtgaa    360
```

-continued atacccgggc ttaacccggg cactgcwttt caaactggat atctakagtg cgggagagga 420
gaatgkaatt cctagtgtag cggtgaaatg cgtakagatt aggaagaaca ccmgtggcga 480
akgcgattct ctggaccgta actgayrctg akgcacgaag cgtggggtak cawacakgat 540
tagatacyct ggtrstccac rccgtaaacg atgagtayta kgtgtakgag kwtcsacccc 600
cttctgtgcc ssmmtaraca ymmyaaktac tcccgcckcr aagtmsawcg cmagatkaaa 660
amtcrwmgsa rtkrwggggg ggcsgcmcta acatcgsast wrkwkkttsr attawarcaa 720

<210> SEQ ID NO 16
<211> LENGTH: 960
<212> TYPE: DNA
<213> ORGANISM: Clostridium autoethanogenum

<400> SEQUENCE: 16
taaaggagta atccgytttg agatggaccc gcggcgcatt agctwgttgg tagggtaacg 60
gcctaccmwg gcgackatgc gtagccgacc tgagagggtg atcggccaca ttggaactga 120
gagacggtcc aractcctac gggaggcagc agtggggaat attgcacaat gggcgaaagc 180
ctgatgcagc aacgccgcgt gagtgaagaa ggttttcgga ttgtaaagct ctgtctttgg 240
ggacgataat gacggtaccc aaggaggaag ccacggstaa ctacgtgcca scagccgcgg 300
taatacgtag gtggcgagcg ttgtccggaa ttactgggcg taaagagtgc gtaggcggat 360
atttaagtga gatgtgaaat acccgggctt aacccgggyw ctgcatttca aactggatat 420
ctagagtgcg ggagaggaga atggaattcc tagtgtagcg gtgaartgcg takagattak 480
gaagaacacc agtggcgaag gcgattctct ggaccgtrac tgacgctgag gcacgaaagc 540
gtgggtagca aacaggatta gataccctgg tagtccacrc cgtaaacgat gagtactakg 600
tgtaggaggt atcgacccct tctgtgccgc agtaaacaca ataagtacty ckcctgggaa 660
gtacgatcgc aagattaaaa ctcaasgaak tgacaggsgc ccgcacwagc akcgasyatg 720
tggtttattc gaagcacgcg aagaacctta cctggacttg acataccctg mwatctwtas 780
ataagagagc scttcgggtc aggatrcagt cgtgcatggt gtcgtcwgct cgtgtcrtga 840
gatgtagtar tctgcaacsa kcgyacyctg tggyagtgct acatgmtsag cmtctagcag 900
actgcgmgta sccgsagagy ggggatgacg tcgakcatca tgycctyagt cmcgyctacr 960

<210> SEQ ID NO 17
<211> LENGTH: 676
<212> TYPE: DNA
<213> ORGANISM: Clostridium autoethanogenum

<400> SEQUENCE: 17
atttkggsar aktccgkakg caaggtgasc cgtargcttg gatccyggga akksryrgsw 60
grgtamcysk kgkstwrswt mccssgraga rggggawags ctcccgaaag ggagattamt 120
accgcataat aatcagtttt cacatggaga ctgatttaaa ggagtaatcc gctttgagat 180
ggacccgcgg cgcattagct agttggtagg gtaacggcct accaaggcga ckatgcgtag 240
ccgacctgag agggtgatcg gccacwttgg aactgagaga cggtccaaac tcctacggga 300
ggcagcagtg gggaatattg cacaatgggc gaaagcctga tgcagcaacg ccgcgtgagt 360
gaagaaggtt ttcggattgt aaagctctgt ctttggggac gataatgacg gtacccmasg 420
aggargccmc ggsyaactac gkgccwscmk ccgcggtaat acrtaggtgg cragcgttgt 480
ccggaattac tgggcgtaaa kagtgcgtak gcggatattt aaktgagatg tgaaryascc 540

-continued gggcttaacc cgggcwctgy atttcwmayt ggatatctmk agtgcgggrg aggagaatgg 600
awgtyctakk gtamcsgtga artgcstaka satwmkgmas aacaycwstg gcgwarrcgr 660
ytcgswggac cgtawc 676

<210> SEQ ID NO 18
<211> LENGTH: 1040
<212> TYPE: DNA
<213> ORGANISM: Clostridium autoethanogenum

<400> SEQUENCE: 18
tagsaaaktc ytakrcaatg gtarycstwa gcttgkatrm krmwmgrsgg acgggtgagt 60
aacmckkggg taamctacyt crragarggg gatagcctcc csaaagggag attaataccg 120
cataataatc agttttcaca tggagactga tttaaaggag taatccgctt tgagatggac 180
ccgcggcgca ttagctagtt ggtagggtaa cggcctacca aggcgackat gcgtagccga 240
cctgagaggg tgatcggcca cattggaact gagagacggt ccagactcct acgggaggca 300
gcagtgggga atattgcaca atgggcgaaa gcctgatgca gcaacgccgc gtgagtgaag 360
aaggttttcg gattgtaaag ctctgtcttt ggggacgata atgacggtac ccaaggagga 420
rgccacggst aactacgkgc cascmkccgc ggtaatacgt asgtggcgag cgttgtccgg 480
aattactggg cgtaaagagt gcgtakgcgg atatttaagt gagatgtgaa atasccggsc 540
ttaacccggg cactgcattt camactggat atctakagtg cgggagagga saatgkratt 600
cctakkgtas cggtgaaatg cstatasatt akgaasaaca ccmktgkcga akgcgawtck 660
ctggaccrtr rctgacrcts akgcaygywa gcstsgstwk cwwrcmksat yatatacccy 720
ggkrgtcmcr wcrymwmcat sagtactakg tgtmkkaggt atckmcmcct yctytgcssc 780
mkwaraamaa yawkmwcytc csccysssgr rkwacaawcr mwakatkaat agwmatggsa 840
kkkamggssg gccsccswma catcysmkct rwtrktkwat ttcaykcamk ymmsmaamka 900
acctgkmytg rsmtasccyg cycysswwtw awctaagmam agcmtcscss tamgrgwkmr 960
gwsrygsstk ygytsrtggc tmtcgtcayy tmgsrymgar aratratwst awacsmwsms 1020
aamccmykyc ywycctkstk 1040

<210> SEQ ID NO 19
<211> LENGTH: 674
<212> TYPE: DNA
<213> ORGANISM: Clostridium autoethanogenum

<400> SEQUENCE: 19
ggggrtakcc tcccsaawgg garaytaatw ccgcataata atcagttttc acatggagac 60
tgatttaaag gagtaatccg ctttgagatg gacccgcggc gcattagcta gttggtaggg 120
taacggccta ccaaggcgac gatgcgtagc cgacctgaga gggtgatcgg scacattgga 180
actgagagac ggtccaract cctacgggag gcagcagtgg ggaatattgc acaatgggcg 240
aaagcctgat gcagcaacgc cgcgtgagtg aagaaggttt tcggattgta aagctctgtc 300
tttggggacg atratgacgg tacccaagga ggaagccacg gstaactacg tgccascakc 360
cgcggtaata cgtaggtggc gagcgttgtc cggaattact gggcgtaaak agtgcgtarg 420
cggatattta agtgagatgt gaaatasccg gscttaaccc gggcwctgca tttcwaactg 480
gatatctaka gtgcgggaga ggagwatkta wttcctagtg trscggtgaa atgsgkasam 540
atyakgmaga acmccagtgk cgaaggcgay tckstggacc ryractgamg ctsawgcwcg 600
maagcgwgss tagcaaasat gattagatay mcyggtagwc mcamcrmmaa csatgagkac 660

-continued trkgtgtmsk asgt 674

<210> SEQ ID NO 20
<211> LENGTH: 1226
<212> TYPE: DNA
<213> ORGANISM: Clostridium autoethanogenum

<400> SEQUENCE: 20
crgrwycttt mggatkgkwg acttgskggg ggtcagtwmc awatactkcm wawggwgggt 60
ttgtargttt atatccttca ttttctaccc attccctcra mtwakywwat wcaragatgt 120
taayyckraa tatgarcccc ttaaaacrga sttcsmacaa aggactccwg gyaakywtct 180
kgttcccttt acawtctcct twaysrraat ggmaakttct gyatcmttgc casawggatt 240
gwwttcascg ctkygwtaaa tagttattgg cttaccwmka aagtcmwtta caaaaatata 300
tataaagaaa gcaaagctac wkatwtyaaa ksattwaagg taaarmtaaa aatatwataa 360
aawwgaamtt atttttctc wtakstaawg ttacwtaata cgaggaggat ttataatgaa 420
aaaagtaata ggawttataa ryattgwmct atttgkactm ktagcacttc aatcctgtgc 480
kgcmkgakwa ggaartgymt yaagwaatra cmwwsawksw mgwgratctg cwggatwatt 540
tttatytkka tgkatgctka ttgctggaat aatakmmatr awaycawamy wwwktamagg 600
tatgacyata acagctatag katttwattt gttakctttt gttgyaggga twgctaaygw 660
tgggcatttt wcagatttgc awatttgrtc aaycwttaac twgatatttg ctggactatw 720
gatatttcat ttrctkaama wtaagmaatt atatwatakc agtggraaaa agwakaatca 780
tatrttgtaa ttatttttaa ttatgtkrrc aamwytgawa ttgwcacwga waacayctct 840
aaatgtttwr aatacatatg tttmaktakt gtgacakatw ctaatastak aaagwagaar 900
wtygctatrw watratgaca tagwggtgaa tgtaatgcsg mckctgwryc catatsacca 960
tgatrcgaat tmsagctsgg tacscsggrk atcctctrga stcgwcgtya ckcgtccatg 1020
kagatmwcga gcctggmgac atgcagctta gcwckggtcg tcatkttacw cgtcgtsact 1080
rsgtaaaacc atgacgtmcc rctgtcgcat gcwgcacrtc yccrtatcgt cagctrcgta 1140
wcgcgacyag ccgatcgatc gcctgccwcg atgccractg atgcatgcct gmcakacggc 1200
aywacaagtc taggcattac tggcca 1226

<210> SEQ ID NO 21
<211> LENGTH: 1236
<212> TYPE: DNA
<213> ORGANISM: Clostridium autoethanogenum

<400> SEQUENCE: 21
twwttwwacm ttactaaata atgacagaat aggtattatt ggacctaatg gaagtggtaa 60
atccactctt atgaatattt tarttcaaaa aattctgccg gacagcggca ctatagatat 120
aggtgaaaca gtaaagatag gatactattc tcagggaatt tctgatatgg atatgaacga 180
aagggtaatt gaatacatac gtgggacatc rraatatgcg tcaacttcat cgggtgaaaa 240
aakaaktgct tctgctgtac ttgaaaattt tttatttgaa ccttcagttc aatggactcc 300
ccttggaaaa ctktcaggag gagaacgaar aagattatat cttctaaaaa tactgatgaa 360
ttaccctaat gtacttttgc tggacgaacc aacaaatgat ctggatatag aaacacttac 420
aatcctagaa gattatatta acgattttga aggagctgtt atagctgtat ctcatgacag 480
gtacttcctt gacaaaacag ttgataaaat attttctttt gaaggaaacg gtaaaatcac 540

-continued

```
tcaatataca ggaaactatt cctattttca caaaactgca aaaatatcag aggaaaaaat    600

aagctctaag aaaaatacag ctaaaaacaa ctatragttg caaaaagaaa agcctctaaa    660

atttacctat gcagaacaaa tggagtttga caaaatagat gaggtaattg aacatctaga    720

aaaatctata tctgaaaaga aaatagaaat ggaagctgct tcatctgatt atgcacttct    780

tgaagatctc ttatccgaaa agaattcact ggaaaaagag ctagacgaaa agatggacag    840

gtggacttac ttaatgaact caatgaaaaa attgagcaag ataaaagcac tagacattgt    900

tattagcact gtctagtgct agcgccattc gccattcatg ctgcgcaact gtgggaaggg    960

cgatcggtgc ggcctcttcg ctaytacgcc agctggcgaa gggatgtgct gcaagscgat   1020

aagttggtac gccaggtttc cagtcacgac gtagwaaacg acgtcagtgc tagctgcatg   1080

tctgcagctc gagattctca tggascgtka cgtcgacytr asgatcctgg tactrrctcg   1140

attcgtatcm tggwcawtgg atmgcggcgc atamctcccc tatgcattaa catgcaattc   1200

acgtctacta tagagtctgt tccaaaatra acgcgt                              1236
```

<210> SEQ ID NO 22
<211> LENGTH: 1224
<212> TYPE: DNA
<213> ORGANISM: Clostridium autoethanogenum

<400> SEQUENCE: 22

```
gawtttttcm acttttataa catactaaat aatgacagaa taggtattat tggacctaat     60

ggaagtggta aatccactct tatgaatatt ttarttcaaa aaattctgcc ggacagcggc    120

actatagata taggtgaaac agtaaagata ggatactatt ctcagggaat ttctgatatg    180

gatatgaacg aaagggtaat tgaatacata cgtgggacat caraatatgc gtcaacttca    240

tcgggtgaaa aaataagtgc ttctgctgta cttgaaaatt ttttatttga accttcagtt    300

caatggactc cccttggaaa actttcagga ggagaacgaa raagattata tcttctaaaa    360

atactgatga attaccctaa tgtacttttg ctggacgaac caacaaatga tctggatata    420

gaaacactta caatcctaga agattatatt aacgattttg aaggagctgt tatagctgta    480

tctcatgaca ggtacttcct tgacaaaaca gttgataaaa tattttcttt tgaaggaaac    540

ggtaaaatca ctcaatatac aggaaactat tcctattttc acaaaactgc aaaaatatca    600

gaggaaaaaa taagctctaa gaaaaataca gctaaaaaca actataagtt gcaaaaagaa    660

aagcctctaa aatttaccta tgcagaacaa atggagtttg acaaaataga tgaggtaatt    720

gaacatctag aaaaatctat atctgaaaag aaaatagaaa tggaagctgc ttcatctgat    780

tatgcacttc ttgaagatct cttatccgaa aagaattcac tggaaaaaga gctagacgaa    840

aagatggaca ggtggactta cttaaatgaa ctcaatgaaa aaattgagca agataaaagc    900

actagacatt gttattagca ctgtctagtg ctagcgccat tcgccattca ggctgmgcaa    960

ctgtgggagg cgatcggtgc gggcctyttc gctattacgc cagctgcgaa aggggatgtg   1020

ctgcaagcga ttagttgggt aacsccaggc tttcccagtc mcgacgtgta aacgacgcag   1080

tgcagctgca tgtctgcagc tcgagatctc atgacgckac gtcgactcta rgatccctgt   1140

wcgagctcga ttcgaatcat gcawtggatc msggccgatc tgmccctakg cataacatgc   1200

aattcmcttt ctcattagaa aygt                                           1224
```

<210> SEQ ID NO 23
<211> LENGTH: 1120
<212> TYPE: DNA
<213> ORGANISM: Clostridium autoethanogenum

<400> SEQUENCE: 23

```
grrammttkw aawttaaraa attkcactta tracatacta aataatgaca gartaggkat      60
tattggacct aatggaagtg gtaaatccac tcttatgaat attttarttc aaaaaattct     120
gccsgacagc ggcactmtwk atataggtga aacagtaaag ataggatact attctcaggg     180
aatttctgat atggatatga acgaaagggk aattgaatac atacktggga catcrraata     240
tgcgtcaact tcrtcgggtg aaaaaakaag tgcttctgct gtacttgaaa attttttatt     300
tgaaccttca gttcaatgga ctycccttgg aaaamtktca ggaggagaac raaraagatt     360
atatcttcta aaaatactga tgaattaccc taatgtactt ttgctggacg aaccaacaaa     420
tgatctggat atagaaacac ttacmatcct agaagattat attwacgatt ttgaaggagc     480
tgttatagct gtrtctcatg acaggtactt ccwtgacaar acagttgatr aaatattttc     540
ttttgaagga aacggtaaaa tcactcaata tacasgaaac tattcctatt ttcacrraac     600
tgcawaaata tcagaggaaa aaatwagctc taagaaaaat acagctaaaa caactatrag     660
ttgcaaaaag aawagcctct aaatttacct atgcagaaca aatggagttt gacaaaatag     720
atgaggtaay tgaacatcta gaaaatctat atctgaaaga aaatagaatg gaagctgctt     780
catctgatta tgcacttctt garatctctt atccgaaaas rattcmctgg aaaagagcta     840
gacgaaagat ggwcagkkga cttactwaat gactcatgaa aatgakcara tawagcmcta     900
gamttgttat tagcactgtc trkgstagcg ccatcgcatt cagctgmgca actgtgggac     960
ggcgatcgtk cggctcytcg ctattacgcc agctggcaag ggaktgcctg caggcatagt    1020
gttacscwgc ttccagtccm srtkaamgac gcakgccagc tgcatgtygc agcctggatc    1080
catggacgka gctcaacyta agaatccggt ccgrcactgt                          1120
```

<210> SEQ ID NO 24
<211> LENGTH: 1210
<212> TYPE: DNA
<213> ORGANISM: Clostridium autoethanogenum

<400> SEQUENCE: 24

```
traaaawttk tcactkkata acatactaaa taatgmcaga rtaggtatta ttggacctaa      60
tggaagtggt aawtccactc ttatgaatat tttarttcaa aaaattctgc cggacagcgg     120
cacymtagat ataggtgaaa cagyaaagat aggatactat tctcagggaa tttctgatat     180
ggatatgaac saaagggkaa ttgaatacat mcktgggaca tcrraakatg cstcaacttc     240
rtcgggtgaa aaaakaaktg cttctgctgt acttgaaaat tttttatttg aaccttcagt     300
tcaatggact ccccttggaa aactktcarg aggagaacga araarattat atcttctaaa     360
aatactgatg aattacccta atgtactttt gctggacgaa ccaacaaatg atctggatat     420
agaaacactt acaatcctag aagattatat taacgatttt gaaggagctg ttatagctgt     480
rtctcatgac aggtacttcc ttgacaarac agttgataaa atattttctt ttgaaggaaa     540
cggtaaratc actcaatata caggaaacta ttcctatttt cacaaaactg cawaaatatc     600
agaggaaaaa ataagctcta agaaaaatac agctaaaaac aackatragt tgcaaaaaga     660
aaagcctcta aratttacct atgcagaaca aatggagttt gacaaaatag atgaggtaat     720
tgaacatcta gaaaaatcta tatctgaaaa gaaaatagaa atggaagctg cttcatctga     780
ttatgcactt cttgaagatc tcttatccga aaagaattca ctggaaaaag agctagacka     840
aaagatggac aggtggactt acttaaatga actcaatgaa raaattgagc aagataaaag     900
```

-continued

```
cactagacat tgttattagc actgtctagt gctagcgcca ttcgccattm agctgmgcac    960

tgtgggaagg cgatcggtgc gggctctcgc tatacgcagc tggcgaaggg gatgtgctgc   1020

agcgatagtg gtacgcakgt ttccagtcac gacgwgaaaa cgacgtcagt gcwagctgca   1080

kkctgcagct cgratctcat ggacgctkac gtcgayctra cgatcccwgt wckrctcgat   1140

cgtatcctgt cawtgatacc gggcgcatac atgccctagt cagttaacat gcaagtckac   1200

cttctcagtg                                                          1210
```

<210> SEQ ID NO 25
<211> LENGTH: 1206
<212> TYPE: DNA
<213> ORGANISM: Clostridium autoethanogenum

<400> SEQUENCE: 25

```
aamywaatwr ggwggggttt sycaakktta tatcsttcat kttctaccca ytccctcrac     60

twagcwwatw carardatgtt arttckraat atgagcccct taaaacrgac ttcscacaaa    120

ggactccwgg yaakywyctk gwtcccttta cawtctcctt waycgraakg gmaakktctg    180

yatcyttgcc agaaggattg wwttcagcgc tgygwtaaat agttattggc ttrccwmkaa    240

agtcaattac aaaaatatat ataaagaaag caaagctacw tatwtyamwk srttwaaggt    300

aaarmtaaaa atattataaa awtgaamttw ttttttctcw takctaaagt tacwtaatac    360

gaggaggatt wataatgaaa aaagtaatwg gaattataar yattgwmcww tttgtactmk    420

tagcacttca atcytgtgck gcakgakwwg gaartgymty awgwaatrac mwwsawkswa    480

gwgratctgc wggatwattt ttatytgkat gkatgctkat tgctggaata atagcaatra    540

waycawamyw wwktamaggt atswctataa cagctatagk atwtwatttg ttakcttttg    600

ttgyagggat wgctaaygwt gggcattttw cagattwgcm wmtttgrtca aycwttrmct    660

tgatatttgc tggactatwg atattkmatt trctkaamaw yaagcaatta tatwatakca    720

gwggraaaaa gtagaatcat atrttgtaat tatttttaat tatgttgrca amtytgawmy    780

trwcacwgaw acmcctmtaa atgttttram tacatrtgtt waaktwtkgt gacakatwct    840

aatagtakra agwagaarwt ygctatgtwa tratgacata gwggtgaatg taatgcggms    900

gctgwrtcca tatsaccatg atrcgamtyc gagctcggta csssggrgat sctctrgast    960

ckacgtcack cgtccatgka gatcwcgagg ctgcmgwcwg cagmtrcwct ggtmcgtcga   1020

tktaywcgtc gtgactrsga aaaccatgac gtmctrctay ggcatgcwgc artcyccgwt   1080

tckcagstag gtawagcgac akgcgatcsm aygcccttgc cacrttgcca tctgaatgyg   1140

akgcctgaca kmcgkccmta cagctagcat gactgaattt catgackcyt agaagacmct   1200

gtgaca                                                              1206
```

<210> SEQ ID NO 26
<211> LENGTH: 1232
<212> TYPE: DNA
<213> ORGANISM: Clostridium autoethanogenum

<400> SEQUENCE: 26

```
accymwaaat aattgmcaga ataggtatta ttggacctaa tggaagtggt aaatccactc     60

ttatgaatat tttarttcaa aaaattctgc cggacagcgg cactmtagat ataggtgaaa    120

cagtaaagat aggatactat tctcagggaa tttctgatat ggatatgaac gaaagggtaa    180

ttgaatacat acktgggaca tcrraakatg cstcaacttc atcgggtgaa aaaataaktg    240

cttctgctgt acttgaaaat tttttatttg aaccttcagt tcaatggact ccccttggaa    300
```

-continued

```
aactktcarg aggagaacra araarattat atcttctaaa aatactgatg aattacccta    360

atgtactttt gctggacgaa ccaacaaatg atctggatat agaaacactt acaatcctag    420

aagattatat taacgatttt gaaggagctg ttatagctgt atctcatgac aggtacttcc    480

ttgacaaaac asttgataaa atattttctt ttgaaggaaa cggtwaaatc actcaatata    540

caggaaacta ttcctatttt cacaaaactg caaaaatatc agaggaaaaa ataagctcta    600

agaaaaatac agctaaaaac aactatragt tgcwaaaaga aaagcctcta aaatttacct    660

atgcagaaca aatggagttt gacaaartag atgaggtaat tgaacatcta gaaaaatcta    720

tatctgaaaa gaaaatagaa atggaagctg cttcatctga ttatgcactt cttgaagatc    780

tcttatccga aaasaattca ctggaaaaag agctagacga aaagatggac aggtggactt    840

acttawatga actcatgaaa aaatwgagca gataaaagca ctagacattg ttattagcac    900

tgtstagtgc tagcgccatt cgmcattcag ctgmgcacwg ytgggaaggg cgatmgygck    960

ggcctcttcg ctwytacgyc akctggcraa ggggatgtgc wgcaagmcga tagttgggta   1020

acgcaggwtw tcccagtcac kacgtagtam aygacgtcmg trctagctgc atgtctgcag   1080

cytsrgatct catgtacgct gacgtcgacy trrmggatcc cwggtacyga gctcgattcg   1140

tatcatgayr atggatgmgc ggcgcataac tcccttatgc mttaacrttc aattsacgtc   1200

ttcwtataga tckctcatag ttgarcmccg gg                                 1232
```

<210> SEQ ID NO 27
<211> LENGTH: 37
<212> TYPE: DNA
<213> ORGANISM: Artificial sequence
<220> FEATURE:
<223> OTHER INFORMATION: Synthetic primer

<400> SEQUENCE: 27

```
ccgaattcgt cgacaacaga gtttgatcct ggctcag                              37
```

<210> SEQ ID NO 28
<211> LENGTH: 37
<212> TYPE: DNA
<213> ORGANISM: Artificial sequence
<220> FEATURE:
<223> OTHER INFORMATION: Synthetic primer

<400> SEQUENCE: 28

```
cccgggatcc aagcttacgg ctaccttgtt acgactt                              37
```

<210> SEQ ID NO 29
<211> LENGTH: 25
<212> TYPE: DNA
<213> ORGANISM: Artificial sequence
<220> FEATURE:
<223> OTHER INFORMATION: Synthetic peptide

<400> SEQUENCE: 29

```
ttgctgtagt cactgaactg gaaaa                                            25
```

<210> SEQ ID NO 30
<211> LENGTH: 25
<212> TYPE: DNA
<213> ORGANISM: Artificial sequence
<220> FEATURE:
<223> OTHER INFORMATION: Synthetic peptide

<400> SEQUENCE: 30
aatcaggaca cctaaatcca accac 25

<210> SEQ ID NO 31
<211> LENGTH: 1940
<212> TYPE: DNA
<213> ORGANISM: artificial sequence
<220> FEATURE:
<223> OTHER INFORMATION: novel methyltransferase gene fused with an inducible lac Promoter

<400> SEQUENCE: 31
gcggccgcgc aacgcaatta atgtgagtta gctcactcat taggcacccc aggctttaca 60
ctttatgctt ccggctcgta tgttgtgtgg aattgtgagc ggataacaat ttcacacagg 120
aaacacatat gtttccgtgc aatgcctata tcgaatatgg tgataaaaat atgaacagct 180
ttatcgaaga tgtggaacag atctacaact tcattaaaaa gaacattgat gtggaagaaa 240
agatgcattt cattgaaacc tataaacaga aaagcaacat gaagaaagag attagcttta 300
gcgaagaata ctataaacag aagattatga acggcaaaaa tggcgttgtg tacaccccgc 360
cggaaatggc ggcctttatg gttaaaaatc tgatcaacgt taacgatgtt attggcaatc 420
cgtttattaa aatcattgac ccgagctgcg gtagcggcaa tctgatttgc aaatgttttc 480
tgtatctgaa tcgcatcttt attaagaaca ttgaggtgat taacagcaaa aataacctga 540
atctgaaact ggaagacatc agctaccaca tcgttcgcaa caatctgttt ggcttcgata 600
ttgacgaaac cgcgatcaaa gtgctgaaaa ttgatctgtt tctgatcagc aaccaattta 660
gcgagaaaaa tttccaggtt aaagactttc tggtggaaaa tattgatcgc aaatatgacg 720
tgttcattgg taatccgccg tatatcggtc acaaaagcgt ggacagcagc tacagctacg 780
tgctgcgcaa aatctacggc agcatctacc gcgacaaagg cgatatcagc tattgtttct 840
ttcagaagag cctgaaatgt ctgaaggaag gtggcaaact ggtgtttgtg accagccgct 900
acttctgcga gagctgcagc ggtaaagaac tgcgtaaatt cctgatcgaa aacacgagca 960
tttacaagat cattgatttt tacggcatcc gcccgttcaa acgcgtgggt atcgatccga 1020
tgattatttt tctggttcgt acgaagaact ggaacaataa cattgaaatt attcgcccga 1080
acaagattga aaagaacgaa aagaacaaat tcctggatag cctgttcctg gacaaaagcg 1140
aaaagtgtaa aaagtttagc attagccaga aaagcattaa taacgatggc tgggttttcg 1200
tggacgaagt ggagaaaaac attatcgaca aaatcaaaga gaaaagcaag ttcattctga 1260
aagatatttg ccatagctgt caaggcatta tcaccggttg tgatcgcgcc tttattgtgg 1320
accgtgatat catcaatagc cgtaagatcg aactgcgtct gattaaaccg tggattaaaa 1380
gcagccatat ccgtaagaat gaagttatta agggcgaaaa attcatcatc tatagcaacc 1440
tgattgagaa tgaaaccgag tgtccgaatg cgattaaata tatcgaacag tacaagaaac 1500
gtctgatgga gcgccgcgaa tgcaaaaagg gcacgcgtaa gtggtatgaa ctgcaatggg 1560
gccgtaaacc ggaaatcttc gaagaaaaga aaattgtttt cccgtataaa agctgtgaca 1620
atcgttttgc actggataag ggtagctatt ttagcgcaga catttatagc ctggttctga 1680
agaaaaatgt gccgttcacc tatgagatcc tgctgaatat cctgaatagc ccgctgtacg 1740
agttttactt taagaccttc gcgaaaaagc tgggcgagaa tctgtacgag tactatccga 1800
acaacctgat gaagctgtgc atcccgagca tcgatttcgg cggtgagaac aatattgaga 1860
aaaagctgta tgatttcttt ggtctgacgg ataaagaaat tgagattgtg gagaagatca 1920
aagataactg ctaagaattc 1940

-continued

<210> SEQ ID NO 32
<211> LENGTH: 601
<212> TYPE: PRT
<213> ORGANISM: Clostridium autoethanogenum

<400> SEQUENCE: 32

```
Met Phe Pro Cys Asn Ala Tyr Ile Glu Tyr Gly Asp Lys Asn Met Asn
1               5                   10                  15

Ser Phe Ile Glu Asp Val Glu Gln Ile Tyr Asn Phe Ile Lys Lys Asn
            20                  25                  30

Ile Asp Val Glu Glu Lys Met His Phe Ile Glu Thr Tyr Lys Gln Lys
        35                  40                  45

Ser Asn Met Lys Lys Glu Ile Ser Phe Ser Glu Glu Tyr Tyr Lys Gln
    50                  55                  60

Lys Ile Met Asn Gly Lys Asn Gly Val Val Tyr Thr Pro Pro Glu Met
65                  70                  75                  80

Ala Ala Phe Met Val Lys Asn Leu Ile Asn Val Asn Asp Val Ile Gly
                85                  90                  95

Asn Pro Phe Ile Lys Ile Ile Asp Pro Ser Cys Gly Ser Gly Asn Leu
            100                 105                 110

Ile Cys Lys Cys Phe Leu Tyr Leu Asn Arg Ile Phe Ile Lys Asn Ile
        115                 120                 125

Glu Val Ile Asn Ser Lys Asn Asn Leu Asn Leu Lys Leu Glu Asp Ile
    130                 135                 140

Ser Tyr His Ile Val Arg Asn Asn Leu Phe Gly Phe Asp Ile Asp Glu
145                 150                 155                 160

Thr Ala Ile Lys Val Leu Lys Ile Asp Leu Phe Leu Ile Ser Asn Gln
                165                 170                 175

Phe Ser Glu Lys Asn Phe Gln Val Lys Asp Phe Leu Val Glu Asn Ile
            180                 185                 190

Asp Arg Lys Tyr Asp Val Phe Ile Gly Asn Pro Pro Tyr Ile Gly His
        195                 200                 205

Lys Ser Val Asp Ser Ser Tyr Ser Tyr Val Leu Arg Lys Ile Tyr Gly
    210                 215                 220

Ser Ile Tyr Arg Asp Lys Gly Asp Ile Ser Tyr Cys Phe Phe Gln Lys
225                 230                 235                 240

Ser Leu Lys Cys Leu Lys Glu Gly Gly Lys Leu Val Phe Val Thr Ser
                245                 250                 255

Arg Tyr Phe Cys Glu Ser Cys Ser Gly Lys Glu Leu Arg Lys Phe Leu
            260                 265                 270

Ile Glu Asn Thr Ser Ile Tyr Lys Ile Ile Asp Phe Tyr Gly Ile Arg
        275                 280                 285

Pro Phe Lys Arg Val Gly Ile Asp Pro Met Ile Ile Phe Leu Val Arg
    290                 295                 300

Thr Lys Asn Trp Asn Asn Asn Ile Glu Ile Ile Arg Pro Asn Lys Ile
305                 310                 315                 320

Glu Lys Asn Glu Lys Asn Lys Phe Leu Asp Ser Leu Phe Leu Asp Lys
                325                 330                 335

Ser Glu Lys Cys Lys Lys Phe Ser Ile Ser Gln Lys Ser Ile Asn Asn
            340                 345                 350

Asp Gly Trp Val Phe Val Asp Glu Val Glu Lys Asn Ile Ile Asp Lys
        355                 360                 365

Ile Lys Glu Lys Ser Lys Phe Ile Leu Lys Asp Ile Cys His Ser Cys
    370                 375                 380
```

```
Gln Gly Ile Ile Thr Gly Cys Asp Arg Ala Phe Ile Val Asp Arg Asp
385                 390                 395                 400

Ile Ile Asn Ser Arg Lys Ile Glu Leu Arg Leu Ile Lys Pro Trp Ile
                405                 410                 415

Lys Ser Ser His Ile Arg Lys Asn Glu Val Ile Lys Gly Glu Lys Phe
            420                 425                 430

Ile Ile Tyr Ser Asn Leu Ile Glu Asn Glu Thr Glu Cys Pro Asn Ala
        435                 440                 445

Ile Lys Tyr Ile Glu Gln Tyr Lys Lys Arg Leu Met Glu Arg Arg Glu
    450                 455                 460

Cys Lys Lys Gly Thr Arg Lys Trp Tyr Glu Leu Gln Trp Gly Arg Lys
465                 470                 475                 480

Pro Glu Ile Phe Glu Glu Lys Lys Ile Val Phe Pro Tyr Lys Ser Cys
                485                 490                 495

Asp Asn Arg Phe Ala Leu Asp Lys Gly Ser Tyr Phe Ser Ala Asp Ile
            500                 505                 510

Tyr Ser Leu Val Leu Lys Lys Asn Val Pro Phe Thr Tyr Glu Ile Leu
        515                 520                 525

Leu Asn Ile Leu Asn Ser Pro Leu Tyr Glu Phe Tyr Phe Lys Thr Phe
    530                 535                 540

Ala Lys Lys Leu Gly Glu Asn Leu Tyr Glu Tyr Tyr Pro Asn Asn Leu
545                 550                 555                 560

Met Lys Leu Cys Ile Pro Ser Ile Asp Phe Gly Gly Glu Asn Asn Ile
                565                 570                 575

Glu Lys Lys Leu Tyr Asp Phe Phe Gly Leu Thr Asp Lys Glu Ile Glu
            580                 585                 590

Ile Val Glu Lys Ile Lys Asp Asn Cys
        595                 600
```

<210> SEQ ID NO 33
<211> LENGTH: 2781
<212> TYPE: DNA
<213> ORGANISM: Artificial sequence
<220> FEATURE:
<223> OTHER INFORMATION: Synthetic plasmid

<400> SEQUENCE: 33

```
tttgccacct gacgtctaag aaaaggaata ttcagcaatt tgcccgtgcc gaagaaaggc      60

ccacccgtga aggtgagcca gtgagttgat tgctacgtaa ttagttagtt agcccttagt     120

gactcgtaat acgactcact atagggctcg agtctagaga attcgatatc acccgggaac     180

tagtctgcag ccctttagtg agggttaatt ggagtcacta agggttagtt agttagatta     240

gcagaaagtc aaaagcctcc gaccggaggc ttttgactaa aacttccctt ggggttatca     300

ttggggctca ctcaaaggcg gtaatcagat aaaaaaaatc cttagctttc gctaaggatg     360

atttctgcta gagatggaat agactggatg gaggcggata aagttgcagg accacttctg     420

cgctcggccc ttccggctgg ctggtttatt gctgataaat ctggagccgg tgagcgtggg     480

tctcgcggta tcattgcagc actggggcca gatggtaagc cctcccgtat cgtagttatc     540

tacacgacgg ggagtcaggc aactatggat gaacgaaata gacagatcgc tgagataggt     600

gcctcactga ttaagcattg gtaactgtca gaccaagttt actcatatat actttagatt     660

gatttaaaac ttcattttta atttaaaagg atctaggtga agatcctttt tgataatctc     720

atgaccaaaa tcccttaacg tgagttttcg ttccactgag cgtcagaccc cttaataaga     780
```

-continued

```
tgatcttctt gagatcgttt tggtctgcgc gtaatctctt gctctgaaaa cgaaaaaacc    840

gccttgcagg gcggtttttc gaaggttctc tgagctacca actctttgaa ccgaggtaac    900

tggcttggag gagcgcagtc accaaaactt gtcctttcag tttagcctta accggcgcat    960

gacttcaaga ctaactcctc taaatcaatt accagtggct gctgccagtg gtgcttttgc   1020

atgtctttcc gggttggact caagacgata gttaccggat aaggcgcagc ggtcggactg   1080

aacggggggt tcgtgcatac agtccagctt ggagcgaact gcctacccgg aactgagtgt   1140

caggcgtgga atgagacaaa cgcggccata acagcggaat gacaccggta aaccgaaagg   1200

caggaacagg agagcgcacg agggagccgc caggggaaac gcctggtatc tttatagtcc   1260

tgtcgggttt cgccaccact gatttgagcg tcagatttcg tgatgcttgt caggggggcg   1320

gagcctatgg aaaaacggct ttgccgcggc cctctcactt ccctgttaag tatcttcctg   1380

gcatcttcca ggaaatctcc gccccgttcg taagccattt ccgctcgccg cagtcgaacg   1440

accgagcgta gcgagtcagt gagcgaggaa gcggaatata tcctgtatca catattctgc   1500

tgacgcaccg gtgcagcctt ttttctcctg ccacatgaag cacttcactg acaccctcat   1560

cagtgccaac atagtaagcc agtatacact ccgctagcgc tgaggtctgc ctcgtgaaga   1620

aggtgttgct gactcatacc aggcctgaat cgccccatca tccagccaga aagtgaggga   1680

gccacggttg atgagagctt tgttgtaggt ggaccagttg gtgattttga acttttgctt   1740

tgccacggaa cggtctgcgt tgtcgggaag atgcgtgatc tgatccttca actcagcaaa   1800

agttcgattt attcaacaaa gccacgttgt gtctcaaaat ctctgatgtt acattgcaca   1860

agataaaaat atatcatcat gaacaataaa actgtctgct tacataaaca gtaatacaag   1920

gggtgtttac tagaggttga tcgggcacgt aagaggttcc aactttcacc ataatgaaat   1980

aagatcacta ccgggcgtat tttttgagtt atcgagattt tcaggagcta aggaagctaa   2040

aatggagaaa aaaatcacgg gatataccac cgttgatata tcccaatggc atcgtaaaga   2100

acattttgag gcatttcagt cagttgctca atgtacctat aaccagaccg ttcagctgga   2160

tattacggcc tttttaaaga ccgtaaagaa aaataagcac aagttttatc cggcctttat   2220

tcacattctt gcccgcctga tgaacgctca cccggagttt cgtatggcca tgaaagacgg   2280

tgagctggtg atctgggata gtgttcaccc ttgttacacc gttttccatg agcaaactga   2340

aacgttttcg tccctctgga gtgaatacca cgacgatttc cggcagtttc tccacatata   2400

ttcgcaagat gtggcgtgtt acggtgaaaa cctggcctat ttccctaaag ggtttattga   2460

gaatatgttt tttgtctcag ccaatccctg ggtgagtttc accagttttg atttaaacgt   2520

ggccaatatg gacaacttct tcgcccccgt tttcacgatg ggcaaatatt atacgcaagg   2580

cgacaaggtg ctgatgccgc tggcgatcca ggttcatcat gccgtttgtg atggcttcca   2640

tgtcggccgc atgcttaatg aattacaaca gtactgtgat gagtggcagg gcggggcgta   2700

ataatactag ctccggcaaa aaaacgggca aggtgtcacc accctgccct tttctttaa    2760

aaccgaaaag attacttcgc g                                              2781
```

<210> SEQ ID NO 34
<211> LENGTH: 351
<212> TYPE: PRT
<213> ORGANISM: Clostridium autoethanogenum

<400> SEQUENCE: 34

```
Met Lys Gly Phe Ala Met Leu Gly Ile Asn Lys Leu Gly Trp Ile Glu
1               5                   10                  15
```

-continued

```
Lys Lys Asn Pro Val Pro Gly Pro Tyr Asp Ala Ile Val His Pro Leu
            20                  25                  30

Ala Val Ser Pro Cys Thr Ser Asp Ile His Thr Val Phe Glu Gly Ala
        35                  40                  45

Leu Gly Asn Arg Glu Asn Met Ile Leu Gly His Glu Ala Val Gly Glu
    50                  55                  60

Ile Ala Glu Val Gly Ser Glu Val Lys Asp Phe Lys Val Gly Asp Arg
65                  70                  75                  80

Val Ile Val Pro Cys Thr Thr Pro Asp Trp Arg Ser Leu Glu Val Gln
                85                  90                  95

Ala Gly Phe Gln Gln His Ser Asn Gly Met Leu Ala Gly Trp Lys Phe
            100                 105                 110

Ser Asn Phe Lys Asp Gly Val Phe Ala Asp Tyr Phe His Val Asn Asp
        115                 120                 125

Ala Asp Met Asn Leu Ala Ile Leu Pro Asp Glu Ile Pro Leu Glu Ser
    130                 135                 140

Ala Val Met Met Thr Asp Met Met Thr Thr Gly Phe His Gly Ala Glu
145                 150                 155                 160

Leu Ala Asp Ile Lys Met Gly Ser Ser Val Val Val Ile Gly Ile Gly
                165                 170                 175

Ala Val Gly Leu Met Gly Ile Ala Gly Ser Lys Leu Arg Gly Ala Gly
            180                 185                 190

Arg Ile Ile Gly Val Gly Ser Arg Pro Val Cys Val Glu Thr Ala Lys
        195                 200                 205

Phe Tyr Gly Ala Thr Asp Ile Val Asn Tyr Lys Asn Gly Asp Ile Val
    210                 215                 220

Glu Gln Ile Met Asp Leu Thr His Gly Lys Gly Val Asp Arg Val Ile
225                 230                 235                 240

Met Ala Gly Gly Gly Ala Glu Thr Leu Ala Gln Ala Val Thr Met Val
                245                 250                 255

Lys Pro Gly Gly Val Ile Ser Asn Ile Asn Tyr His Gly Ser Gly Asp
            260                 265                 270

Thr Leu Pro Ile Pro Arg Val Gln Trp Gly Cys Gly Met Ala His Lys
        275                 280                 285

Thr Ile Arg Gly Gly Leu Cys Pro Gly Gly Arg Leu Arg Met Glu Met
    290                 295                 300

Leu Arg Asp Leu Val Leu Tyr Lys Arg Val Asp Leu Ser Lys Leu Val
305                 310                 315                 320

Thr His Val Phe Asp Gly Ala Glu Asn Ile Glu Lys Ala Leu Leu Leu
                325                 330                 335

Met Lys Asn Lys Pro Lys Asp Leu Ile Lys Ser Val Val Thr Phe
            340                 345                 350
```

<210> SEQ ID NO 35
<211> LENGTH: 1056
<212> TYPE: DNA
<213> ORGANISM: Clostridium autoethanogenum

<400> SEQUENCE: 35

```
atgaaaggtt ttgcaatgtt aggtattaac aaattaggat ggattgaaaa gaaaaaccca      60

gtgccaggtc cttatgatgc gattgtacat cctctagctg tatccccatg tacatcagat     120

atacatacgg tttttgaagg agcacttggt aatagggaaa atatgatttt aggccatgaa     180

gctgtaggtg aaatagccga agttggcagc gaagttaaag attttaaagt tggcgataga     240
```

-continued

```
gttatcgtac catgcacaac acctgactgg agatctttag aagtccaagc tggttttcag    300

cagcattcaa acggtatgct tgcaggatgg aagttttcca attttaaaga cggtgtattt    360

gcagattact ttcatgtaaa cgatgcagat atgaatcttg ccatactccc agatgaaata    420

cctttagaaa gtgcagttat gatgacagac atgatgacta ctggttttca tggagcagaa    480

cttgcagaca taaaaatggg ctccagcgtt gtagtaattg gtataggagc tgttggatta    540

atgggaatag ccggttccaa acttcgagga gcaggcagaa ttatcggtgt tggaagcaga    600

cctgtttgtg ttgaaacagc taaattttat ggagcaactg atattgtaaa ttataaaaat    660

ggtgatatag ttgaacaaat catggactta actcatggta aaggtgtaga ccgtgtaatc    720

atggcaggcg gtggtgctga aacactagca caagcagtaa ctatggttaa acctggcggc    780

gtaatttcta acatcaacta ccatggaagc ggtgatactt taccaatacc tcgtgttcaa    840

tggggctgcg gcatggctca caaaactata agaggaggat tatgccccgg cggacgtctt    900

agaatggaaa tgctaagaga tcttgttcta tataaacgtg ttgatttgag taaacttgtt    960

actcatgtat ttgatggtgc agaaaatatt gaaaaggccc ttttgcttat gaaaaataag   1020

ccaaaagatt taattaaatc agtagttaca ttctaa                             1056
```

<210> SEQ ID NO 36
<211> LENGTH: 1056
<212> TYPE: DNA
<213> ORGANISM: Clostridium ljungdahlii

<400> SEQUENCE: 36

```
atgaaaggtt ttgcaatgtt aggtattaac aaattaggat ggattgaaaa gaaaaaccca     60

gtgccaggtc cttatgatgc gattgtacat cctctagctg tatccccatg tacatcagat    120

atacatacgg tttttgaagg agcacttggt aatagggaaa atatgatttt aggccatgaa    180

gctgtaggtg aaatagccga agttggcagc gaagttaaag attttaaagt tggcgataga    240

gttatcgtac catgcacaac acctgactgg agatctttag aagtccaagc tggttttcag    300

cagcattcaa acggtatgct tgcaggatgg aagttttcca attttaaaga tggtgtattt    360

gcagattact ttcatgtaaa cgatgcagat atgaatcttg ccatactccc agatgaaata    420

cctttagaaa gtgcagttat gatgacagac atgatgacta ctggttttca tggagcagaa    480

cttgcagaca taaaaatggg ctccagcgtt gtagtaattg gtataggagc tgttggatta    540

atgggaatag ccggttccaa acttcgagga gcaggcagaa ttatcggtgt tggaagcaga    600

cctgtttgtg ttgaaacagc taaattttat ggagcaactg atattgtaaa ttataaaaat    660

ggtgatatag ttgaacaaat catggactta actcatggta aaggtgtaga ccgtgtaatc    720

atggcaggcg gtggtgctga aacactagca caagcagtaa ctatggttaa acctggcggc    780

gtaatttcta acatcaacta ccatggaagc ggtgatactt taccaatacc tcgtgttcaa    840

tggggctgcg gcatggctca caaaactata agaggaggat tatgccccgg cggacgtctt    900

agaatggaaa tgctaagaga tcttgttcta tataaacgtg ttgatttgag taaacttgtt    960

actcatgtat ttgatggtgc agaaaatatt gaaaaggccc ttttgcttat gaaaaataag   1020

ccaaaagatt taattaaatc agtagttaca ttctaa                             1056
```

<210> SEQ ID NO 37
<211> LENGTH: 1056
<212> TYPE: DNA
<213> ORGANISM: Clostridium ragsdalei

<400> SEQUENCE: 37

```
atgaaaggtt ttgcaatgtt aggtattaac aagttaggat ggattgaaaa gaaaaaccca     60
gtaccaggtc cttatgatgc gattgtacat cctctagctg tatccccatg tacatcagat    120
atacatacgg tttttgaagg agcacttggt aatagggaaa atatgatttt aggtcacgaa    180
gctgtaggtg aaatagctga agttggcagt gaagttaaag attttaaagt tggcgataga    240
gttatcgtac catgcacaac acctgactgg agatccttag aagtccaagc tggttttcaa    300
cagcattcaa acggtatgct tgcaggatgg aagttttcca attttaaaga cggtgtattt    360
gcagattact ttcatgtaaa cgatgcagat atgaatcttg caatacttcc agatgaaata    420
cctttagaaa gtgcagttat gatgacagac atgatgacta ctggttttca tggggcagaa    480
cttgctgaca taaaaatggg ttccagtgtt gtcgtaattg gtataggagc tgttggatta    540
atgggaatag ccggttccaa acttcgagga gcaggtagaa ttatcggtgt tggaagcaga    600
cccgtttgtg ttgaaacagc taaattttat ggagcaactg atattgtaaa ttataaaaat    660
ggtgatatag ttgaacaaat aatggactta actcatggta aaggtgtaga ccgtgtaatc    720
atggcaggcg gtggtgctga aacactagca caagcagtaa ctatggttaa acctggcggc    780
gtaatttcta acatcaacta ccatggaagc ggtgatactt tgccaatacc tcgtgttcaa    840
tggggctgcg gcatggctca caaaactata agaggagggt tatgtcccgg cggacgtctt    900
agaatggaaa tgctaagaga ccttgttcta tataaacgtg ttgatttgag caaacttgtt    960
actcatgtat ttgatggtgc agaaaatatt gaaaaggccc ttttgcttat gaaaaataag   1020
ccaaaagatt taattaaatc agtagttaca ttctaa                             1056
```

<210> SEQ ID NO 38
<211> LENGTH: 1230
<212> TYPE: DNA
<213> ORGANISM: Clostridium autoethanogenum

<400> SEQUENCE: 38

```
atgaacaatt taaaggaaga agcattaaag tttcataaag aacatgaagg taaaatagca     60
cttaaaagta aagtatctgt taaaactaga gaggacctag gcttagcata tactccaggt    120
gttgctgaac catgtcttga aatcaacagg gactataata cgttatacga ttatacttct    180
aagggaaatt atgtagcagt agtaactaac ggcagtgcag ttttgggact tggaaatata    240
ggtgctgcag ctggcttacc tgtaatggaa ggtaaatcta ttctatttaa gacttttgca    300
ggagtagacg cttttcctat ttgtgttgac agcaaagatc ctgacaagat tgtagaaaca    360
gtaaaattaa tagaatccac atttggagga ataaacctag aagatataaa agcacctgag    420
tgctttgaaa tagaagataa attaaaaaag gtctgcaata taccagtttt tcatgacgac    480
cagcacggaa cagcagtagt aactttagct gctatgataa atgcacttaa aatagtaaac    540
aaaaaatttg aagacttaaa agtaataata aatggtgcag gagctgcagg tacagcaatt    600
gcaaaactgc ttgtaagtag aggagttaaa aacattattg tatgcgatag aaaaggtgct    660
atatcaaaag atagagaaaa tttaagtgct gcaaaaaaag acctagcaga agttacaaat    720
cctagtatga taaaaggtgc acttaaagat gtactaaaag aagctgatgt attcataggt    780
gtatctgctc ctggagtaat tactcctgaa atgataaaaa caatggctaa agatcccctc    840
atttttgcta tggccaatcc taagcctgaa atctaccctg atgaagcaaa agctgcaggt    900
gccagagtag ttggtacggg aagatcagat ttcccaaatc aaataaataa tgttcttgca    960
tttcctggaa tatttagagg agcacttgat gtaagggcat caaaaataaa tgaagaaatg   1020
```

```
aaaatagctg ctgcatgtgc tatagcagac ataataactg aaaaagaact taatgaagat   1080

tatgttatac cagatgcttt tgactcaaga atagcaccaa aggtagctta ttatgtagca   1140

aaggctgcca tagaaagtgg agttgcaaga agaactgaca tcactcctga aatggtagaa   1200

gaacatacta aaaagcttgt acaagcataa                                   1230


<210> SEQ ID NO 39
<211> LENGTH: 409
<212> TYPE: PRT
<213> ORGANISM: Clostridium autoethanogenum

<400> SEQUENCE: 39

Met Asn Asn Leu Lys Glu Glu Ala Leu Lys Phe His Lys Glu His Glu
1               5                   10                  15

Gly Lys Ile Ala Leu Lys Ser Lys Val Ser Val Lys Thr Arg Glu Asp
            20                  25                  30

Leu Gly Leu Ala Tyr Thr Pro Gly Val Ala Glu Pro Cys Leu Glu Ile
        35                  40                  45

Asn Arg Asp Tyr Asn Thr Leu Tyr Asp Tyr Thr Ser Lys Gly Asn Tyr
    50                  55                  60

Val Ala Val Val Thr Asn Gly Ser Ala Val Leu Gly Leu Gly Asn Ile
65                  70                  75                  80

Gly Ala Ala Ala Gly Leu Pro Val Met Glu Gly Lys Ser Ile Leu Phe
                85                  90                  95

Lys Thr Phe Ala Gly Val Asp Ala Phe Pro Ile Cys Val Asp Ser Lys
            100                 105                 110

Asp Pro Asp Lys Ile Val Glu Thr Val Lys Leu Ile Glu Ser Thr Phe
        115                 120                 125

Gly Gly Ile Asn Leu Glu Asp Ile Lys Ala Pro Glu Cys Phe Glu Ile
    130                 135                 140

Glu Asp Lys Leu Lys Lys Val Cys Asn Ile Pro Val Phe His Asp Asp
145                 150                 155                 160

Gln His Gly Thr Ala Val Val Thr Leu Ala Ala Met Ile Asn Ala Leu
                165                 170                 175

Lys Ile Val Asn Lys Lys Phe Glu Asp Leu Lys Val Ile Ile Asn Gly
            180                 185                 190

Ala Gly Ala Ala Gly Thr Ala Ile Ala Lys Leu Leu Val Ser Arg Gly
        195                 200                 205

Val Lys Asn Ile Ile Val Cys Asp Arg Lys Gly Ala Ile Ser Lys Asp
    210                 215                 220

Arg Glu Asn Leu Ser Ala Ala Lys Lys Asp Leu Ala Glu Val Thr Asn
225                 230                 235                 240

Pro Ser Met Ile Lys Gly Ala Leu Lys Asp Val Leu Lys Glu Ala Asp
                245                 250                 255

Val Phe Ile Gly Val Ser Ala Pro Gly Val Ile Thr Pro Glu Met Ile
            260                 265                 270

Lys Thr Met Ala Lys Asp Pro Leu Ile Phe Ala Met Ala Asn Pro Lys
        275                 280                 285

Pro Glu Ile Tyr Pro Asp Glu Ala Lys Ala Ala Gly Ala Arg Val Val
    290                 295                 300

Gly Thr Gly Arg Ser Asp Phe Pro Asn Gln Ile Asn Asn Val Leu Ala
305                 310                 315                 320

Phe Pro Gly Ile Phe Arg Gly Ala Leu Asp Val Arg Ala Ser Lys Ile
                325                 330                 335
```

Asn Glu Glu Met Lys Ile Ala Ala Ala Cys Ala Ile Ala Asp Ile Ile
            340                 345                 350

Thr Glu Lys Glu Leu Asn Glu Asp Tyr Val Ile Pro Asp Ala Phe Asp
        355                 360                 365

Ser Arg Ile Ala Pro Lys Val Ala Tyr Tyr Val Ala Lys Ala Ala Ile
    370                 375                 380

Glu Ser Gly Val Ala Arg Arg Thr Asp Ile Thr Pro Glu Met Val Glu
385                 390                 395                 400

Glu His Thr Lys Lys Leu Val Gln Ala
                405

<210> SEQ ID NO 40
<211> LENGTH: 1230
<212> TYPE: DNA
<213> ORGANISM: Clostridium autoethanogenum

<400> SEQUENCE: 40
atgaatctaa gagaaactgc attaaaattt cacaaagaca acgaaggtaa aattgcacta 60
aaatgcaagg tgccggttaa aaacaaagaa gacctaacgt tagcatatac acctggagtt 120
gcagaacctt gcttagaaat taataaaaat ccagaatgca tttatgacta tacatcaaaa 180
gggaattggg tagctgttgt aacaaatggt acagctgttc ttggccttgg aaatataggt 240
gcaggtgcag gacttcctgt tatggaggga aaatccgttt tatttaaaac ttttgctgga 300
gtagatgcat ttccaatatg tctggaaagc aaggatatca atgaaattgt agcagctgta 360
aaacttatgg aaccaacttt tggaggaata aatctagagg acatcaaagc tccagaatgc 420
tttgaaattg aatcaaagct taaagaagtt tgtaacatcc ctgtatttca tgacgatcaa 480
catggaacgg cagttgtttc atcagcctgt cttataaatg cattaaagat agtaaataaa 540
aaatttgaag acttaaaaat tgttgtaaat ggagcaggag cagcaggaac tgccattaca 600
aaacttttaa taaagatggg aacaaaaaat gtaatacttt gcgacactaa aggtgctata 660
tacaagagaa gaccaattgg aatgaataag tttaaggatg aaatggcaga aataacaaat 720
cctaatcttc agaaaggaac tcttgctgat gttttaaaag gtgcagatgt atttttagga 780
gtatctgcag ctaattgtgt aactgaagaa atggtaaagt ccatgaataa agattcaata 840
attatggcaa tggcaaatcc aaatccagaa atacttcctg atttagctat aaaagctgga 900
gctaaagtgg tatgtacagg aaggtcggat tttccaaatc aggttaacaa tgtacttgct 960
tttccaggaa tatttagggg agctttagat gtaagggcaa gtgaaataaa tgatgagatg 1020
aaaatagctg cagcatatgc aatagcagaa cttgtaagtg aagaagaatt gaaaccagac 1080
tatataatac ctaatgcttt tgacttgaga atagccccaa aagtagccgc atacgtagca 1140
aaagctgcta ttgatacagg tgttgcgagg aaaaaggatg tcactccaga gatggttgaa 1200
aaacatacta agactttgct tggaatctaa 1230

<210> SEQ ID NO 41
<211> LENGTH: 409
<212> TYPE: PRT
<213> ORGANISM: Clostridium autoethanogenum

<400> SEQUENCE: 41

Met Asn Leu Arg Glu Thr Ala Leu Lys Phe His Lys Asp Asn Glu Gly
1               5                   10                  15

Lys Ile Ala Leu Lys Cys Lys Val Pro Val Lys Asn Lys Glu Asp Leu
            20                  25                  30

-continued

```
Thr Leu Ala Tyr Thr Pro Gly Val Ala Glu Pro Cys Leu Glu Ile Asn
        35                  40                  45

Lys Asn Pro Glu Cys Ile Tyr Asp Tyr Thr Ser Lys Gly Asn Trp Val
    50                  55                  60

Ala Val Val Thr Asn Gly Thr Ala Val Leu Gly Leu Gly Asn Ile Gly
65                  70                  75                  80

Ala Gly Ala Gly Leu Pro Val Met Glu Gly Lys Ser Val Leu Phe Lys
                85                  90                  95

Thr Phe Ala Gly Val Asp Ala Phe Pro Ile Cys Leu Glu Ser Lys Asp
            100                 105                 110

Ile Asn Glu Ile Val Ala Ala Val Lys Leu Met Glu Pro Thr Phe Gly
        115                 120                 125

Gly Ile Asn Leu Glu Asp Ile Lys Ala Pro Glu Cys Phe Glu Ile Glu
    130                 135                 140

Ser Lys Leu Lys Glu Val Cys Asn Ile Pro Val Phe His Asp Asp Gln
145                 150                 155                 160

His Gly Thr Ala Val Val Ser Ser Ala Cys Leu Ile Asn Ala Leu Lys
                165                 170                 175

Ile Val Asn Lys Lys Phe Glu Asp Leu Lys Ile Val Val Asn Gly Ala
            180                 185                 190

Gly Ala Ala Gly Thr Ala Ile Thr Lys Leu Leu Ile Lys Met Gly Thr
        195                 200                 205

Lys Asn Val Ile Leu Cys Asp Thr Lys Gly Ala Ile Tyr Lys Arg Arg
    210                 215                 220

Pro Ile Gly Met Asn Lys Phe Lys Asp Glu Met Ala Glu Ile Thr Asn
225                 230                 235                 240

Pro Asn Leu Gln Lys Gly Thr Leu Ala Asp Val Leu Lys Gly Ala Asp
                245                 250                 255

Val Phe Leu Gly Val Ser Ala Ala Asn Cys Val Thr Glu Glu Met Val
            260                 265                 270

Lys Ser Met Asn Lys Asp Ser Ile Ile Met Ala Met Ala Asn Pro Asn
        275                 280                 285

Pro Glu Ile Leu Pro Asp Leu Ala Ile Lys Ala Gly Ala Lys Val Val
    290                 295                 300

Cys Thr Gly Arg Ser Asp Phe Pro Asn Gln Val Asn Asn Val Leu Ala
305                 310                 315                 320

Phe Pro Gly Ile Phe Arg Gly Ala Leu Asp Val Arg Ala Ser Glu Ile
                325                 330                 335

Asn Asp Glu Met Lys Ile Ala Ala Ala Tyr Ala Ile Ala Glu Leu Val
            340                 345                 350

Ser Glu Glu Glu Leu Lys Pro Asp Tyr Ile Ile Pro Asn Ala Phe Asp
        355                 360                 365

Leu Arg Ile Ala Pro Lys Val Ala Ala Tyr Val Ala Lys Ala Ala Ile
    370                 375                 380

Asp Thr Gly Val Ala Arg Lys Lys Asp Val Thr Pro Glu Met Val Glu
385                 390                 395                 400

Lys His Thr Lys Thr Leu Leu Gly Ile
                405
```

<210> SEQ ID NO 42
<211> LENGTH: 1098
<212> TYPE: DNA
<213> ORGANISM: Clostridium autoethanogenum

<400> SEQUENCE: 42

```
atgtcataca ccaaagttaa atatgaagat ataaaaaagc tgtgtaattt ggtctttgag     60

aaatttggat tcaaccggga agatagtgaa accataacta gcgttttgct tttatcagat    120

ctatatggaa ttgaatccca tggtattcaa aggctggtaa agtactacag tgaaataaaa    180

agtggtctta taaatatcaa ttctaaaata aaaatagtaa aggaaacacc tgtatctgca    240

acaatagatg gcatgggcgg tatgggacag ctaattggta aaaaagctat gaatctggca    300

attaaaaaag ctaaaacttc aggaatgagt atggtagtgg ttagaaattc aaatcactat    360

ggtattgcag gctactatgc caaaatggct gaggaggaag gacttcttgg aatttcaatg    420

accaactctc cagctgtaat ggtaccaacc tttggaaaag atgctatgct tggcacaaat    480

cctattgcca tatcttttcc agctaaaccc tacccatttt taatggatat ggctactagc    540

gtagttacta ggggaaaaat tgaagtttat aacaaaaggc atgaacctct tccccttggt    600

ctagctttaa atagtgatgg tgaagatact acagatccct tagatgtact tcttaatgta    660

cgaaaaaatt ctggaggagg actgcttcct cttggaggat caaaagaatc aactggagga    720

cataaaggtt atggatttgc acttgcagtt gaaatgttta cagcaatttt atctggagga    780

tttactgcaa ataaagttag cttagatagg gaaaatggat ctggaacatg tcattatttc    840

tttgcagtgg attatggtat atttggggat aaacaatcca ttgaagagaa cttttccagc    900

tacctaaatg aacttagaaa ttcaaagaaa gcaaaaggcg ccacaagaat atatactcat    960

ggtgagaaag aagtagaatc ctataaggat aaaatgaaaa atggaattcc agtaaacgac   1020

actactctta aagaaatata cgacatatgt gactacttta gcataaaagc tagtgactat   1080

gtaactaaag tagtataa                                                 1098
```

```
<210> SEQ ID NO 43
<211> LENGTH: 365
<212> TYPE: PRT
<213> ORGANISM: Clostridium autoethanogenum

<400> SEQUENCE: 43

Met Ser Tyr Thr Lys Val Lys Tyr Glu Asp Ile Lys Lys Leu Cys Asn
1               5                   10                  15

Leu Val Phe Glu Lys Phe Gly Phe Asn Arg Glu Asp Ser Glu Thr Ile
            20                  25                  30

Thr Ser Val Leu Leu Leu Ser Asp Leu Tyr Gly Ile Glu Ser His Gly
        35                  40                  45

Ile Gln Arg Leu Val Lys Tyr Tyr Ser Glu Ile Lys Ser Gly Leu Ile
    50                  55                  60

Asn Ile Asn Ser Lys Ile Lys Ile Val Lys Glu Thr Pro Val Ser Ala
65                  70                  75                  80

Thr Ile Asp Gly Met Gly Gly Met Gly Gln Leu Ile Gly Lys Lys Ala
                85                  90                  95

Met Asn Leu Ala Ile Lys Lys Ala Lys Thr Ser Gly Met Ser Met Val
            100                 105                 110

Val Val Arg Asn Ser Asn His Tyr Gly Ile Ala Gly Tyr Tyr Ala Lys
        115                 120                 125

Met Ala Glu Glu Glu Gly Leu Leu Gly Ile Ser Met Thr Asn Ser Pro
    130                 135                 140

Ala Val Met Val Pro Thr Phe Gly Lys Asp Ala Met Leu Gly Thr Asn
145                 150                 155                 160

Pro Ile Ala Ile Ser Phe Pro Ala Lys Pro Tyr Pro Phe Leu Met Asp
                165                 170                 175
```

```
Met Ala Thr Ser Val Val Thr Arg Gly Lys Ile Glu Val Tyr Asn Lys
            180                 185                 190

Arg His Glu Pro Leu Pro Leu Gly Leu Ala Leu Asn Ser Asp Gly Glu
        195                 200                 205

Asp Thr Thr Asp Pro Leu Asp Val Leu Leu Asn Val Arg Lys Asn Ser
    210                 215                 220

Gly Gly Gly Leu Leu Pro Leu Gly Gly Ser Lys Glu Ser Thr Gly Gly
225                 230                 235                 240

His Lys Gly Tyr Gly Phe Ala Leu Ala Val Glu Met Phe Thr Ala Ile
                245                 250                 255

Leu Ser Gly Gly Phe Thr Ala Asn Lys Val Ser Leu Asp Arg Glu Asn
            260                 265                 270

Gly Ser Gly Thr Cys His Tyr Phe Phe Ala Val Asp Tyr Gly Ile Phe
        275                 280                 285

Gly Asp Lys Gln Ser Ile Glu Glu Asn Phe Ser Ser Tyr Leu Asn Glu
    290                 295                 300

Leu Arg Asn Ser Lys Lys Ala Lys Gly Ala Thr Arg Ile Tyr Thr His
305                 310                 315                 320

Gly Glu Lys Glu Val Glu Ser Tyr Lys Asp Lys Met Lys Asn Gly Ile
                325                 330                 335

Pro Val Asn Asp Thr Thr Leu Lys Glu Ile Tyr Asp Ile Cys Asp Tyr
            340                 345                 350

Phe Ser Ile Lys Ala Ser Asp Tyr Val Thr Lys Val Val
        355                 360                 365
```

<210> SEQ ID NO 44
<211> LENGTH: 2640
<212> TYPE: DNA
<213> ORGANISM: Clostridium autoethanogenum

<400> SEQUENCE: 44

```
atgaatggta agaagtacgt ttatcttttc aatgaaggaa atgctggcat gagaaattta     60

cttggaggca agggagctaa tcttgcagaa atgaccaatc ttggcatacc cgttcccggt    120

ggatttacta tatccacaga ggcatgtacc aaatattatg aagatggtaa atctatatcg    180

cagcaagtta tagatcaaat ttatgatgca cttaaaaatg tggaagagac aacaggaaaa    240

aaatttggaa gcatagaaaa tccattgtta gtttcagtaa gatcaggagc cagagtttct    300

atgccaggaa tgatggatac tatattaaat ttaggattaa atgatgatac tgtaatagga    360

cttaaaaagt tgacaggaaa tgaaagattt gcgtatgatt cttatagaag atttattcaa    420

atgttttcag atgtagttat gggaattgaa aagagagaat ttgaagatgt attggatgat    480

gtaaaaaatg ctaaaggagt aaaatacgat acagatttag atgagtccga tttaaagaat    540

ataatccaga gatttaagga tatttataaa aaagaagtaa aggaagactt tcctcaagat    600

cctaaagaac aattaattca gtcagttact gcagtattca gatcttggga aaatcctaga    660

gcaataattt atagaaggtt aaacgacata tcaggtgatt ggggaactgc agtaaatgtt    720

caatcaatgg tatttggaaa tatgggagaa acttcaggaa ctggagttgc atttactaga    780

aatccatcta caggagaaaa gtccatattt ggtgaatatc tcataaatgc tcaaggagag    840

gatgtagttg caggaataag aacacctcaa cctataacaa agctaaaaga agaccttcca    900

gaatgttatt ctcaatttat gagtatagca aataagcttg aaaatcatta taaagatatg    960

caggatatgg agttcactat agaacaggga aaattgtatt tccttcagac aagaaacggt   1020
```

-continued

```
aagagaacag ctcaagctgc acttagaata gcagtaaata tggtagatga aggtctcatc   1080
actaaagaag aggccatact taaagttgag cctaaacagc tcgatacact attgcatcca   1140
aactttgaca gtgatgaatt gaaacgggca gttgtaatag caaatggact tcctgcatca   1200
ccaggagcag cttgtggtaa gatatatttt acagcagatg atgctaagaa acatcatgat   1260
caaggtgaaa aggtaatact tgtaaggcta gagacttctc cagaagatat agaaggaatg   1320
gcagcttctg aaggaatact tacagttaga ggaggcatga catctcatgc agctgttgta   1380
gcaagaggta tgggaacatg ctgtgtagct ggatgtggtg atcttatcgt aagtgaaaag   1440
gaaaagcttt tcaaaagatt agataaggtt tacaaagaag ggattacat atctttagat   1500
ggaagtactg gaaatgtata tggagagcct ataaagactg tagcaccaga aatatcagga   1560
gattttggaa tcttcatggg atgggctgac aatataagaa aattgggagt tagaacaaat   1620
gcagatacac caagagatgc aaaccaggct attagctttg gtgccgaagg aataggactt   1680
tgtagaacag agcatatgtt ctttgatgaa gatagaatac cagaaatgag ggaaatgata   1740
gtttcaaaaa cggaagagca gaggagaaaa gctttagata aattactacc aagacaaaag   1800
aaagatttta ttggaatata tgaggcaatg gaaggaaaac ctgtcacaat tagatttttg   1860
gatccaccac ttcatgaatt cttacctact gaaactgagg atatagagtc tttagccaag   1920
gaaatgggag taagttttca agaactaaaa gatactatag attctctaca tgaatttaat   1980
cctatgatgg ggcatagagg atgcaggctt actgtttcat atccagaaat agctgaaatg   2040
caaacaaggg ctattataga agcagctata gatgttaaaa agagaaaagg gtatgatata   2100
gttccagaaa ttatgatacc tcttgtagga gaaataaaag aattaaaata tgttaaagac   2160
gtagttgtga gggtagcaga tgaaataata caaaaagagg gaatcaattt aaaatatgaa   2220
gtaggaacta tgatagaaat tccaagagca gctattacag ctgatgaaat agctaaagaa   2280
gctgagttct tctcatttgg aactaatgat ttaactcaaa tgacttttgg attttcaaga   2340
gatgatgcag gtaaattttt gaatgattat tatgataaaa aagtatatga gtttgatcca   2400
ttccaaaggt tagatcaagt tggagtagga aaacttgtag agactgctgt aaaattaggt   2460
aaaaagacta gacctgacat tcatcttgga atatgtggag aacatggagg agatccatct   2520
tctgtagagt ttttccacaa tgtaggactt gactatgtat cttgttcacc atttagggta   2580
cctgtggcaa gacttgctgc agctcaggct cagataaaga atccaagacc aatcaaataa   2640
```

<210> SEQ ID NO 45
<211> LENGTH: 879
<212> TYPE: PRT
<213> ORGANISM: Clostridium autoethanogenum

<400> SEQUENCE: 45

```
Met Asn Gly Lys Lys Tyr Val Tyr Leu Phe Asn Glu Gly Asn Ala Gly
1               5                   10                  15

Met Arg Asn Leu Leu Gly Gly Lys Gly Ala Asn Leu Ala Glu Met Thr
            20                  25                  30

Asn Leu Gly Ile Pro Val Pro Gly Gly Phe Thr Ile Ser Thr Glu Ala
        35                  40                  45

Cys Thr Lys Tyr Tyr Glu Asp Gly Lys Ser Ile Ser Gln Gln Val Ile
    50                  55                  60

Asp Gln Ile Tyr Asp Ala Leu Lys Asn Val Glu Glu Thr Thr Gly Lys
65                  70                  75                  80

Lys Phe Gly Ser Ile Glu Asn Pro Leu Leu Val Ser Val Arg Ser Gly
                85                  90                  95
```

-continued

```
Ala Arg Val Ser Met Pro Gly Met Met Asp Thr Ile Leu Asn Leu Gly
            100                 105                 110

Leu Asn Asp Asp Thr Val Ile Gly Leu Lys Lys Leu Thr Gly Asn Glu
        115                 120                 125

Arg Phe Ala Tyr Asp Ser Tyr Arg Arg Phe Ile Gln Met Phe Ser Asp
    130                 135                 140

Val Val Met Gly Ile Glu Lys Arg Glu Phe Glu Asp Val Leu Asp Asp
145                 150                 155                 160

Val Lys Asn Ala Lys Gly Val Lys Tyr Asp Thr Asp Leu Asp Glu Ser
                165                 170                 175

Asp Leu Lys Asn Ile Ile Gln Arg Phe Lys Asp Ile Tyr Lys Lys Glu
            180                 185                 190

Val Lys Glu Asp Phe Pro Gln Asp Pro Lys Glu Gln Leu Ile Gln Ser
        195                 200                 205

Val Thr Ala Val Phe Arg Ser Trp Glu Asn Pro Arg Ala Ile Ile Tyr
    210                 215                 220

Arg Arg Leu Asn Asp Ile Ser Gly Asp Trp Gly Thr Ala Val Asn Val
225                 230                 235                 240

Gln Ser Met Val Phe Gly Asn Met Gly Glu Thr Ser Gly Thr Gly Val
                245                 250                 255

Ala Phe Thr Arg Asn Pro Ser Thr Gly Glu Lys Ser Ile Phe Gly Glu
            260                 265                 270

Tyr Leu Ile Asn Ala Gln Gly Glu Asp Val Val Ala Gly Ile Arg Thr
        275                 280                 285

Pro Gln Pro Ile Thr Lys Leu Lys Glu Asp Leu Pro Glu Cys Tyr Ser
    290                 295                 300

Gln Phe Met Ser Ile Ala Asn Lys Leu Glu Asn His Tyr Lys Asp Met
305                 310                 315                 320

Gln Asp Met Glu Phe Thr Ile Glu Gln Gly Lys Leu Tyr Phe Leu Gln
                325                 330                 335

Thr Arg Asn Gly Lys Arg Thr Ala Gln Ala Ala Leu Arg Ile Ala Val
            340                 345                 350

Asn Met Val Asp Glu Gly Leu Ile Thr Lys Glu Glu Ala Ile Leu Lys
        355                 360                 365

Val Glu Pro Lys Gln Leu Asp Thr Leu Leu His Pro Asn Phe Asp Ser
    370                 375                 380

Asp Glu Leu Lys Arg Ala Val Val Ile Ala Asn Gly Leu Pro Ala Ser
385                 390                 395                 400

Pro Gly Ala Ala Cys Gly Lys Ile Tyr Phe Thr Ala Asp Asp Ala Lys
                405                 410                 415

Lys His His Asp Gln Gly Glu Lys Val Ile Leu Val Arg Leu Glu Thr
            420                 425                 430

Ser Pro Glu Asp Ile Glu Gly Met Ala Ala Ser Glu Gly Ile Leu Thr
        435                 440                 445

Val Arg Gly Gly Met Thr Ser His Ala Ala Val Val Ala Arg Gly Met
    450                 455                 460

Gly Thr Cys Cys Val Ala Gly Cys Gly Asp Leu Ile Val Ser Glu Lys
465                 470                 475                 480

Glu Lys Leu Phe Lys Arg Leu Asp Lys Val Tyr Lys Glu Gly Asp Tyr
                485                 490                 495

Ile Ser Leu Asp Gly Ser Thr Gly Asn Val Tyr Gly Glu Pro Ile Lys
            500                 505                 510
```

-continued

```
Thr Val Ala Pro Glu Ile Ser Gly Asp Phe Gly Ile Phe Met Gly Trp
        515                 520                 525

Ala Asp Asn Ile Arg Lys Leu Gly Val Arg Thr Asn Ala Asp Thr Pro
    530                 535                 540

Arg Asp Ala Asn Gln Ala Ile Ser Phe Gly Ala Glu Gly Ile Gly Leu
545                 550                 555                 560

Cys Arg Thr Glu His Met Phe Phe Asp Glu Asp Arg Ile Pro Glu Met
                565                 570                 575

Arg Glu Met Ile Val Ser Lys Thr Glu Glu Gln Arg Arg Lys Ala Leu
            580                 585                 590

Asp Lys Leu Leu Pro Arg Gln Lys Lys Asp Phe Ile Gly Ile Tyr Glu
        595                 600                 605

Ala Met Glu Gly Lys Pro Val Thr Ile Arg Phe Leu Asp Pro Pro Leu
    610                 615                 620

His Glu Phe Leu Pro Thr Glu Thr Glu Asp Ile Glu Ser Leu Ala Lys
625                 630                 635                 640

Glu Met Gly Val Ser Phe Gln Glu Leu Lys Asp Thr Ile Asp Ser Leu
                645                 650                 655

His Glu Phe Asn Pro Met Met Gly His Arg Gly Cys Arg Leu Thr Val
            660                 665                 670

Ser Tyr Pro Glu Ile Ala Glu Met Gln Thr Arg Ala Ile Ile Glu Ala
        675                 680                 685

Ala Ile Asp Val Lys Lys Arg Lys Gly Tyr Asp Ile Val Pro Glu Ile
    690                 695                 700

Met Ile Pro Leu Val Gly Glu Ile Lys Glu Leu Lys Tyr Val Lys Asp
705                 710                 715                 720

Val Val Val Arg Val Ala Asp Glu Ile Ile Gln Lys Glu Gly Ile Asn
                725                 730                 735

Leu Lys Tyr Glu Val Gly Thr Met Ile Glu Ile Pro Arg Ala Ala Ile
            740                 745                 750

Thr Ala Asp Glu Ile Ala Lys Glu Ala Glu Phe Phe Ser Phe Gly Thr
        755                 760                 765

Asn Asp Leu Thr Gln Met Thr Phe Gly Phe Ser Arg Asp Asp Ala Gly
    770                 775                 780

Lys Phe Leu Asn Asp Tyr Tyr Asp Lys Lys Val Tyr Glu Phe Asp Pro
785                 790                 795                 800

Phe Gln Arg Leu Asp Gln Val Gly Val Gly Lys Leu Val Glu Thr Ala
                805                 810                 815

Val Lys Leu Gly Lys Lys Thr Arg Pro Asp Ile His Leu Gly Ile Cys
            820                 825                 830

Gly Glu His Gly Gly Asp Pro Ser Ser Val Glu Phe Phe His Asn Val
        835                 840                 845

Gly Leu Asp Tyr Val Ser Cys Ser Pro Phe Arg Val Pro Val Ala Arg
    850                 855                 860

Leu Ala Ala Ala Gln Ala Gln Ile Lys Asn Pro Arg Pro Ile Lys
865                 870                 875
```

<210> SEQ ID NO 46
<211> LENGTH: 3447
<212> TYPE: DNA
<213> ORGANISM: Clostridium autoethanogenum

<400> SEQUENCE: 46
atggattact tgttaaagag gtttaagagg gttcttgtag cgaatagagg agaaatagcc      60

-continued

```
ataagaatat tcagagcatg caaagaattg ggaataacta ctgtagcaat atattcaaat    120

gaggataaga gatctctttt cagaactaaa gctgatgaat cctatatgat agggaaaaat    180

aagggacctg tagaagcata tttggatatt gatgaaataa tagatatagc tttgaagaaa    240

aatgtagatg caatacatcc gggttatgga ttcctatcag aaaatcctga attggcaaaa    300

aagtgtaaag aagcaggtat tgaatttata ggacctacat cagatatgat ggagatgctt    360

ggtgataaga taaaatctaa aattgttgca caaaaggctg gagtaccaac aataccagga    420

gttcaagaag ctataaagac agaagaagaa gctttaaaat ttgctaactt ctgtggatat    480

cctgttatga ttaaagcagc tgacggtggc ggcggcagag gaatgagaat agtaagggaa    540

gaaaaagatc tcatagaatc ctataacagt gctaaaaatg aatctagaaa agcttttggt    600

tcagaaaaaa tatacattga aaaatatatt gaaaatccaa aacacataga ggtgcaggta    660

cttggagata agtacggcaa tattgttcat ctatatgaaa gagattgttc catacagaga    720

agacatcaaa aggttataga atttacacca tctttagccc tctcagaaga aaaaagacaa    780

caaatatgtg aagatgcttt aaaaattgcg agaactgtag gatatacaag tgcaggtacc    840

ttggagtttt tagttgacaa aaatgaaaat cactatttta tagagatgaa tactagaatt    900

caggtagaac acactgtaac tgaaatggtt acaggaatag atatagttca agatcaaata    960

cttattgcag aagggcattc acttgattct aaggaaatag gaataaaatc tcaagatgat   1020

atagagttaa aaggatatgc aatacaatgc agaattacta cagaagatcc tttaaataat   1080

tttgcgccag atacaggaag aatagatatg tatagaactg gttctggatt tggtataaga   1140

cttgatggag gaaatggatt tacaggtgca gtaataagtc cttattatga tagcttactg   1200

gtaaaaactg tatcttggtc aagaactttt gaagatgcta taagaaaggc aataaggtct   1260

ataaatgaga ctgttatatc aggggtaaag acaaatgcag actttataat aaaagtgtta   1320

agtcatgaaa agtttataaa aggtgaatgt gatactaatt ttattgaaga taatccagat   1380

ttatttgata taaaaccaaa attagataaa gaaatgagtg tacttaaatt tataggaaat   1440

aaagtagtaa atgagactcg tggaaagaag aagaaattta atatacctat tgtaccaaaa   1500

gtagaagaaa atattaaatt gagtggaaca aagcaaatac ttgatacaaa aggagcagat   1560

ggattagttg attggataaa atcacaagat aagcttctta ttacagatac tactatgaga   1620

gacgctcatc agtcacttat ggcaactagg gtgagaacta gagatttgct taagatagca   1680

aaagcccaat cagctttggc aaacgatctt ttctccatgg aaatgtgggg aggagcaact   1740

tttgatgtag cgtatagatt tttaaatgaa tctccttggg aaagacttga aaaacttaga   1800

gaaaaggttc ctaatatact attccagatg ctcataagag gagctaatgc agtaggatat   1860

aagaactatc ctgataatgt tattagagaa tttataaaac aatcttcaac ttcaggcatt   1920

gatgtattta gaatatttga ttcactaaac tggcttaaag gaatgaaagt tgctatagat   1980

cagacattaa aagaaggaaa gatagctgaa gcatgcatgt gctatacagg agatgtatta   2040

gatgacaagg aggataaata tacgcttcag tactatataa acttagctaa agaaatagag   2100

aaaactggag cacagattct tggaataaag gatatgtctg ctttgttaaa gccatattct   2160

gcttataaac ttgtaaaagc acttaagaat gaaatctcta ttccaataca tcttcatact   2220

catgatacta caggtaatgg tgtggcaaca gtacttatgg ctgctgatgc aggacttgat   2280

atagctgata ctgcattcaa tagtatgtct gggcttacta gccagccagc tttgaattca   2340

atagcagcag cacttaaaaa tacaaataga gatactaagt tagatgcaga taatcttcaa   2400

aaaatatcta actactggga agatgtaaga cctatatata gtcagtttga gtcgggactt   2460
```

```
aagtcaagta ctgcagaaat atacaagtat gagataccag gaggccagta ttcaaactta   2520

aaacctcagg ttgaaagttt tgggttggga gatcgttttg aagatgtaaa agaaatgtat   2580

aagagagtta ataaaatgct tggaaatata attaaagtaa ctccttcttc aaaaatggta   2640

ggagatctgg ctatatttat gatacaaaat gatttggatg aaaagaatat ttatgaaaaa   2700

ggtaagaatt taactttccc agattctaca atttcttttct tcaagggaat gatgggtcag   2760

cctatgggag gatttccaaa agaacttcaa aaaatagttc taaagggaga ggaaccttta   2820

aagggaagac caggagaatt tttgccacca gaagattttg gcaagataga agatcattta   2880

actaaaaaat ataagagaaa atttgaaaat aaagaactct tgagttatgc tatgtatcct   2940

gatgtatttg aaaattacct taaattcata gatgaatatg gtgatctcag cagaatggaa   3000

agtgaaacat tcttctatgg acttgcagaa ggagaacttt gtgaagttga aataggagaa   3060

ggaaaaagtt tatttgtaca attactagag attacaaaag ttgacgatga aggatataga   3120

ttcttagtgt ttgaggttaa tggtattaag agagacataa ggataaaaga taacttggct   3180

ttctctggat caggaataaa agaaaattca tgtgttatgg cagatgaaga taatgaaaaa   3240

gaaataggat caagtatacc tggaaacatt gttaaagtac ttgtaaaacc aggagataaa   3300

gtagaagagg gccagagctt aattgtaata gaagctatga aaatggaaac aaatgtttca   3360

gctgctgaag caggagtaat tgatggagta tttgtaaaag aaggccagag agttaaaact   3420

ggagaacttt taattaaatt aaagtaa                                       3447
```

```
<210> SEQ ID NO 47
<211> LENGTH: 1148
<212> TYPE: PRT
<213> ORGANISM: Clostridium autoethanogenum

<400> SEQUENCE: 47

Met Asp Tyr Leu Leu Lys Arg Phe Lys Arg Val Leu Val Ala Asn Arg
1               5                   10                  15

Gly Glu Ile Ala Ile Arg Ile Phe Arg Ala Cys Lys Glu Leu Gly Ile
            20                  25                  30

Thr Thr Val Ala Ile Tyr Ser Asn Glu Asp Lys Arg Ser Leu Phe Arg
        35                  40                  45

Thr Lys Ala Asp Glu Ser Tyr Met Ile Gly Lys Asn Lys Gly Pro Val
    50                  55                  60

Glu Ala Tyr Leu Asp Ile Asp Glu Ile Ile Asp Ile Ala Leu Lys Lys
65                  70                  75                  80

Asn Val Asp Ala Ile His Pro Gly Tyr Gly Phe Leu Ser Glu Asn Pro
                85                  90                  95

Glu Leu Ala Lys Lys Cys Lys Glu Ala Gly Ile Glu Phe Ile Gly Pro
            100                 105                 110

Thr Ser Asp Met Met Glu Met Leu Gly Asp Lys Ile Lys Ser Lys Ile
        115                 120                 125

Val Ala Gln Lys Ala Gly Val Pro Thr Ile Pro Gly Val Gln Glu Ala
    130                 135                 140

Ile Lys Thr Glu Glu Glu Ala Leu Lys Phe Ala Asn Phe Cys Gly Tyr
145                 150                 155                 160

Pro Val Met Ile Lys Ala Ala Asp Gly Gly Gly Gly Arg Gly Met Arg
                165                 170                 175

Ile Val Arg Glu Glu Lys Asp Leu Ile Glu Ser Tyr Asn Ser Ala Lys
            180                 185                 190
```

```
Asn Glu Ser Arg Lys Ala Phe Gly Ser Glu Lys Ile Tyr Ile Glu Lys
        195                 200                 205

Tyr Ile Glu Asn Pro Lys His Ile Glu Val Gln Val Leu Gly Asp Lys
    210                 215                 220

Tyr Gly Asn Ile Val His Leu Tyr Glu Arg Asp Cys Ser Ile Gln Arg
225                 230                 235                 240

Arg His Gln Lys Val Ile Glu Phe Thr Pro Ser Leu Ala Leu Ser Glu
                245                 250                 255

Glu Lys Arg Gln Gln Ile Cys Glu Asp Ala Leu Lys Ile Ala Arg Thr
            260                 265                 270

Val Gly Tyr Thr Ser Ala Gly Thr Leu Glu Phe Leu Val Asp Lys Asn
        275                 280                 285

Glu Asn His Tyr Phe Ile Glu Met Asn Thr Arg Ile Gln Val Glu His
    290                 295                 300

Thr Val Thr Glu Met Val Thr Gly Ile Asp Ile Val Gln Asp Gln Ile
305                 310                 315                 320

Leu Ile Ala Glu Gly His Ser Leu Asp Ser Lys Glu Ile Gly Ile Lys
                325                 330                 335

Ser Gln Asp Asp Ile Glu Leu Lys Gly Tyr Ala Ile Gln Cys Arg Ile
            340                 345                 350

Thr Thr Glu Asp Pro Leu Asn Asn Phe Ala Pro Asp Thr Gly Arg Ile
        355                 360                 365

Asp Met Tyr Arg Thr Gly Ser Gly Phe Gly Ile Arg Leu Asp Gly Gly
    370                 375                 380

Asn Gly Phe Thr Gly Ala Val Ile Ser Pro Tyr Tyr Asp Ser Leu Leu
385                 390                 395                 400

Val Lys Thr Val Ser Trp Ser Arg Thr Phe Glu Asp Ala Ile Arg Lys
                405                 410                 415

Ala Ile Arg Ser Ile Asn Glu Thr Val Ile Ser Gly Val Lys Thr Asn
            420                 425                 430

Ala Asp Phe Ile Ile Lys Val Leu Ser His Glu Lys Phe Ile Lys Gly
        435                 440                 445

Glu Cys Asp Thr Asn Phe Ile Glu Asp Asn Pro Asp Leu Phe Asp Ile
    450                 455                 460

Lys Pro Lys Leu Asp Lys Glu Met Ser Val Leu Lys Phe Ile Gly Asn
465                 470                 475                 480

Lys Val Val Asn Glu Thr Arg Gly Lys Lys Lys Lys Phe Asn Ile Pro
                485                 490                 495

Ile Val Pro Lys Val Glu Glu Asn Ile Lys Leu Ser Gly Thr Lys Gln
            500                 505                 510

Ile Leu Asp Thr Lys Gly Ala Asp Gly Leu Val Asp Trp Ile Lys Ser
        515                 520                 525

Gln Asp Lys Leu Leu Ile Thr Asp Thr Thr Met Arg Asp Ala His Gln
    530                 535                 540

Ser Leu Met Ala Thr Arg Val Arg Thr Arg Asp Leu Leu Lys Ile Ala
545                 550                 555                 560

Lys Ala Gln Ser Ala Leu Ala Asn Asp Leu Phe Ser Met Glu Met Trp
                565                 570                 575

Gly Gly Ala Thr Phe Asp Val Ala Tyr Arg Phe Leu Asn Glu Ser Pro
            580                 585                 590

Trp Glu Arg Leu Glu Lys Leu Arg Glu Lys Val Pro Asn Ile Leu Phe
        595                 600                 605

Gln Met Leu Ile Arg Gly Ala Asn Ala Val Gly Tyr Lys Asn Tyr Pro
```

```
    610                 615                 620

Asp Asn Val Ile Arg Glu Phe Ile Lys Gln Ser Ser Thr Ser Gly Ile
625                 630                 635                 640

Asp Val Phe Arg Ile Phe Asp Ser Leu Asn Trp Leu Lys Gly Met Lys
                645                 650                 655

Val Ala Ile Asp Gln Thr Leu Lys Glu Gly Lys Ile Ala Glu Ala Cys
            660                 665                 670

Met Cys Tyr Thr Gly Asp Val Leu Asp Asp Lys Glu Asp Lys Tyr Thr
        675                 680                 685

Leu Gln Tyr Tyr Ile Asn Leu Ala Lys Glu Ile Glu Lys Thr Gly Ala
    690                 695                 700

Gln Ile Leu Gly Ile Lys Asp Met Ser Ala Leu Leu Lys Pro Tyr Ser
705                 710                 715                 720

Ala Tyr Lys Leu Val Lys Ala Leu Lys Asn Glu Ile Ser Ile Pro Ile
                725                 730                 735

His Leu His Thr His Asp Thr Thr Gly Asn Gly Val Ala Thr Val Leu
            740                 745                 750

Met Ala Ala Asp Ala Gly Leu Asp Ile Ala Asp Thr Ala Phe Asn Ser
        755                 760                 765

Met Ser Gly Leu Thr Ser Gln Pro Ala Leu Asn Ser Ile Ala Ala Ala
    770                 775                 780

Leu Lys Asn Thr Asn Arg Asp Thr Lys Leu Asp Ala Asp Asn Leu Gln
785                 790                 795                 800

Lys Ile Ser Asn Tyr Trp Glu Asp Val Arg Pro Ile Tyr Ser Gln Phe
                805                 810                 815

Glu Ser Gly Leu Lys Ser Ser Thr Ala Glu Ile Tyr Lys Tyr Glu Ile
            820                 825                 830

Pro Gly Gly Gln Tyr Ser Asn Leu Lys Pro Gln Val Glu Ser Phe Gly
        835                 840                 845

Leu Gly Asp Arg Phe Glu Asp Val Lys Glu Met Tyr Lys Arg Val Asn
    850                 855                 860

Lys Met Leu Gly Asn Ile Ile Lys Val Thr Pro Ser Ser Lys Met Val
865                 870                 875                 880

Gly Asp Leu Ala Ile Phe Met Ile Gln Asn Asp Leu Asp Glu Lys Asn
                885                 890                 895

Ile Tyr Glu Lys Gly Lys Asn Leu Thr Phe Pro Asp Ser Thr Ile Ser
            900                 905                 910

Phe Phe Lys Gly Met Met Gly Gln Pro Met Gly Gly Phe Pro Lys Glu
        915                 920                 925

Leu Gln Lys Ile Val Leu Lys Gly Glu Glu Pro Leu Lys Gly Arg Pro
    930                 935                 940

Gly Glu Phe Leu Pro Pro Glu Asp Phe Gly Lys Ile Glu Asp His Leu
945                 950                 955                 960

Thr Lys Lys Tyr Lys Arg Lys Phe Glu Asn Lys Glu Leu Leu Ser Tyr
                965                 970                 975

Ala Met Tyr Pro Asp Val Phe Glu Asn Tyr Leu Lys Phe Ile Asp Glu
            980                 985                 990

Tyr Gly Asp Leu Ser Arg Met Glu  Ser Glu Thr Phe Phe  Tyr Gly Leu
        995                 1000                 1005

Ala Glu  Gly Glu Leu Cys Glu  Val Glu Ile Gly Glu  Gly Lys Ser
    1010                 1015                 1020

Leu Phe  Val Gln Leu Leu Glu  Ile Thr Lys Val Asp  Asp Glu Gly
    1025                 1030                 1035
```

```
Tyr Arg  Phe Leu Val Phe Glu  Val Asn Gly Ile Lys  Arg Asp Ile
    1040                 1045                 1050

Arg Ile  Lys Asp Asn Leu Ala  Phe Ser Gly Ser Gly  Ile Lys Glu
    1055                 1060                 1065

Asn Ser  Cys Val Met Ala Asp  Glu Asp Asn Glu Lys  Glu Ile Gly
    1070                 1075                 1080

Ser Ser  Ile Pro Gly Asn Ile  Val Lys Val Leu Val  Lys Pro Gly
    1085                 1090                 1095

Asp Lys  Val Glu Glu Gly Gln  Ser Leu Ile Val Ile  Glu Ala Met
    1100                 1105                 1110

Lys Met  Glu Thr Asn Val Ser  Ala Ala Glu Ala Gly  Val Ile Asp
    1115                 1120                 1125

Gly Val  Phe Val Lys Glu Gly  Gln Arg Val Lys Thr  Gly Glu Leu
    1130                 1135                 1140

Leu Ile  Lys Leu Lys
    1145


<210> SEQ ID NO 48
<211> LENGTH: 1524
<212> TYPE: DNA
<213> ORGANISM: Clostridium autoethanogenum

<400> SEQUENCE: 48

atgtataaaa atttatcacc atcagaatta acggaatttt caattaaaag aggagaagga     60

tttttatcaa ataagggagc tcttatgatt aatactggaa agtacacagg aagatctcct    120

aaagatagat ttatagttaa tcaagaaagc attaggaaca aaataaactg gggaaatgta    180

aatctttcta tagaagaaga tatttttaat aaaatgtatg ataagatttt aaattatata    240

agtgataaag atatttttgt gtttgatgga tttgttggag ctttaaaaaa atataccctt    300

cctataagag taatatgcga aagggcatcc caggcgttgt ttgcaaatca attgtttaga    360

agaccaacgg aggaggattt aaagtgtttt actcctgaat ttaatattat atcggcacct    420

ggatttaagg ctaagggcaa agaagacggt ttaaattcag atgcctttat tttagtaaat    480

ttcgataaaa aaattatatt aataggtgga accagttact cgggagaaat aaaaaaatca    540

gtattttcag taatgaactt cttgcttcca caaaaaggag tcatgcctat gcactgttct    600

gctaatatag gacaagataa taaaacttgc ttatttttg gattgtcagg aacaggaaaa    660

actactttat cagcagatgg tgaaagaaga ctgattggtg atgacgaaca tggatggtct    720

aatgaaggtg tatttaattt tgagggtgga tgttatgcta aaactataag acttgataag    780

gaaaaggaaa gtcagatata caatgccata aaatttggaa ctgtagttga aaatgtagtg    840

gcagatggga atagagtacc tgattataat gatgctagat atactgaaaa tacaagggca    900

gcatatccta taaattatat agataatata gaagaaagtg gtgtaggagg aaatccagag    960

actataatat ttttaaccgc agatgctttt ggtgtaatgc cacctatatc aaggctttct   1020

aaagaagcag caatgtatca ctttatgtct ggatatacta gcaagatagc tggaactgaa   1080

agaggaataa ttgaacctca agctactttt tcctcttgct ttggtgaacc gtttatgtta   1140

atgaatcctg ctgtctatgc aaaattgtta ggcgaaagaa tagacaagta taacactcag   1200

gtatatttag tgaatactgg atggctatct ggaggatatg gaaatggaga tagaataaaa   1260

ctttcctata caagggctat gattagagaa gctttgaaag ggaagttcaa ggatgttgaa   1320

tttgtggaac atcctgtatt taaagtaatg atgcctaaaa gatgtccagg tgtacctgat   1380
```

-continued

```
gaaatattaa atcctagaaa tatatgggaa gataaagaag catatgatga gacagcgaga   1440

aagctggcgc tgaagtttag taaaaacttt gagaagttta aagatgtttc cgaagatata   1500

gcaaaagctg gacctgaagc ttaa                                          1524


<210> SEQ ID NO 49
<211> LENGTH: 507
<212> TYPE: PRT
<213> ORGANISM: Clostridium autoethanogenum

<400> SEQUENCE: 49

Met Tyr Lys Asn Leu Ser Pro Ser Glu Leu Thr Glu Phe Ser Ile Lys
1               5                   10                  15

Arg Gly Glu Gly Phe Leu Ser Asn Lys Gly Ala Leu Met Ile Asn Thr
            20                  25                  30

Gly Lys Tyr Thr Gly Arg Ser Pro Lys Asp Arg Phe Ile Val Asn Gln
        35                  40                  45

Glu Ser Ile Arg Asn Lys Ile Asn Trp Gly Asn Val Asn Leu Ser Ile
    50                  55                  60

Glu Glu Asp Ile Phe Asn Lys Met Tyr Asp Lys Ile Leu Asn Tyr Ile
65                  70                  75                  80

Ser Asp Lys Asp Ile Phe Val Phe Asp Gly Phe Val Gly Ala Leu Lys
                85                  90                  95

Lys Tyr Thr Leu Pro Ile Arg Val Ile Cys Glu Arg Ala Ser Gln Ala
            100                 105                 110

Leu Phe Ala Asn Gln Leu Phe Arg Arg Pro Thr Glu Glu Asp Leu Lys
        115                 120                 125

Cys Phe Thr Pro Glu Phe Asn Ile Ile Ser Ala Pro Gly Phe Lys Ala
    130                 135                 140

Lys Gly Lys Glu Asp Gly Leu Asn Ser Asp Ala Phe Ile Leu Val Asn
145                 150                 155                 160

Phe Asp Lys Lys Ile Ile Leu Ile Gly Gly Thr Ser Tyr Ser Gly Glu
                165                 170                 175

Ile Lys Lys Ser Val Phe Ser Val Met Asn Phe Leu Leu Pro Gln Lys
            180                 185                 190

Gly Val Met Pro Met His Cys Ser Ala Asn Ile Gly Gln Asp Asn Lys
        195                 200                 205

Thr Cys Leu Phe Phe Gly Leu Ser Gly Thr Gly Lys Thr Thr Leu Ser
    210                 215                 220

Ala Asp Gly Glu Arg Arg Leu Ile Gly Asp Asp Glu His Gly Trp Ser
225                 230                 235                 240

Asn Glu Gly Val Phe Asn Phe Glu Gly Gly Cys Tyr Ala Lys Thr Ile
                245                 250                 255

Arg Leu Asp Lys Glu Lys Glu Ser Gln Ile Tyr Asn Ala Ile Lys Phe
            260                 265                 270

Gly Thr Val Val Glu Asn Val Val Ala Asp Gly Asn Arg Val Pro Asp
        275                 280                 285

Tyr Asn Asp Ala Arg Tyr Thr Glu Asn Thr Arg Ala Ala Tyr Pro Ile
    290                 295                 300

Asn Tyr Ile Asp Asn Ile Glu Glu Ser Gly Val Gly Gly Asn Pro Glu
305                 310                 315                 320

Thr Ile Ile Phe Leu Thr Ala Asp Ala Phe Gly Val Met Pro Pro Ile
                325                 330                 335

Ser Arg Leu Ser Lys Glu Ala Ala Met Tyr His Phe Met Ser Gly Tyr
            340                 345                 350
```

-continued

```
Thr Ser Lys Ile Ala Gly Thr Glu Arg Gly Ile Ile Glu Pro Gln Ala
        355                 360                 365

Thr Phe Ser Ser Cys Phe Gly Glu Pro Phe Met Leu Met Asn Pro Ala
    370                 375                 380

Val Tyr Ala Lys Leu Leu Gly Glu Arg Ile Asp Lys Tyr Asn Thr Gln
385                 390                 395                 400

Val Tyr Leu Val Asn Thr Gly Trp Leu Ser Gly Gly Tyr Gly Asn Gly
                405                 410                 415

Asp Arg Ile Lys Leu Ser Tyr Thr Arg Ala Met Ile Arg Glu Ala Leu
            420                 425                 430

Lys Gly Lys Phe Lys Asp Val Glu Phe Val Glu His Pro Val Phe Lys
        435                 440                 445

Val Met Met Pro Lys Arg Cys Pro Gly Val Pro Asp Glu Ile Leu Asn
    450                 455                 460

Pro Arg Asn Ile Trp Glu Asp Lys Glu Ala Tyr Asp Glu Thr Ala Arg
465                 470                 475                 480

Lys Leu Ala Leu Lys Phe Ser Lys Asn Phe Glu Lys Phe Lys Asp Val
                485                 490                 495

Ser Glu Asp Ile Ala Lys Ala Gly Pro Glu Ala
            500                 505


<210> SEQ ID NO 50
<211> LENGTH: 843
<212> TYPE: DNA
<213> ORGANISM: Clostridium autoethanogenum

<400> SEQUENCE: 50

atgagagaag tagatgtatc cactataact aaagctgtta gaaatctctg tatagatgcc      60

aattattatc tttcggagga tgttaagaaa aagataaaag aatgtgaaga ggacgaaaaa     120

tggcctactg caaaagacat tttaggtaaa atacttgaaa atatagatat atctaaaaat     180

gaagatgtgc ctatgtgtca agatacagga atggcttgtg tatttataac aattggccag     240

gatgttcata tagtaggagg aagtttagaa gacgcaataa ataagggagt aggccagggg     300

tatgtagaag ggtatttaag aaaatctgta gtctctgatc ctataaatag agttaatact     360

aaggacaata ctcctgcagt aatatattat gaaatagttc caggagataa acttaacata     420

aaagtggctc ctaaaggatt tggatcagaa aatatgagtc agataaaaat gcttaaacca     480

gcagatggtc ttaagggtgt taaagatttt gtaataaaag tagtaaagga cgcaggacca     540

aatccatgtc ctcctatggt tgtaggagta ggtataggag gaacttttga caaggctgca     600

aatcttgcaa agaaagctct tgtaagacca ttatctgaaa gaaataaaaa taagttttat     660

tcagatttag aaaatgaact tttagacaaa ataaatctcc ttggtatagg acctcaagga     720

ctagggggaa agactacagc tcttgcagta aatatagaaa cttatcctac ccatatagca     780

ggattacctg tagccgtaaa tataaattgt cacgttacaa gacataagga aatagaattg     840

taa                                                                   843


<210> SEQ ID NO 51
<211> LENGTH: 280
<212> TYPE: PRT
<213> ORGANISM: Clostridium autoethanogenum

<400> SEQUENCE: 51

Met Arg Glu Val Asp Val Ser Thr Ile Thr Lys Ala Val Arg Asn Leu
1               5                   10                  15
```

-continued

```
Cys Ile Asp Ala Asn Tyr Tyr Leu Ser Glu Asp Val Lys Lys Lys Ile
            20                  25                  30

Lys Glu Cys Glu Glu Asp Glu Lys Trp Pro Thr Ala Lys Asp Ile Leu
        35                  40                  45

Gly Lys Ile Leu Glu Asn Ile Asp Ile Ser Lys Asn Glu Asp Val Pro
    50                  55                  60

Met Cys Gln Asp Thr Gly Met Ala Cys Val Phe Ile Thr Ile Gly Gln
65                  70                  75                  80

Asp Val His Ile Val Gly Gly Ser Leu Glu Asp Ala Ile Asn Lys Gly
                85                  90                  95

Val Gly Gln Gly Tyr Val Glu Gly Tyr Leu Arg Lys Ser Val Val Ser
            100                 105                 110

Asp Pro Ile Asn Arg Val Asn Thr Lys Asp Asn Thr Pro Ala Val Ile
        115                 120                 125

Tyr Tyr Glu Ile Val Pro Gly Asp Lys Leu Asn Ile Lys Val Ala Pro
    130                 135                 140

Lys Gly Phe Gly Ser Glu Asn Met Ser Gln Ile Lys Met Leu Lys Pro
145                 150                 155                 160

Ala Asp Gly Leu Lys Gly Val Lys Asp Phe Val Ile Lys Val Val Lys
                165                 170                 175

Asp Ala Gly Pro Asn Pro Cys Pro Pro Met Val Val Gly Val Gly Ile
            180                 185                 190

Gly Gly Thr Phe Asp Lys Ala Ala Asn Leu Ala Lys Lys Ala Leu Val
        195                 200                 205

Arg Pro Leu Ser Glu Arg Asn Lys Asn Lys Phe Tyr Ser Asp Leu Glu
    210                 215                 220

Asn Glu Leu Leu Asp Lys Ile Asn Leu Leu Gly Ile Gly Pro Gln Gly
225                 230                 235                 240

Leu Gly Gly Lys Thr Thr Ala Leu Ala Val Asn Ile Glu Thr Tyr Pro
                245                 250                 255

Thr His Ile Ala Gly Leu Pro Val Ala Val Asn Ile Asn Cys His Val
            260                 265                 270

Thr Arg His Lys Glu Ile Glu Leu
        275                 280


<210> SEQ ID NO 52
<211> LENGTH: 573
<212> TYPE: DNA
<213> ORGANISM: Clostridium autoethanogenum

<400> SEQUENCE: 52

atgtatatgg aaaaaaagat aactactccg ttaacggaag aaaaggttaa aactttaaaa      60

gcaggggata gtgttttaat atcagggaca atatatactg ctagagatgc tgctcataag     120

agattagttg aattattaga tgaaggtaaa tcacttccta taaatgtaaa agatgaaata     180

atatattacg caggaccaag tcctgcaaaa ccaggccatg taataggttc agcaggacca     240

acaagtagtt atagaatgga tccatttgca ccaagactgc ttgatatagg tttaaaggga     300

atgataggaa aaggccttcg ttcaaaagaa gttatagaat ccatgaagaa aaataaagct     360

gtttactttg ctgcaatagg cggggctgca gcacttgtag caaaatccat aaagaaagca     420

gaagtagtag cttatgaaga tttggattct gaagctataa gaaaattaga agtaaaagac     480

ttacctgtaa ttgtagtaat agattcagag ggcaataatt tatatgaatc aggacgaaaa     540

gagtacttgg actctgtgga ccagtctaag tag                                  573
```

<210> SEQ ID NO 53
<211> LENGTH: 190
<212> TYPE: PRT
<213> ORGANISM: Clostridium autoethanogenum

<400> SEQUENCE: 53

```
Met Tyr Met Glu Lys Lys Ile Thr Thr Pro Leu Thr Glu Glu Lys Val
1               5                   10                  15

Lys Thr Leu Lys Ala Gly Asp Ser Val Leu Ile Ser Gly Thr Ile Tyr
            20                  25                  30

Thr Ala Arg Asp Ala Ala His Lys Arg Leu Val Glu Leu Leu Asp Glu
        35                  40                  45

Gly Lys Ser Leu Pro Ile Asn Val Lys Asp Glu Ile Ile Tyr Tyr Ala
    50                  55                  60

Gly Pro Ser Pro Ala Lys Pro Gly His Val Ile Gly Ser Ala Gly Pro
65                  70                  75                  80

Thr Ser Ser Tyr Arg Met Asp Pro Phe Ala Pro Arg Leu Leu Asp Ile
                85                  90                  95

Gly Leu Lys Gly Met Ile Gly Lys Gly Leu Arg Ser Lys Glu Val Ile
            100                 105                 110

Glu Ser Met Lys Lys Asn Lys Ala Val Tyr Phe Ala Ala Ile Gly Gly
        115                 120                 125

Ala Ala Ala Leu Val Ala Lys Ser Ile Lys Lys Ala Glu Val Val Ala
    130                 135                 140

Tyr Glu Asp Leu Asp Ser Glu Ala Ile Arg Lys Leu Glu Val Lys Asp
145                 150                 155                 160

Leu Pro Val Ile Val Val Ile Asp Ser Glu Gly Asn Asn Leu Tyr Glu
                165                 170                 175

Ser Gly Arg Lys Glu Tyr Leu Asp Ser Val Asp Gln Ser Lys
            180                 185                 190
```

<210> SEQ ID NO 54
<211> LENGTH: 1797
<212> TYPE: DNA
<213> ORGANISM: Clostridium autoethanogenum

<400> SEQUENCE: 54

```
atgcaaatag ataagataat tgatactgac atattagttg ttggaggttc tggagcagga      60

tcaatggcag ctgtaacagc tgcgagaaaa ggagcaaaag tactacttgc agtaaaaggg     120

aagcttggaa aaagcggaaa tgccattatg gcaggggcag gattttctat ggatggagaa     180

acagcatatt ataaatatgg actcaaggaa gcagatccta aaaatacaaa gggaaaatta     240

tttgaacaaa ttgtaaaaca gtctttttat ttaagtgatc aaaatatggt tgagcagttt     300

gtaagtgatt gtgatgagtg ctgctgggaa cttaaacagt ggattgaaaa agcaggacac     360

aaggttgtat tttttggaga agaaggatat ataagctcgg gtaaagctgt gggagttggc     420

tgccgatatg gagtttcaaa agcaggtggt attgatgtta tagaagattt tatagcagtg     480

gatattttaa tggaagataa aaaagctgta ggtgcagtgg gcatagaagt atatacagga     540

aaaattattg aaatcagatc aaagtcagtt attttagcta ctggcggata tcagccttat     600

tcctttaaat gtactgtttc cgatatgact ggcgatggaa tggctatggc ataccgtgca     660

ggagccaagc ttgcagatat ggaattttta ttatatatac cagcagttgc cctttcacca     720

tcagtatata aaggttcaat ttatcccttc ttacactcca gtatgttaat gcctattgtt     780
```

-continued

```
aaaaatggta agggagaatc aattttagat aatatacctg aaaatttact taaaatggcc    840
aaggaaagtg aaatgggaaa gcttatattt acgtattatt atggagatca aattgcaaga    900
ggaaaaggaa ctccaaatgg aggagtatat tttgattatt ccaatgtacc ttttgatatt    960
tatgaaaaag ctttaaaaaa agctgaacca ttaatgaaca tatggtatag aaaaggattc   1020
tatcaaggaa acaacttgga tacttttgtt gaaaatatta gaaagggcat tccatgggaa   1080
gtaggtattg gcagtgaata cagcatgggc ggcattgaag tagacgaaaa tatgtacact   1140
ggagtaccag gactttatgc agctggtgag actacaagtg gtgtatttgg agctatgagg   1200
gttgcagatg gacttattga aatgcttgta cagggttata gagcagcatt gtccgcttgc   1260
aaatatatac aaaatgtaaa tgagccaagt atgaaaaata ccaatattga tagtataatt   1320
aaagatattt tttcacctct tgaaagaaaa gaaggagtta gtcctataaa aatacacaga   1380
aatatagaaa aaacggctga tgttggattc aactttagaa gaaatgaaga gggacttaca   1440
aaagctttag atgaaatttt aaaaatacac aaatatgaca taagcgcaat gagtactaaa   1500
agtaaaaata gagtttataa ctatgaatgg atagaatcag tacaggctcg aaatctttta   1560
acttgtacag aagcaggtgt aagagctgcc cttatgagaa aggaaagtag gggtacacac   1620
atacgtgatg attatgaatt tgtagataat gataactggc ttttaaggat tatgagttcg   1680
aaaggtgaag acgaaaccat gaaattatca accagaaagc ctaaagtaac aacaatggaa   1740
cttccaggtg gtaaaaataa gaatattcct gattatatgc tttcaatgtt aaagtaa      1797
```

```
<210> SEQ ID NO 55
<211> LENGTH: 598
<212> TYPE: PRT
<213> ORGANISM: Clostridium autoethanogenum

<400> SEQUENCE: 55

Met Gln Ile Asp Lys Ile Ile Asp Thr Asp Ile Leu Val Val Gly Gly
1               5                   10                  15

Ser Gly Ala Gly Ser Met Ala Ala Val Thr Ala Ala Arg Lys Gly Ala
            20                  25                  30

Lys Val Leu Leu Ala Val Lys Gly Lys Leu Gly Lys Ser Gly Asn Ala
        35                  40                  45

Ile Met Ala Gly Ala Gly Phe Ser Met Asp Gly Glu Thr Ala Tyr Tyr
    50                  55                  60

Lys Tyr Gly Leu Lys Glu Ala Asp Pro Lys Asn Thr Lys Gly Lys Leu
65                  70                  75                  80

Phe Glu Gln Ile Val Lys Gln Ser Phe Tyr Leu Ser Asp Gln Asn Met
                85                  90                  95

Val Glu Gln Phe Val Ser Asp Cys Asp Glu Cys Cys Trp Glu Leu Lys
            100                 105                 110

Gln Trp Ile Glu Lys Ala Gly His Lys Val Val Phe Phe Gly Glu Glu
        115                 120                 125

Gly Tyr Ile Ser Ser Gly Lys Ala Val Gly Val Gly Cys Arg Tyr Gly
    130                 135                 140

Val Ser Lys Ala Gly Gly Ile Asp Val Ile Glu Asp Phe Ile Ala Val
145                 150                 155                 160

Asp Ile Leu Met Glu Asp Lys Lys Ala Val Gly Ala Val Gly Ile Glu
                165                 170                 175

Val Tyr Thr Gly Lys Ile Ile Glu Ile Arg Ser Lys Ser Val Ile Leu
            180                 185                 190

Ala Thr Gly Gly Tyr Gln Pro Tyr Ser Phe Lys Cys Thr Val Ser Asp
```

```
        195                 200                 205

Met Thr Gly Asp Gly Met Ala Met Ala Tyr Arg Ala Gly Ala Lys Leu
    210                 215                 220

Ala Asp Met Glu Phe Leu Leu Tyr Ile Pro Ala Val Ala Leu Ser Pro
225                 230                 235                 240

Ser Val Tyr Lys Gly Ser Ile Tyr Pro Phe Leu His Ser Ser Met Leu
                245                 250                 255

Met Pro Ile Val Lys Asn Gly Lys Gly Glu Ser Ile Leu Asp Asn Ile
            260                 265                 270

Pro Glu Asn Leu Leu Lys Met Ala Lys Glu Ser Glu Met Gly Lys Leu
        275                 280                 285

Ile Phe Thr Tyr Tyr Tyr Gly Asp Gln Ile Ala Arg Gly Lys Gly Thr
    290                 295                 300

Pro Asn Gly Gly Val Tyr Phe Asp Tyr Ser Asn Val Pro Phe Asp Ile
305                 310                 315                 320

Tyr Glu Lys Ala Leu Lys Lys Ala Glu Pro Leu Met Asn Ile Trp Tyr
                325                 330                 335

Arg Lys Gly Phe Tyr Gln Gly Asn Asn Leu Asp Thr Phe Val Glu Asn
            340                 345                 350

Ile Arg Lys Gly Ile Pro Trp Glu Val Gly Ile Gly Ser Glu Tyr Ser
        355                 360                 365

Met Gly Gly Ile Glu Val Asp Glu Asn Met Tyr Thr Gly Val Pro Gly
    370                 375                 380

Leu Tyr Ala Ala Gly Glu Thr Thr Ser Gly Val Phe Gly Ala Met Arg
385                 390                 395                 400

Val Ala Asp Gly Leu Ile Glu Met Leu Val Gln Gly Tyr Arg Ala Ala
                405                 410                 415

Leu Ser Ala Cys Lys Tyr Ile Gln Asn Val Asn Glu Pro Ser Met Lys
            420                 425                 430

Asn Thr Asn Ile Asp Ser Ile Ile Lys Asp Ile Phe Ser Pro Leu Glu
        435                 440                 445

Arg Lys Glu Gly Val Ser Pro Ile Lys Ile His Arg Asn Ile Glu Lys
    450                 455                 460

Thr Ala Asp Val Gly Phe Asn Phe Arg Arg Asn Glu Glu Gly Leu Thr
465                 470                 475                 480

Lys Ala Leu Asp Glu Ile Leu Lys Ile His Lys Tyr Asp Ile Ser Ala
                485                 490                 495

Met Ser Thr Lys Ser Lys Asn Arg Val Tyr Asn Tyr Glu Trp Ile Glu
            500                 505                 510

Ser Val Gln Ala Arg Asn Leu Leu Thr Cys Thr Glu Ala Gly Val Arg
        515                 520                 525

Ala Ala Leu Met Arg Lys Glu Ser Arg Gly Thr His Ile Arg Asp Asp
    530                 535                 540

Tyr Glu Phe Val Asp Asn Asp Asn Trp Leu Leu Arg Ile Met Ser Ser
545                 550                 555                 560

Lys Gly Glu Asp Glu Thr Met Lys Leu Ser Thr Arg Lys Pro Lys Val
                565                 570                 575

Thr Thr Met Glu Leu Pro Gly Gly Lys Asn Lys Asn Ile Pro Asp Tyr
            580                 585                 590

Met Leu Ser Met Leu Lys
        595

<210> SEQ ID NO 56
```

-continued

<211> LENGTH: 2781
<212> TYPE: DNA
<213> ORGANISM: Clostridium autoethanogenum

<400> SEQUENCE: 56
atgctaacta ataatactga ggcacttata ttggcagaaa agattggaaa agaagctgca 60
ctatcatgtt tacagggaat gtatgattat ggcacaagtc ctatgaaagt tttagatatg 120
ataaaggaaa aacctaattg taaagttata gttggagcac taaacaattc ggatacagat 180
ggaatgctta atattttggc aaaaacaaat ccagctggac ttgcagcagg tctttcagta 240
ttagcaaagg catcaggagc agaagaggcc ctattagaac ttcgtaatac ggataatgaa 300
gctgaattat tagccagtgc aaaaacagca ggagtaaaac ttagagtaga agtaggtgaa 360
ctagttgatg taagggcaca taaagagcat attattttta atttagaaac tttagccgga 420
attgccgata aaattacggg cacagcacca ggaattatta tagcagtaga tgaagatgta 480
cctaaggaag ttaaattcgg tacaaaactt gtggattttt tagacacagc taaggttaaa 540
tcggttatga ttaaccacca tttttataga ttagatgtat taaataatgg cattataaag 600
gaaaactcct atggaagtgg tgttattcat ataatttacg aaaatgattg catagtagaa 660
aaaacaaaaa aagaactaga aaatcttaga aagcaaagct gtggaaaatg tactttttgc 720
cgtgaaggat tatatcagct tgatgttata tttgatgaca tgataaaagg cagatcagag 780
aaagaggatc ttgctatggt agaagagtta acaagtgcaa tgaaattttc atgtaattgc 840
tcattaggaa aatgctcagg agaaccagca gcaagtgcaa taacagaatt taaattagaa 900
gtagagcagc atataaagaa gaggggatgt cctgctggcc agtgtttagc ctttacaaat 960
atatacgtag atcctagaaa atgcaaaggt tgtggaaaat gcttggaagt ttgtccagag 1020
gattgtattg aagcaaaaaa gggctatatt tccatgattg acgaatttga ttgcactaaa 1080
tgcggcatat gtatagatga atgtcccaat aatgcaattg ttaaggtaaa tggcaaaacc 1140
cctaaacttc ctacaaaact aacaagagta aaaggaagta aaaatataac agaagaggac 1200
acagagaaga aaaaacggca caatttaaaa agacacagaa ctaagcttgt tattccactt 1260
aaaaaagata ataataaagc atctgagaaa atatcagaga ttaaaaagtc aaaggagggt 1320
actattatga aaaagatgga aacagatatt ataatcgcag caggaggccc agcaggactg 1380
gcagcagcta ttacagctgg agagaacaat ttaaaatcta ttctttttga aaaatctagt 1440
acaacaggtg gagcagcaaa catgggtatg ggaccacttg gaatagatac taaaattcag 1500
aaagataact ttaacaatat aagtgtagca gaagcccttg acatgcatat gaaatatact 1560
cattatcgtg tagatgagga tttagttcag acatacttta ataagagtgc agaaacaatt 1620
gaatggttac aggatatggg agtagaattt gcaggagcat ttcgctattt taaagaatca 1680
gcggcaactt ggcatatagt taagccggaa aatggagtta ttggaccacg tgcagctagt 1740
ggaatggcaa aaataatgac agaacgtgca aaagaacttg gaacaaaaat cctattggaa 1800
acaccagtgg tttctttaat aaaggaaaat ggaagaatat gtggtgttaa agcacaagat 1860
agtgaaggta atattattga agtcagggca aaagctgtta ttgttgcaac tggtggtttt 1920
ggcaataaca agaatatgat aaaatctgaa tttggtttga caattggaga agattatttc 1980
ccatttatgg ttcctggaat aacaggtgat ggcttgaaaa tgatgtggga agcaggtgca 2040
atgaaatatg gagaaaatat tgaggcaatt tatcagcttc ctgataattt aaactggttt 2100
ttactagatg cagtgctgcg tcagccaaat cttttaatta atcaacttgg tgatcgtttt 2160
atgaatgaag gagatatggg aaatactaca tttactggaa atgccattgc aatgcagccg 2220

-continued

```
ggcaattatg cttactgcat tatggatgaa ggaattttaa aacattataa aaagaatggt   2280

ccagatattt ttgatattgt tcatccagca gatgctttcc ttgcagttga tggagagatt   2340

gctaaggcag tagaacaagg ttatgaatca tattttgaag cacgaacagt agaagagctt   2400

gctaaaaaac ttaatattga tgctgaaaaa ttacaagata ctattgatga atataatgaa   2460

gcctgtgaaa cgggagtaga cactaaattc cataaaaaac aggcatatct ccatcctatc   2520

actggaaagg gaaaatattt agttggaaaa ttctaccttg gagcttatgg aacaattggt   2580

ggtgttcgta tcaataaata ttgtgaagtt ttagatgaaa gctttaatcc aattgaggga   2640

ctttatagcg ctggtactga tgctaataca atttatggag acagctataa ttttactctt   2700

cctggtaaca gcatgggatt tgcaattaat tcaggacgta tggctggaga aagtgccgca   2760

gagtatattg aagaagtata a                                               2781
```

<210> SEQ ID NO 57
<211> LENGTH: 926
<212> TYPE: PRT
<213> ORGANISM: Clostridium autoethanogenum

<400> SEQUENCE: 57

```
Met Leu Thr Asn Asn Thr Glu Ala Leu Ile Leu Ala Glu Lys Ile Gly
1               5                   10                  15

Lys Glu Ala Ala Leu Ser Cys Leu Gln Gly Met Tyr Asp Tyr Gly Thr
            20                  25                  30

Ser Pro Met Lys Val Leu Asp Met Ile Lys Glu Lys Pro Asn Cys Lys
        35                  40                  45

Val Ile Val Gly Ala Leu Asn Asn Ser Asp Thr Asp Gly Met Leu Asn
    50                  55                  60

Ile Leu Ala Lys Thr Asn Pro Ala Gly Leu Ala Ala Gly Leu Ser Val
65                  70                  75                  80

Leu Ala Lys Ala Ser Gly Ala Glu Glu Ala Leu Leu Glu Leu Arg Asn
                85                  90                  95

Thr Asp Asn Glu Ala Glu Leu Leu Ala Ser Ala Lys Thr Ala Gly Val
            100                 105                 110

Lys Leu Arg Val Glu Val Gly Glu Leu Val Asp Val Arg Ala His Lys
        115                 120                 125

Glu His Ile Ile Phe Asn Leu Glu Thr Leu Ala Gly Ile Ala Asp Lys
    130                 135                 140

Ile Thr Gly Thr Ala Pro Gly Ile Ile Ile Ala Val Asp Glu Asp Val
145                 150                 155                 160

Pro Lys Glu Val Lys Phe Gly Thr Lys Leu Val Asp Phe Leu Asp Thr
                165                 170                 175

Ala Lys Val Lys Ser Val Met Ile Asn His His Phe Tyr Arg Leu Asp
            180                 185                 190

Val Leu Asn Asn Gly Ile Ile Lys Glu Asn Ser Tyr Gly Ser Gly Val
        195                 200                 205

Ile His Ile Ile Tyr Glu Asn Asp Cys Ile Val Glu Lys Thr Lys Lys
    210                 215                 220

Glu Leu Glu Asn Leu Arg Lys Gln Ser Cys Gly Lys Cys Thr Phe Cys
225                 230                 235                 240

Arg Glu Gly Leu Tyr Gln Leu Asp Val Ile Phe Asp Asp Met Ile Lys
                245                 250                 255

Gly Arg Ser Glu Lys Glu Asp Leu Ala Met Val Glu Glu Leu Thr Ser
            260                 265                 270
```

-continued

```
Ala Met Lys Phe Ser Cys Asn Cys Ser Leu Gly Lys Cys Ser Gly Glu
        275                 280                 285

Pro Ala Ala Ser Ala Ile Thr Glu Phe Lys Leu Glu Val Glu Gln His
    290                 295                 300

Ile Lys Lys Arg Gly Cys Pro Ala Gly Gln Cys Leu Ala Phe Thr Asn
305                 310                 315                 320

Ile Tyr Val Asp Pro Arg Lys Cys Lys Gly Cys Gly Lys Cys Leu Glu
                325                 330                 335

Val Cys Pro Glu Asp Cys Ile Glu Ala Lys Lys Gly Tyr Ile Ser Met
            340                 345                 350

Ile Asp Glu Phe Asp Cys Thr Lys Cys Gly Ile Cys Ile Asp Glu Cys
        355                 360                 365

Pro Asn Asn Ala Ile Val Lys Val Asn Gly Lys Thr Pro Lys Leu Pro
    370                 375                 380

Thr Lys Leu Thr Arg Val Lys Gly Ser Lys Asn Ile Thr Glu Glu Asp
385                 390                 395                 400

Thr Glu Lys Lys Lys Arg His Asn Leu Lys Arg His Arg Thr Lys Leu
                405                 410                 415

Val Ile Pro Leu Lys Lys Asp Asn Asn Lys Ala Ser Glu Lys Ile Ser
            420                 425                 430

Glu Ile Lys Lys Ser Lys Glu Gly Thr Ile Met Lys Lys Met Glu Thr
        435                 440                 445

Asp Ile Ile Ile Ala Ala Gly Gly Pro Ala Gly Leu Ala Ala Ala Ile
    450                 455                 460

Thr Ala Gly Glu Asn Asn Leu Lys Ser Ile Leu Phe Glu Lys Ser Ser
465                 470                 475                 480

Thr Thr Gly Gly Ala Ala Asn Met Gly Met Gly Pro Leu Gly Ile Asp
                485                 490                 495

Thr Lys Ile Gln Lys Asp Asn Phe Asn Asn Ile Ser Val Ala Glu Ala
            500                 505                 510

Leu Asp Met His Met Lys Tyr Thr His Tyr Arg Val Asp Glu Asp Leu
        515                 520                 525

Val Gln Thr Tyr Phe Asn Lys Ser Ala Glu Thr Ile Glu Trp Leu Gln
    530                 535                 540

Asp Met Gly Val Glu Phe Ala Gly Ala Phe Arg Tyr Phe Lys Glu Ser
545                 550                 555                 560

Ala Ala Thr Trp His Ile Val Lys Pro Glu Asn Gly Val Ile Gly Pro
                565                 570                 575

Arg Ala Ala Ser Gly Met Ala Lys Ile Met Thr Glu Arg Ala Lys Glu
            580                 585                 590

Leu Gly Thr Lys Ile Leu Leu Glu Thr Pro Val Val Ser Leu Ile Lys
        595                 600                 605

Glu Asn Gly Arg Ile Cys Gly Val Lys Ala Gln Asp Ser Glu Gly Asn
    610                 615                 620

Ile Ile Glu Val Arg Ala Lys Ala Val Ile Val Ala Thr Gly Gly Phe
625                 630                 635                 640

Gly Asn Asn Lys Asn Met Ile Lys Ser Glu Phe Gly Leu Thr Ile Gly
                645                 650                 655

Glu Asp Tyr Phe Pro Phe Met Val Pro Gly Ile Thr Gly Asp Gly Leu
            660                 665                 670

Lys Met Met Trp Glu Ala Gly Ala Met Lys Tyr Gly Glu Asn Ile Glu
        675                 680                 685
```

```
Ala Ile Tyr Gln Leu Pro Asp Asn Leu Asn Trp Phe Leu Leu Asp Ala
    690                 695                 700

Val Leu Arg Gln Pro Asn Leu Leu Ile Asn Gln Leu Gly Asp Arg Phe
705                 710                 715                 720

Met Asn Glu Gly Asp Met Gly Asn Thr Thr Phe Thr Gly Asn Ala Ile
                725                 730                 735

Ala Met Gln Pro Gly Asn Tyr Ala Tyr Cys Ile Met Asp Glu Gly Ile
            740                 745                 750

Leu Lys His Tyr Lys Lys Asn Gly Pro Asp Ile Phe Asp Ile Val His
        755                 760                 765

Pro Ala Asp Ala Phe Leu Ala Val Asp Gly Glu Ile Ala Lys Ala Val
    770                 775                 780

Glu Gln Gly Tyr Glu Ser Tyr Phe Glu Ala Arg Thr Val Glu Glu Leu
785                 790                 795                 800

Ala Lys Lys Leu Asn Ile Asp Ala Glu Lys Leu Gln Asp Thr Ile Asp
                805                 810                 815

Glu Tyr Asn Glu Ala Cys Glu Thr Gly Val Asp Thr Lys Phe His Lys
            820                 825                 830

Lys Gln Ala Tyr Leu His Pro Ile Thr Gly Lys Gly Lys Tyr Leu Val
        835                 840                 845

Gly Lys Phe Tyr Leu Gly Ala Tyr Gly Thr Ile Gly Gly Val Arg Ile
    850                 855                 860

Asn Lys Tyr Cys Glu Val Leu Asp Glu Ser Phe Asn Pro Ile Glu Gly
865                 870                 875                 880

Leu Tyr Ser Ala Gly Thr Asp Ala Asn Thr Ile Tyr Gly Asp Ser Tyr
                885                 890                 895

Asn Phe Thr Leu Pro Gly Asn Ser Met Gly Phe Ala Ile Asn Ser Gly
            900                 905                 910

Arg Met Ala Gly Glu Ser Ala Ala Glu Tyr Ile Glu Glu Val
        915                 920                 925
```

<210> SEQ ID NO 58
<211> LENGTH: 1461
<212> TYPE: DNA
<213> ORGANISM: Clostridium autoethanogenum

<400> SEQUENCE: 58

```
atgagagaat ttgaaacaga tgtagttgtt gttggtggag gagcatcagg gctagctgca     60

gcagttactg ctgcagaaaa tggtgcaaaa gtaatggtgc ttgaaaaagc taatactaca    120

ggtggatgtg ctaatatggc aatggggcct ctaggtgttg aaacaagaat gcaaagagaa    180

agacttatag atatctctgt agatagagct tttaataagt tcatggaata ttctcactgg    240

agatcagatg caagattgat aagaagatat ttggagcagt cagcaggaac tattgaatgg    300

ttagaaaata tgggagtaga attcgcatta ccttcaaagt attttccagc ttcagaagca    360

acctggcata ttgttaaacc taaaacaggg aaaccgggac ttcgtgcagc tgctactatg    420

attaaaatta tgacagaaag agcagaagaa ttaggcgtta aaatattatt agaaacacct    480

gtaaaaagta ttattaaaga tcaaggagaa gtaattggcg taacagctag tgataaagat    540

ggtgaattag aagtatatgc tggagcagtt atcatcggta caggtggatt tggtgataat    600

ccagacttta ttaagaagta tgttggactt gaatggggaa aagatttgtt ctcatataga    660

attcctggat taactggaga tggaatccag atggcttggg atgctggtgc ttcaaaagat    720

tttatgacta tggaaatggt attttttgct cctaacactg gtggatatgc tcctatagag    780
```

-continued

```
ttacctttcc gtcaacctaa tctcttagtt aacctggacg gtgaaagatt tataaatgaa    840
gaagttatag aaaatcctgt atttaccgca aatgctattg aaaaacaaaa aagaaaaatt    900
gcatattcta taatagatga agaactaatc aagcattatg aagaaaaggg cttagatctt    960
ataaatgtgg ttacttctag tatggatatg agttatttta gacaagaaga agaagaagct   1020
aagaaaaatg gaagtgatgt attatttatt gctgattcta tagaagagtt agctgaaaaa   1080
actggcattg atgcagaaaa cttaaaaaat accattgata cttataattc ttattgtgat   1140
tcaaaagatg agttattcca taaaaatcct aaatacttat taccaattaa aggctctaaa   1200
tattacgcat taaaacttgg tttaagtgca tatggaagtg ctggcggtat aaaaataaac   1260
tataatactg aagttcttaa tgatgattta aatgttataa agggacttta tgctgctgga   1320
actgatgcta attcactata taatcctgat tatgcttttg tactacctgg aaattcccta   1380
ggttttgctt tgaacagcgg aagaatagca gggtctagcg ctgttgaata tattaaagca   1440
aatcttatgg aagaacaata a                                             1461
```

<210> SEQ ID NO 59
<211> LENGTH: 486
<212> TYPE: PRT
<213> ORGANISM: Clostridium autoethanogenum

<400> SEQUENCE: 59

```
Met Arg Glu Phe Glu Thr Asp Val Val Val Val Gly Gly Gly Ala Ser
1               5                   10                  15

Gly Leu Ala Ala Ala Val Thr Ala Ala Glu Asn Gly Ala Lys Val Met
            20                  25                  30

Val Leu Glu Lys Ala Asn Thr Thr Gly Gly Cys Ala Asn Met Ala Met
        35                  40                  45

Gly Pro Leu Gly Val Glu Thr Arg Met Gln Arg Glu Arg Leu Ile Asp
    50                  55                  60

Ile Ser Val Asp Arg Ala Phe Asn Lys Phe Met Glu Tyr Ser His Trp
65                  70                  75                  80

Arg Ser Asp Ala Arg Leu Ile Arg Arg Tyr Leu Glu Gln Ser Ala Gly
                85                  90                  95

Thr Ile Glu Trp Leu Glu Asn Met Gly Val Glu Phe Ala Leu Pro Ser
            100                 105                 110

Lys Tyr Phe Pro Ala Ser Glu Ala Thr Trp His Ile Val Lys Pro Lys
        115                 120                 125

Thr Gly Lys Pro Gly Leu Arg Ala Ala Ala Thr Met Ile Lys Ile Met
    130                 135                 140

Thr Glu Arg Ala Glu Glu Leu Gly Val Lys Ile Leu Leu Glu Thr Pro
145                 150                 155                 160

Val Lys Ser Ile Ile Lys Asp Gln Gly Glu Val Ile Gly Val Thr Ala
                165                 170                 175

Ser Asp Lys Asp Gly Glu Leu Glu Val Tyr Ala Gly Ala Val Ile Ile
            180                 185                 190

Gly Thr Gly Gly Phe Gly Asp Asn Pro Asp Phe Ile Lys Lys Tyr Val
        195                 200                 205

Gly Leu Glu Trp Gly Lys Asp Leu Phe Ser Tyr Arg Ile Pro Gly Leu
    210                 215                 220

Thr Gly Asp Gly Ile Gln Met Ala Trp Asp Ala Gly Ala Ser Lys Asp
225                 230                 235                 240

Phe Met Thr Met Glu Met Val Phe Phe Ala Pro Asn Thr Gly Gly Tyr
                245                 250                 255
```

```
Ala Pro Ile Glu Leu Pro Phe Arg Gln Pro Asn Leu Leu Val Asn Leu
            260                 265                 270

Asp Gly Glu Arg Phe Ile Asn Glu Glu Val Ile Glu Asn Pro Val Phe
        275                 280                 285

Thr Ala Asn Ala Ile Glu Lys Gln Lys Arg Lys Ile Ala Tyr Ser Ile
    290                 295                 300

Ile Asp Glu Glu Leu Ile Lys His Tyr Glu Glu Lys Gly Leu Asp Leu
305                 310                 315                 320

Ile Asn Val Val Thr Ser Ser Met Asp Met Ser Tyr Phe Arg Gln Glu
                325                 330                 335

Glu Glu Glu Ala Lys Lys Asn Gly Ser Asp Val Leu Phe Ile Ala Asp
            340                 345                 350

Ser Ile Glu Glu Leu Ala Glu Lys Thr Gly Ile Asp Ala Glu Asn Leu
        355                 360                 365

Lys Asn Thr Ile Asp Thr Tyr Asn Ser Tyr Cys Asp Ser Lys Asp Glu
    370                 375                 380

Leu Phe His Lys Asn Pro Lys Tyr Leu Leu Pro Ile Lys Gly Ser Lys
385                 390                 395                 400

Tyr Tyr Ala Leu Lys Leu Gly Leu Ser Ala Tyr Gly Ser Ala Gly Gly
                405                 410                 415

Ile Lys Ile Asn Tyr Asn Thr Glu Val Leu Asn Asp Asp Leu Asn Val
            420                 425                 430

Ile Lys Gly Leu Tyr Ala Ala Gly Thr Asp Ala Asn Ser Leu Tyr Asn
        435                 440                 445

Pro Asp Tyr Ala Phe Val Leu Pro Gly Asn Ser Leu Gly Phe Ala Leu
    450                 455                 460

Asn Ser Gly Arg Ile Ala Gly Ser Ser Ala Val Glu Tyr Ile Lys Ala
465                 470                 475                 480

Asn Leu Met Glu Glu Gln
                485
```

<210> SEQ ID NO 60
<211> LENGTH: 1230
<212> TYPE: DNA
<213> ORGANISM: Clostridium ragsdalei

<400> SEQUENCE: 60

```
atgaacaatt taaaagaaga agcattaaag tttcataaag aacatgaagg taaaatagaa     60

cttaaaagta aagtagctgt taaaacaaga gaggatctgg gtttagcata tactccaggt    120

gttgctgaac catgtcttga aatcaacaaa aactataatg ccctatacga ttatacttct    180

aagggaaatt atgtagcagt agtaactaac ggcagtgcag ttttgggact tggaaatata    240

ggtgctgcag ctggcttgcc tgtaatggaa ggtaaatcta ttctatttaa gacttttgca    300

ggagtagacg cttttcctat ttgtgttgac agcaaagatc ctgacaagat tgtagaaaca    360

gtaaaattaa tagaatccac atttggagga ataaacctag aagatataaa agcccctgaa    420

tgctttgaaa tagaagataa attaaaaaag gtctgcaata taccagtttt tcatgacgac    480

caacacggaa cagcagtagt aactttagct gctatgataa acgcgcttaa aatagtaaac    540

aaaaaatttg aagacttaaa agtaataata aatggtgcag gagctgcagg tacagcaatc    600

gcaaagctgc ttgtaagtag aggagttaaa aacattattg tatgcgatag aaaaggtgct    660

atatcaaaag atagagaaaa tttaagtgct gcaaaaaaag acctggcaga aattacaaat    720

cctagcatgg taaaaggtgc gcttaaagat gtactaaaag aagctgatgt atttataggt    780
```

```
gtatctgctc ctggagtaat tactcctgaa atgataaaaa caatggataa agatcccctc    840

atttttgcta tggccaatcc taaacctgaa atctaccctg atgaagcaaa agctgcaggt    900

gccagagtag ttggtacagg aagatcggat tttccaaatc aaataaataa tgttcttgca    960

ttccctggaa tatttagagg agcacttgat gtaagagcat caaaaataaa cgaagaaatg   1020

aaaatagctg ctgcatgtgc tatagcagat ataataactg aaaaagaact taatgaagat   1080

tatgttatac cagatgcttt cgactcaaga atagcaccaa aggtagctta ctatgtagca   1140

aaagctgcca tagaaagtgg agttgcaaga agaactgaca tcactcctga aatggtagaa   1200

gaacatacta aaaagcttgt acaagcataa                                    1230


<210> SEQ ID NO 61
<211> LENGTH: 409
<212> TYPE: PRT
<213> ORGANISM: Clostridium ragsdalei

<400> SEQUENCE: 61

Met Asn Asn Leu Lys Glu Glu Ala Leu Lys Phe His Lys Glu His Glu
1               5                   10                  15

Gly Lys Ile Glu Leu Lys Ser Lys Val Ala Val Lys Thr Arg Glu Asp
            20                  25                  30

Leu Gly Leu Ala Tyr Thr Pro Gly Val Ala Glu Pro Cys Leu Glu Ile
        35                  40                  45

Asn Lys Asn Tyr Asn Ala Leu Tyr Asp Tyr Thr Ser Lys Gly Asn Tyr
    50                  55                  60

Val Ala Val Val Thr Asn Gly Ser Ala Val Leu Gly Leu Gly Asn Ile
65                  70                  75                  80

Gly Ala Ala Ala Gly Leu Pro Val Met Glu Gly Lys Ser Ile Leu Phe
                85                  90                  95

Lys Thr Phe Ala Gly Val Asp Ala Phe Pro Ile Cys Val Asp Ser Lys
            100                 105                 110

Asp Pro Asp Lys Ile Val Glu Thr Val Lys Leu Ile Glu Ser Thr Phe
        115                 120                 125

Gly Gly Ile Asn Leu Glu Asp Ile Lys Ala Pro Glu Cys Phe Glu Ile
    130                 135                 140

Glu Asp Lys Leu Lys Lys Val Cys Asn Ile Pro Val Phe His Asp Asp
145                 150                 155                 160

Gln His Gly Thr Ala Val Val Thr Leu Ala Ala Met Ile Asn Ala Leu
                165                 170                 175

Lys Ile Val Asn Lys Lys Phe Glu Asp Leu Lys Val Ile Ile Asn Gly
            180                 185                 190

Ala Gly Ala Ala Gly Thr Ala Ile Ala Lys Leu Leu Val Ser Arg Gly
        195                 200                 205

Val Lys Asn Ile Ile Val Cys Asp Arg Lys Gly Ala Ile Ser Lys Asp
    210                 215                 220

Arg Glu Asn Leu Ser Ala Ala Lys Lys Asp Leu Ala Glu Ile Thr Asn
225                 230                 235                 240

Pro Ser Met Val Lys Gly Ala Leu Lys Asp Val Leu Lys Glu Ala Asp
                245                 250                 255

Val Phe Ile Gly Val Ser Ala Pro Gly Val Ile Thr Pro Glu Met Ile
            260                 265                 270

Lys Thr Met Asp Lys Asp Pro Leu Ile Phe Ala Met Ala Asn Pro Lys
        275                 280                 285
```

-continued

```
Pro Glu Ile Tyr Pro Asp Glu Ala Lys Ala Ala Gly Ala Arg Val Val
    290                 295                 300

Gly Thr Gly Arg Ser Asp Phe Pro Asn Gln Ile Asn Asn Val Leu Ala
305                 310                 315                 320

Phe Pro Gly Ile Phe Arg Gly Ala Leu Asp Val Arg Ala Ser Lys Ile
                325                 330                 335

Asn Glu Glu Met Lys Ile Ala Ala Ala Cys Ala Ile Ala Asp Ile Ile
            340                 345                 350

Thr Glu Lys Glu Leu Asn Glu Asp Tyr Val Ile Pro Asp Ala Phe Asp
        355                 360                 365

Ser Arg Ile Ala Pro Lys Val Ala Tyr Tyr Val Ala Lys Ala Ala Ile
    370                 375                 380

Glu Ser Gly Val Ala Arg Arg Thr Asp Ile Thr Pro Glu Met Val Glu
385                 390                 395                 400

Glu His Thr Lys Lys Leu Val Gln Ala
                405
```

<210> SEQ ID NO 62
<211> LENGTH: 1098
<212> TYPE: DNA
<213> ORGANISM: Clostridium ragsdalei

<400> SEQUENCE: 62

```
atgtcataca ccaaggttaa gtatgaagat ataaaaaagt tgtgtaattt ggtttttgag      60

aaatttggat tcaaccagga agatagtaaa accataacta gcgttttgct tttatcagat     120

ctatatggaa ttgaatcaca tggtatccaa aggctagtca aatactacag tgaaataaaa     180

agtggcctta taaatatcaa ttctaaaatg aaaatagtaa aggaaacacc tgtatctgca     240

acaatagatg gcatgggagg tatgggacaa ctaattggta aaaaagccat gaatctggca     300

attaaaaaag ctaaaacttc aggaatgggt atggtagtag ttagaaattc aaatcactat     360

ggtattgcag gctactatgc caaaatggct gaggaggaag gacttcttgg aatttcaatg     420

accaattctc cagctgtaat ggtaccaacc tttggaaaag atgctatgct tggtacaaat     480

cctattgcca tatcttttcc agctaaaccc tacccatttt taatggatat ggctactagc     540

gtagttacca gaggaaaaat tgaagtttat aacaaaaggc atgaacctct tccacttggt     600

ctcgctttaa atagtgacgg tgaagatact acagatcccc tagatgtact tcttaatgta     660

cgaaaaaatt ctggaggagg cctgcttcct cttggaggat caaaagaatc aactggagga     720

cataaaggtt atggatttgc acttgcagtt gaaatgttta cagcaatttt gtctggagga     780

tttactgcaa ataaagttag cttagataga gaaaatggat ctggaacatg tcattatttc     840

tttgcagtgg attatggtat atttggggat aaacaatcca ttgaagagaa cttttccagt     900

tacctaaatg aacttagaaa ttcaaaaaaa gcaaaaggcg ccacaagaat atatactcat     960

ggtgagaaag aagtagaatc ctataaggat aaaatggaaa atggaattcc agtaaatgag    1020

actactctta aagaaatata cgacatatgt gactacttta atataaaagc tagtgattat    1080

gtaactaaag taatataa                                                  1098
```

<210> SEQ ID NO 63
<211> LENGTH: 365
<212> TYPE: PRT
<213> ORGANISM: Clostridium ragsdalei

<400> SEQUENCE: 63

```
Met Ser Tyr Thr Lys Val Lys Tyr Glu Asp Ile Lys Lys Leu Cys Asn
```

-continued

```
1               5                   10                  15

Leu Val Phe Glu Lys Phe Gly Phe Asn Gln Glu Asp Ser Lys Thr Ile
            20                  25                  30

Thr Ser Val Leu Leu Leu Ser Asp Leu Tyr Gly Ile Glu Ser His Gly
        35                  40                  45

Ile Gln Arg Leu Val Lys Tyr Tyr Ser Glu Ile Lys Ser Gly Leu Ile
    50                  55                  60

Asn Ile Asn Ser Lys Met Lys Ile Val Lys Glu Thr Pro Val Ser Ala
65                  70                  75                  80

Thr Ile Asp Gly Met Gly Gly Met Gly Gln Leu Ile Gly Lys Lys Ala
                85                  90                  95

Met Asn Leu Ala Ile Lys Lys Ala Lys Thr Ser Gly Met Gly Met Val
            100                 105                 110

Val Val Arg Asn Ser Asn His Tyr Gly Ile Ala Gly Tyr Tyr Ala Lys
        115                 120                 125

Met Ala Glu Glu Glu Gly Leu Leu Gly Ile Ser Met Thr Asn Ser Pro
    130                 135                 140

Ala Val Met Val Pro Thr Phe Gly Lys Asp Ala Met Leu Gly Thr Asn
145                 150                 155                 160

Pro Ile Ala Ile Ser Phe Pro Ala Lys Pro Tyr Pro Phe Leu Met Asp
                165                 170                 175

Met Ala Thr Ser Val Val Thr Arg Gly Lys Ile Glu Val Tyr Asn Lys
            180                 185                 190

Arg His Glu Pro Leu Pro Leu Gly Leu Ala Leu Asn Ser Asp Gly Glu
        195                 200                 205

Asp Thr Thr Asp Pro Leu Asp Val Leu Leu Asn Val Arg Lys Asn Ser
    210                 215                 220

Gly Gly Gly Leu Leu Pro Leu Gly Gly Ser Lys Glu Ser Thr Gly Gly
225                 230                 235                 240

His Lys Gly Tyr Gly Phe Ala Leu Ala Val Glu Met Phe Thr Ala Ile
                245                 250                 255

Leu Ser Gly Gly Phe Thr Ala Asn Lys Val Ser Leu Asp Arg Glu Asn
            260                 265                 270

Gly Ser Gly Thr Cys His Tyr Phe Phe Ala Val Asp Tyr Gly Ile Phe
        275                 280                 285

Gly Asp Lys Gln Ser Ile Glu Glu Asn Phe Ser Ser Tyr Leu Asn Glu
    290                 295                 300

Leu Arg Asn Ser Lys Lys Ala Lys Gly Ala Thr Arg Ile Tyr Thr His
305                 310                 315                 320

Gly Glu Lys Glu Val Glu Ser Tyr Lys Asp Lys Met Glu Asn Gly Ile
                325                 330                 335

Pro Val Asn Glu Thr Thr Leu Lys Glu Ile Tyr Asp Ile Cys Asp Tyr
            340                 345                 350

Phe Asn Ile Lys Ala Ser Asp Tyr Val Thr Lys Val Ile
        355                 360                 365


<210> SEQ ID NO 64
<211> LENGTH: 2634
<212> TYPE: DNA
<213> ORGANISM: Clostridium ragsdalei

<400> SEQUENCE: 64

atgaatggta agaagtacgt ttatcttttc aatgaaggaa atgctggcat gagaaattta      60

cttggaggca agggagctaa tcttgcagaa atgaccaatc ttggcatacc cgttcctggt     120
```

-continued

```
ggatttacta tatccacaga ggcatgtacc aaatattatg aagatggtaa atccatatca    180
cagcaagtta tagatcaaat ttatgatgca cttaaaaatg tggaagagac aacaggaaaa    240
aagtttggaa gtatagagaa tccactgtta gtttcagtaa ggtcaggagc cagagtttct    300
atgccaggaa tgatggatac tatattaaat ttgggattaa atgatgatac tgtaatagga    360
cttaaaaagc taacaggaaa tgaaagattt gcgtatgatt cttatagaag atttattcaa    420
atgttttcag atgtagttat gggaattgaa aagagagaat ttgaagatgt gctggatgac    480
gtaaaaaatg ctaaaggagt aaaatacgat acagatttag atgaatccga tttaaaggat    540
ataatccaga aatttaaaga tatttacaaa aaagaagtaa aggaagactt tcctcaagat    600
cctaaggaac agttaattca gtcagttact gcagtgttta gatcttggga aaaccctaga    660
gcaataattt acagaaggtt aaacgatata tcaggtgatt ggggaactgc agtaaatgtt    720
caatcaatgg tatttggaaa tatgggagag acttcaggaa caggagttgc atttactaga    780
aacccatcta caggggaaaa gtccatattt ggtgaatatc tcataaacgc tcaaggagag    840
gatgtagttg cagggataag aacacctcaa cctataacaa agctaaaaga agaccttcca    900
aaatgttatt ctcaatttat gagtatagcg aataaactcg aaaatcatta taaagatatg    960
caggatatgg agtttactat agagcagggg aaattatatt tccttcagac gagaaacggt   1020
aagagaacag ctcaggctgc acttagaata gcagtaaata tggtagatga aggtctcatc   1080
actaaagaag aggccatact taaagttgag cctaaacagc ttgacacact attgcatcca   1140
aactttgaca gtgatgaatt gaaacgggca gctgtaatag caaatggact tcctgcatca   1200
ccaggagcag cttgtggtaa gatatatttt acagcagatg atgctaagaa acatcatgat   1260
caaggtgaaa aggtaatact tgtaaggtta gagacttccc cagaagatat agaaggaatg   1320
gcagcttctg aaggaatact tacagttaga ggaggtatga catctcatgc agctgttgta   1380
gcaagaggta tgggaacatg ctgtgtagct ggatgtggtg atcttatagt aagtgaaaag   1440
gaaaagcttt tcaaaagatt agataaggtt tataaagaag gagattacat atctttagat   1500
ggaagtactg gaaatgttta tggagagcct ataaagactg tagcaccaga aatatcggga   1560
gattttggaa tcttcatggg atgggctgat aatataagaa aattaggagt tagaaccaat   1620
gcagatacac caagagatgc aaaccaggct attagttttg gtgccgaagg aataggactt   1680
tgtagaacag agcatatgtt cttcgatgaa gatagaatac cagaaatgag agaaatgata   1740
gtttcaaaaa cggaagagca gagaagaaaa gctttagata aattgctacc aagacaaaag   1800
aaagatttta ttggaatata tgaggcaatg gaaggaaaac ctgtcacaat tagatttttg   1860
gatccaccac ttcatgaatt cttacctact gaaactgagg atatagaggc tttagcaaag   1920
gaagtgggag taagttttca agaattgaaa gatactatag attctctaca tgaatttaat   1980
cctatgatgg gacatagagg atgcaggctt actgtttcat atccagaaat agctgaaatg   2040
caaacaaggg ctattataga agcagctata gatgttaaga agagaaaagg gtatgatata   2100
gttccagaaa ttatgatacc tcttgtagga gaagtaaaag aattaaaata tgttaaagat   2160
gtagttgtaa aggtagcaga tgaaataata caaaaagagg gagtcaattt aaaatatgaa   2220
gtaggaacta tgatagaaat tccaagagcg gctattacag ctgatgaaat agcaaaagaa   2280
gctgagttct tctcatttgg aactaatgat ttaactcaaa tgacttttgg attttcaaga   2340
gatgatgcag gtaaattttt aaatgattat tatgataaaa aagtatatga gtttgatcca   2400
ttccaaaagt tagatcagat tggagtagga aaacttgtag agactgctgt aaaattaggt   2460
```

-continued

```
aaaaagacta gacctgacat tcatcttgga atatgtggag aacatggagg ggatccatct   2520

tctgtagaat ttttccacaa tgtaggactt gactatgtat cttgttcacc atttagggta   2580

cctgtggcaa gacttgctgc agctcaagct caaataaaga atccaagaaa gtaa         2634


<210> SEQ ID NO 65
<211> LENGTH: 877
<212> TYPE: PRT
<213> ORGANISM: Clostridium ragsdalei

<400> SEQUENCE: 65

Met Asn Gly Lys Lys Tyr Val Tyr Leu Phe Asn Glu Gly Asn Ala Gly
1               5                   10                  15

Met Arg Asn Leu Leu Gly Gly Lys Gly Ala Asn Leu Ala Glu Met Thr
            20                  25                  30

Asn Leu Gly Ile Pro Val Pro Gly Gly Phe Thr Ile Ser Thr Glu Ala
        35                  40                  45

Cys Thr Lys Tyr Tyr Glu Asp Gly Lys Ser Ile Ser Gln Gln Val Ile
    50                  55                  60

Asp Gln Ile Tyr Asp Ala Leu Lys Asn Val Glu Glu Thr Thr Gly Lys
65                  70                  75                  80

Lys Phe Gly Ser Ile Glu Asn Pro Leu Leu Val Ser Val Arg Ser Gly
                85                  90                  95

Ala Arg Val Ser Met Pro Gly Met Met Asp Thr Ile Leu Asn Leu Gly
            100                 105                 110

Leu Asn Asp Asp Thr Val Ile Gly Leu Lys Lys Leu Thr Gly Asn Glu
        115                 120                 125

Arg Phe Ala Tyr Asp Ser Tyr Arg Arg Phe Ile Gln Met Phe Ser Asp
    130                 135                 140

Val Val Met Gly Ile Glu Lys Arg Glu Phe Glu Asp Val Leu Asp Asp
145                 150                 155                 160

Val Lys Asn Ala Lys Gly Val Lys Tyr Asp Thr Asp Leu Asp Glu Ser
                165                 170                 175

Asp Leu Lys Asp Ile Ile Gln Lys Phe Lys Asp Ile Tyr Lys Lys Glu
            180                 185                 190

Val Lys Glu Asp Phe Pro Gln Asp Pro Lys Glu Gln Leu Ile Gln Ser
        195                 200                 205

Val Thr Ala Val Phe Arg Ser Trp Glu Asn Pro Arg Ala Ile Ile Tyr
    210                 215                 220

Arg Arg Leu Asn Asp Ile Ser Gly Asp Trp Gly Thr Ala Val Asn Val
225                 230                 235                 240

Gln Ser Met Val Phe Gly Asn Met Gly Glu Thr Ser Gly Thr Gly Val
                245                 250                 255

Ala Phe Thr Arg Asn Pro Ser Thr Gly Glu Lys Ser Ile Phe Gly Glu
            260                 265                 270

Tyr Leu Ile Asn Ala Gln Gly Glu Asp Val Val Ala Gly Ile Arg Thr
        275                 280                 285

Pro Gln Pro Ile Thr Lys Leu Lys Glu Asp Leu Pro Lys Cys Tyr Ser
    290                 295                 300

Gln Phe Met Ser Ile Ala Asn Lys Leu Glu Asn His Tyr Lys Asp Met
305                 310                 315                 320

Gln Asp Met Glu Phe Thr Ile Glu Gln Gly Lys Leu Tyr Phe Leu Gln
                325                 330                 335

Thr Arg Asn Gly Lys Arg Thr Ala Gln Ala Ala Leu Arg Ile Ala Val
            340                 345                 350
```

-continued

```
Asn Met Val Asp Glu Gly Leu Ile Thr Lys Glu Glu Ala Ile Leu Lys
        355                 360                 365

Val Glu Pro Lys Gln Leu Asp Thr Leu Leu His Pro Asn Phe Asp Ser
    370                 375                 380

Asp Glu Leu Lys Arg Ala Ala Val Ile Ala Asn Gly Leu Pro Ala Ser
385                 390                 395                 400

Pro Gly Ala Ala Cys Gly Lys Ile Tyr Phe Thr Ala Asp Asp Ala Lys
                405                 410                 415

Lys His His Asp Gln Gly Glu Lys Val Ile Leu Val Arg Leu Glu Thr
            420                 425                 430

Ser Pro Glu Asp Ile Glu Gly Met Ala Ala Ser Glu Gly Ile Leu Thr
        435                 440                 445

Val Arg Gly Gly Met Thr Ser His Ala Ala Val Val Ala Arg Gly Met
    450                 455                 460

Gly Thr Cys Cys Val Ala Gly Cys Gly Asp Leu Ile Val Ser Glu Lys
465                 470                 475                 480

Glu Lys Leu Phe Lys Arg Leu Asp Lys Val Tyr Lys Glu Gly Asp Tyr
                485                 490                 495

Ile Ser Leu Asp Gly Ser Thr Gly Asn Val Tyr Gly Glu Pro Ile Lys
            500                 505                 510

Thr Val Ala Pro Glu Ile Ser Gly Asp Phe Gly Ile Phe Met Gly Trp
        515                 520                 525

Ala Asp Asn Ile Arg Lys Leu Gly Val Arg Thr Asn Ala Asp Thr Pro
    530                 535                 540

Arg Asp Ala Asn Gln Ala Ile Ser Phe Gly Ala Glu Gly Ile Gly Leu
545                 550                 555                 560

Cys Arg Thr Glu His Met Phe Phe Asp Glu Asp Arg Ile Pro Glu Met
                565                 570                 575

Arg Glu Met Ile Val Ser Lys Thr Glu Glu Gln Arg Arg Lys Ala Leu
            580                 585                 590

Asp Lys Leu Leu Pro Arg Gln Lys Lys Asp Phe Ile Gly Ile Tyr Glu
        595                 600                 605

Ala Met Glu Gly Lys Pro Val Thr Ile Arg Phe Leu Asp Pro Pro Leu
    610                 615                 620

His Glu Phe Leu Pro Thr Glu Thr Glu Asp Ile Glu Ala Leu Ala Lys
625                 630                 635                 640

Glu Val Gly Val Ser Phe Gln Glu Leu Lys Asp Thr Ile Asp Ser Leu
                645                 650                 655

His Glu Phe Asn Pro Met Met Gly His Arg Gly Cys Arg Leu Thr Val
            660                 665                 670

Ser Tyr Pro Glu Ile Ala Glu Met Gln Thr Arg Ala Ile Ile Glu Ala
        675                 680                 685

Ala Ile Asp Val Lys Lys Arg Lys Gly Tyr Asp Ile Val Pro Glu Ile
    690                 695                 700

Met Ile Pro Leu Val Gly Glu Val Lys Glu Leu Lys Tyr Val Lys Asp
705                 710                 715                 720

Val Val Val Lys Val Ala Asp Glu Ile Ile Gln Lys Glu Gly Val Asn
                725                 730                 735

Leu Lys Tyr Glu Val Gly Thr Met Ile Glu Ile Pro Arg Ala Ala Ile
            740                 745                 750

Thr Ala Asp Glu Ile Ala Lys Glu Ala Glu Phe Phe Ser Phe Gly Thr
        755                 760                 765
```

```
Asn Asp Leu Thr Gln Met Thr Phe Gly Phe Ser Arg Asp Asp Ala Gly
    770                 775                 780

Lys Phe Leu Asn Asp Tyr Tyr Asp Lys Lys Val Tyr Glu Phe Asp Pro
785                 790                 795                 800

Phe Gln Lys Leu Asp Gln Ile Gly Val Gly Lys Leu Val Glu Thr Ala
                805                 810                 815

Val Lys Leu Gly Lys Lys Thr Arg Pro Asp Ile His Leu Gly Ile Cys
            820                 825                 830

Gly Glu His Gly Gly Asp Pro Ser Ser Val Glu Phe Phe His Asn Val
        835                 840                 845

Gly Leu Asp Tyr Val Ser Cys Ser Pro Phe Arg Val Pro Val Ala Arg
    850                 855                 860

Leu Ala Ala Ala Gln Ala Gln Ile Lys Asn Pro Arg Lys
865                 870                 875


<210> SEQ ID NO 66
<211> LENGTH: 3447
<212> TYPE: DNA
<213> ORGANISM: Clostridium ragsdalei

<400> SEQUENCE: 66

atggcgtact tgttaaagag gtttaagagg gttcttgtag cgaatagagg agaaatagcc      60

ataagaatat tcagagcatg taaagaattg ggaataacta ctgtagcagt atattcaaat     120

gaggataaga gatctctttt cagaactaaa gctgatgaat cctatatgat agggaaaaat     180

aagggacctg tagaagcata tttagatatt gatgaaataa tagatatagc tttgaagaaa     240

aatgtagatg caatacatcc gggttatgga tttctatcag aaaatcctga attggcaaaa     300

aagtgtaaag aagcaggtat tgaatttata ggacctacat cagatatgat ggagatgctt     360

ggtgataaga taaaatctaa gattgttgca caaaaggctg gggttccaac aataccagga     420

gttcaagagg ctataaagac agaagaagaa gctttaaaat ttgctaagtt ctgtggatat     480

cctgtcatga ttaaagcagc tgatggcggt ggcggcagag gaatgagaat agtaagggaa     540

gaaaaagatc tcgtagaatc ctacaacagt gctaaaaacg aatccagaaa agcttttggt     600

tcagaaaaaa tatatattga aaaatatatt gaaagtccaa aacacataga ggtgcaggta     660

ctcggagata agtacggcaa tattgtccat ctgtatgaaa gagattgttc tatacagagg     720

agacatcaaa aggtgataga atttacacca tctttagccc tctcagaaga aaaaagacaa     780

caaatatgtg aagatgcttt aaaaattgca agaactgtag gatatacaag tgcaggtacc     840

ttggagtttt tggttgataa aaacggaaat cactatttca tagagatgaa tactagaatt     900

caggtagaac atactgtaac tgaaatggtt acaggaatag atatagttca agatcaaata     960

cttattgcag aagggcattc acttgattct aaggaaatag gaataaaatc tcaagatgat    1020

atagagttaa aaggatatgc aatacaatgc agaattacga cagaagatcc tttaaataat    1080

tttgcaccag atacaggaag aatagatatg tatagaactg gttctggatt tggtataaga    1140

cttgatggag ggaatggatt tacaggcgca gtaataagtc ctcattatga tagtttgcta    1200

gtaaaaactg tatcttggtc aagaactttt gaagatgcca taagaaaggc aataaggtct    1260

ataaatgaga ctgttatatc aggagtaaag acaaatgcag actttataat aaaagtgtta    1320

agtcatgaaa agtttataaa aggtgaatgt gatactaatt ttattgaaga taatccagat    1380

ttatttgata taaaaccaaa actagataaa gagatgagtg tacttaaatt tataggaaat    1440

aaagtagtaa atgagactcg tggaaagaag aagaaattta atatacctat tgtaccaaaa    1500
```

-continued gtagaagaaa atattaaatt gagtggaacg aagcagatac ttgataccaa aggagcagat 1560
ggattagttg attggataaa atcacaagat aagcttctta ttacagatac tactatgaga 1620
gatgcccatc agtcgcttat ggcaactagg gtgagaacta gagatttgct taagatagca 1680
aaagcacaat cagtattgac aaacgatctt ttctccatgg aaatgtgggg aggagcaact 1740
tttgatgtag cttatagatt tttaaatgaa tctccttggg aaagactaga aaaacttaga 1800
gaaaaggttc ctaatatact attccagatg ctcataagag gagctaatgc agtaggatat 1860
aagaactatc ctgataatgt tattagagaa tttataaaac aatctgcagc ttcaggtatt 1920
gatgtattta gagtatttga tgctttaaac tggcttaaag gaatggaagt ttctatagat 1980
cagacattaa aagaaggaaa aatagctgaa gcatgtatgt gctatacagg agatgtatta 2040
gatgacaagg aagataaata tacacttcag tactatgtaa acttagctaa agaaatagag 2100
aaaactggag cacagattct tggaataaag gatatgtctg ccctattaaa gccatattct 2160
gcttataaac ttgtaaaagc acttaagaat gaggtatcta ttccaataca tcttcatact 2220
catgatacta caggtaatgg tgtggcaaca gtactcatgg ctgccgatgc aggacttgat 2280
atagctgata ctgcattcaa tagtatgtct gggcttacta gccagccagc tttgaattca 2340
atagcagcag cacttaaaaa tacacctaga gatactaagt tagatgcaga taatcttcaa 2400
aaaatatcta actattggga agatgtaagg cctatataca gtcagtttga gtcaggactt 2460
aagtcgagta ctgcagaaat atacaagtat gagataccag gaggtcaata ttcaaactta 2520
aaacctcagg ttgaaagttt tgggttgggg gatcgttttg aagatgtaaa ggaaatgtat 2580
aagagagtta ataaaatgct tggcaacata attaaagtaa ctccttcttc aaaaatggta 2640
ggagacctgg ctatattcat gatacaaaat gatttagatg aaaagaatat ttatgaaaaa 2700
ggtaagagct taactttccc agattctaca atttcttact ttaagggaat gatgggtcag 2760
cctatgggag gattcccaaa ggaacttcaa aaagtagttt taaagggaga agaacctttt 2820
acggtaagac caggagaact tttaccacca gaagattttg ccaaaataaa agagtattta 2880
actaaaaaat ataagagaga atttaataat aaagaactta taagctatgc tatgtatcct 2940
gatgtatatg aaggttatct taaattctta agtgaatatg gtgatcttag cagaatggaa 3000
agtgaaacat tcttctatgg acttgcggaa ggagaacttt gtgaagttga aataggagaa 3060
ggaaagagtt tatttgtaca gttattagag attacaaaag ttgatgatga aggatacaga 3120
ttcttagtat ttgaggtaaa tggtattaag agagacataa ggataaaaga taacttggct 3180
ttctctggat caggaataaa agaaaattca tgtgttatgg cagatgaaga tgatgaaaaa 3240
gaaataggat caagtatacc tggaaacatt gttaaagtac ttgtaaaacc aggagataaa 3300
gtagaagagg gccagagctt aattgtaata gaagctatga aaatggaaac aaatgtttca 3360
gctgctgaag caggagtaat tgatggagta tttgtaaaag aaggccagag agttaaaact 3420
ggagaacttt taattagatt aaaatag 3447

<210> SEQ ID NO 67
<211> LENGTH: 1148
<212> TYPE: PRT
<213> ORGANISM: Clostridium ragsdalei

<400> SEQUENCE: 67

Met Ala Tyr Leu Leu Lys Arg Phe Lys Arg Val Leu Val Ala Asn Arg
1 5 10 15

Gly Glu Ile Ala Ile Arg Ile Phe Arg Ala Cys Lys Glu Leu Gly Ile
20 25 30

-continued

```
Thr Thr Val Ala Val Tyr Ser Asn Glu Asp Lys Arg Ser Leu Phe Arg
        35                  40                  45

Thr Lys Ala Asp Glu Ser Tyr Met Ile Gly Lys Asn Lys Gly Pro Val
    50                  55                  60

Glu Ala Tyr Leu Asp Ile Asp Glu Ile Ile Asp Ile Ala Leu Lys Lys
65                  70                  75                  80

Asn Val Asp Ala Ile His Pro Gly Tyr Gly Phe Leu Ser Glu Asn Pro
                85                  90                  95

Glu Leu Ala Lys Lys Cys Lys Glu Ala Gly Ile Glu Phe Ile Gly Pro
            100                 105                 110

Thr Ser Asp Met Met Glu Met Leu Gly Asp Lys Ile Lys Ser Lys Ile
        115                 120                 125

Val Ala Gln Lys Ala Gly Val Pro Thr Ile Pro Gly Val Gln Glu Ala
    130                 135                 140

Ile Lys Thr Glu Glu Glu Ala Leu Lys Phe Ala Lys Phe Cys Gly Tyr
145                 150                 155                 160

Pro Val Met Ile Lys Ala Ala Asp Gly Gly Gly Gly Arg Gly Met Arg
                165                 170                 175

Ile Val Arg Glu Glu Lys Asp Leu Val Glu Ser Tyr Asn Ser Ala Lys
            180                 185                 190

Asn Glu Ser Arg Lys Ala Phe Gly Ser Glu Lys Ile Tyr Ile Glu Lys
        195                 200                 205

Tyr Ile Glu Ser Pro Lys His Ile Glu Val Gln Val Leu Gly Asp Lys
    210                 215                 220

Tyr Gly Asn Ile Val His Leu Tyr Glu Arg Asp Cys Ser Ile Gln Arg
225                 230                 235                 240

Arg His Gln Lys Val Ile Glu Phe Thr Pro Ser Leu Ala Leu Ser Glu
                245                 250                 255

Glu Lys Arg Gln Gln Ile Cys Glu Asp Ala Leu Lys Ile Ala Arg Thr
            260                 265                 270

Val Gly Tyr Thr Ser Ala Gly Thr Leu Glu Phe Leu Val Asp Lys Asn
        275                 280                 285

Gly Asn His Tyr Phe Ile Glu Met Asn Thr Arg Ile Gln Val Glu His
    290                 295                 300

Thr Val Thr Glu Met Val Thr Gly Ile Asp Ile Val Gln Asp Gln Ile
305                 310                 315                 320

Leu Ile Ala Glu Gly His Ser Leu Asp Ser Lys Glu Ile Gly Ile Lys
                325                 330                 335

Ser Gln Asp Asp Ile Glu Leu Lys Gly Tyr Ala Ile Gln Cys Arg Ile
            340                 345                 350

Thr Thr Glu Asp Pro Leu Asn Asn Phe Ala Pro Asp Thr Gly Arg Ile
        355                 360                 365

Asp Met Tyr Arg Thr Gly Ser Gly Phe Gly Ile Arg Leu Asp Gly Gly
    370                 375                 380

Asn Gly Phe Thr Gly Ala Val Ile Ser Pro His Tyr Asp Ser Leu Leu
385                 390                 395                 400

Val Lys Thr Val Ser Trp Ser Arg Thr Phe Glu Asp Ala Ile Arg Lys
                405                 410                 415

Ala Ile Arg Ser Ile Asn Glu Thr Val Ile Ser Gly Val Lys Thr Asn
            420                 425                 430

Ala Asp Phe Ile Ile Lys Val Leu Ser His Glu Lys Phe Ile Lys Gly
        435                 440                 445
```

-continued

```
Glu Cys Asp Thr Asn Phe Ile Glu Asp Asn Pro Asp Leu Phe Asp Ile
    450                 455                 460

Lys Pro Lys Leu Asp Lys Glu Met Ser Val Leu Lys Phe Ile Gly Asn
465                 470                 475                 480

Lys Val Val Asn Glu Thr Arg Gly Lys Lys Lys Lys Phe Asn Ile Pro
                485                 490                 495

Ile Val Pro Lys Val Glu Glu Asn Ile Lys Leu Ser Gly Thr Lys Gln
            500                 505                 510

Ile Leu Asp Thr Lys Gly Ala Asp Gly Leu Val Asp Trp Ile Lys Ser
        515                 520                 525

Gln Asp Lys Leu Leu Ile Thr Asp Thr Thr Met Arg Asp Ala His Gln
    530                 535                 540

Ser Leu Met Ala Thr Arg Val Arg Thr Arg Asp Leu Leu Lys Ile Ala
545                 550                 555                 560

Lys Ala Gln Ser Val Leu Thr Asn Asp Leu Phe Ser Met Glu Met Trp
                565                 570                 575

Gly Gly Ala Thr Phe Asp Val Ala Tyr Arg Phe Leu Asn Glu Ser Pro
            580                 585                 590

Trp Glu Arg Leu Glu Lys Leu Arg Glu Lys Val Pro Asn Ile Leu Phe
        595                 600                 605

Gln Met Leu Ile Arg Gly Ala Asn Ala Val Gly Tyr Lys Asn Tyr Pro
    610                 615                 620

Asp Asn Val Ile Arg Glu Phe Ile Lys Gln Ser Ala Ala Ser Gly Ile
625                 630                 635                 640

Asp Val Phe Arg Val Phe Asp Ala Leu Asn Trp Leu Lys Gly Met Glu
                645                 650                 655

Val Ser Ile Asp Gln Thr Leu Lys Glu Gly Lys Ile Ala Glu Ala Cys
            660                 665                 670

Met Cys Tyr Thr Gly Asp Val Leu Asp Asp Lys Glu Asp Lys Tyr Thr
        675                 680                 685

Leu Gln Tyr Tyr Val Asn Leu Ala Lys Glu Ile Glu Lys Thr Gly Ala
    690                 695                 700

Gln Ile Leu Gly Ile Lys Asp Met Ser Ala Leu Leu Lys Pro Tyr Ser
705                 710                 715                 720

Ala Tyr Lys Leu Val Lys Ala Leu Lys Asn Glu Val Ser Ile Pro Ile
                725                 730                 735

His Leu His Thr His Asp Thr Thr Gly Asn Gly Val Ala Thr Val Leu
            740                 745                 750

Met Ala Ala Asp Ala Gly Leu Asp Ile Ala Asp Thr Ala Phe Asn Ser
        755                 760                 765

Met Ser Gly Leu Thr Ser Gln Pro Ala Leu Asn Ser Ile Ala Ala Ala
    770                 775                 780

Leu Lys Asn Thr Pro Arg Asp Thr Lys Leu Asp Ala Asp Asn Leu Gln
785                 790                 795                 800

Lys Ile Ser Asn Tyr Trp Glu Asp Val Arg Pro Ile Tyr Ser Gln Phe
                805                 810                 815

Glu Ser Gly Leu Lys Ser Ser Thr Ala Glu Ile Tyr Lys Tyr Glu Ile
            820                 825                 830

Pro Gly Gly Gln Tyr Ser Asn Leu Lys Pro Gln Val Glu Ser Phe Gly
        835                 840                 845

Leu Gly Asp Arg Phe Glu Asp Val Lys Glu Met Tyr Lys Arg Val Asn
    850                 855                 860

Lys Met Leu Gly Asn Ile Ile Lys Val Thr Pro Ser Ser Lys Met Val
```

```
865                 870                 875                 880

Gly Asp Leu Ala Ile Phe Met Ile Gln Asn Asp Leu Asp Glu Lys Asn
                885                 890                 895

Ile Tyr Glu Lys Gly Lys Ser Leu Thr Phe Pro Asp Ser Thr Ile Ser
            900                 905                 910

Tyr Phe Lys Gly Met Met Gly Gln Pro Met Gly Gly Phe Pro Lys Glu
        915                 920                 925

Leu Gln Lys Val Val Leu Lys Gly Glu Glu Pro Phe Thr Val Arg Pro
    930                 935                 940

Gly Glu Leu Leu Pro Pro Glu Asp Phe Ala Lys Ile Lys Glu Tyr Leu
945                 950                 955                 960

Thr Lys Lys Tyr Lys Arg Glu Phe Asn Asn Lys Glu Leu Ile Ser Tyr
                965                 970                 975

Ala Met Tyr Pro Asp Val Tyr Glu Gly Tyr Leu Lys Phe Leu Ser Glu
            980                 985                 990

Tyr Gly Asp Leu Ser Arg Met Glu  Ser Glu Thr Phe Phe  Tyr Gly Leu
        995                 1000                 1005

Ala Glu  Gly Glu Leu Cys Glu  Val Glu Ile Gly Glu  Gly Lys Ser
    1010                 1015                 1020

Leu Phe  Val Gln Leu Leu Glu  Ile Thr Lys Val Asp  Asp Glu Gly
    1025                 1030                 1035

Tyr Arg  Phe Leu Val Phe Glu  Val Asn Gly Ile Lys  Arg Asp Ile
    1040                 1045                 1050

Arg Ile  Lys Asp Asn Leu Ala  Phe Ser Gly Ser Gly  Ile Lys Glu
    1055                 1060                 1065

Asn Ser  Cys Val Met Ala Asp  Glu Asp Asp Glu Lys  Glu Ile Gly
    1070                 1075                 1080

Ser Ser  Ile Pro Gly Asn Ile  Val Lys Val Leu Val  Lys Pro Gly
    1085                 1090                 1095

Asp Lys  Val Glu Glu Gly Gln  Ser Leu Ile Val Ile  Glu Ala Met
    1100                 1105                 1110

Lys Met  Glu Thr Asn Val Ser  Ala Ala Glu Ala Gly  Val Ile Asp
    1115                 1120                 1125

Gly Val  Phe Val Lys Glu Gly  Gln Arg Val Lys Thr  Gly Glu Leu
    1130                 1135                 1140

Leu Ile  Arg Leu Lys
    1145


<210> SEQ ID NO 68
<211> LENGTH: 1506
<212> TYPE: DNA
<213> ORGANISM: Clostridium ragsdalei

<400> SEQUENCE: 68

ttgaatatta ataaatatag aaatatgtat aaaaatttat caccatcgga attaacggaa     60

ttttcaatta aaaggggaga aggattttta tcaaataagg gagctcttat gattaatact    120

ggaaagtata caggaagatc tcctaaagat agatttatag ttaatcaaga aagcattagg    180

aacaaaataa actggggaaa tgtaaatctt tctatagaag aagatatttt taataaaatg    240

tatgataaga ttttaaatta tataagtgat aaagacattt ttgtgtttga tggatttgtt    300

ggagctttaa aaaaatatac ccttcctata agagtaatat gcgaaagagc atcccaggcg    360

ttgtttgcaa atcaattgtt tagaaggcca acggaggagg atttaaagtg ttttactcct    420

gaatttaata ttatatcggt acctggattt aaagctaagg ggaaagagga cggtttaaat    480
```

```
tcagatgcct ttattttagt aaattttgat aaaaaaatta tattaatagg gggaaccagt    540

tactcgggag aaataaaaaa atcagtattt tcagtaatga actttttgct tccacaaaaa    600

ggggtcatgc ctatgcactg ttctgctaat ataggacaag acaataaaac ttgcttattt    660

tttgggttgt caggaacagg aaaaaccact ttatcagcag atggtgaaag aagattaatt    720

ggtgatgacg aacatggatg gtctaatgaa ggtgtattta attttgaggg tggatgttat    780

gctaaaacta taaggcttga taaggaaaag gaaagccaga tatacaatgc cataaaattt    840

ggaactgtag ttgaaaatgt agtggcagat gagaataggg tacctgatta taatgatggt    900

aggtatactg aaaatacaag ggcagcatat cctataaatt atatagataa tatagaagaa    960

agcggtgtag gaggaaatcc agagactata atatttttaa ctgcagatgc ttttggtgta   1020

atgccaccta tatcaagact ttctaaagaa gcagcaatgt atcactttat gtctggatat   1080

accagcaaga tagctggaac tgaaagagga ataattgaac ctcaagctac tttttcctct   1140

tgctttggtg aacctttat gttaatgaat cctgctgtct atgcaaagct gttaggcgaa    1200

agaatagaca agtataacac ccaggtatat ttagtgaata ctggatggct atctggagga   1260

tatggaaatg gagatagaat aaaactttcc tatacaagaa ctatgattag agaagctttg   1320

aaaggaaaat tcaaagatgt tgattttgtg gaacatcctg tgtttaaagt aatgatgcct   1380

acaagatgtc caggtgtacc tgatgaaata ttaaacccta gaaatacatg gcaagataaa   1440

gaagcgtatg atgagacagc gagaaagctg gcaatgaagt ttagtaaaaa ctttgagaag   1500

ttttaa                                                              1506
```

<210> SEQ ID NO 69
<211> LENGTH: 501
<212> TYPE: PRT
<213> ORGANISM: Clostridium ragsdalei

<400> SEQUENCE: 69

```
Met Asn Ile Asn Lys Tyr Arg Asn Met Tyr Lys Asn Leu Ser Pro Ser
1               5                   10                  15

Glu Leu Thr Glu Phe Ser Ile Lys Arg Gly Glu Gly Phe Leu Ser Asn
            20                  25                  30

Lys Gly Ala Leu Met Ile Asn Thr Gly Lys Tyr Thr Gly Arg Ser Pro
        35                  40                  45

Lys Asp Arg Phe Ile Val Asn Gln Glu Ser Ile Arg Asn Lys Ile Asn
    50                  55                  60

Trp Gly Asn Val Asn Leu Ser Ile Glu Glu Asp Ile Phe Asn Lys Met
65                  70                  75                  80

Tyr Asp Lys Ile Leu Asn Tyr Ile Ser Asp Lys Asp Ile Phe Val Phe
                85                  90                  95

Asp Gly Phe Val Gly Ala Leu Lys Lys Tyr Thr Leu Pro Ile Arg Val
            100                 105                 110

Ile Cys Glu Arg Ala Ser Gln Ala Leu Phe Ala Asn Gln Leu Phe Arg
        115                 120                 125

Arg Pro Thr Glu Glu Asp Leu Lys Cys Phe Thr Pro Glu Phe Asn Ile
    130                 135                 140

Ile Ser Val Pro Gly Phe Lys Ala Lys Gly Lys Glu Asp Gly Leu Asn
145                 150                 155                 160

Ser Asp Ala Phe Ile Leu Val Asn Phe Asp Lys Lys Ile Ile Leu Ile
                165                 170                 175

Gly Gly Thr Ser Tyr Ser Gly Glu Ile Lys Lys Ser Val Phe Ser Val
```

```
            180                 185                 190

Met Asn Phe Leu Leu Pro Gln Lys Gly Val Met Pro Met His Cys Ser
        195                 200                 205

Ala Asn Ile Gly Gln Asp Asn Lys Thr Cys Leu Phe Phe Gly Leu Ser
    210                 215                 220

Gly Thr Gly Lys Thr Thr Leu Ser Ala Asp Gly Glu Arg Arg Leu Ile
225                 230                 235                 240

Gly Asp Asp Glu His Gly Trp Ser Asn Glu Gly Val Phe Asn Phe Glu
                245                 250                 255

Gly Gly Cys Tyr Ala Lys Thr Ile Arg Leu Asp Lys Glu Lys Glu Ser
            260                 265                 270

Gln Ile Tyr Asn Ala Ile Lys Phe Gly Thr Val Val Glu Asn Val Val
        275                 280                 285

Ala Asp Glu Asn Arg Val Pro Asp Tyr Asn Asp Gly Arg Tyr Thr Glu
    290                 295                 300

Asn Thr Arg Ala Ala Tyr Pro Ile Asn Tyr Ile Asp Asn Ile Glu Glu
305                 310                 315                 320

Ser Gly Val Gly Gly Asn Pro Glu Thr Ile Ile Phe Leu Thr Ala Asp
                325                 330                 335

Ala Phe Gly Val Met Pro Pro Ile Ser Arg Leu Ser Lys Glu Ala Ala
            340                 345                 350

Met Tyr His Phe Met Ser Gly Tyr Thr Ser Lys Ile Ala Gly Thr Glu
        355                 360                 365

Arg Gly Ile Ile Glu Pro Gln Ala Thr Phe Ser Ser Cys Phe Gly Glu
    370                 375                 380

Pro Phe Met Leu Met Asn Pro Ala Val Tyr Ala Lys Leu Leu Gly Glu
385                 390                 395                 400

Arg Ile Asp Lys Tyr Asn Thr Gln Val Tyr Leu Val Asn Thr Gly Trp
                405                 410                 415

Leu Ser Gly Gly Tyr Gly Asn Gly Asp Arg Ile Lys Leu Ser Tyr Thr
            420                 425                 430

Arg Thr Met Ile Arg Glu Ala Leu Lys Gly Lys Phe Lys Asp Val Asp
        435                 440                 445

Phe Val Glu His Pro Val Phe Lys Val Met Met Pro Thr Arg Cys Pro
    450                 455                 460

Gly Val Pro Asp Glu Ile Leu Asn Pro Arg Asn Thr Trp Gln Asp Lys
465                 470                 475                 480

Glu Ala Tyr Asp Glu Thr Ala Arg Lys Leu Ala Met Lys Phe Ser Lys
                485                 490                 495

Asn Phe Glu Lys Phe
            500


<210> SEQ ID NO 70
<211> LENGTH: 843
<212> TYPE: DNA
<213> ORGANISM: Clostridium ragsdalei

<400> SEQUENCE: 70

atgagagaag tagatgtatc cactataaca aaagctgtta gaaatctctg tatagatgcc      60

aattattatc tttcggagga tgttaagaaa aagataaaag aatgtgaaga ggacgaaaaa     120

tggcctactg caaaagacat tttaggtaaa atacttgaaa atatagatat atctaaaaat     180

gaagatgtgc ctatgtgtca ggatacagga atggcttgtg tatttgtaac aattggccag     240

gatgttcata tagtaggagg aagtttagaa gacgcaataa ataagggagt aagtcaggga     300
```

```
tatgtagaag ggtatttaag aaagtctgta gtctctgatc ctataaatag agttaatact    360

aaggataata ctcctgcagt aatatattat gaaatagttc caggagataa acttaacata    420

aaagtggctc ctaaaggatt tggatcagaa aatatgagcc agataaaaat gcttaaacca    480

gcagatggac ttaagggtgt taaagatttc gtaataaaag tagtaaagga cgcaggacca    540

aatccatgtc ctcctatggt tgtaggagta ggtataggag gaacttttga caaggctgca    600

aatcttgcaa agaaagctct tgtaagacca ttatctgaaa gaaataaaaa taagttttat    660

tcagatttag aaaatgaact tttagacaaa ataaatttcc taggtatagg acctcaagga    720

ctagggggaa agactacagc tcttgcagta aatatagaaa cttatcctac gcatatagca    780

ggattacctg tagccgtaaa tataaattgc catgttacaa gacataagga aatagaattg    840

taa                                                                  843
```

<210> SEQ ID NO 71
<211> LENGTH: 280
<212> TYPE: PRT
<213> ORGANISM: Clostridium ragsdalei

<400> SEQUENCE: 71

```
Met Arg Glu Val Asp Val Ser Thr Ile Thr Lys Ala Val Arg Asn Leu
1               5                   10                  15

Cys Ile Asp Ala Asn Tyr Tyr Leu Ser Glu Asp Val Lys Lys Lys Ile
            20                  25                  30

Lys Glu Cys Glu Glu Asp Glu Lys Trp Pro Thr Ala Lys Asp Ile Leu
        35                  40                  45

Gly Lys Ile Leu Glu Asn Ile Asp Ile Ser Lys Asn Glu Asp Val Pro
    50                  55                  60

Met Cys Gln Asp Thr Gly Met Ala Cys Val Phe Val Thr Ile Gly Gln
65                  70                  75                  80

Asp Val His Ile Val Gly Gly Ser Leu Glu Asp Ala Ile Asn Lys Gly
                85                  90                  95

Val Ser Gln Gly Tyr Val Glu Gly Tyr Leu Arg Lys Ser Val Val Ser
            100                 105                 110

Asp Pro Ile Asn Arg Val Asn Thr Lys Asp Asn Thr Pro Ala Val Ile
        115                 120                 125

Tyr Tyr Glu Ile Val Pro Gly Asp Lys Leu Asn Ile Lys Val Ala Pro
    130                 135                 140

Lys Gly Phe Gly Ser Glu Asn Met Ser Gln Ile Lys Met Leu Lys Pro
145                 150                 155                 160

Ala Asp Gly Leu Lys Gly Val Lys Asp Phe Val Ile Lys Val Val Lys
                165                 170                 175

Asp Ala Gly Pro Asn Pro Cys Pro Pro Met Val Val Gly Val Gly Ile
            180                 185                 190

Gly Gly Thr Phe Asp Lys Ala Ala Asn Leu Ala Lys Lys Ala Leu Val
        195                 200                 205

Arg Pro Leu Ser Glu Arg Asn Lys Asn Lys Phe Tyr Ser Asp Leu Glu
    210                 215                 220

Asn Glu Leu Leu Asp Lys Ile Asn Phe Leu Gly Ile Gly Pro Gln Gly
225                 230                 235                 240

Leu Gly Gly Lys Thr Thr Ala Leu Ala Val Asn Ile Glu Thr Tyr Pro
                245                 250                 255

Thr His Ile Ala Gly Leu Pro Val Ala Val Asn Ile Asn Cys His Val
            260                 265                 270
```

```
Thr Arg His Lys Glu Ile Glu Leu
        275                 280


<210> SEQ ID NO 72
<211> LENGTH: 574
<212> TYPE: DNA
<213> ORGANISM: Clostridium ragsdalei

<400> SEQUENCE: 72

atgtatatgg aaaaaaagat aactactccg ttaacggaag waaaaggtta aaactttaaa      60

agcaggggat agtgttttaa tatcagggac aatatatact gctagagatg ctgctcataa     120

gagattggtc gagttattag atgaaggtaa atctcttcct atagatgtaa aagatgcaat     180

aatatattac gcaggaccaa gtcctgcaaa accaggccat gtaataggtt cagctggacc     240

aacaagtagt tatagaatgg acccatttgc accaagactg cttgatatag ggttaaaagg     300

aatgatagga aaaggccttc gttcaaaaga agttatagaa tccatgaaga aaaatggagc     360

tgtttacttt gctgcaatag gcggggctgc agcacttgta gcaaaatcca taaagaaagc     420

agaagtagta gcttatgaag atttggattc tgaagctata agaaaattag aagtaaaaga     480

tttacctgta attgtagtaa tagattcaga gggcaataat ttatatgaat caggacgaaa     540

agagtacttg gactctgtgg gccagtctaa gtaa                                 574


<210> SEQ ID NO 73
<211> LENGTH: 190
<212> TYPE: PRT
<213> ORGANISM: Clostridium ragsdalei

<400> SEQUENCE: 73

Met Tyr Met Glu Lys Lys Ile Thr Thr Pro Leu Thr Glu Glu Lys Val
1               5                   10                  15

Lys Thr Leu Lys Ala Gly Asp Ser Val Leu Ile Ser Gly Thr Ile Tyr
            20                  25                  30

Thr Ala Arg Asp Ala Ala His Lys Arg Leu Val Glu Leu Leu Asp Glu
        35                  40                  45

Gly Lys Ser Leu Pro Ile Asp Val Lys Asp Ala Ile Ile Tyr Tyr Ala
    50                  55                  60

Gly Pro Ser Pro Ala Lys Pro Gly His Val Ile Gly Ser Ala Gly Pro
65                  70                  75                  80

Thr Ser Ser Tyr Arg Met Asp Pro Phe Ala Pro Arg Leu Leu Asp Ile
                85                  90                  95

Gly Leu Lys Gly Met Ile Gly Lys Gly Leu Arg Ser Lys Glu Val Ile
            100                 105                 110

Glu Ser Met Lys Lys Asn Gly Ala Val Tyr Phe Ala Ala Ile Gly Gly
        115                 120                 125

Ala Ala Ala Leu Val Ala Lys Ser Ile Lys Lys Ala Glu Val Val Ala
    130                 135                 140

Tyr Glu Asp Leu Asp Ser Glu Ala Ile Arg Lys Leu Glu Val Lys Asp
145                 150                 155                 160

Leu Pro Val Ile Val Val Ile Asp Ser Glu Gly Asn Asn Leu Tyr Glu
                165                 170                 175

Ser Gly Arg Lys Glu Tyr Leu Asp Ser Val Gly Gln Ser Lys
            180                 185                 190


<210> SEQ ID NO 74
<211> LENGTH: 1797
```

<212> TYPE: DNA
<213> ORGANISM: Clostridium ragsdalei

<400> SEQUENCE: 74

```
atgcaaatag ataagataat tgatactgac atattagttg ttggaggctc tggagcaggg     60

tcaatggcag ctgtaacagc tgctgaaaaa ggagcaaaag tactgcttgc attaaaagga    120

aagcttggga aaagtggtaa tgctattatg gcaggagcag gattttctat ggatggagaa    180

actgcatatt ataaatatgg actcaaggaa gcagatccta gaaatacgaa ggaaaaatta    240

tttgaacaaa ttgtaaagca gtctttttat ctaagtgatc aaaatatggt tgagcagttt    300

gttaatgatt gtggtgaatg ctgctggaaa cttaaacagt ggattgaaaa agcaggacat    360

aaggttgcat tctttggaga agaaggatat ataacatcag gtaaagctgt tgcagatgga    420

tgccgatatg gagtttctga ggcaggcagc attgatgtta tacaagattt tatggttgca    480

gatgttttga tggaagatgg aagagctgta ggtgcagttg gaatagatat atattcagga    540

gagattattg aaattagatc aaagtcagtt attttagcta ctggcggata tcagccctat    600

tcctttaaat gcactgtttc cgatatgact ggcgatggaa tggctatggc gtaccgtgca    660

ggagtcaagc ttgcagatat ggaattttta ttatatatac cagcagttgc cctttcacca    720

tcagtatata aaggttcaat ttatcctttc ttacattcca gtatgcttat gcccattgtt    780

aaaaatggca aaggagaatc aattttagac aatatacctg aaactttact taaaatggcc    840

aaggaaagtg aaatgggaaa gcttatattt acgtattatt atggagatca aattgcaaaa    900

ggaaaagcaa ctccaaatgg aggagtatat tttgattatt ccaatgtacc ttttgatatt    960

tatgaaaaag ccttaaaaaa atctgagcca ttaatgaaca tgtggtatag aaaaggattc   1020

tatcaaggaa acaacttgga tacttttgtt gaaaatataa gaaagggcat tccatgggaa   1080

gtaggtattg gctcagaata cagcatgggt ggcattgaag tagacgaaaa tatgtacact   1140

ggagtaccag gactttatgc agctggtgag actacaagtg gtgtatttgg agctatgagg   1200

gttgcagacg gacttattga aatgcttgta catggttata gagcagcatt gtccgcttgc   1260

aaatatatac aaaatgtaaa tgagccaagt atgaaaaata ctaatattga tagtataatt   1320

aaagatattt tttcacctct tgaaagaaaa gaagggataa gtcctataaa aatacacaga   1380

aatatagaaa agacagctga tgctggattc aactttagaa gaaatgaaga gggacttaca   1440

aaagctttag atgatatttt aaaaatacac aaatatgaca taagcgcaat gagtactaaa   1500

agtaaaaata gagtttataa ctatgaatgg atagaatcag tacaggttcg aaatctttta   1560

acttgcacag aagcaggtgt aagagctgcc cttatgagaa aagaaagtag gggtacacat   1620

atacgtgatg attatgaatt tgtagataat gataactggc ttttaaggat tatgagttta   1680

aaaagtgaag acggaactat gaaattatca accagaaagc ctaaagtaac aacaatggaa   1740

ctcccaaatg gtaaaaataa gaatattcct gattatatgc tttcaatgtt aaagtaa      1797
```

<210> SEQ ID NO 75
<211> LENGTH: 598
<212> TYPE: PRT
<213> ORGANISM: Clostridium ragsdalei

<400> SEQUENCE: 75

```
Met Gln Ile Asp Lys Ile Ile Asp Thr Asp Ile Leu Val Val Gly Gly
1               5                   10                  15

Ser Gly Ala Gly Ser Met Ala Ala Val Thr Ala Ala Glu Lys Gly Ala
            20                  25                  30
```

-continued

```
Lys Val Leu Leu Ala Leu Lys Gly Lys Leu Gly Lys Ser Gly Asn Ala
        35                  40                  45

Ile Met Ala Gly Ala Gly Phe Ser Met Asp Gly Glu Thr Ala Tyr Tyr
    50                  55                  60

Lys Tyr Gly Leu Lys Glu Ala Asp Pro Arg Asn Thr Lys Glu Lys Leu
65                  70                  75                  80

Phe Glu Gln Ile Val Lys Gln Ser Phe Tyr Leu Ser Asp Gln Asn Met
                85                  90                  95

Val Glu Gln Phe Val Asn Asp Cys Gly Glu Cys Cys Trp Lys Leu Lys
            100                 105                 110

Gln Trp Ile Glu Lys Ala Gly His Lys Val Ala Phe Phe Gly Glu Glu
        115                 120                 125

Gly Tyr Ile Thr Ser Gly Lys Ala Val Ala Asp Gly Cys Arg Tyr Gly
    130                 135                 140

Val Ser Glu Ala Gly Ser Ile Asp Val Ile Gln Asp Phe Met Val Ala
145                 150                 155                 160

Asp Val Leu Met Glu Asp Gly Arg Ala Val Gly Ala Val Gly Ile Asp
                165                 170                 175

Ile Tyr Ser Gly Glu Ile Ile Glu Ile Arg Ser Lys Ser Val Ile Leu
            180                 185                 190

Ala Thr Gly Gly Tyr Gln Pro Tyr Ser Phe Lys Cys Thr Val Ser Asp
        195                 200                 205

Met Thr Gly Asp Gly Met Ala Met Ala Tyr Arg Ala Gly Val Lys Leu
    210                 215                 220

Ala Asp Met Glu Phe Leu Leu Tyr Ile Pro Ala Val Ala Leu Ser Pro
225                 230                 235                 240

Ser Val Tyr Lys Gly Ser Ile Tyr Pro Phe Leu His Ser Ser Met Leu
                245                 250                 255

Met Pro Ile Val Lys Asn Gly Lys Gly Glu Ser Ile Leu Asp Asn Ile
            260                 265                 270

Pro Glu Thr Leu Leu Lys Met Ala Lys Glu Ser Glu Met Gly Lys Leu
        275                 280                 285

Ile Phe Thr Tyr Tyr Tyr Gly Asp Gln Ile Ala Lys Gly Lys Ala Thr
    290                 295                 300

Pro Asn Gly Gly Val Tyr Phe Asp Tyr Ser Asn Val Pro Phe Asp Ile
305                 310                 315                 320

Tyr Glu Lys Ala Leu Lys Lys Ser Glu Pro Leu Met Asn Met Trp Tyr
                325                 330                 335

Arg Lys Gly Phe Tyr Gln Gly Asn Asn Leu Asp Thr Phe Val Glu Asn
            340                 345                 350

Ile Arg Lys Gly Ile Pro Trp Glu Val Gly Ile Gly Ser Glu Tyr Ser
        355                 360                 365

Met Gly Gly Ile Glu Val Asp Glu Asn Met Tyr Thr Gly Val Pro Gly
    370                 375                 380

Leu Tyr Ala Ala Gly Glu Thr Thr Ser Gly Val Phe Gly Ala Met Arg
385                 390                 395                 400

Val Ala Asp Gly Leu Ile Glu Met Leu Val His Gly Tyr Arg Ala Ala
                405                 410                 415

Leu Ser Ala Cys Lys Tyr Ile Gln Asn Val Asn Glu Pro Ser Met Lys
            420                 425                 430

Asn Thr Asn Ile Asp Ser Ile Ile Lys Asp Ile Phe Ser Pro Leu Glu
        435                 440                 445

Arg Lys Glu Gly Ile Ser Pro Ile Lys Ile His Arg Asn Ile Glu Lys
```

```
    450                 455                 460

Thr Ala Asp Ala Gly Phe Asn Phe Arg Arg Asn Glu Glu Gly Leu Thr
465                 470                 475                 480

Lys Ala Leu Asp Asp Ile Leu Lys Ile His Lys Tyr Asp Ile Ser Ala
                485                 490                 495

Met Ser Thr Lys Ser Lys Asn Arg Val Tyr Asn Tyr Glu Trp Ile Glu
            500                 505                 510

Ser Val Gln Val Arg Asn Leu Leu Thr Cys Thr Glu Ala Gly Val Arg
        515                 520                 525

Ala Ala Leu Met Arg Lys Glu Ser Arg Gly Thr His Ile Arg Asp Asp
    530                 535                 540

Tyr Glu Phe Val Asp Asn Asp Asn Trp Leu Leu Arg Ile Met Ser Leu
545                 550                 555                 560

Lys Ser Glu Asp Gly Thr Met Lys Leu Ser Thr Arg Lys Pro Lys Val
                565                 570                 575

Thr Thr Met Glu Leu Pro Asn Gly Lys Asn Lys Asn Ile Pro Asp Tyr
            580                 585                 590

Met Leu Ser Met Leu Lys
        595
```

<210> SEQ ID NO 76
<211> LENGTH: 912
<212> TYPE: DNA
<213> ORGANISM: Clostridium ragsdalei

<400> SEQUENCE: 76

```
atgagagagt ttgaaacaga tgttgttgtt gttggaggag gagcatcagg gcttgctgca     60

gcagttactg ctgctgaaaa tggtgcaaaa gtaatggtgc ttgaaaaagc taatactaca    120

ggtggatgtg ctaatatggc aatgggccct ctaggtgttg aaacaagaat gcaaagagaa    180

aggcttatag atatatctgt agatagagca tttaataagt tcatggaata ttctcactgg    240

agatcagatg caagattgat aagaagatat ttagagcagt cagcaggaac tattgaatgg    300

ttagaaaata tgggagtaga attcgcatta ccttcaaaat attttccagc ttcagaagca    360

acttggcata ttgttaaacc taaaactgga aaaccaggac tccgtgcagc tgctactatg    420

attaaaatca tgacagaaag agcagaagaa ttaggcgtta aaatattatt agaaacacct    480

gtaaagagta ttattaaaga tcaaggagag ataattggcg taacagctag cgataaagat    540

ggtgaattag aagtatatgc tggagcagtt atcatcggta caggcggatt tggtgataat    600

ccagatttta ttaagaagta tgttggactt gaatggggaa aagatttgtt ctcatataga    660

attcctggat taactggaga tggaatccag atggcttggg atgctggcgc ttcaaaagat    720

tttatgacta tggaaatggt attctttgct cctaacactg gtggatatgc tcctatagag    780

ttacccttcc gtcaacctaa ccttttagtt aacctggatg gtgaaagatt tataaatgaa    840

gaagttatag aaaatcctgt atttaccgca aatgctattg aaaaacaaaa aagaaagttg    900

catattctat aa                                                        912
```

<210> SEQ ID NO 77
<211> LENGTH: 303
<212> TYPE: PRT
<213> ORGANISM: Clostridium ragsdalei

<400> SEQUENCE: 77

```
Met Arg Glu Phe Glu Thr Asp Val Val Val Val Gly Gly Gly Ala Ser
1               5                   10                  15
```

Gly Leu Ala Ala Ala Val Thr Ala Ala Glu Asn Gly Ala Lys Val Met
20 25 30

Val Leu Glu Lys Ala Asn Thr Thr Gly Gly Cys Ala Asn Met Ala Met
35 40 45

Gly Pro Leu Gly Val Glu Thr Arg Met Gln Arg Glu Arg Leu Ile Asp
50 55 60

Ile Ser Val Asp Arg Ala Phe Asn Lys Phe Met Glu Tyr Ser His Trp
65 70 75 80

Arg Ser Asp Ala Arg Leu Ile Arg Arg Tyr Leu Glu Gln Ser Ala Gly
85 90 95

Thr Ile Glu Trp Leu Glu Asn Met Gly Val Glu Phe Ala Leu Pro Ser
100 105 110

Lys Tyr Phe Pro Ala Ser Glu Ala Thr Trp His Ile Val Lys Pro Lys
115 120 125

Thr Gly Lys Pro Gly Leu Arg Ala Ala Ala Thr Met Ile Lys Ile Met
130 135 140

Thr Glu Arg Ala Glu Glu Leu Gly Val Lys Ile Leu Leu Glu Thr Pro
145 150 155 160

Val Lys Ser Ile Ile Lys Asp Gln Gly Glu Ile Ile Gly Val Thr Ala
165 170 175

Ser Asp Lys Asp Gly Glu Leu Glu Val Tyr Ala Gly Ala Val Ile Ile
180 185 190

Gly Thr Gly Gly Phe Gly Asp Asn Pro Asp Phe Ile Lys Lys Tyr Val
195 200 205

Gly Leu Glu Trp Gly Lys Asp Leu Phe Ser Tyr Arg Ile Pro Gly Leu
210 215 220

Thr Gly Asp Gly Ile Gln Met Ala Trp Asp Ala Gly Ala Ser Lys Asp
225 230 235 240

Phe Met Thr Met Glu Met Val Phe Phe Ala Pro Asn Thr Gly Gly Tyr
245 250 255

Ala Pro Ile Glu Leu Pro Phe Arg Gln Pro Asn Leu Leu Val Asn Leu
260 265 270

Asp Gly Glu Arg Phe Ile Asn Glu Glu Val Ile Glu Asn Pro Val Phe
275 280 285

Thr Ala Asn Ala Ile Glu Lys Gln Lys Arg Lys Leu His Ile Leu
290 295 300

<210> SEQ ID NO 78
<211> LENGTH: 962
<212> TYPE: DNA
<213> ORGANISM: Clostridium ljungdahlii

<400> SEQUENCE: 78
tttcttcaca ggaaaatata cttcagtaac aagatcttta ggaatggtga cttggtgggg 60
gtcagttaca tatacttcat atggtgggtt tgtaagttta tatccttcat tttctaccca 120
ttccctcaac ttagcatata cagatgttaa ttctgaatat gagcccctta aaacagactt 180
cgcacaaagg actccaggca agtatcttgt tccctttaca atctccttta tcggaatggc 240
aagttctgta tcattgccag aaggattgta ttcagcgctg tgataaatag ttattggctt 300
accaagaaag tcaattacaa aaatatatat aaagaaagca aagctacata tattaaagca 360
tttaaggtaa aactaaaaat attataaaaa tgaaattatt ttttctcata gctaaagtta 420
cataatacga ggaggattta taatgaaaaa agtaatagga attataagta ttgtactatt 480

-continued

```
tgtactcgta gcacttcaat cctgtgctgc aggagtagga aatgcattaa gtaataacaa    540

agaagctagt ggatctgctg gattattttt atctgtatgt atgcttattg ctggaataat    600

agcaataata tcaaaatata gtaaaggtat gactataaca gctatagtat tttatttgtt    660

agcttttgtt gtagggattg ctaatgttgg gcatttttca gatttgcaaa tttggtcaat    720

cattaacttg atatttgctg gactattgat atttcatttg cttaaaaata agcaattata    780

taatagcagt gggaaaaagt agaatcatat attgtaatta tttttaatta tgttggcaaa    840

attgaaattg tcactgaaac acctctaaat gttttaaata catatgttta attattgtga    900

cagattctaa tagtagaaag tagaaatttg ctatgttata atgacataga ggtgaatgta    960

at                                                                   962
```

<210> SEQ ID NO 79
<211> LENGTH: 977
<212> TYPE: DNA
<213> ORGANISM: Clostridium ljungdahlii

<400> SEQUENCE: 79

```
actagacagt gctaataaca atgtctagtg ctttttatct tgctcaattt tttcattgag     60

ttcatttaag taagtccacc tgtccatctt ttcgtctagc tctttttcca gtgaattctt    120

ttcggataag agatcttcaa gaagtgcata atcagatgaa gcagcttcca tttctatttt    180

cttttcagat atagattttt ctagatgttc aattacctca tctattttgt caaactccat    240

ttgttctgca taggtaaatt ttagaggctt ttctttttgc aacttatagt tgtttttagc    300

tgtatttttc ttagagctta ttttttcctc tgatattttt gcagttttgt gaaaatagga    360

atagtttcct gtatattgag tgattttacc gtttccttca aaagaaaata ttttatcaac    420

tgttttgtca aggaagtacc tgtcatgaga tacagctata acagctcctt caaaatcgtt    480

aatataatct tctaggattg taagtgtttc tatatccaga tcatttgttg gttcgtccag    540

caaaagtaca ttagggtaat tcatcaatat ttttagaaga tataatcttc ttcgttctcc    600

tcctgaaagt tttccaaggg gagtccattg aactgaaggt tcaaataaaa aattttcaag    660

tacagcagaa gcacttattt tttcacccga tgaagttgac gcatattctg atgtcccacg    720

tatgtattca attacccttt cgttcatatc catatcagaa attccctgag aatagtatcc    780

tatctttact gtttcaccta tatctatagt gccgctgtcc ggcagaattt tttgaactaa    840

aatattcata agagtggatt taccacttcc attaggtcca ataataccta ttctgtcatt    900

atttagtatg ttataagtga aatttttaat taatgtcttt tcaccaaaac ttttgcttat    960

gttatccagg tttatga                                                   977
```

<210> SEQ ID NO 80
<211> LENGTH: 962
<212> TYPE: DNA
<213> ORGANISM: Clostridium ragsdalei

<400> SEQUENCE: 80

```
tttcttcaca ggaaaatata cttcagtaac aagatcttta ggaatggtga cttggtgggg     60

gtcagttaca tatacttcat atggtgggtt tgtaagttta tatccttcat tttctaccca    120

ttccctcaac ttagcatata cagatgttaa ttctgaatat gagcccctta aaacagactt    180

cgcacaaagg actccaggca agtatcttgt tccctttaca atctccttta tcggaatggc    240

aagttctgta tcattgccag aaggattgta ttcagcgctg tgataaatag ttattggctt    300

accaagaaag tcaattacaa aaatatatat aaagaaagca aagctacata tattaaagca    360
```

```
tttaaggtaa aactaaaaat attataaaaa tgaaattatt ttttctcata gctaaagtta    420

cataatacga ggaggattta taatgaaaaa agtaatagga attataagta ttgtactatt    480

tgtactcgta gcacttcaat cctgtgctgc aggagtagga aatgcattaa gtaataacaa    540

agaagctagt ggatctgctg gattattttt atctgtatgt atgcttattg ctggaataat    600

agcaataata tcaaaatata gtaaaggtat gactataaca gctatagtat tttatttgtt    660

agcttttgtt gtagggattg ctaatgttgg gcatttttca gatttgcaaa tttggtcaat    720

cattaacttg atatttgctg gactattgat atttcatttg cttaaaaata agcaattata    780

taatagcagt gggaaaaagt agaatcatat attgtaatta tttttaatta tgttggcaaa    840

attgaaattg tcactgaaac acctctaaat gttttaaata catatgttta attattgtga    900

cagattctaa tagtagaaag tagaaatttg ctatgttata atgacataga ggtgaatgta    960

at                                                                   962
```

<210> SEQ ID NO 81
<211> LENGTH: 975
<212> TYPE: DNA
<213> ORGANISM: Clostridium ragsdalei

<400> SEQUENCE: 81

```
ctagacagtg ttaataacaa tgtctagtgt ttttctcttg ttcaattttt tcattgagtt     60

catttaggta agtccacctg tccatctttt cttctaattc tttttccagt gaattctttt    120

cagataagag atcttcaaga agtgcataat cagatgaagc agcttccatt tctattttct    180

tttcagatat agatttttct agattttcaa ttacctcatc tattttgtca aactccattt    240

gttctgcata ggtaaatttt aaaggctttt ctttttgcaa cctataattg tttttagctg    300

tattgttctt agtggttatt ttttcttgtg gtatttttgc agtttcgtga aaatgggagt    360

agtttcctgt atattgagcg attttaccat ttccttcaaa agaaaatatt ttatcaactg    420

ttttgtcaag gaagtatctg tcatgggata cagctataac agttccttca aaatcattaa    480

tataatcctc taggattgta agtgtttcta tatccagatc atttgttggt tcgtccagta    540

aaagtacatt aggataattc atcagtattt ttagaaggta taatcttctt cgttcccctc    600

ctgaaagttt tccaagggga gtccattgaa ctgaaggttc aaatagaaaa ttttcaagta    660

cagcagaagc acttattttt tcacccgatg aagttgaggc atattctgat gtcccacgta    720

tgtattcaat taccctttcg ttcatatcca tatcagaaat tccctgagaa tagtatccta    780

tttttactgt ttcacctata tctatagtac cgctgtccgg cagaattttt tgagttaaaa    840

tattcataag agtggattta ccacttccat taggtccaat aatacctatt ctatcattat    900

ttagtacgtt ataagtgaaa tttttaatta atgttttttc accaaaactt ttgcttatgt    960

tatccaggtt tatga                                                     975
```

<210> SEQ ID NO 82
<211> LENGTH: 353
<212> TYPE: DNA
<213> ORGANISM: Clostridium autoethanogenum

<400> SEQUENCE: 82

```
aaaaaagctt ataattatcc ttagttaacg atcaggtgcg cccagatagg gtgttaagtc     60

aagtagttta aggtactact ctgtaagata acacagaaaa cagccaacct aaccgaaaag    120

cgaaagctga tacgggaaca gagcacggtt ggaaagcgat gagttaccta aagacaatcg    180
```

-continued

```
ggtacgactg agtcgcaatg ttaatcagat ataaggtata agttgtgttt actgaacgca    240

agtttctaat ttcgatttta actcgataga ggaaagtgtc tgaaacctct agtacaaaga    300

aaggtaagtt aggctgatcg acttatctgt tatcaccaca tttgtacaat ctg           353


<210> SEQ ID NO 83
<211> LENGTH: 353
<212> TYPE: DNA
<213> ORGANISM: Clostridium autoethanogenum

<400> SEQUENCE: 83

aaaaaagctt ataattatcc ttagcactcg ttgaggtgcg cccagatagg gtgttaagtc     60

aagtagttta aggtactact ctgtaagata acacagaaaa cagccaacct aaccgaaaag    120

cgaaagctga tacgggaaca gagcacggtt ggaaagcgat gagttaccta aagacaatcg    180

ggtacgactg agtcgcaatg ttaatcagat ataaggtata agttgtgttt actgaacgca    240

agtttctaat ttcgattagt gctcgataga ggaaagtgtc tgaaacctct agtacaaaga    300

aaggtaagtt aggctcaacg acttatctgt tatcaccaca tttgtacaat ctg           353


<210> SEQ ID NO 84
<211> LENGTH: 25
<212> TYPE: DNA
<213> ORGANISM: Artificial sequence
<220> FEATURE:
<223> OTHER INFORMATION: Synthetic primer

<400> SEQUENCE: 84

ctgcacctaa aaccaaagca gtatt                                           25


<210> SEQ ID NO 85
<211> LENGTH: 25
<212> TYPE: DNA
<213> ORGANISM: Artificial sequence
<220> FEATURE:
<223> OTHER INFORMATION: Synthetic primer

<400> SEQUENCE: 85

atcctttaag caagagtact gcacc                                           25


<210> SEQ ID NO 86
<211> LENGTH: 520
<212> TYPE: DNA
<213> ORGANISM: Clostridium autoethanogenum

<400> SEQUENCE: 86

ccggatwgka ysctrwgmgw gmarrcytwa saymtksgmk ycsssrcsag gkagccgtaa     60

gcttggatcc cgggawtmgk rgrwggkwsy ckgtksktgs mtccygggra gagggggatw    120

scctcccgaa agggaratta mtacsgcata ataatcagtt ttcwcatgga gactgattta    180

aaggagtaat ccsctttgag atggacccgc ggcgcattag ctagttggta gggtaacggc    240

ctaccaaggc gacratgcgt agcckacctg agagggtgat cggccmcmtt ggaactgaga    300

gacggtccmg actyctacgg gaggcakcag kggggaatwt tgcacaatgg gcgaaagcct    360

gatgcarcaa csccgcgtga gtgaagaagg ttttcggatt gtaaagctwt gtctttgggg    420

acgataatga cggtwcckwa ggaggaagcc mcsgstaact acgtgyywgc mkcckcggta    480

atacgtyggt ggmgagygtt gtyyggaatm wckwgkykta                          520


<210> SEQ ID NO 87
<211> LENGTH: 639
```

```
<212> TYPE: DNA
<213> ORGANISM: Clostridium autoethanogenum

<400> SEQUENCE: 87

gggrraystr amyscwgycr wrmmymmssm tmssskkmrw ckragmcrgr wtcaarctct      60

gttgtcgacr aattcgamwr awccrggatc aaactctgtt gtcgamsaat kcsgrkwaac     120

swaktyacmr cymcrttkts attcrmkatt actagcaact ccaacttcwt gtaggcgagt     180

ttcagcctgc aatccgaact gggggcagtt tttgaggttt gctccacctt gcggtcttgc     240

ttctctctgt actgcccatt gtarcacgtg kgttgccctg racataaggg gcatgatgat     300

ttwacstcwt ccccaccttc ytccgcgtta accmcggcag tcttgctara rtgctcaact     360

aaatgttakc aactaacamc aggggttgck ctckttgcag gacttaacct aacwtctcac     420

gacacgagct gacracaacc atgcaccacc tgtatycctg ccccgaaggg yttctcttat     480

ctctaarata ttmagggtat gtcmwgtcca ggwawggttc ttcgcgttgc ttcgaattaa     540

accacatgct ccgctgcttg tgcgggcccc cgtcaattcc tttgagtttt aatmttgcga     600

tcgtacttcc caggcggagt acttattgtg tttactgcg                            639


<210> SEQ ID NO 88
<211> LENGTH: 1028
<212> TYPE: DNA
<213> ORGANISM: Clostridium autoethanogenum

<400> SEQUENCE: 88

ccgatwgwaa ysctsgmrgc asrsytwasa ymtksarkyc sysrcaaggk agccgtaagc      60

ttggatcccg ggaaccgsrg aaggkasccs krgsktgsmt mccgggraga gggggatagc     120

cwcccsaaag ggagawtmmy rssrcataat awtcagtttt cacwtggaga ctgwtttaaa     180

ggaktaatcc gctttgagat ggacccgcgg cgcattagct agttggtagg gtaacggcct     240

accaaggcga cgatgcgtag ccgacctgag agggtgatcg gccacattgg aactgagaga     300

cggyccarac tcctacggga ggcakcagtg gggaatattg cacaatgggc gaaagcctga     360

tgcagcaacg ccgcgtgagt gaagaaggtt ttcggattgt aaagctctgt ctttggggac     420

gataatgacg gtacccaagg aggaagccac ggstaactac gkgccascag ccgcggtaat     480

acgtaggtgg cgagcgttgt ccggaattac tggkcgtaaa gagtgcgtag gcggatattt     540

aagtgasatg tgaaataccc gggcttaacy cgggcactgc wtttyaaact ggatatctar     600

agtgcgggag aggakaatgg aattcctwkt gtagcggrtg aaatgcgtak agattaggaa     660

gaacaccagt ggcgaargcg attctctgga ccrtaactga crctgaggya cgaaagcrtg     720

ggtagcaakm aggattagat accctggkta gwccacrccg taaacratga ktactakktg     780

twggaggtwt cacccccttyt ktgccrsmkt aaacacaata aktactccsc cckggraagt     840

ackatygcaa gawttaaaac tcaaaggrwt tgayggggggs cccgcycaag yagcggaagc     900

atgtggkttw wttycaakca mtsckaykaa ccttwcctkg rayttkrwmt wmccmgcaww     960

cytwataawt aaagaakccc ttysgkgymr gggwawmmgg gkkggtgyat gkktkgtygt    1020

ywatmycg                                                             1028


<210> SEQ ID NO 89
<211> LENGTH: 716
<212> TYPE: DNA
<213> ORGANISM: Clostridium autoethanogenum

<400> SEQUENCE: 89
```

```
gggtaygtsa ayswgyyatr mrysyskmtm rwskkmrwck ragmcrgrat caarctctgt      60

tgtckacraa ttcggmkrak ccrggatcaa actctgttgk cgacsaattc sgrkgaaccy    120

rkwymcmrck mcrttstsat ycrckaytac tagcaactcc aacttcatgt aggcgagttt    180

cagcctgcaa tccgaactgg gggcagtttt tgaggtttgc tccmccttgc ggtcttgctt    240

ctctctgtac tgcccattgt ascacgtgtg ttgccctgga cataaggggc atgatgattt    300

gacgtcatcc ccaccttcct ccgcgttaac cgcggcagtc ttgctagagt gctcaactaa    360

atgttagcaa ctaacaacag gggttgcgct cgttgcagga cttaacctaa catctcacga    420

cacgagctga cgacaaccat gcaccacctg tatccctgyc ccraagggyt tctcttatct    480

ctaagatawt cagggtatkt yaagtccagg waaggttctt cscrttgytt csaattaaac    540

cacatgctcc gctgcttgtg cgggcccccg tcaattcctt tgagttttaa tcttgcgatc    600

gtacttccya ggcggagtac twattgtgtt tactgyggca sasaarrggt cgatacctcc    660

tacacctagt actcatcgtt tackgmgtgy actaccaggr watstaatwc tgtttg       716

<210> SEQ ID NO 90
<211> LENGTH: 556
<212> TYPE: DNA
<213> ORGANISM: Clostridium autoethanogenum

<400> SEQUENCE: 90

ccggatwkaw awsctmsmgg cwrrcytwas aymtksgmky csyrrcaagg kagccgtaag     60

cttggatccc gggawscgkr gswggkagcc skwksktgsm tccysggrrg aggggggrwws  120

ccwcccgrrr gggagaytmm yrssgsataa taatcakttt tcwcatggar actgatttaa   180

aggagtaatc csctttgaga tggacccscg gcgcattakc tagkkggtag ggtaacggyc   240

taccaaggcg acrktgcgta gccgacctga ragggtgatc ggscacattg kaactgagag   300

amggtccara ctcytacggg aygyagcart ggggaatatt gmacaatggg cgaaagccmg   360

atgcagcaac gccscgtgag tgaagaaggt tttcggattg twaarytctg tctttgggga   420

mgataatgac kgtacccaag gasyaagccw cggstaacta cgtgccagya kyckcggtaa   480

tamktaggtg gcgagcgttg tccggaatta cygggmgtaa agartgcgta rgcggatatt   540

tarkgakatg tgaaat                                                    556

<210> SEQ ID NO 91
<211> LENGTH: 478
<212> TYPE: DNA
<213> ORGANISM: Clostridium autoethanogenum

<400> SEQUENCE: 91

gggwayytsa mkcwgycrwr maykyrgwta rcskkmrwck ragmcrgrat caarctctgt     60

tgtckacraa ttcgakwrar ccrggatcaa actctgttgt csacmaattc sgmkraawcm   120

rgwyymmact myrttstsaw ycamtwytac tagcaactcc aacttcwtgt akgcgagttt   180

cagcctgcaa tccraactgg gggcagtttt tgaggtttgc tccmccttgc ggtcttgctt   240

ctcyctgtac tgcccattgt agcmcgtgtg ttgcwctggw mataaggggc atgatgattt   300

gacgtcatcc ccaccttcct ccgcgtkaac cgcggsagtc ttgcyagagw gytcaaytaa   360

atgttrscra cwaacaacag gggttgcgct cgttgcagga cmtaamctaa yatctcayga   420

camgagctga cgamaayyat gcaccaccty tatccctgwc yckaagggct tctyttat     478

<210> SEQ ID NO 92
<211> LENGTH: 561
```

<212> TYPE: DNA
<213> ORGANISM: Clostridium autoethanogenum

<400> SEQUENCE: 92
ccgawwrgka aygstmwsmr wgcwrrsktw asaymsksam kycskrrcaa ggkagccgta 60
agcttggatc ccgggawycg krgraggkas ycskkksktr sawmyykggr ararggggat 120
wsccwcccgr awggmarawt amtascrcat aataatcagt tttcmcatgg agactgattt 180
awaggagtaa tccgctttga gatggacccg cggcgcwtta gcwagttggt agggtaacgg 240
cctaccaagg cgacgatgcg takccsacct gasagggtga tcggccacat tggaactgar 300
agacggtcca ractcctacg ggaggyakca gtggggaata ttgcacaatg ggcgaaagcc 360
tgatgcakca acgccgcgtg agtgaagaag gttttcsgat tgyaaagctc tgtctttggg 420
gacgataatg acggwaccca aggaggaarc cacggctrac tacgtgccws csgycgyggt 480
aatacrtagg tggkkagcgt tgtccggaat tyctyggckt aatgagtgcg wargcggatm 540
yttaagtgas atstgaaama c 561

<210> SEQ ID NO 93
<211> LENGTH: 362
<212> TYPE: DNA
<213> ORGANISM: Clostridium autoethanogenum

<400> SEQUENCE: 93
agggwaaysk maakgawgat matrmatgas katarcskka awckragmcr ggatcaarct 60
ctgttgtcga craattcgmk wrakccagga tcaaactctg ttgtcgacma attcsgmwra 120
accwaktcmm crckmcrttc tgatyrkmkw ctactagcaa ctccaacttc atgtaggcga 180
gtttcakcct gsaatccgaa ytgggggyag tttttgaggt tyyctccayc ttgcggtctt 240
gcttctytct gtactgccca ttgtakcacg tgtgttgccc tggacataag gggcatgatg 300
atttgacgtc atccccawct tyctccgmgt waaccgcggc agtyttycta rartgctyaa 360 yt 362

<210> SEQ ID NO 94
<211> LENGTH: 1160
<212> TYPE: DNA
<213> ORGANISM: Clostridium autoethanogenum

<400> SEQUENCE: 94
agtggcactg gaaaagaact cttagctcaa tctattcaca attatagtga aagatgtgaa 60
ggcccttttg tagctataaa ttgtagttct atacctagag aacttgtaga aagtgagctt 120
tttggttatg aaaaaggagc ttttacggga gctttaaagc aaggaaagcc tggaaagttt 180
gaattagcag atggaggaac tatttttttg gatgaagtag gagagcttcc tcttgatata 240
cagtcaaagc ttttaagggt tcttgataat aataaaatta caagagttgg aggaacttat 300
gaaaaacagc taaatgtaag gataatagga gctacaaaca gggtgctcaa ggatgaaatt 360
aaaaagaaaa atttcagaag tgacctttat tatagattga gtgtgatgaa tataaaaact 420
gtcccactta gggaaagaaa agaagatata gagcttttaa ttaaatattt tatggaagaa 480
ttgaattcta aaagtttgtg taagaagaaa gtagtggaaa aagcatacat agaaaagatt 540
aaagcttatg attggcctgg aaatgttaga gaacttagaa atgtaataga gagggattac 600
tatttaagtg aggataagat ggcccctttg gattatttag aaaaagaagt ttatgaaaaa 660
aatgtctcct ctgatccagt aaatattagt gtgcttccaa tggatgtttt agaaaaagaa 720

-continued

```
aacattgaaa atgcacttaa aaagtgtaag ggaaatatat taaaagctgc aaaatcttta    780

aatatcagta gatctaccat gtatagaaaa atgaaaaagt atggaataaa aagtgtgtca    840

aaatgaccag aaaagagtaa gattctcaaa ataggacact aagtatgtgt cataatggca    900

catagtgatt ttaaatgtct ttttaacagg tttcttgttt ttggtatggc ttttgcttat    960

aaaatatagt gaatatatta acaggtatat gtaaatttta atattgccat actattataa   1020

aaaaggagag ataattatga aagctgtatt gtggtatgat aaaaaagatg taagagtaga   1080

ggaaattgag gaacctaagg taaaagaaaa tgctgtaaaa attaaagtga aatggtgtgg   1140

tatatgtggt tctgacttgc                                               1160


<210> SEQ ID NO 95
<211> LENGTH: 834
<212> TYPE: DNA
<213> ORGANISM: Clostridium autoethanogenum

<400> SEQUENCE: 95

tattgaggag gccaaaaatg agctttaaga aaaatgtata cgatacaatg agggaactaa     60

tatctgtgcc aagcatatct ggtacaaaag aagagtgtgc ggcagcagaa aaaatatatg    120

aaaaaatttt ggaaatacct tattttaagg acaatcctga aaatctagga atagagcaaa    180

ttgaagatga tcctttagga agaagctttg tatgggcagt agtaaatgga aatgaaaatt    240

caccaaattc gtttatactt tcaggtcatt tggatgtagt tggagtagaa gaatttggac    300

atttaaaatc tatggctttt gatgtagatg aatgtactaa aagaatctca gaattgaatt    360

tagatgaaga tgctatggag gattttaaat caggagattg gatatttgga aggggaactg    420

cagacatgaa gtttggagtg gccctcaata tggaactttt aagagaattc agtaaagaga    480

gaaactttaa gggaaactta ttacttttag tagttcctgg tgaagagagt aattccgaag    540

gaatgattgc tgcagctcca tttcttctta aattaaagga agagaggaag tacaattact    600

gtggtatgat aatatcagag ccaagtatac ctgaaagagg agaaaaagaa ggcaagagat    660

tatatatagg tagtgtaggt aaaattatgc ctttattttt ttgtgtggga aaagaaactc    720

atgtagggga atctttaaga ggattgaatc caaatttgct agtttcagag ataaacaaat    780

taatggaatg taatccagat ctctcagata gcgtttatga tactgtgact ccac          834


<210> SEQ ID NO 96
<211> LENGTH: 39
<212> TYPE: DNA
<213> ORGANISM: Artificial sequence
<220> FEATURE:
<223> OTHER INFORMATION: Synthetic primer

<400> SEQUENCE: 96

attcatcctg caggagtggc actggaaaag aactcttag                            39


<210> SEQ ID NO 97
<211> LENGTH: 37
<212> TYPE: DNA
<213> ORGANISM: Artificial sequence
<220> FEATURE:
<223> OTHER INFORMATION: Synthetic primer

<400> SEQUENCE: 97

gactgcggcc gcgcaagtca gaaccacata taccaca                              37


<210> SEQ ID NO 98
<211> LENGTH: 35
```

-continued

<212> TYPE: DNA
<213> ORGANISM: Artificial sequence
<220> FEATURE:
<223> OTHER INFORMATION: Synthetic primer

<400> SEQUENCE: 98
atatgctagc tattgaggag gccaaaaatg agctt 35

<210> SEQ ID NO 99
<211> LENGTH: 37
<212> TYPE: DNA
<213> ORGANISM: Artificial sequence
<220> FEATURE:
<223> OTHER INFORMATION: Synthetic primer

<400> SEQUENCE: 99
gactggcgcg ccgtggagtc acagtatcat aaacgct 37

<210> SEQ ID NO 100
<211> LENGTH: 25
<212> TYPE: DNA
<213> ORGANISM: Artificial sequence
<220> FEATURE:
<223> OTHER INFORMATION: Synthetic primer

<400> SEQUENCE: 100
aatggcaggg cagataattg taatg 25

<210> SEQ ID NO 101
<211> LENGTH: 25
<212> TYPE: DNA
<213> ORGANISM: Artificial sequence
<220> FEATURE:
<223> OTHER INFORMATION: Synthetic primer

<400> SEQUENCE: 101
aaggcattct gagccagttc tttta 25

<210> SEQ ID NO 102
<211> LENGTH: 1062
<212> TYPE: DNA
<213> ORGANISM: Clostridium autoethanogenum

<400> SEQUENCE: 102
acagttaaaa agcatatcta acagtccttc cactgtacta attcaaggcg aaagcggtac 60
aggtaaagaa cttattgcgc agtccatcca caatgacagc agcagaaaaa ataacagctt 120
tatagcaata aattgcggtg ccatacccaa aaatttaata gaaagtgaat tattcggata 180
tgaagatgga tcattcacag gtgcaaaaca tggagggcgt gcaggaaaat ttgaacttgc 240
aaatggtggt actttatttt tagatgaaat tggggaaatg cctttagata tgcaagtaaa 300
tcttttaaga gttctccaag aaaactgtat tacaagaata ggcgggaaca gatgtgtaaa 360
aatagatata agaatcattg cagctactaa taaaaatttg agggaagaaa tacataaagg 420
aacttttcgc gaagatttat actatagact aaatgtaata cctatatatg taccaccact 480
gcgggaaaga gatatggata ttaaaatact gataaactat tttttaaaga taaaagcttt 540
taaacttaaa aaacctattc caatagtaag acctgatata tatcaaaagc tcttaaatta 600
taattggccc ggaaatgtaa gagaattgga aaattgtatt gaaaatatcg taaatatgaa 660
tggaaataca tctttcaact tcgaaaatag tatttcagta aatacgcaaa ctagtccttg 720
tactacaaaa tttaaatatg atatgtattc attaaaagag ttggaaaaag aagcaataac 780

-continued aaattgtatg agtaattgca atggtaacat tgcaaaagct tctaaaattc tgggaataaa 840
tagaagtact ttgtatacaa aaataaaaaa atatcaaatt aatttttctt aaagtgtatg 900
taaacacaac tttgttgtaa aaagcaacat tattttctta aaaaatgttg ctttttacag 960
catttttcaa ttatatatat taaccttata aagtcctacc cccctaaatt caaccttttc 1020
atgataaaaa acatactggc acaacatttg cttatatatt ta 1062

<210> SEQ ID NO 103
<211> LENGTH: 823
<212> TYPE: DNA
<213> ORGANISM: Clostridium autoethanogenum

<400> SEQUENCE: 103
cgtattttta attgcgaact taagatttaa ttaatatcta ctatgagtaa gtcaacatat 60
atacctaaat tatgataaaa ttatatatta taatttcaaa ataaacataa ctataataat 120
acactaagat aaagctattt atctgatggc tacctactgt aacactccct cttctatcaa 180
agtgagagat aacagtagct acgcccctag ataattcatc taaacttagt gggagaaaca 240
aaactctaaa gagaaagcga ttcactttaa atcaaagatt tgagatatct gcttctccca 300
ctaagtaaga ttcattgata taaaaaggaa ggtaatctaa taatgtttaa accatttact 360
catagtgaaa tagtcagtag gtctcttaat agatgcatta aataccatat agaaaaaggt 420
ataccaaaac ctaaacgaac acttagtcgc aaagaattgg acaacttaat aaaagaaaac 480
aacgatatta taaaaatagc aaaaccattt atggaaatac tttatgattt tttaagtgga 540
tcaggtttct cattatatct cacagacaaa aatggaattg tattaactat cataggtgac 600
aaagatattg taatggagca ggcaaaggct ggaatagcag aaggtattga tctgagtgaa 660
caaagtgcag gtacaaatgc agcaggaact gctatttttg aaaatttgtc agttcaactt 720
tcaggcaaag aacattttat aaatactttt cagatttata cctgctctgc atctgtcata 780
cataacgaac aaggaaatat aatcggatgt ctaactttaa ctg 823

<210> SEQ ID NO 104
<211> LENGTH: 39
<212> TYPE: DNA
<213> ORGANISM: Artificial sequence
<220> FEATURE:
<223> OTHER INFORMATION: Synthetic primer

<400> SEQUENCE: 104
attcatcctg caggacagtt aaaaagcata tctaacagt 39

<210> SEQ ID NO 105
<211> LENGTH: 37
<212> TYPE: DNA
<213> ORGANISM: Artificial sequence
<220> FEATURE:
<223> OTHER INFORMATION: Synthetic primer

<400> SEQUENCE: 105
gactgcggcc gctaaatata taagcaaatg ttgtgcc 37

<210> SEQ ID NO 106
<211> LENGTH: 34
<212> TYPE: DNA
<213> ORGANISM: Artificial sequence
<220> FEATURE:
<223> OTHER INFORMATION: Synthetic primer

<400> SEQUENCE: 106
atatgctagc gtatttttaa ttgcgaactt aaga 34

<210> SEQ ID NO 107
<211> LENGTH: 36
<212> TYPE: DNA
<213> ORGANISM: Artificial sequence
<220> FEATURE:
<223> OTHER INFORMATION: Synthetic primer

<400> SEQUENCE: 107
gactggcgcg ccagttaaag ttagacatcc gattat 36

<210> SEQ ID NO 108
<211> LENGTH: 25
<212> TYPE: DNA
<213> ORGANISM: Artificial sequence
<220> FEATURE:
<223> OTHER INFORMATION: Synthetic primer

<400> SEQUENCE: 108
ttggaatttt agctgtagat aacaa 25

<210> SEQ ID NO 109
<211> LENGTH: 25
<212> TYPE: DNA
<213> ORGANISM: Artificial sequence
<220> FEATURE:
<223> OTHER INFORMATION: Synthetic primer

<400> SEQUENCE: 109
taagtgattt tcaatggact ttact 25

<210> SEQ ID NO 110
<211> LENGTH: 344
<212> TYPE: DNA
<213> ORGANISM: Artificial sequence
<220> FEATURE:
<223> OTHER INFORMATION: Intron targeting cassette

<400> SEQUENCE: 110
aagcttataa ttatccttag atatcaatct tgtgcgccca gatagggtgt taagtcaagt 60
agtttaaggt actactctgt aagataacac agaaaacagc caacctaacc gaaaagcgaa 120
agctgatacg ggaacagagc acggttggaa agcgatgagt tacctaaaga caatcgggta 180
cgactgagtc gcaatgttaa tcagatataa ggtataagtt gtgtttactg aacgcaagtt 240
tctaatttcg attatatctc gatagaggaa agtgtctgaa acctctagta caaagaaagg 300
taagttagca agattgactt atctgttatc accacatttg taca 344

<210> SEQ ID NO 111
<211> LENGTH: 25
<212> TYPE: DNA
<213> ORGANISM: Artificial sequence
<220> FEATURE:
<223> OTHER INFORMATION: Synthetic primer

<400> SEQUENCE: 111
tgattttagg ccatgaagct gtagg 25

<210> SEQ ID NO 112
<211> LENGTH: 24
<212> TYPE: DNA
<213> ORGANISM: Artificial sequence
<220> FEATURE:

<223> OTHER INFORMATION: Synthetic primer

<400> SEQUENCE: 112
catgatttgt tcaactatat cacc 24

<210> SEQ ID NO 113
<211> LENGTH: 1005
<212> TYPE: DNA
<213> ORGANISM: Clostridium autoethanogenum

<400> SEQUENCE: 113
catatgcact tttaggtaaa taagcatgct tccctgcttc cacagataaa tctggagata 60
atccaagcat aaccaagtct ttttttggac tttgtgaatt tttcaaaata ccgtaaaaaa 120
ctgaattaaa ttttgtatct acaccacaag agctatcaat tttacaatat actcctttta 180
cataaaaaat taacgttaga gtagtaataa caagaaatat attagtttta ttaaaaattt 240
gttttctatc aattttcact atccttagca taataagaac tacaagtggc aattcaacaa 300
aacattgggc tttagctcca agaaacaaaa tggacgagat aaatataaat aaaaattttt 360
tataagacct atcttctcta tgttttaaaa agtaaataat acttgaaata aacaaaagaa 420
aacctacaat catcattggt tctccataaa ggctgttaaa ccatacaata tagtttccat 480
ctactaatat tattatagat aatatactaa aaaaaactgc tgcagctata tttttaaaat 540
gaatacagct aaagcatata tataatcctg tcatatacaa aattaagtaa ataaaagcta 600
aaattctagt gtcaaaataa ttataaccaa ttaccttaca taataatttt ccaaatgtaa 660
taggataaat catgcttgta gttggaataa ttcctaaaag ccttgaaaaa ctggttggaa 720
gcattttata ttcagttaca acatacttaa accagtgagc tgaatctttc cctttggcat 780
ctgttaaacc agtagctttc attactcttt caaaatctcc ttgatctgct atacctggca 840
taggaggata aaaaagtata aataaagctg ctatgaaagc tcctaggata ctaataattg 900
gtatatatct acataaactt gaattttccc taagagacca cctattttct ttcatatttt 960
agtaataact ctccccttc ctgggactta tccaaaaata taaca 1005

<210> SEQ ID NO 114
<211> LENGTH: 959
<212> TYPE: DNA
<213> ORGANISM: Clostridium autoethanogenum

<400> SEQUENCE: 114
attacaagtg agcatactta tgtttcatat ttttctaaat ataaccttga taccaatgta 60
atctttatta gaaaatacgg cactggagag ccaagtgata caatggtaga agcaatttgt 120
aaggatataa aagatattac ttataaaaga gtaattgcta ttggcggcgg aagtgtcctt 180
gacgtttcaa aattgtttgc attaaagaaa gtctcgccag tacttgattt atttgatcac 240
aaattagaat ttgtaaaaga taaggaattg atcctaattc caacaacttg cggaacaggc 300
agtgaagtaa ctaatatttc tattcttgaa ttgaagtcaa gacatacaaa attaggtctt 360
gctatagatg aactatatgc agattttgct gttatgattc cagaacttct agagaattta 420
ccctttaaat tttttgcaac tagttccatt gatgccttga ttcattccat tgaatccagt 480
gtttcaccaa aagctacaag ctatacagaa atgttttcct ataaagcaat ggaaatgatc 540
ttaaaaggat atcaggagat ttcaaaaaat ggcccagacg ccaggttttc cttgttagat 600
aaatttttac ttgcaagcaa ttatgctgga attgcatttg gcaatgcagg gtgtggtgca 660
gtacatgcta tgagttatcc tttaggtgct aattaccatg ttcctcatgg agaagcaaat 720

```
tatcaaatgt tcattggagt atttaaaacc tattatcgtt taaaaccaca aggtaaaatt    780

acaaaactaa ataaattctt agcatccatt ttaaactgca aagaaaatga agtttacatt    840

aaaatagaag agttattaaa tgtattgatt cctaaaaaac aattacgtga gtatggggta    900

aaagaaaaag aattaaagga atttacacaa agtgttatga ctaaacaagg tcgtttaat     959


<210> SEQ ID NO 115
<211> LENGTH: 39
<212> TYPE: DNA
<213> ORGANISM: Artificial sequence
<220> FEATURE:
<223> OTHER INFORMATION: Synthetic primer

<400> SEQUENCE: 115

attcatcctg caggcatatg cacttttagg taaataagc                            39


<210> SEQ ID NO 116
<211> LENGTH: 37
<212> TYPE: DNA
<213> ORGANISM: Artificial sequence
<220> FEATURE:
<223> OTHER INFORMATION: Synthetic peptide

<400> SEQUENCE: 116

gactgcggcc gctgttatat ttttggataa gtcccag                              37


<210> SEQ ID NO 117
<211> LENGTH: 35
<212> TYPE: DNA
<213> ORGANISM: Artificial sequence
<220> FEATURE:
<223> OTHER INFORMATION: Synthetic primer

<400> SEQUENCE: 117

atatgctagc attacaagtg agcatactta tgttt                                35


<210> SEQ ID NO 118
<211> LENGTH: 37
<212> TYPE: DNA
<213> ORGANISM: Artificial sequence
<220> FEATURE:
<223> OTHER INFORMATION: Synthetic primer

<400> SEQUENCE: 118

gactggcgcg ccattaaacg accttgttta gtcataa                              37


<210> SEQ ID NO 119
<211> LENGTH: 25
<212> TYPE: DNA
<213> ORGANISM: Artificial sequence
<220> FEATURE:
<223> OTHER INFORMATION: Synthetic primer

<400> SEQUENCE: 119

agaattttgc aagttttata ttgct                                           25


<210> SEQ ID NO 120
<211> LENGTH: 25
<212> TYPE: DNA
<213> ORGANISM: Artificial sequence
<220> FEATURE:
<223> OTHER INFORMATION: Synthetic primer

<400> SEQUENCE: 120
```

aagtcaagct ctaactttga aatat 25

<210> SEQ ID NO 121
<211> LENGTH: 1041
<212> TYPE: DNA
<213> ORGANISM: Clostridium autoethanogenum

<400> SEQUENCE: 121
tacatacaca cactaaattt ttcgataaaa taaatttaaa aacaaataaa cttaaaatag 60
agtataaaaa aaacagacat acaccccaat ggggcgaagg tctgtcgctg taccacccaa 120
attattactc gtatatataa cggctgtgcc ggcataactt actttatata aagttcagtc 180
tgcaacttag gagtgatttt caacaactgt agcttatggg ttcccaccaa atccccattc 240
tctgaaagca tatttttgtt tactcttctc cgtcatcgtt tttttatttg cactaactat 300
actataaaaa aatatgtatg tcaacaattt ttttgaaata tataattaac tctataaaga 360
aatcctaaat aaaaaatcaa ggtacaattc aaatattttt acaatcttca gctcggttaa 420
atattttgat aagcctaagc aataaattct aaaaagctaa aagtttaaat tgagtatttg 480
cttttataaa attatgaaaa atattttta cggtaatata atgtaagaaa aacataatgc 540
aataaaaaaa taaaaaaatt ttaaaaaaac tattgacatt attctcataa ggtattatta 600
tcgtcacata cactaaatat tgataaagta aatttcaaaa acaaataaat ttttcaaagt 660
gatttaaaac caattaggtt tattttagtt ttaataaaat aaatgatatt tattagtcat 720
atccatgggg gttatttcta attgatattt tgaattggta caattgtaga gtacaaagac 780
aatgataggg aagagtaaat aggaagtatt ttttagagag tgagattttg gtgaaaactc 840
ataaatatga ctattgaagg tagccttgga gtcgtgagct gaaactaagt aggctttacc 900
ggtaaaaccg ttattacttt gagtaaaaaa ttgggtggta ccgcgcgacc aaacttctcg 960
ccccaagcag agaatgttgg ttgttttttt atacaaaaaa ttagtggtaa ttgctcaaat 1020
gctggttctt aaaattgaaa t 1041

<210> SEQ ID NO 122
<211> LENGTH: 1016
<212> TYPE: DNA
<213> ORGANISM: Clostridium autoethanogenum

<400> SEQUENCE: 122
agattcattg attaaattgg ggtaatattt taacagtata tcaataagaa aatacttatg 60
aataacgctt atgaataagg gggcttatca tttagcggat gacttaaatt tacaggagaa 120
gtaggggagg tacttttccc cactaattcc tgtaatgtaa atatctatct ttttaggggc 180
aaaataatta taggtagata ttacttgtaa ataaaaaagg gcttataaat ataaattttt 240
ttataaaatg tgcgaaaatt attacgaaat tatatatagg tattataaaa actatgatgg 300
agaagagtaa atagtggagt atttttagag aattgggata aggtgaaaac ccatgaatac 360
gaaacttttg aaaatcactc ctaagttaca agctgaaatt agtaagctgt gtcggtatta 420
ccgttattag aattagaaaa aagttgggtg gtaccgcaaa gcttcttgcc ctaggcaggc 480
ggttattttt ttacaaaaaa tttccagatt taaggaggat actaaaaatg aaaagtgatt 540
cagtaaaaaa ggggattaag gcagctccag caagagcact tatgtatgga atgggatata 600
caaaagagga aattgaaaga cctcttatag gaatagtaaa ttcacaaaac gaaatagttg 660
caggtcacat gcatttagat gaaatagcaa aagctgcaaa acttggagta gcaatgtctg 720
ggggtactcc tatagagttt cctgctattg cagtttgcga tggaattgca atgggtcatg 780

-continued

```
ttggaatgaa gtattctctt gcttcaagag aactaatagc agattcaatt gaagctatgg    840

caacagctca tggttttgac ggattggtac tcatacctaa ctgtgacaaa attgtacctg    900

gaatgcttat ggcagctgca agacttaata taccagctgt tgtagtaagt ggaggaccta    960

tgagggcagg taagctaaat aacaaagcac ttgattttag cacttgtatt gaaaag       1016
```

<210> SEQ ID NO 123
<211> LENGTH: 39
<212> TYPE: DNA
<213> ORGANISM: Artificial sequence
<220> FEATURE:
<223> OTHER INFORMATION: Synthetic primer

<400> SEQUENCE: 123

```
attcatcctg caggtacata cacacactaa atttttcga                            39
```

<210> SEQ ID NO 124
<211> LENGTH: 37
<212> TYPE: DNA
<213> ORGANISM: Artificial sequence
<220> FEATURE:
<223> OTHER INFORMATION: Synthetic primer

<400> SEQUENCE: 124

```
gactgcggcc gcatttcaat tttaagaacc agcattt                              37
```

<210> SEQ ID NO 125
<211> LENGTH: 35
<212> TYPE: DNA
<213> ORGANISM: Artificial sequence
<220> FEATURE:
<223> OTHER INFORMATION: Synthetic primer

<400> SEQUENCE: 125

```
atatgctagc agattcattg attaaattgg ggtaa                                35
```

<210> SEQ ID NO 126
<211> LENGTH: 36
<212> TYPE: DNA
<213> ORGANISM: Artificial sequence
<220> FEATURE:
<223> OTHER INFORMATION: Synthetic primer

<400> SEQUENCE: 126

```
gactggcgcg ccttttcaat acaagtgcta aaatca                               36
```

<210> SEQ ID NO 127
<211> LENGTH: 25
<212> TYPE: DNA
<213> ORGANISM: Artificial sequence
<220> FEATURE:
<223> OTHER INFORMATION: Synthetic primer

<400> SEQUENCE: 127

```
tgagagttag tatttactct caact                                           25
```

<210> SEQ ID NO 128
<211> LENGTH: 25
<212> TYPE: DNA
<213> ORGANISM: Artificial sequence
<220> FEATURE:
<223> OTHER INFORMATION: Synthetic primer

<400> SEQUENCE: 128

-continued

```
ttctttacac aatccattac ataca                                          25


<210> SEQ ID NO 129
<211> LENGTH: 978
<212> TYPE: DNA
<213> ORGANISM: Clostridium autoethanogenum

<400> SEQUENCE: 129

taaggctata tttggcaatg aaataaataa aggcgatgta attgtaataa gatatgaagg     60

accaaaaggc ggacctggaa tgagagaaat gctttcacca acttctgcta tagcaggtat    120

gggtttagat aaagatgtag cacttttaac agatggaaga ttctcaggag ctacaagagg    180

ggcatctata ggccatgtgt caccagaagc tatggaaggt ggactaatag gacttgtaga    240

agaaggagat actatatttg tagatattac aaataaaaaa ttagagctaa aagtaagtga    300

ggaagaactt gaaaagagaa gaaagaacta tgtaaagcct gaacctaaga taaaaacagg    360

atatttatca agatatgcaa aattggttac ttctgcaaat acaggtgcag ttcttaaata    420

attggagttt cttaatgtac ttttaatttg taaatatact caactttcaa ctaaaaatat    480

ttcatatatg tgaaagttga gtaaatatat tatttaataa aaattcagaa taaactattg    540

acatttaagt tgttttatag taacatatac tcatatttaa ataataaaag ctttgacagg    600

gactattaaa tatgatgtat attttaaagc gagtgggatc tggtgtaaac ccataaatat    660

ttcatattga aactcaccct tgagctgtaa gctgaaatta tagtaagctg tgccggtgtg    720

aatcgttatt gaattaagta ataaaattgg gtggtaccgc gaacagactt ctcgcctcaa    780

gagaaaggct gtttttttgt gctaattttt aacctaaaat tacctatatt aattactttg    840

aattataaat atttagtgtg tatcaagttt aaatttgatt taagtaattt aatttttaga    900

aactatttat aaatgtaaat tagaaagtat aaaatacgta ttaatatatg aaagctttga    960

aagggataag tagatatt                                                  978


<210> SEQ ID NO 130
<211> LENGTH: 1002
<212> TYPE: DNA
<213> ORGANISM: Clostridium autoethanogenum

<400> SEQUENCE: 130

aagttataga tgaaatgcca taagggtggt atgaaaatta aatttagagg agggacacag     60

acatggacaa tacaatatta ttgagtaaga tatcccaggg cttaatggaa tgctgtaaat    120

caaaaaattt ttcaagagta aataaattaa ctgtgaatgt aaatgaaaac agcaatatta    180

attcttgtaa tctttatgag tatcttaaaa attttaataa aggcatagta gatgaatcta    240

cagaaattaa aattgaaatt gaagatttgc cggatcaagt tgtaatcata agcagcatag    300

aaggtgatat atcacaagag tgcatataaa gtatgtataa ggtttccaca cgaaaaatca    360

aggaaatggg tatagatttg gtttttacac aaatctatac ccattcccac taagcaagat    420

taaatttctt tctaatcata ttaactaata cttttgctgt atcatcaact ccgccgaaca    480

ggctgctgtt aattaagatg tctttgtaaa gtacattatc actgtatgac tttgcataac    540

ttaggctgta tagctgacgc gcttcatcaa cttctttaat caacttatca gcttcatctg    600

gctttatatg aagtatattg atacaatttt cctttcgtat ctcataggga gcatagataa    660

atatgctgaa atgatttgaa tggtttctta aaatatagtc agaacacctt cctacaaata    720

tacaggatga tttatctgcc agatcacaga tgattttctt ttgggcttca aatatttctt    780

cttgtgtctt ttctgaacta gttcctagtg gaaatttcat ttttttgtat tcatttttat    840
```

ctatttcttc tccactgtca atagtagata caggcaaatt catctttttt gcagcttctt 900
caacgatatc cctgtcgtaa tattcaacgc ctaacaattc agccattttt ttagcaatgg 960
gacgtcccag actcccgaat tgacgggaaa tagttattac at 1002

<210> SEQ ID NO 131
<211> LENGTH: 39
<212> TYPE: DNA
<213> ORGANISM: Artificial sequence
<220> FEATURE:
<223> OTHER INFORMATION: Synthetic primer

<400> SEQUENCE: 131
attcatcctg caggtaaggc tatatttggc aatgaaata 39

<210> SEQ ID NO 132
<211> LENGTH: 37
<212> TYPE: DNA
<213> ORGANISM: Artificial sequence
<220> FEATURE:
<223> OTHER INFORMATION: Synthetic primer

<400> SEQUENCE: 132
gactgcggcc gcaatatcta cttatccctt tcaaagc 37

<210> SEQ ID NO 133
<211> LENGTH: 35
<212> TYPE: DNA
<213> ORGANISM: Artificial sequence
<220> FEATURE:
<223> OTHER INFORMATION: Synthetic primer

<400> SEQUENCE: 133
atatgctagc aagttataga tgaaatgcca taagg 35

<210> SEQ ID NO 134
<211> LENGTH: 37
<212> TYPE: DNA
<213> ORGANISM: Artificial sequence
<220> FEATURE:
<223> OTHER INFORMATION: Synthetic primer

<400> SEQUENCE: 134
gactggcgcg ccatgtaata actatttccc gtcaatt 37

<210> SEQ ID NO 135
<211> LENGTH: 25
<212> TYPE: DNA
<213> ORGANISM: Artificial sequence
<220> FEATURE:
<223> OTHER INFORMATION: Synthetic primer

<400> SEQUENCE: 135
ataaatgaag atgcacttac tgtta 25

<210> SEQ ID NO 136
<211> LENGTH: 25
<212> TYPE: DNA
<213> ORGANISM: Artificial sequence
<220> FEATURE:
<223> OTHER INFORMATION: Synthetic primer

<400> SEQUENCE: 136
aaaatttctc cattttacga tccta 25

<210> SEQ ID NO 137
<211> LENGTH: 1115
<212> TYPE: DNA
<213> ORGANISM: Clostridium autoethanogenum

<400> SEQUENCE: 137
agtaaatatt acgcgtaaag tgttagagaa tgggaggttg tctctaaacg aaaagcttaa 60
ataattttac tttataattt aaagcttatg atgtgatatt gcttccgctg ttacattaaa 120
gagattttgt acttacctct tttctcttta atgtgactac attaaagaga aaagaggtgt 180
ttctatgtag attttttgct ctgtgtaaat taatttaata ttataacact gggggtaaaa 240
agtatgaaaa gtagaatgaa cacaaaattt cttgttacta ccgctgtttt tgttgccgtc 300
gcagttgttt tgagatcgtt ttctatagca atagctgcag gtggcatact cactatgaga 360
ataagttttg acgccatatg ttatataatg cctggtatat tatttggacc attatatggg 420
ggaatttcag gtggattaat cgatatactt ggctatataa taagacctat gggtggatac 480
atccctttgt ttactataac taatatagca gctggtattt tgcctgcact tatatggaga 540
tatattaaaa atgctaaaga atataaagta aggaattgtt atattgcttt ctttggattg 600
ctcttagtag taggtttttt taattttatc ataatgaaat ttgcatatca tactacttta 660
ggacaactgc tatcatcttt aggaaaaaaa tctcaatacc ttagtaccgg acttatgtta 720
ataggtgcta taggcgttat tatatttata ataaatgtat ttattaagaa aagcatggta 780
aaatcctatg attttgtaaa taacaattat tttaaattaa taattgcaat tggtatatct 840
ggaattttaa tatgcactat aaatacttat atattgctta tatttactcc tgctctcatt 900
gccaaaggct ttatgttctt atggatacct agaataattg aggctcttct tatgactata 960
gtaaattcct atataacctg tatgattatg tactgttata gcttatttca aggtagggta 1020
gtaaaaaaag cttaaaacgt aaaagaaatg gggtcaaaca aatgtcccca ttttttattt 1080
ctctgtttac tcttctacta aatctgatat agccg 1115

<210> SEQ ID NO 138
<211> LENGTH: 956
<212> TYPE: DNA
<213> ORGANISM: Clostridium autoethanogenum

<400> SEQUENCE: 138
atctaagtcc cccttttatt tatatattaa tcaattattt tatcaaataa tataataatt 60
tatacttagt tagactaaaa aatagattgc ttgttatttt tttcacatac ttatttattc 120 ttttttaca cttatttact tagctaagtt agaattacac cttttatatt atatttatat 180
aatataaaag accaaacttc tcccctctgg ggcgagaagt ttggtccgcg gtaccaccca 240
attttttact taattcaatt aacggctctg ccggtataac ttacttatat ttcagttaaa 300
caactccagg gtgattttca ctagctaata atttatgagc tttcacctaa cctcattctc 360
tttgaaatct ttcaccaatt acttttccct atcctcattt ttactatcta attttcaatt 420
taattacact ttcacattta gtatatattt taataatact atcttatttt ttaaatgtca 480
atagcttttt taaattttta gaaaataaat tcaaaaatat acatgaatac ctaggttgtt 540
aaaaaatcag accatataaa catggtctga taagcagaaa ttattttgct gcatcttgtg 600
tacttgcaaa atcttcatcg ttcataacac tatgactatt cccatataca aagtatatta 660
taagtccaac aacaagccat actgcaaatc tcaccaaagt taccttttgc agattatata 720
tcaagaaagc acaagctgcc atagcaaaaa caggtgtaac cggtgaaaat ggaactttaa 780
atgatctagg tctatccggt tctctttttc ttaaaactat aactgatgca gatactatta 840
taaatgctgc tagtgtacct atattagtta gttctgaaac aacacttatt ggtgtaaatc 900
cagctattat catagttata atgccaacaa gtaaagtact ttttacaggt gtatgg 956

<210> SEQ ID NO 139
<211> LENGTH: 39
<212> TYPE: DNA
<213> ORGANISM: Artificial sequence
<220> FEATURE:
<223> OTHER INFORMATION: Synthetic primer

<400> SEQUENCE: 139
attcatcctg caggagtaaa tattacgcgt aaagtgtta 39

<210> SEQ ID NO 140
<211> LENGTH: 36
<212> TYPE: DNA
<213> ORGANISM: Artificial sequence
<220> FEATURE:
<223> OTHER INFORMATION: Synthetic primer

<400> SEQUENCE: 140
gactgcggcc gcggctatat cagatttagt agaaga 36

<210> SEQ ID NO 141
<211> LENGTH: 35
<212> TYPE: DNA
<213> ORGANISM: Artificial sequence
<220> FEATURE:
<223> OTHER INFORMATION: Synthetic primer

<400> SEQUENCE: 141
atatgctagc atctaagtcc cccttttatt tatat 35

<210> SEQ ID NO 142
<211> LENGTH: 35
<212> TYPE: DNA
<213> ORGANISM: Artificial sequence
<220> FEATURE:
<223> OTHER INFORMATION: Synthetic primer

<400> SEQUENCE: 142
gactggcgcg ccatacacct gtaaaaagta cttta 35

<210> SEQ ID NO 143
<211> LENGTH: 25
<212> TYPE: DNA
<213> ORGANISM: Artificial sequence
<220> FEATURE:
<223> OTHER INFORMATION: Synthetic primer

<400> SEQUENCE: 143
atgctggtat atcaaatgtt ttagt 25

<210> SEQ ID NO 144
<211> LENGTH: 25
<212> TYPE: DNA
<213> ORGANISM: Artificial sequence
<220> FEATURE:
<223> OTHER INFORMATION: Synthetic primer

<400> SEQUENCE: 144
attgcagtat cagctatatt aacag 25

-continued

<210> SEQ ID NO 145
<211> LENGTH: 353
<212> TYPE: DNA
<213> ORGANISM: Clostridium autoethanogenum

<400> SEQUENCE: 145
aaaaaagctt ataattatcc ttagatggcg ctccggtgcg cccagatagg gtgttaagtc 60
aagtagttta aggtactact ctgtaagata acacagaaaa cagccaacct aaccgaaaag 120
cgaaagctga tacgggaaca gagcacggtt ggaaagcgat gagttaccta aagacaatcg 180
ggtacgactg agtcgcaatg ttaatcagat ataaggtata agttgtgttt actgaacgca 240
agtttctaat ttcgattcca tctcgataga ggaaagtgtc tgaaacctct agtacaaaga 300
aaggtaagtt aaccggagcg acttatctgt tatcaccaca tttgtacaat ctg 353

<210> SEQ ID NO 146
<211> LENGTH: 353
<212> TYPE: DNA
<213> ORGANISM: Clostridium autoethanogenum

<400> SEQUENCE: 146
aaaaaagctt ataattatcc ttagttaacc aagcagtgcg cccagatagg gtgttaagtc 60
aagtagttta aggtactact ctgtaagata acacagaaaa cagccaacct aaccgaaaag 120
cgaaagctga tacgggaaca gagcacggtt ggaaagcgat gagttaccta aagacaatcg 180
ggtacgactg agtcgcaatg ttaatcagat ataaggtata agttgtgttt actgaacgca 240
agtttctaat ttcgatttta actcgataga ggaaagtgtc tgaaacctct agtacaaaga 300
aaggtaagtt atctgcttgg acttatctgt tatcaccaca tttgtacaat ctg 353

<210> SEQ ID NO 147
<211> LENGTH: 353
<212> TYPE: DNA
<213> ORGANISM: Clostridium autoethanogenum

<400> SEQUENCE: 147
aaaaaagctt ataattatcc ttaagtgtct tatcggtgcg cccagatagg gtgttaagtc 60
aagtagttta aggtactact ctgtaagata acacagaaaa cagccaacct aaccgaaaag 120
cgaaagctga tacgggaaca gagcacggtt ggaaagcgat gagttaccta aagacaatcg 180
ggtacgactg agtcgcaatg ttaatcagat ataaggtata agttgtgttt actgaacgca 240
agtttctaat ttcgattaca cttcgataga ggaaagtgtc tgaaacctct agtacaaaga 300
aaggtaagtt atccgataag acttatctgt tatcaccaca tttgtacaat ctg 353

<210> SEQ ID NO 148
<211> LENGTH: 353
<212> TYPE: DNA
<213> ORGANISM: Clostridium autoethanogenum

<400> SEQUENCE: 148
aaaaaagctt ataattatcc ttacatgacc agcccgtgcg cccagatagg gtgttaagtc 60
aagtagttta aggtactact ctgtaagata acacagaaaa cagccaacct aaccgaaaag 120
cgaaagctga tacgggaaca gagcacggtt ggaaagcgat gagttaccta aagacaatcg 180
ggtacgactg agtcgcaatg ttaatcagat ataaggtata agttgtgttt actgaacgca 240
agtttctaat ttcggtttca tgtcgataga ggaaagtgtc tgaaacctct agtacaaaga 300
aaggtaagtt aaggggctgg acttatctgt tatcaccaca tttgtacaat ctg 353

-continued

<210> SEQ ID NO 149
<211> LENGTH: 24
<212> TYPE: DNA
<213> ORGANISM: Artificial sequence
<220> FEATURE:
<223> OTHER INFORMATION: Synthetic primer

<400> SEQUENCE: 149
cacaacccgt catgagcaag gtgc 24

<210> SEQ ID NO 150
<211> LENGTH: 19
<212> TYPE: DNA
<213> ORGANISM: Artificial sequence
<220> FEATURE:
<223> OTHER INFORMATION: Synthetic primer

<400> SEQUENCE: 150
tgtaattact aaatcagcc 19

<210> SEQ ID NO 151
<211> LENGTH: 24
<212> TYPE: DNA
<213> ORGANISM: Artificial sequence
<220> FEATURE:
<223> OTHER INFORMATION: Synthetic primer

<400> SEQUENCE: 151
ggaagtcagg gacatgcaca tgct 24

<210> SEQ ID NO 152
<211> LENGTH: 25
<212> TYPE: DNA
<213> ORGANISM: Artificial sequence
<220> FEATURE:
<223> OTHER INFORMATION: Synthetic primer

<400> SEQUENCE: 152
cattttcagg agcatatcca gcttc 25

<210> SEQ ID NO 153
<211> LENGTH: 25
<212> TYPE: DNA
<213> ORGANISM: Artificial sequence
<220> FEATURE:
<223> OTHER INFORMATION: Synthetic primer

<400> SEQUENCE: 153
gtgcaggtgg cggagttata ctggc 25

<210> SEQ ID NO 154
<211> LENGTH: 21
<212> TYPE: DNA
<213> ORGANISM: Artificial sequence
<220> FEATURE:
<223> OTHER INFORMATION: Synthetic primer

<400> SEQUENCE: 154
ccatagttcc gaggcctcca g 21

<210> SEQ ID NO 155
<211> LENGTH: 23
<212> TYPE: DNA
<213> ORGANISM: Artificial sequence
<220> FEATURE:

-continued

```
<223> OTHER INFORMATION: Synthetic primer

<400> SEQUENCE: 155

ggagctgaag tactattaaa atg                                        23


<210> SEQ ID NO 156
<211> LENGTH: 22
<212> TYPE: DNA
<213> ORGANISM: Artificial sequence
<220> FEATURE:
<223> OTHER INFORMATION: Synthetic primer

<400> SEQUENCE: 156

ctacttcagc tgattgtacg tc                                         22
```